(12) United States Patent
Malek et al.

(10) Patent No.: US 11,771,875 B2
(45) Date of Patent: Oct. 3, 2023

(54) CATHETER SYSTEMS AND METHODS FOR MEDICAL PROCEDURES USING CATHETERS

(71) Applicant: CereVasc, Inc., Auburndale, MA (US)

(72) Inventors: Adel M. Malek, Weston, MA (US); Carl Heilman, Wayland, MA (US); David A. Rezac, Westborough, MA (US); Jack B. Sattell, Boston, MA (US); Alexander Bonin, Bellingham, MA (US)

(73) Assignee: CereVasc, Inc., Auburndale, MA (US)

( * ) Notice: Subject to any disclaimer, the term of this patent is extended or adjusted under 35 U.S.C. 154(b) by 985 days.

(21) Appl. No.: 16/489,624

(22) PCT Filed: Mar. 2, 2018

(86) PCT No.: PCT/US2018/020667
§ 371 (c)(1),
(2) Date: Aug. 28, 2019

(87) PCT Pub. No.: WO2018/160966
PCT Pub. Date: Sep. 7, 2018

(65) Prior Publication Data
US 2020/0069927 A1    Mar. 5, 2020

Related U.S. Application Data

(63) Continuation-in-part of application No. PCT/US2017/056227, filed on Oct. 11, 2017.
(Continued)

(51) Int. Cl.
*A61M 27/00* (2006.01)
*A61M 25/00* (2006.01)
*A61F 2/95* (2013.01)

(52) U.S. Cl.
CPC ...... *A61M 27/006* (2013.01); *A61M 25/0051* (2013.01); *A61M 25/0053* (2013.01);
(Continued)

(58) Field of Classification Search
CPC ............ A61M 27/006; A61M 25/0051; A61M 25/0053; A61M 25/0054;
(Continued)

(56) References Cited

U.S. PATENT DOCUMENTS 575,997 A    1/1897 Spencer
5,562,641 A   10/1996 Flomenblit et al.
(Continued)

FOREIGN PATENT DOCUMENTS

EP    2271390      1/2011
WO    WO 2002/22028    3/2002
(Continued)

OTHER PUBLICATIONS

CereVasc, "Trevo XP 3x20mm," 2015, 56 pages.
(Continued)

*Primary Examiner* — Theodore J Stigell
(74) *Attorney, Agent, or Firm* — Fish & Richardson P.C.

(57) ABSTRACT

In some aspects, catheter devices can include: a reinforcing member having a proximal and distal ends, the reinforcing member comprising: discrete longitudinally arranged structural regions between the proximal and distal ends comprising: a first, proximal, structural region defining a first series of wall perforations that generate structural properties within the first structural region, the first series of wall perforations setting a first stiffness of the first structural region; and a second structural region, disposed distally relative to the first structural region, defining a second series of wall perforations that generate structural properties within the second structural region, the second series of wall perforations
(Continued)

setting a second stiffness of the second structural region, which is less than the first stiffness, wherein the second series of wall perforations differs from the first series of wall perforations by at least one of: cut balance, cut frequency, or pitch.

18 Claims, 98 Drawing Sheets

Related U.S. Application Data

(60) Provisional application No. 62/473,729, filed on Mar. 20, 2017, provisional application No. 62/466,272, filed on Mar. 2, 2017.

(52) U.S. Cl.
CPC . *A61M 25/0054* (2013.01); *A61F 2002/9528* (2013.01); *A61M 2025/0042* (2013.01); *A61M 2025/0047* (2013.01)

(58) Field of Classification Search
CPC ... A61M 2025/0042; A61M 2025/0047; A61F 2002/9528; A61F 2/95
See application file for complete search history.

(56) References Cited

U.S. PATENT DOCUMENTS

| | | | |
|---|---|---|---|
| 5,605,543 | A | 2/1997 | Swanson |
| 5,618,301 | A | 4/1997 | Hauenstein et al. |
| 5,725,571 | A | 3/1998 | Imbert et al. |
| 5,769,796 | A | 6/1998 | Palmer et al. |
| 5,792,157 | A | 8/1998 | Mische et al. |
| 5,885,258 | A | 3/1999 | Sachdeva et al. |
| 6,066,158 | A | 5/2000 | Engelson et al. |
| 6,096,053 | A | 8/2000 | Bates |
| 6,350,271 | B1 | 2/2002 | Kurz et al. |
| 6,425,909 | B1 | 7/2002 | Dieck et al. |
| 6,530,935 | B2 | 3/2003 | Wensel et al. |
| 6,663,650 | B2 | 12/2003 | Sepetka et al. |
| 6,730,104 | B1 | 5/2004 | Sepetka et al. |
| 7,316,692 | B2 | 1/2008 | Huffmaster |
| 7,507,252 | B2 | 3/2009 | Lashinski et al. |
| 7,621,950 | B1 | 11/2009 | Globernnan |
| 7,989,042 | B2 | 8/2011 | Obara et al. |
| 8,088,140 | B2 | 1/2012 | Ferrera et al. |
| 8,118,827 | B2 | 2/2012 | Duerig |
| 8,317,748 | B2 | 11/2012 | Fiorella et al. |
| 8,486,104 | B2 | 7/2013 | Samson et al. |
| 8,715,314 | B1 | 5/2014 | Janardhan et al. |
| 8,852,205 | B2 | 10/2014 | Brady et al. |
| 9,113,936 | B2 | 8/2015 | Palmer et al. |
| 9,119,656 | B2 | 9/2015 | Bose et al. |
| 11,383,068 | B2 | 7/2022 | Tran et al. |
| 2001/0041899 | A1 | 11/2001 | Foster |
| 2003/0040754 | A1 | 2/2003 | Mitchell |
| 2004/0073242 | A1 | 4/2004 | Cbanduszko |
| 2004/0153110 | A1 | 8/2004 | Kurz et al. |
| 2005/0033334 | A1 | 2/2005 | Santra et al. |
| 2005/0119668 | A1 | 6/2005 | Teague |
| 2005/0234509 | A1 | 10/2005 | Widomski et al. |
| 2005/0251151 | A1 | 11/2005 | Teague |
| 2005/0026752 | A1 | 12/2005 | Chanduszko |
| 2006/0100687 | A1 | 5/2006 | Fahey et al. |
| 2006/0241687 | A1 | 10/2006 | Glaser et al. |
| 2007/0005125 | A1 | 1/2007 | Berenstein et al. |
| 2007/0073337 | A1 | 3/2007 | Abbott et al. |
| 2007/0208376 | A1 | 9/2007 | Meng |
| 2008/0097398 | A1* | 4/2008 | Mitelberg ......... A61M 25/0043 604/525 |
| 2009/0069828 | A1 | 3/2009 | Martin et al. |
| 2010/0010476 | A1 | 1/2010 | Galdonik et al. |
| 2011/0301630 | A1 | 12/2011 | Hendriksen et al. |
| 2011/0319917 | A1 | 12/2011 | Ferrara et al. |
| 2013/0144328 | A1 | 6/2013 | Weber et al. |
| 2013/0184739 | A1 | 7/2013 | Brady et al. |
| 2013/0345739 | A1 | 12/2013 | Brady et al. |
| 2014/0128905 | A1 | 5/2014 | Molaei |
| 2014/0277079 | A1 | 9/2014 | Vale et al. |
| 2014/0371778 | A1 | 12/2014 | Rudakov et al. |
| 2015/0209058 | A1 | 7/2015 | Ferrera et al. |
| 2015/0305756 | A1 | 10/2015 | Rosenbluth et al. |
| 2016/0136398 | A1 | 5/2016 | Heilman et al. |
| 2016/0287276 | A1 | 10/2016 | Cox et al. |
| 2019/0021750 | A1 | 1/2019 | Heilman et al. |

FOREIGN PATENT DOCUMENTS

| | | |
|---|---|---|
| WO | WO 2006/080113 | 8/2006 |
| WO | WO 2007/115314 | 10/2007 |
| WO | WO 2009/088783 | 7/2009 |
| WO | WO 2012/158152 | 11/2012 |
| WO | WO 2017075544 A1 | 5/2017 |
| WO | WO 2018/071600 | 4/2018 |

OTHER PUBLICATIONS

Medtronic, "Mechanical Thrombectomy for treatment of acute ischemic stroke," 98 pages.
PCT International Search Report and Written Opinion in International Appln. No. PCT/US2016/069280, dated Mar. 27, 2017, 8 pages.
PCT International Preliminary Report on Patentability in International Appln. No. PCT/US2016/069280, dated Jul. 3, 2018, 10 pages.
PCT International Preliminary Report on Patentability in International Appln. No. PCT/US2018/020667, dated Sep. 12, 2019, 13 pages.
PCT International Search Report and Written Opinion in International Appln. No. PCT/US2018/020667, dated Jan. 8, 2018, 17 pages.
U.S. Office Action in U.S. Appl. No. 16/067,486, dated Feb. 3, 2020, 12 pages.
U.S. Office Action in U.S. Appl. No. 16/067,486, dated Sep. 10, 2020, 14 pages.

\* cited by examiner

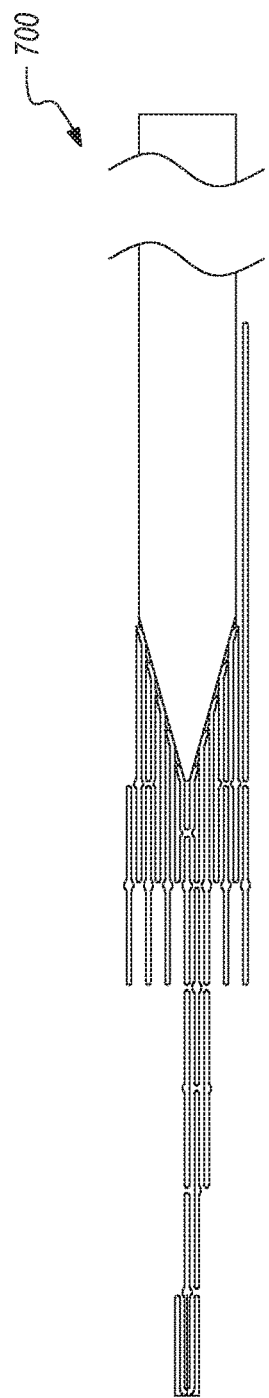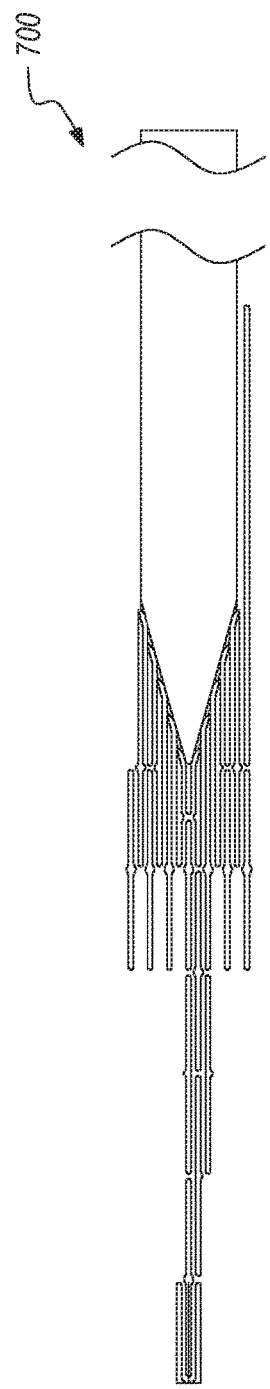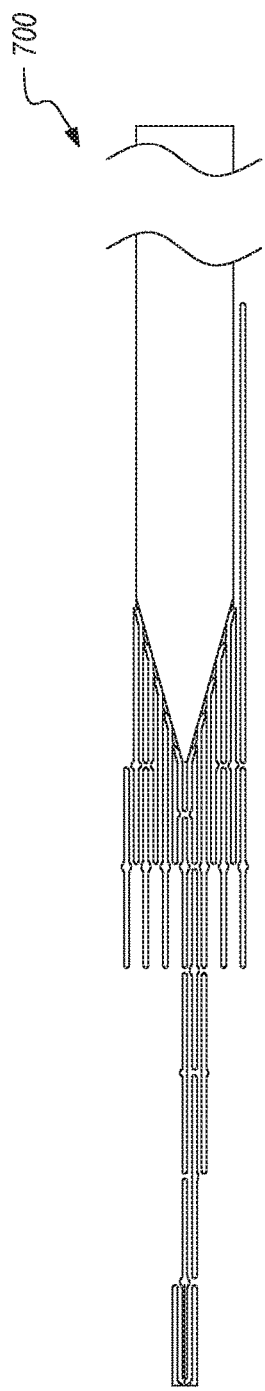

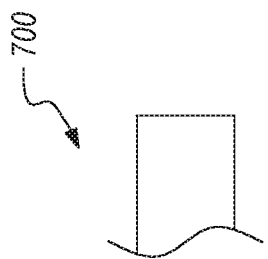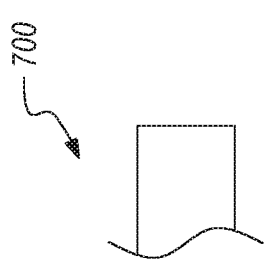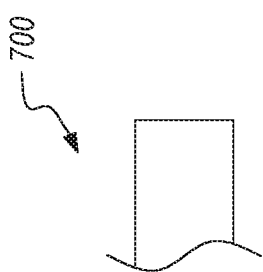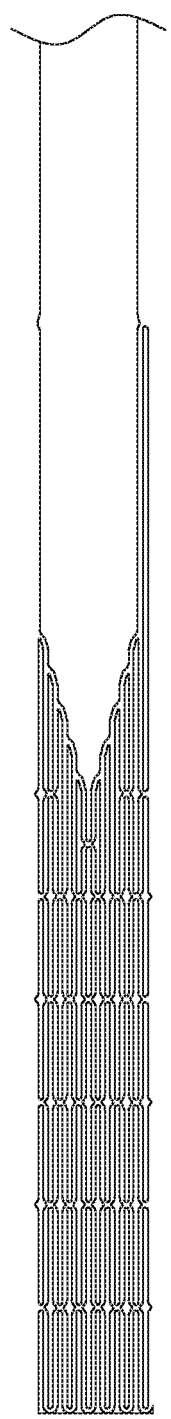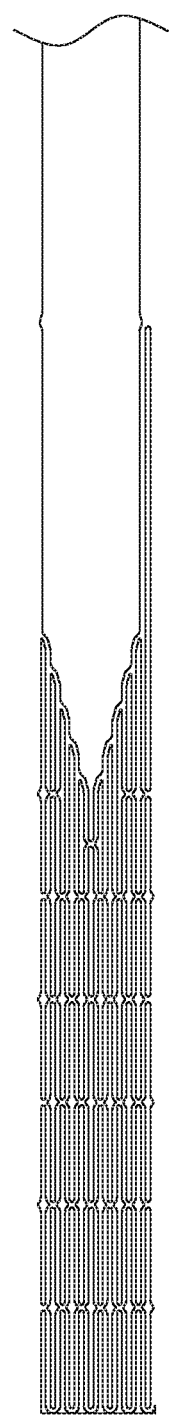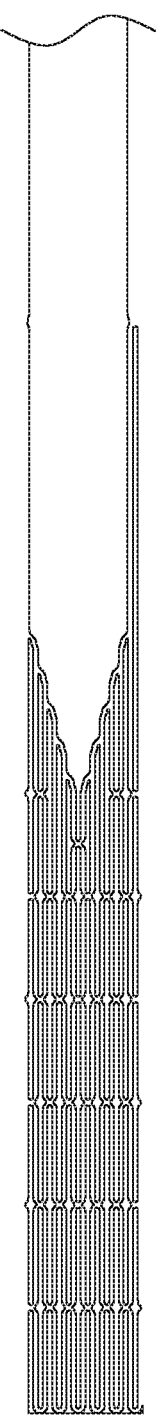
FIG. 5D   FIG. 5E   FIG. 5F

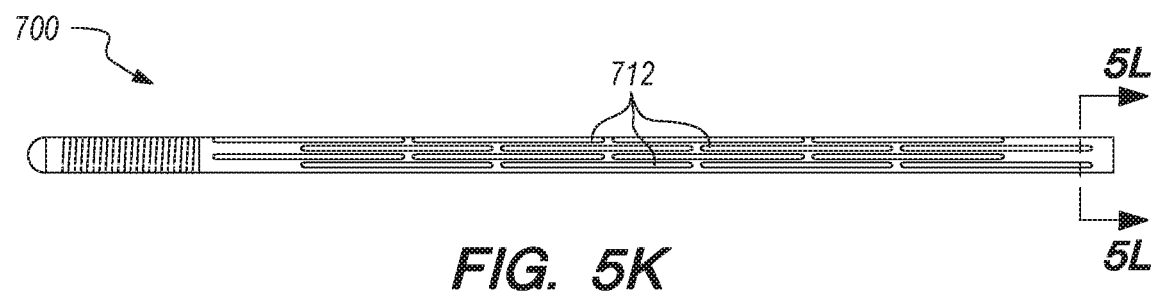
FIG. 5K
FIG. 5L
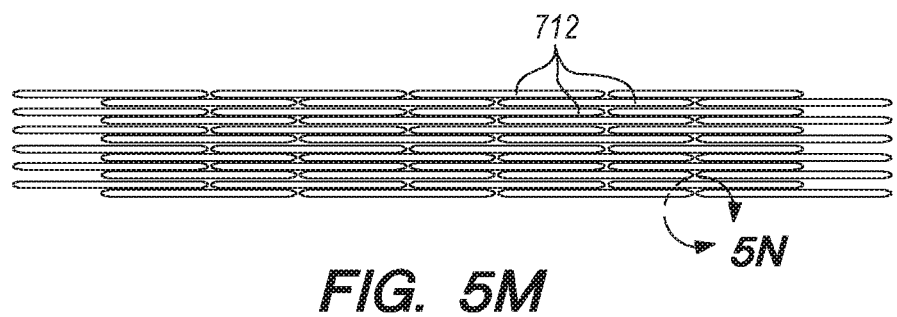
FIG. 5M
FIG. 5N

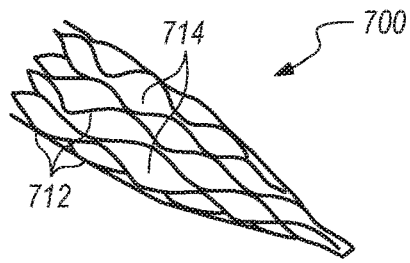
FIG. 5O
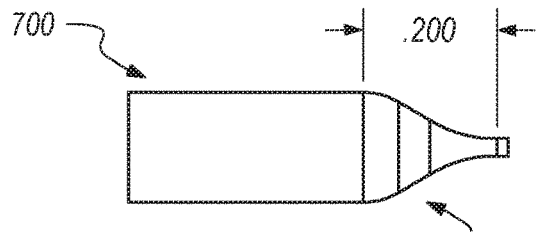
FIG. 5P
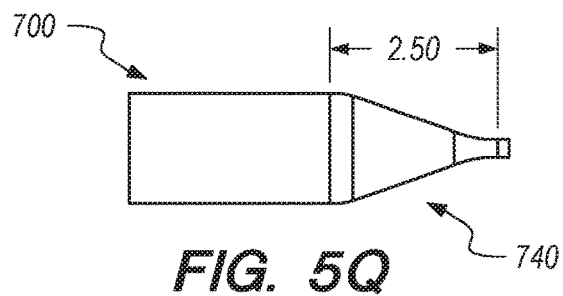
FIG. 5Q
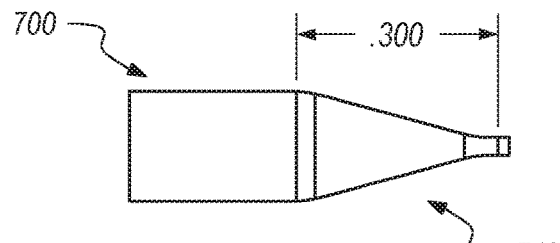
FIG. 5R
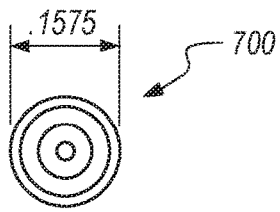
FIG. 5S
| DASH NO. | TRANSITION LENGTH |
|---|---|
| -01 | 0.200 |
| -02 | 0.250 |
| -03 | 0.300 |
FIG. 5T

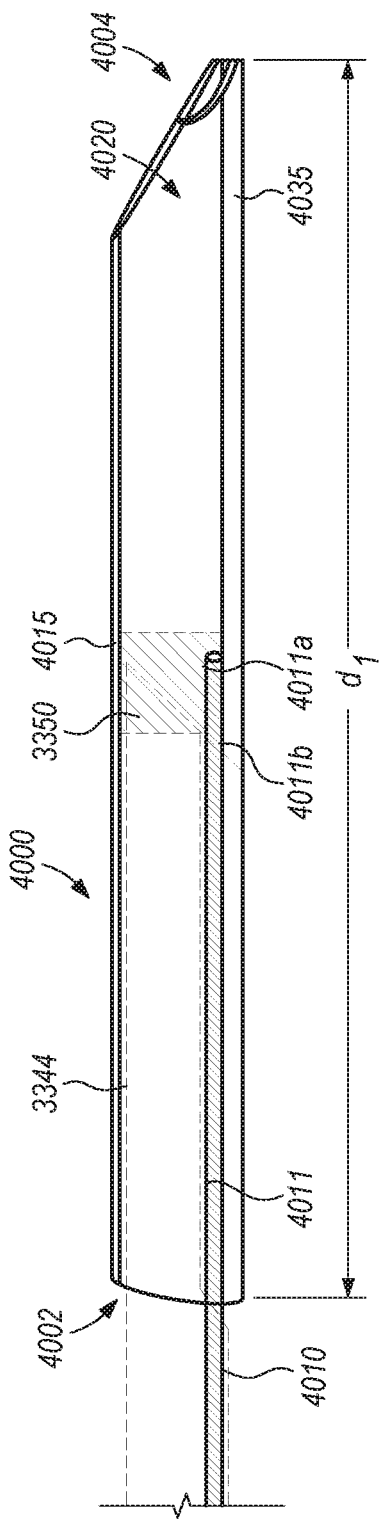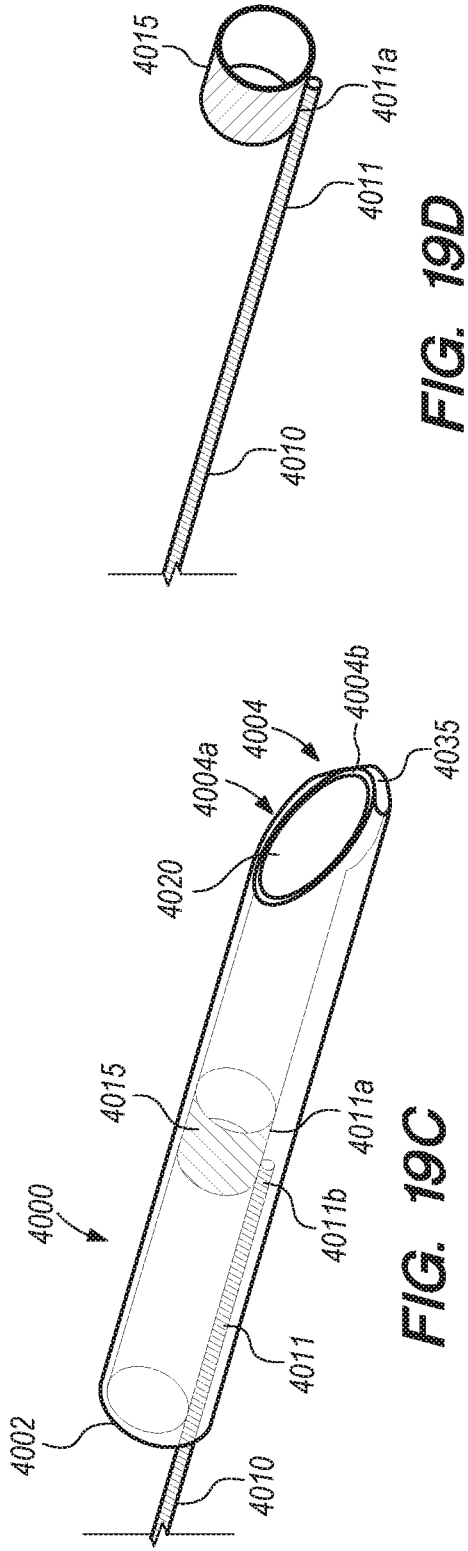

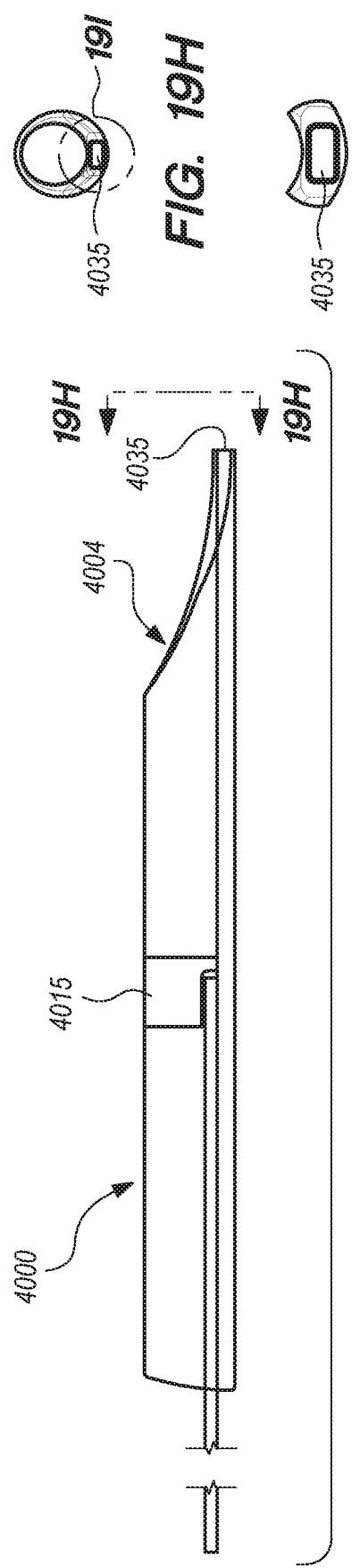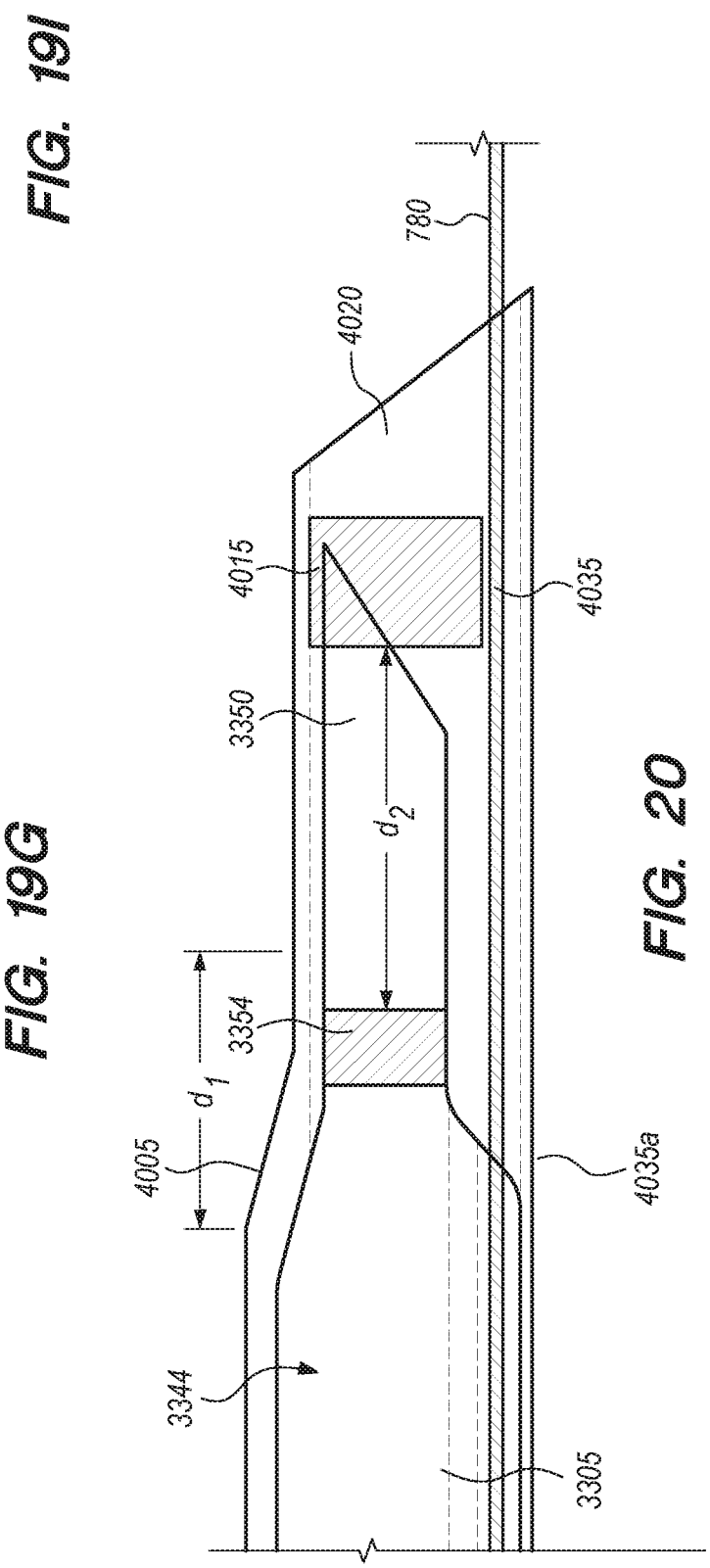

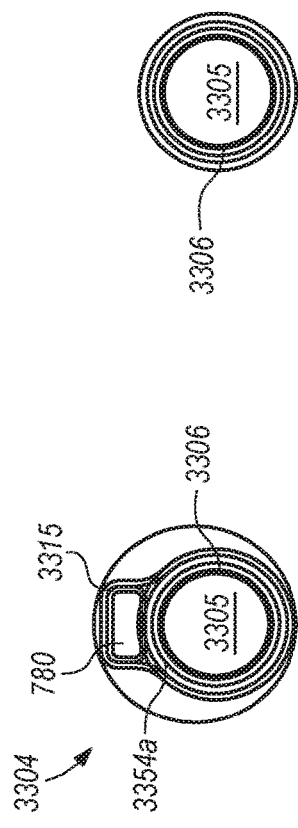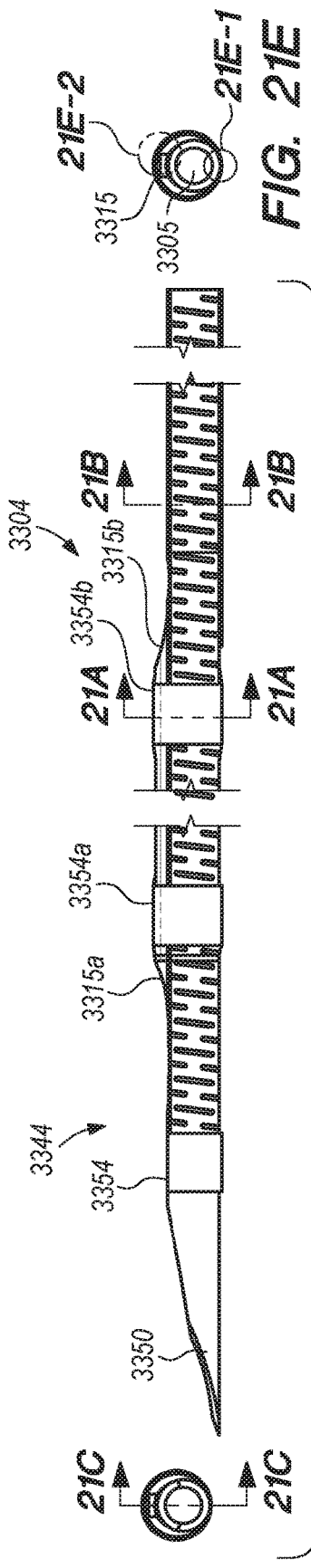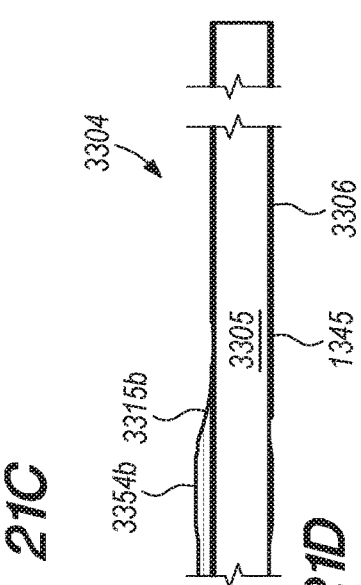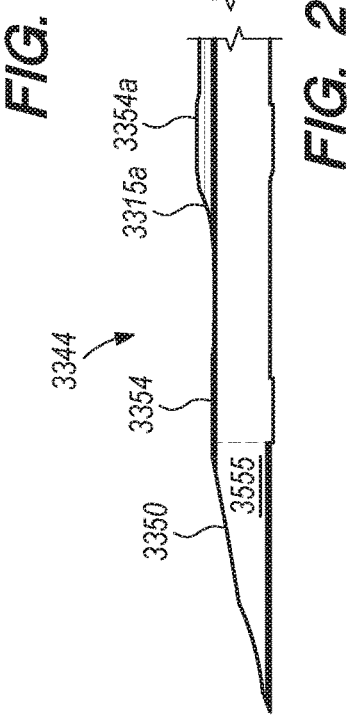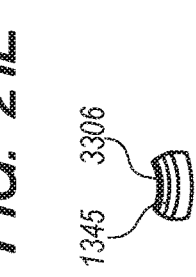
FIG. 21A
FIG. 21B
FIG. 21C
FIG. 21D
FIG. 21E
FIG. 21E-1
FIG. 21E-2

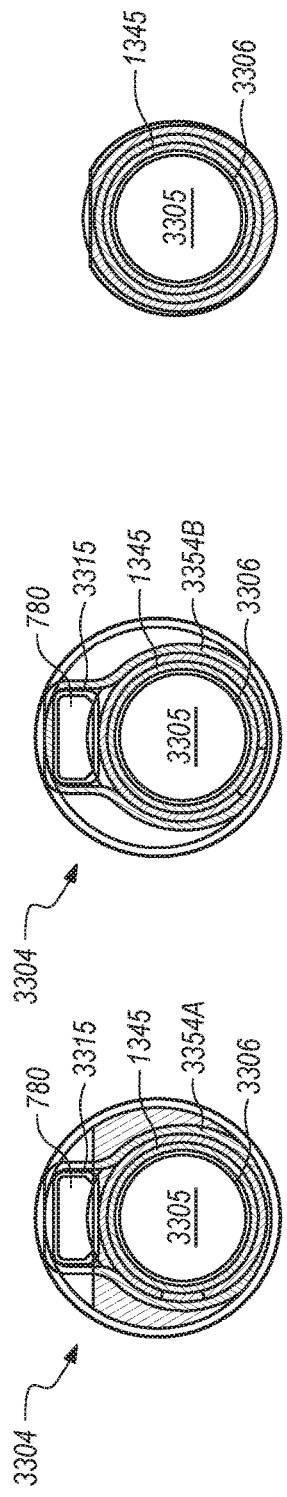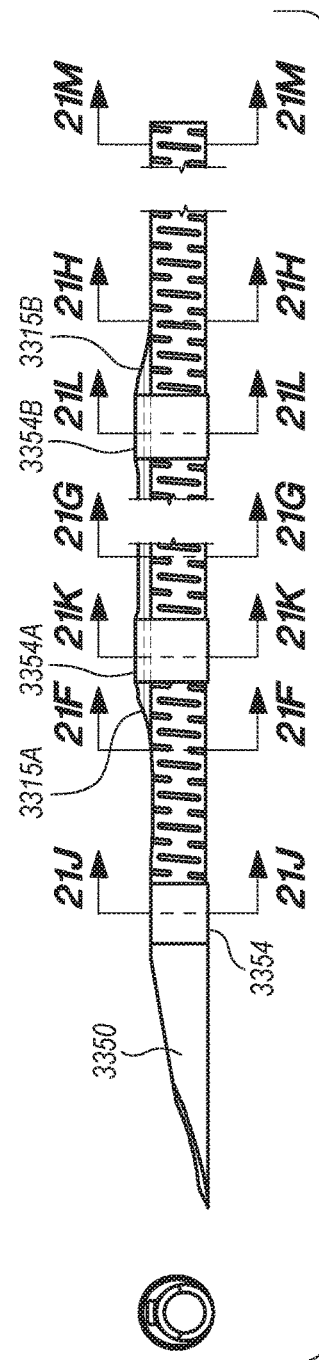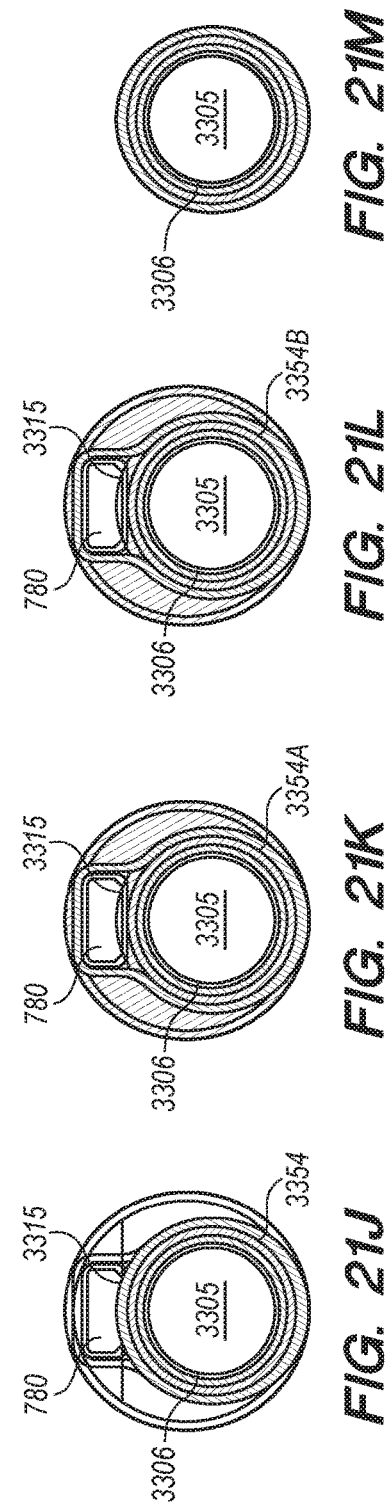

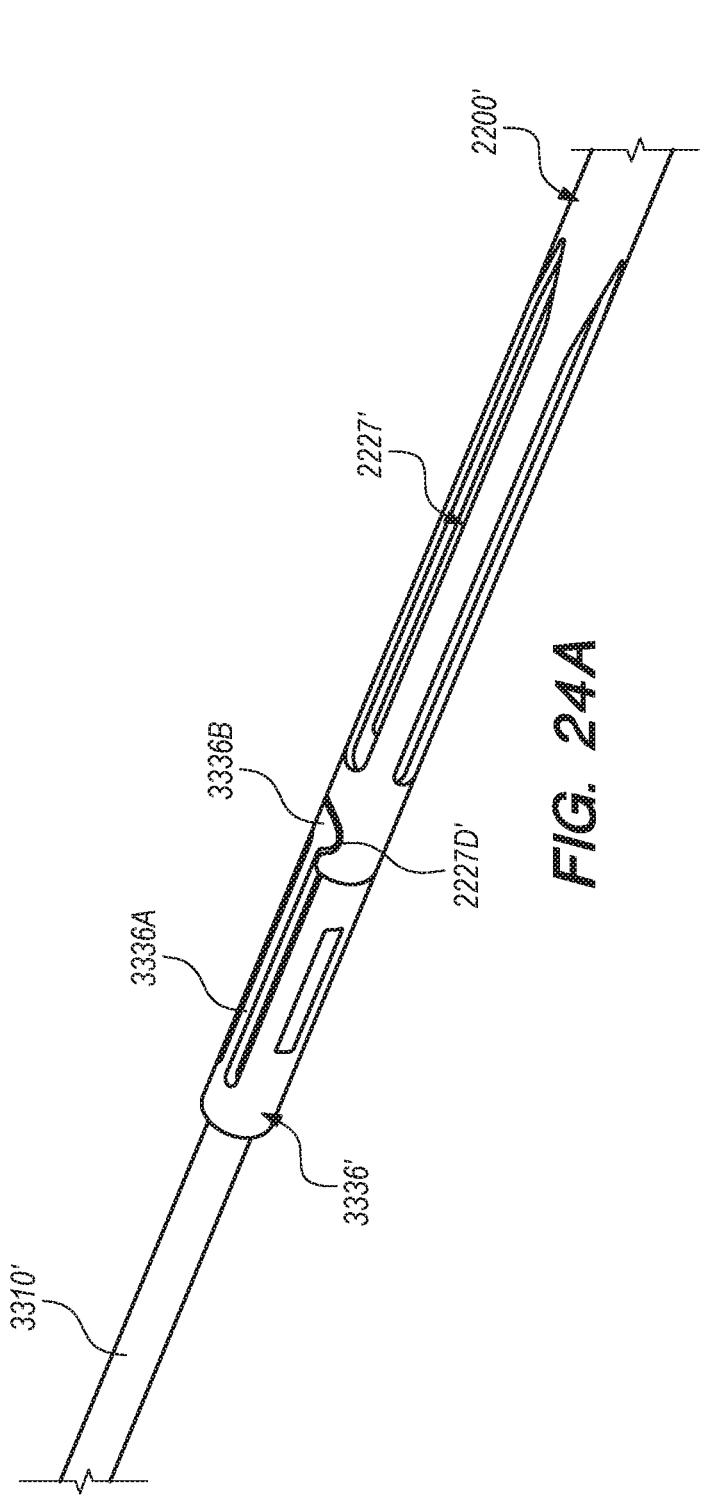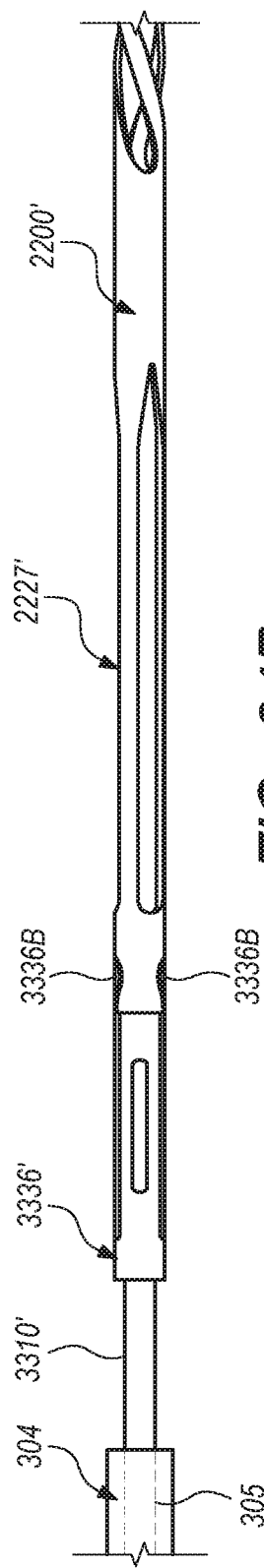

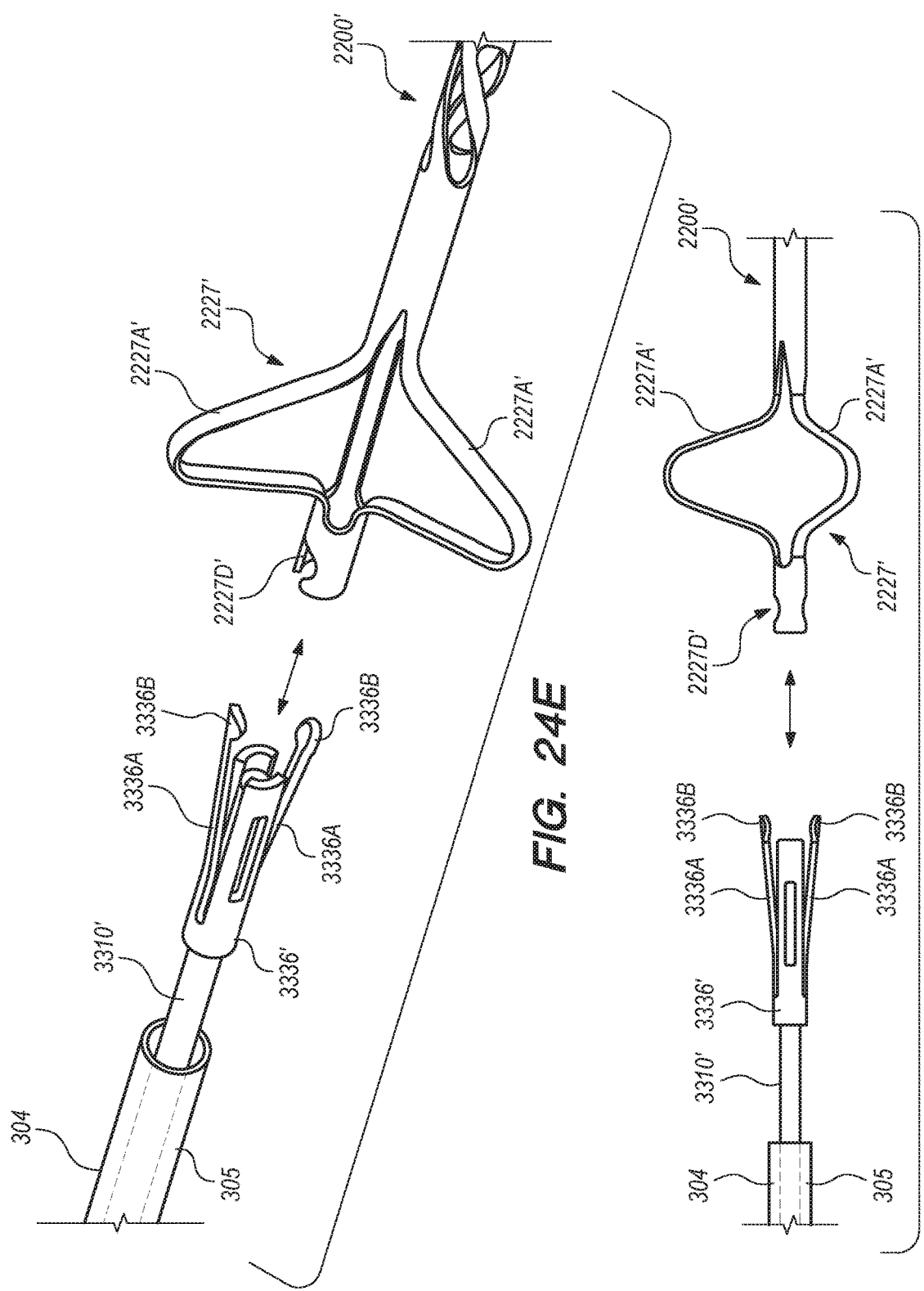

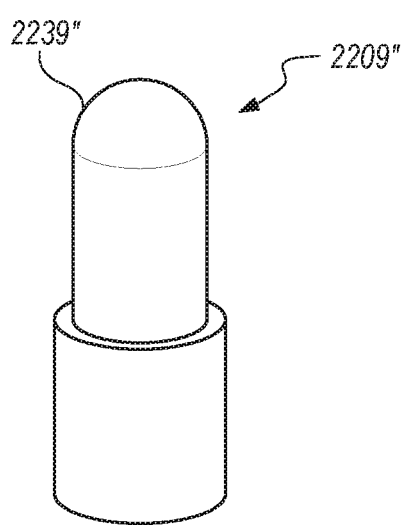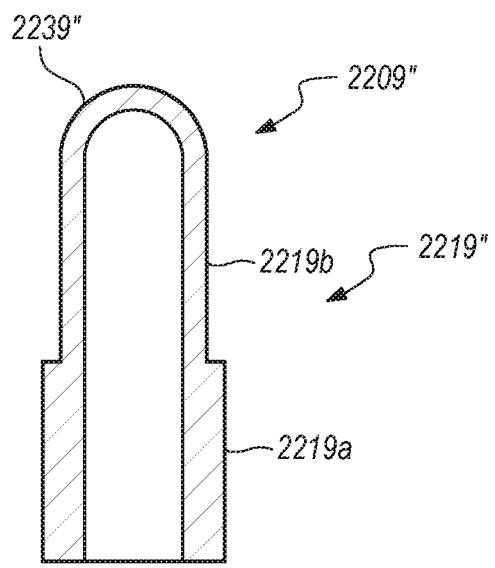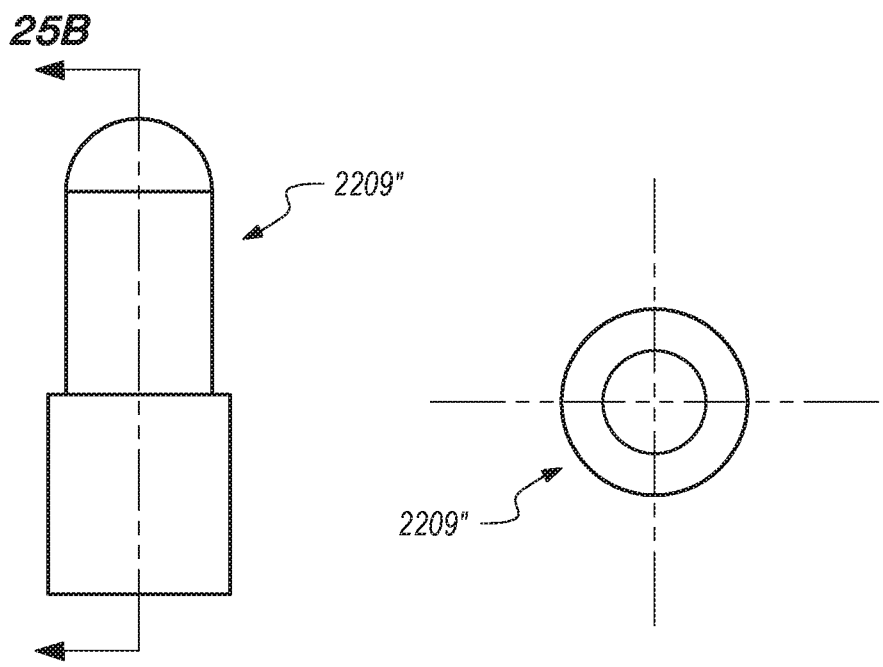
FIG. 25A
FIG. 25B
FIG. 25C
FIG. 25D

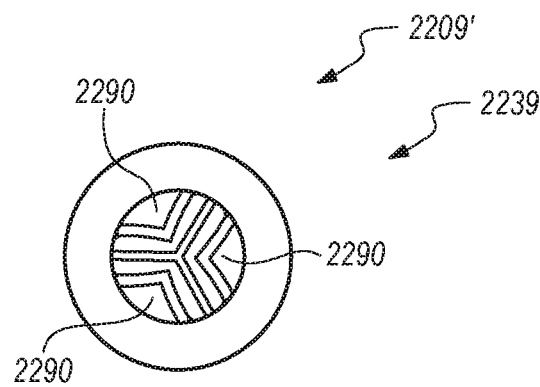
FIG. 25H
| DESIGN TABLE | | |
|---|---|---|
| DASH NO. | DOME THICKNESS | MIN THICKNESS |
| -01 | 0.005 | 0.001 |
| -02 | 0.007 | 0.002 |
| -03 | 0.009 | 0.003 |
FIG. 25I
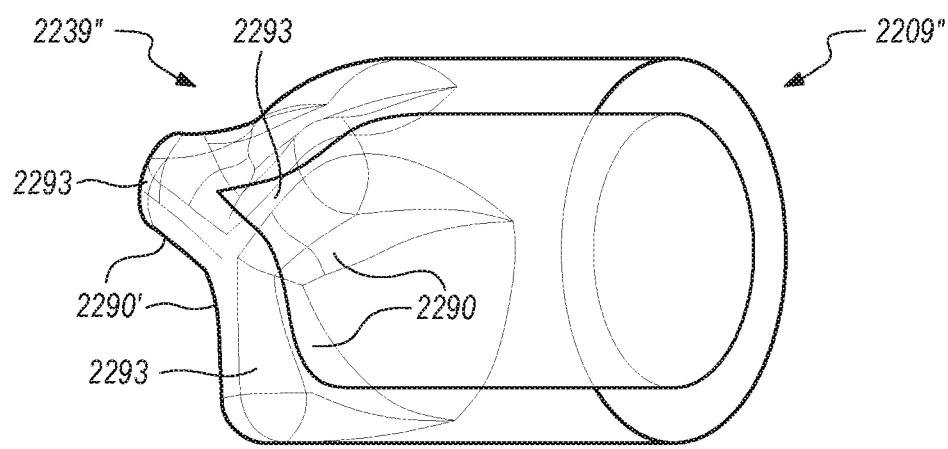
FIG. 25J

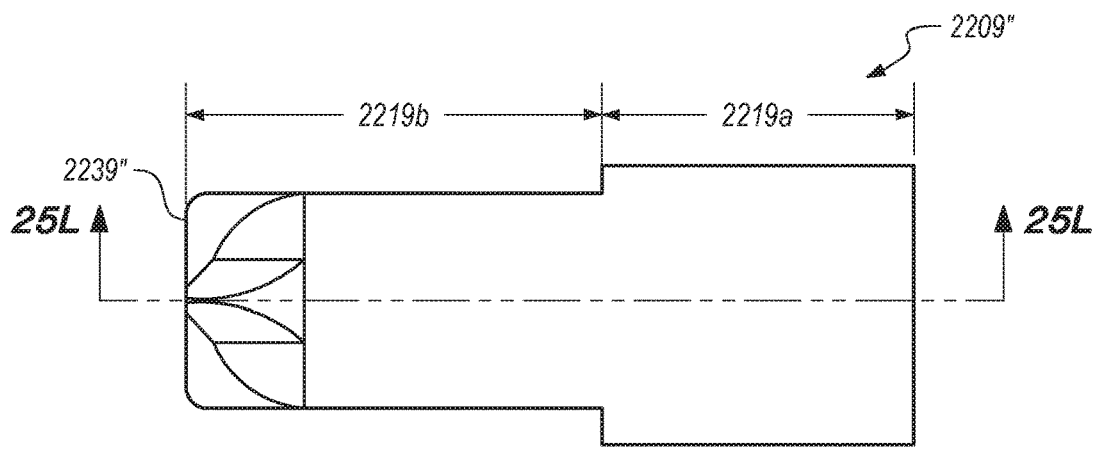
FIG. 25K
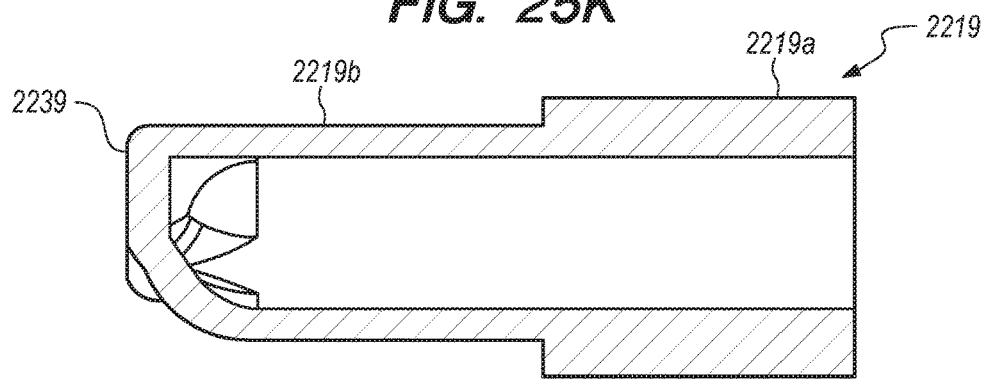
FIG. 25L
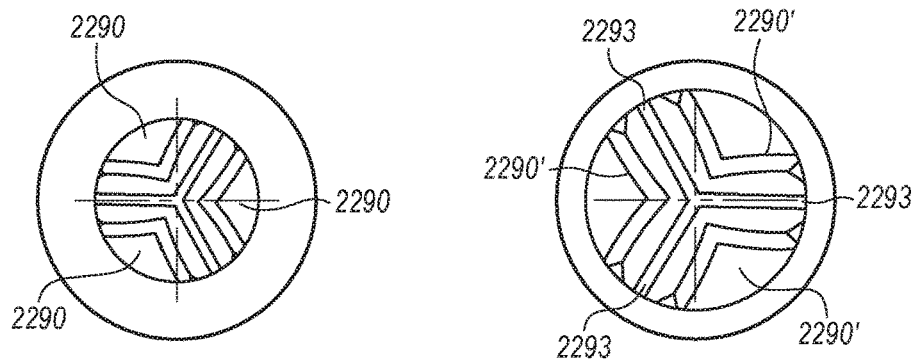
FIG. 25M          FIG. 25N
| DESIGN TABLE | |
|---|---|
| DASH NO. | DOME THICKNESS |
| -01 | 0.002 |
| -02 | 0.003 |
| -03 | 0.004 |
FIG. 25O

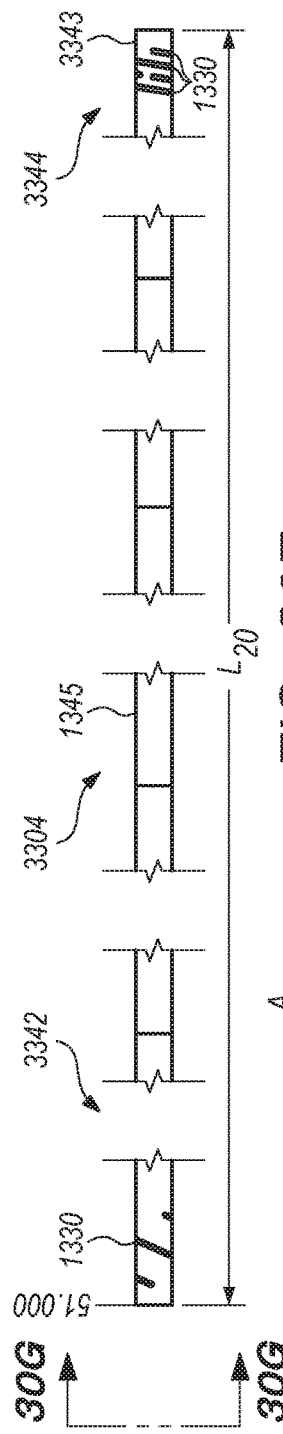
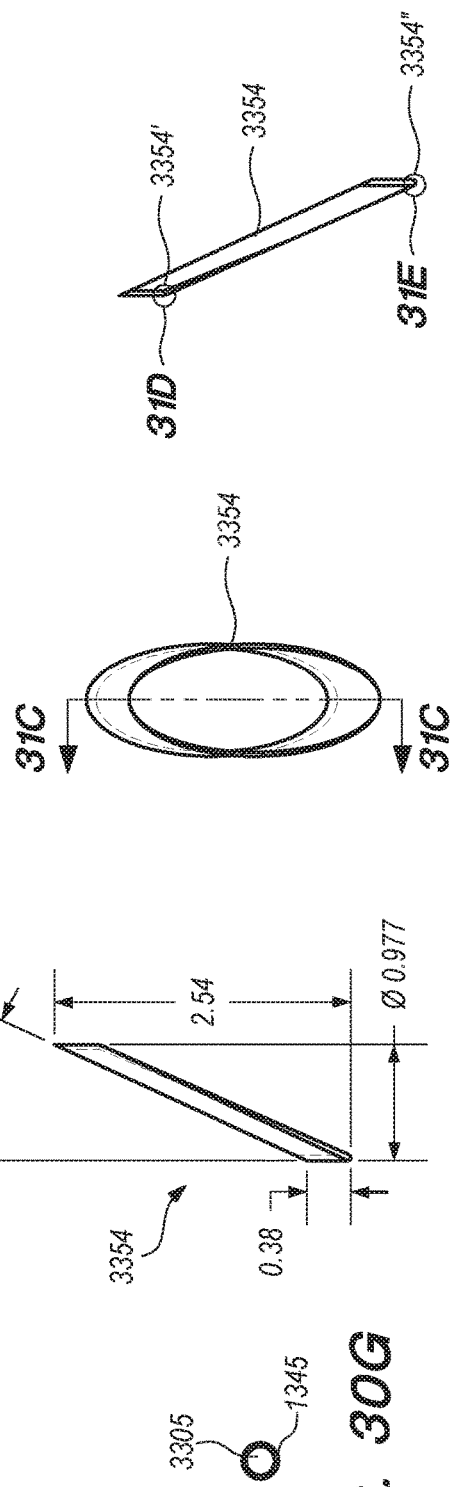

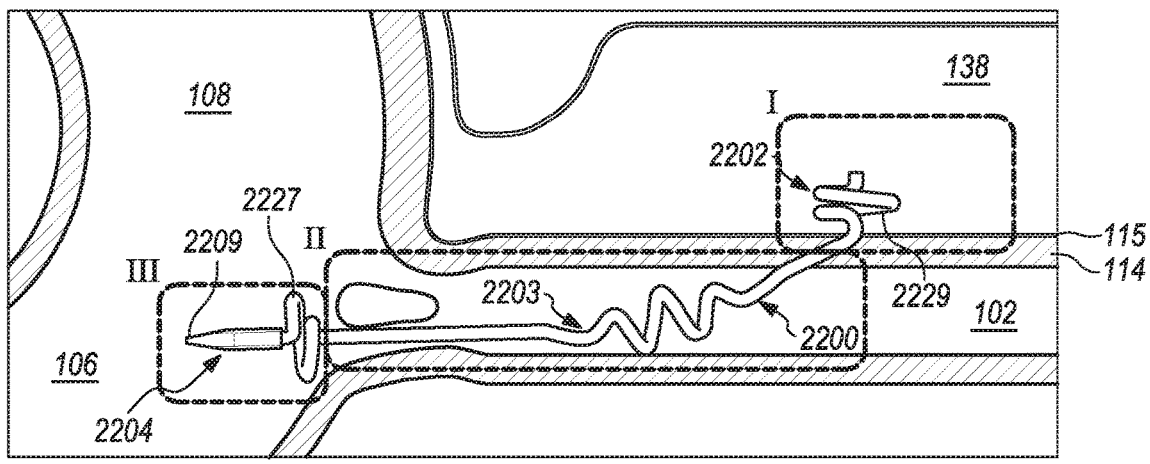
FIG. 32
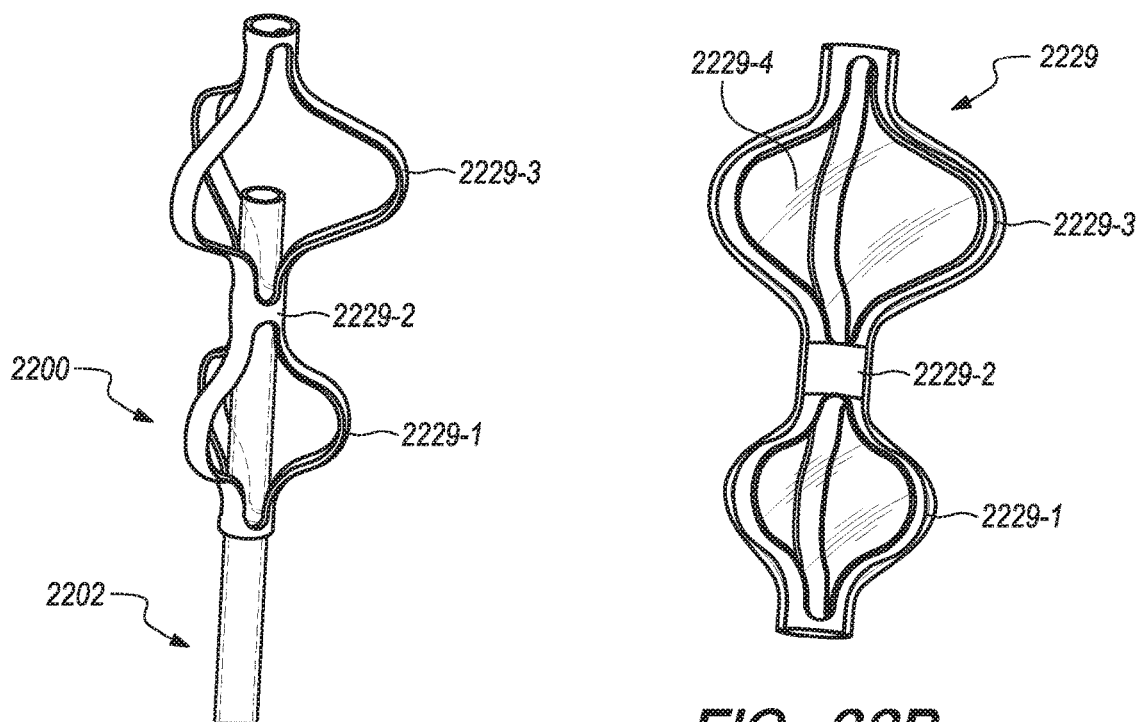
FIG. 33A
FIG. 33B

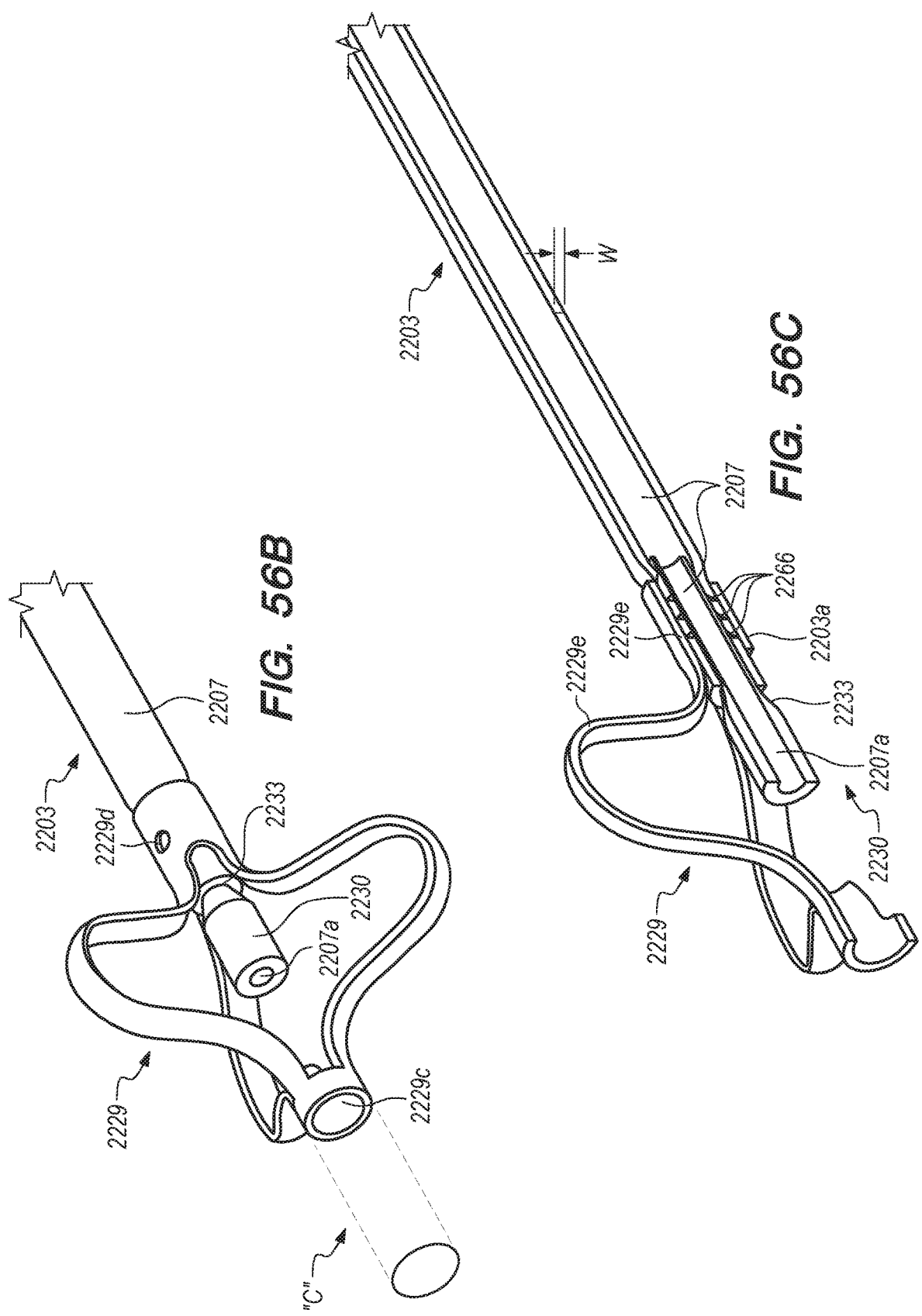

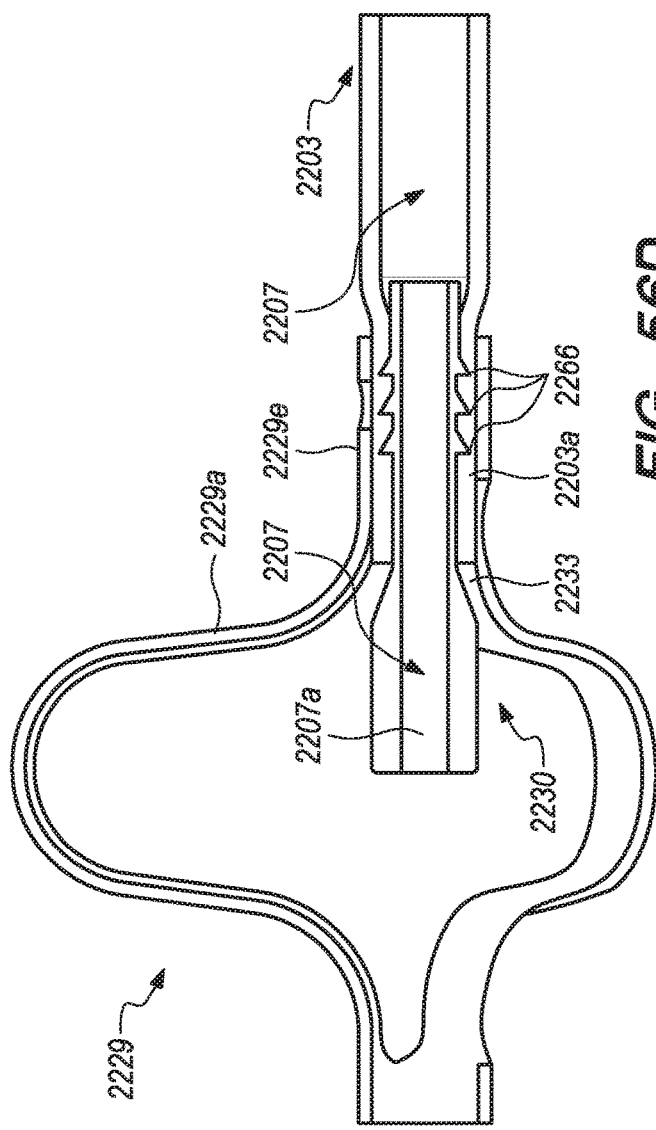
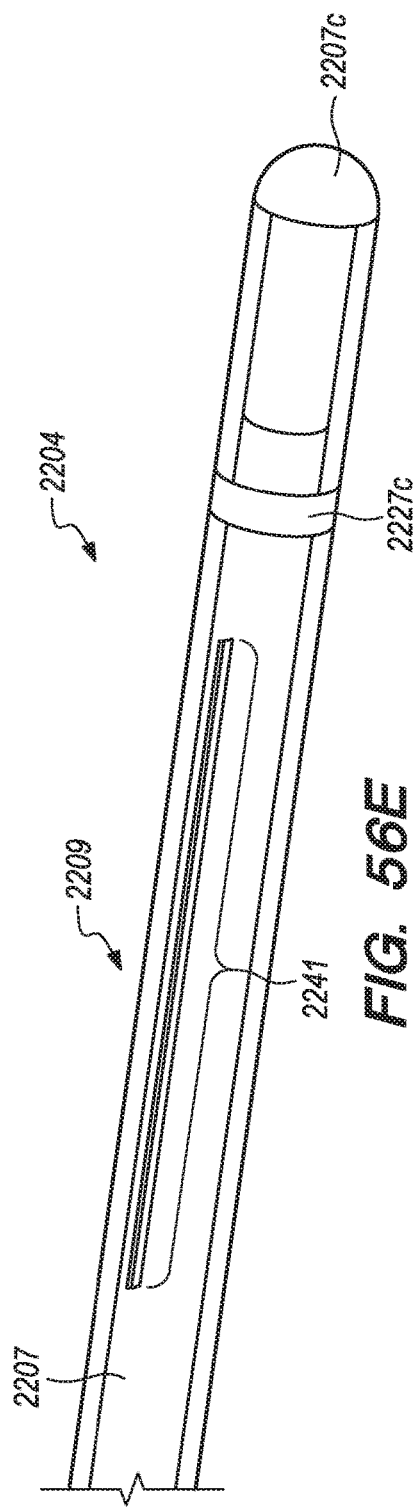

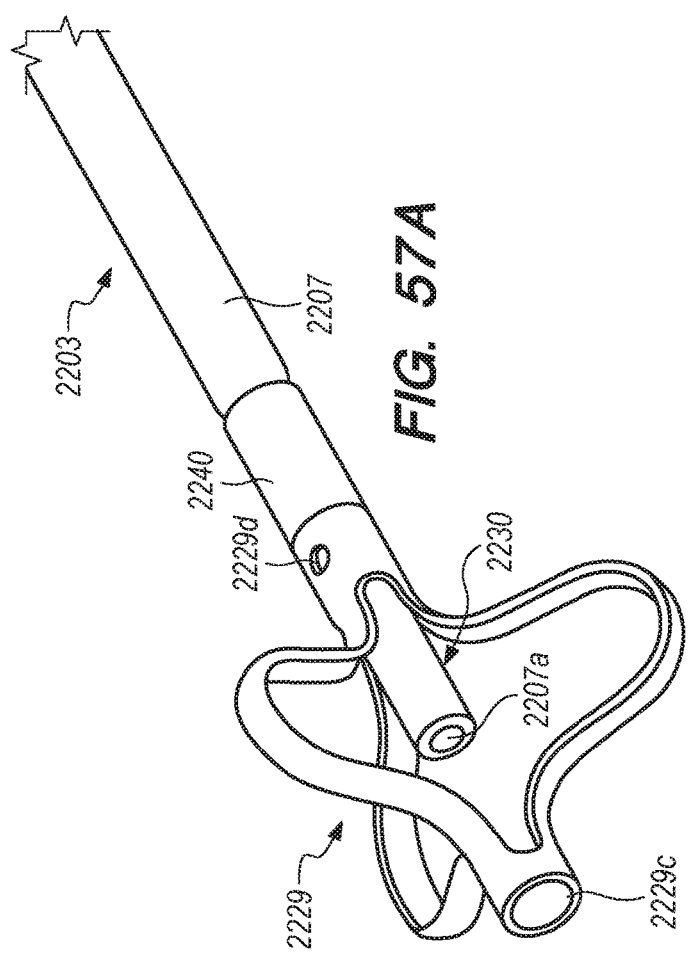
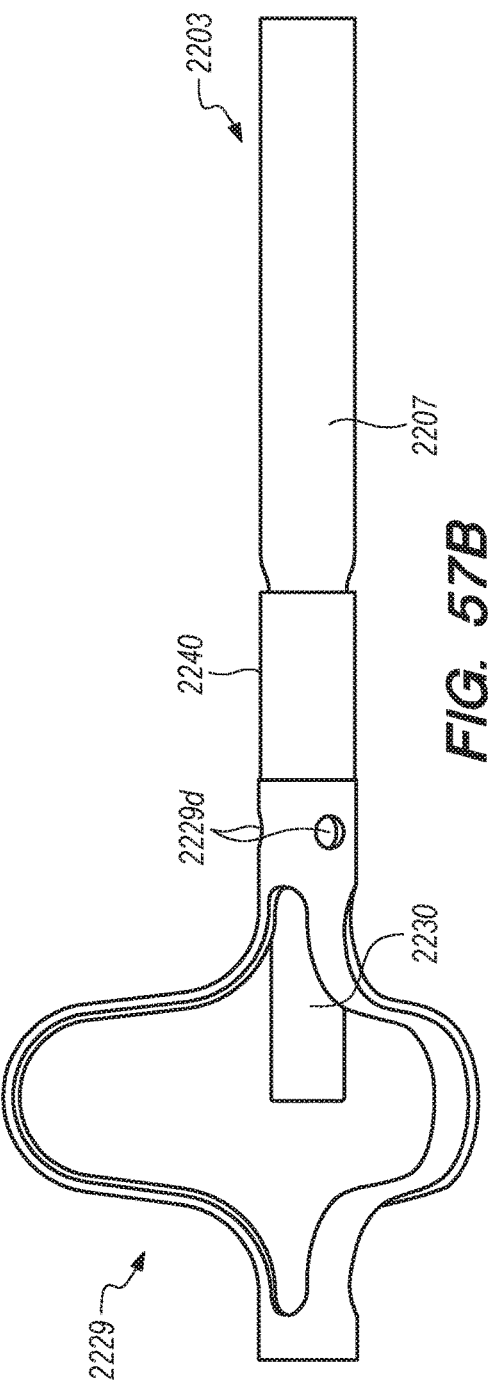

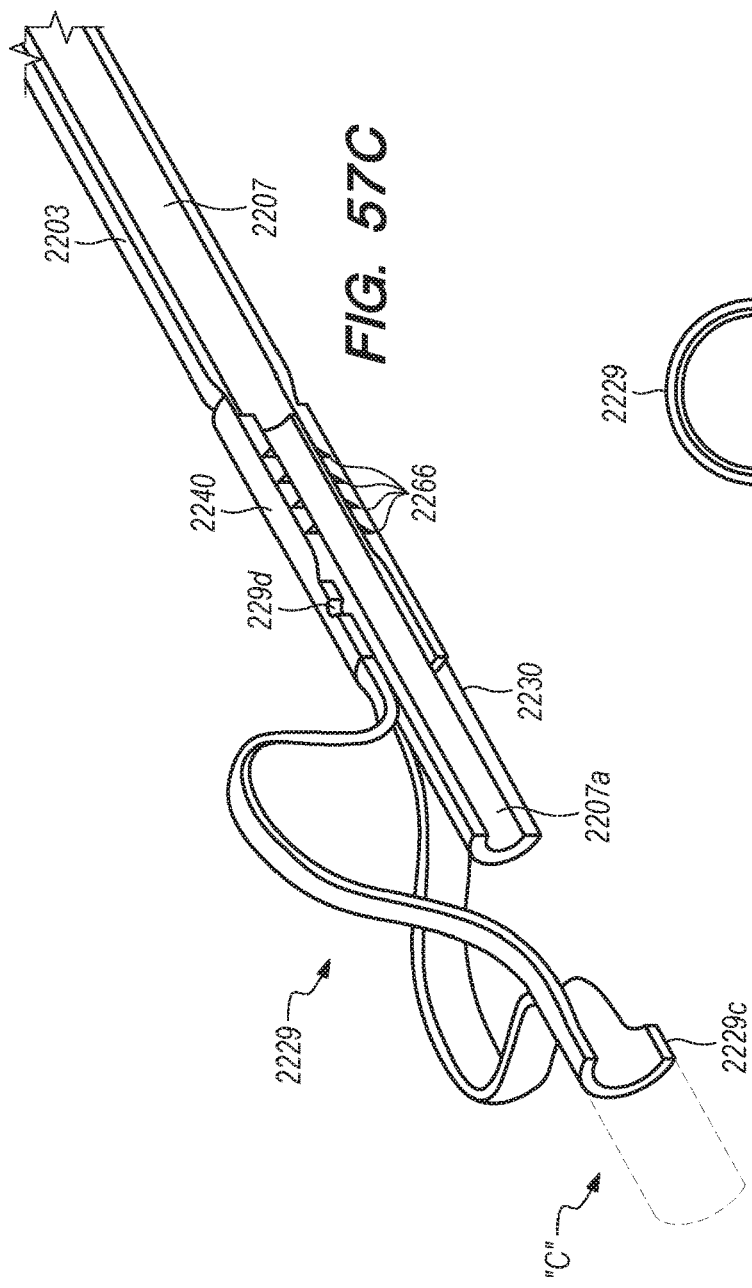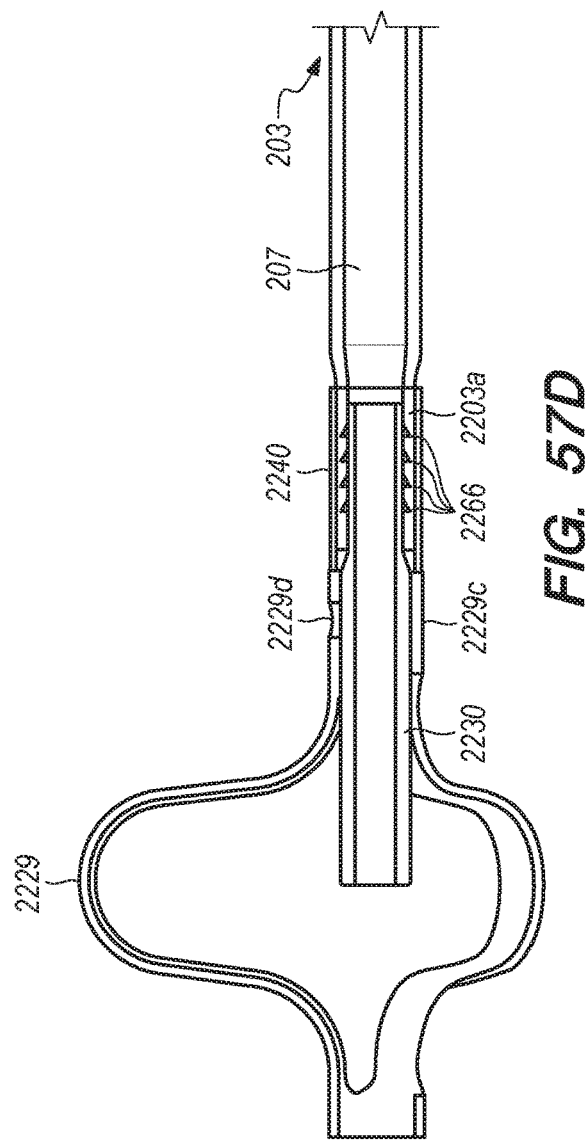

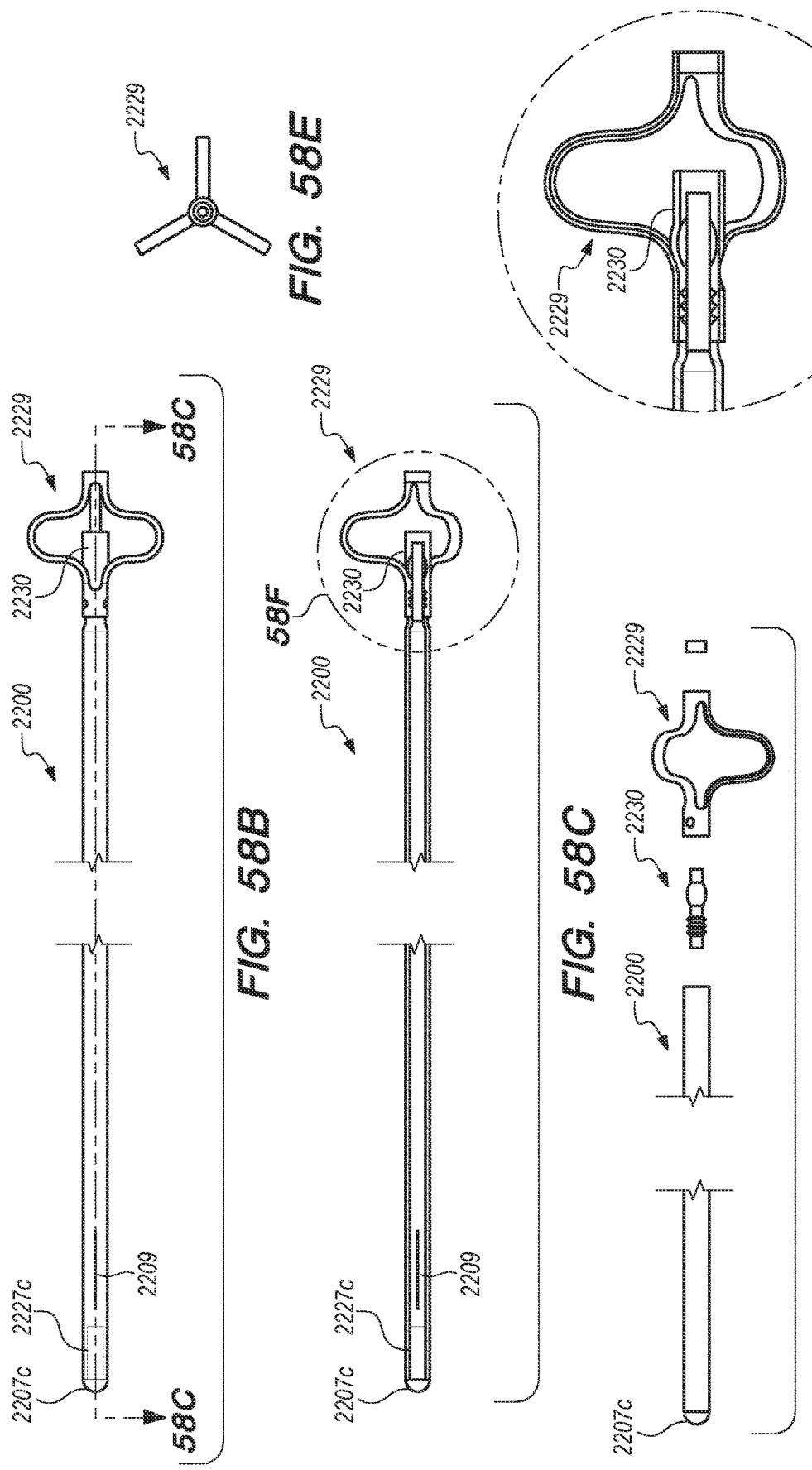

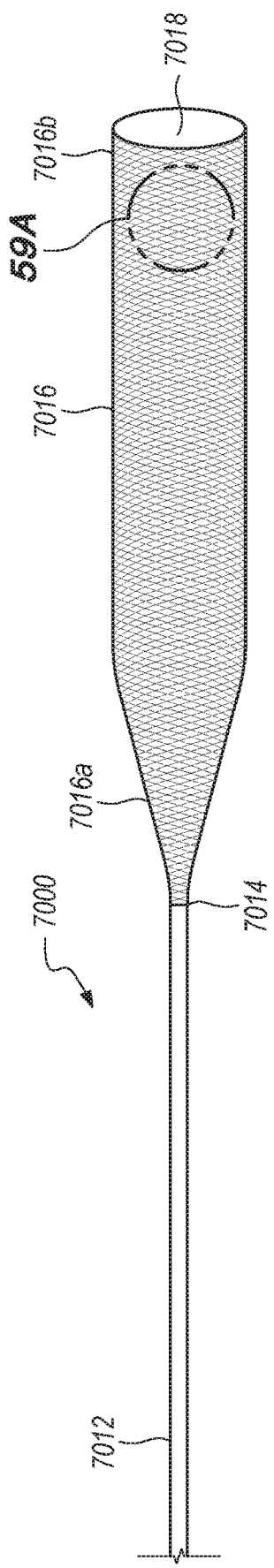
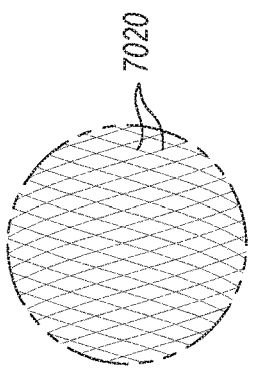
FIG. 59
FIG. 59A

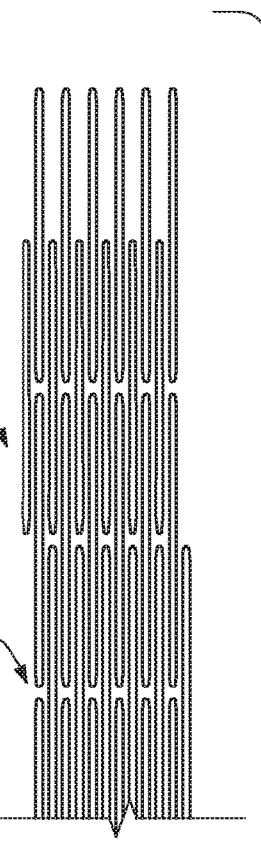
FIG. 60B
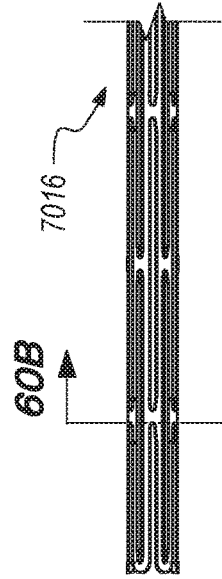
FIG. 60A
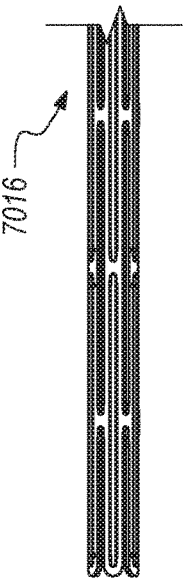
FIG. 60C
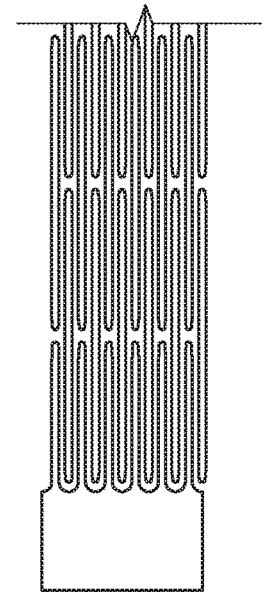
FIG. 60D

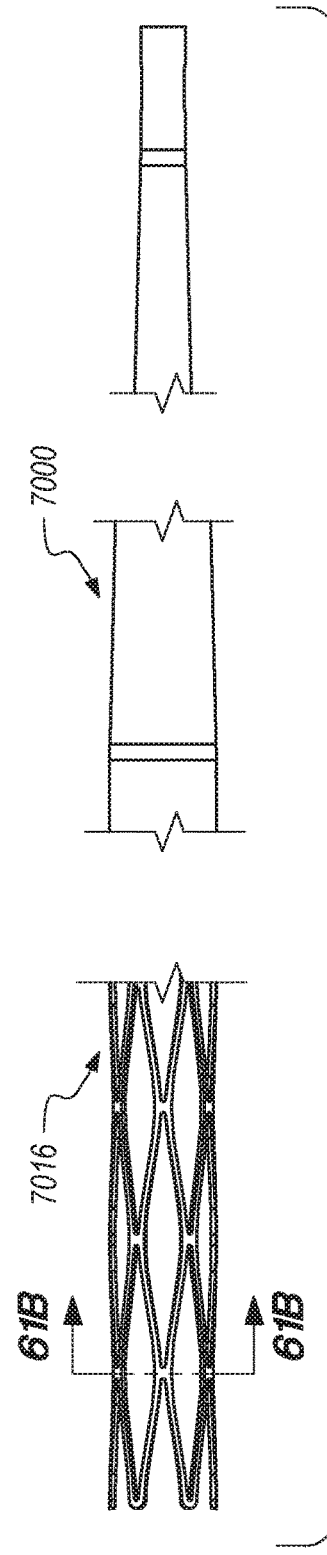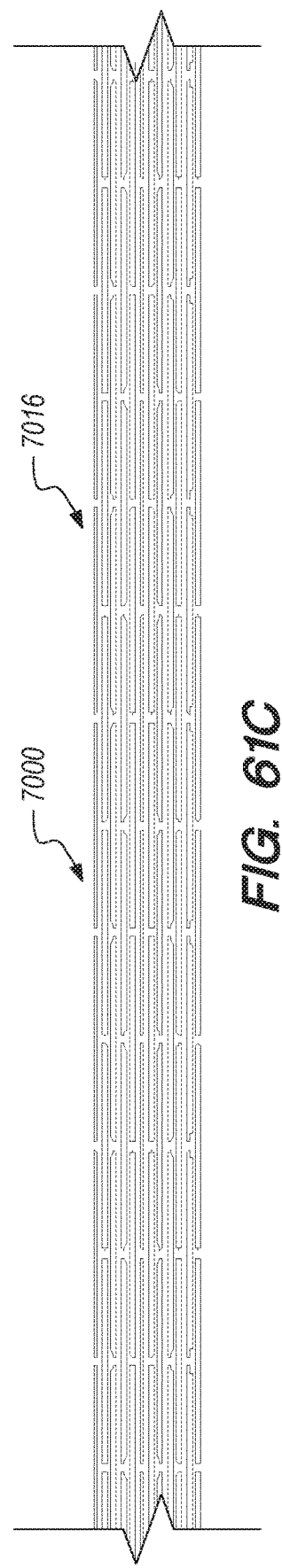
FIG. 61B
FIG. 61A
FIG. 61C

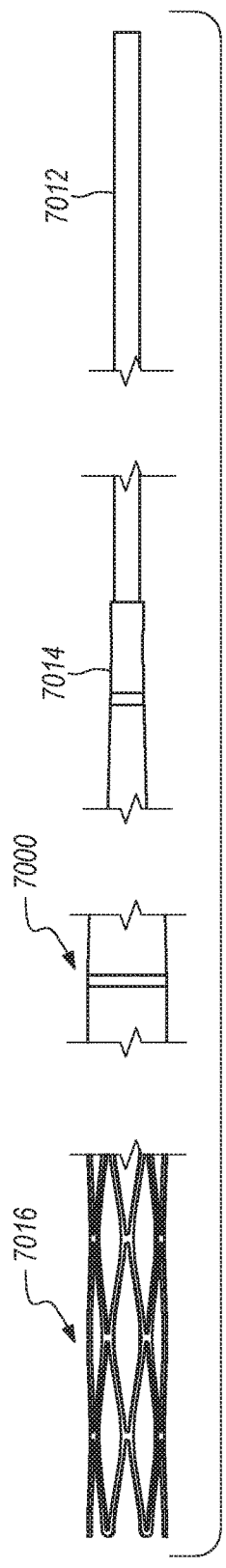
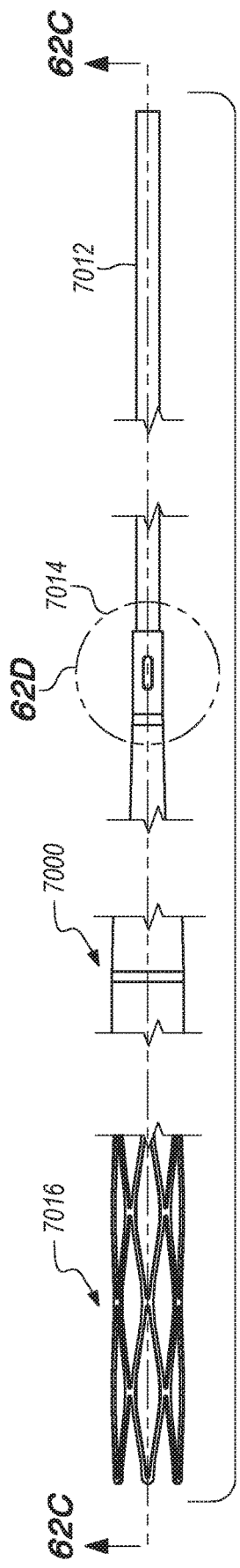
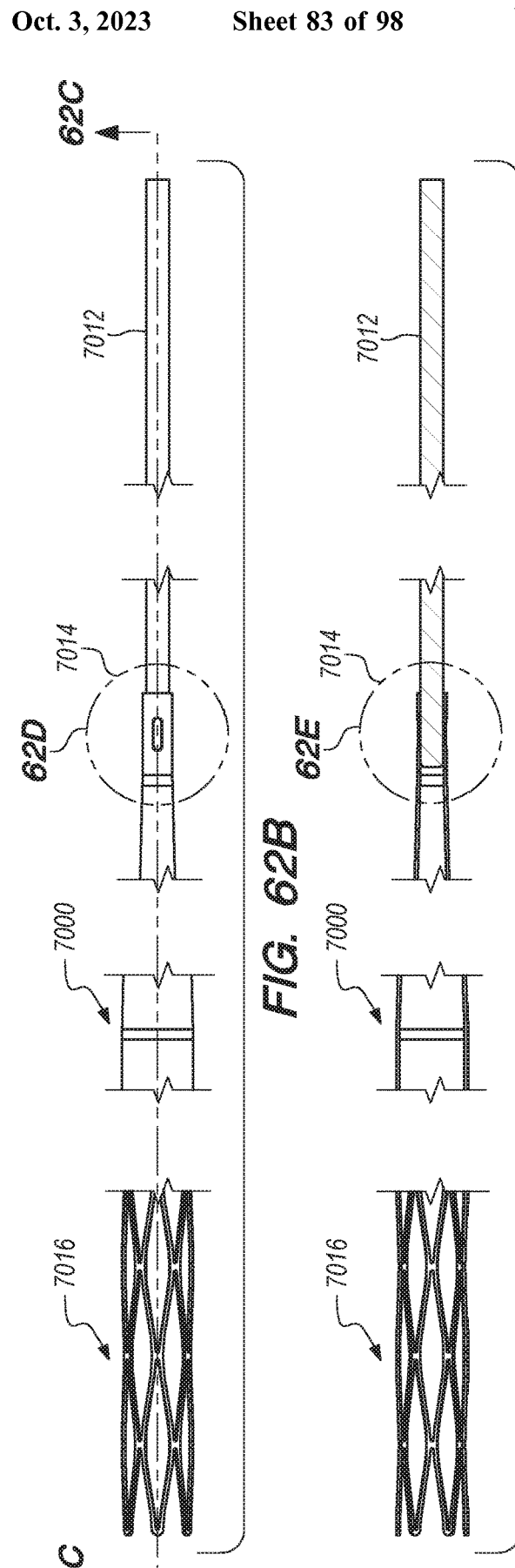
FIG. 62A
FIG. 62B
FIG. 62C
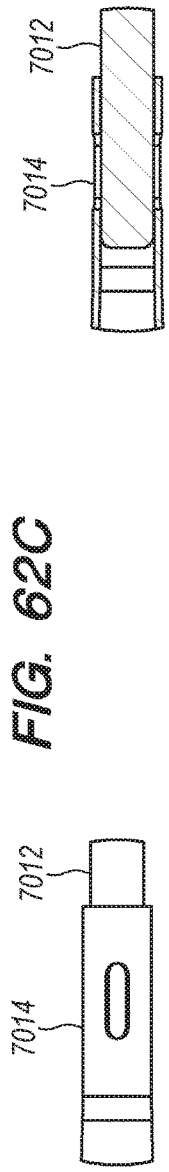
FIG. 62D
FIG. 62E

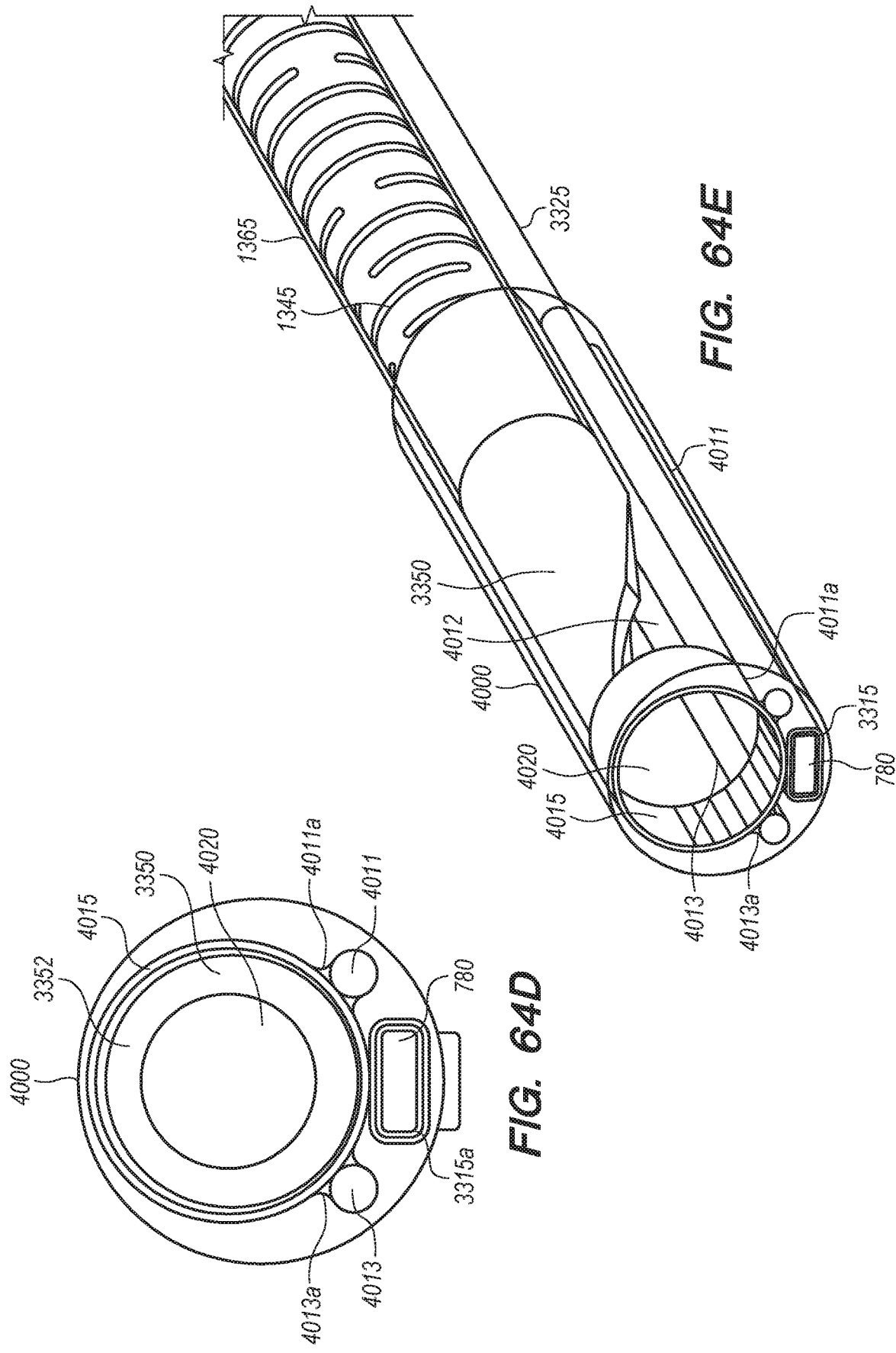

CATHETER SYSTEMS AND METHODS FOR MEDICAL PROCEDURES USING CATHETERS

RELATED APPLICATIONS

This application is a § 371 National Stage Application of PCT/US2018/020667, filed on Mar. 2, 2018, which claims the benefit of U.S. Provisional Patent Application Ser. No. 62/466,272, filed on Mar. 2, 2017, entitled "Microcatheter Devices and Related Systems and Methods," U.S. Provisional Patent Application Ser. No. 62/473,729, filed on Mar. 20, 2017, entitled "Methods and Systems for Treating Hydrocephalus," and International Patent Application No. PCT/US2017/056227, filed on Oct. 11, 2017, entitled "Systems and Methods for Treating Hydrocephalus," the contents of all of which are hereby incorporated herein by reference in their entireties.

FIELD OF THE INVENTION

This disclosure relates generally to catheter devices, and more specifically catheter devices having different structural property regions and to related systems and methods. The catheter devices described herein can be implemented in systems and methods for accessing cerebral cisterns and draining cerebrospinal fluid (CSF), (e.g., to relieve elevated intracranial pressure), using an endovascular approach. More particularly, the present disclosure pertains to catheter devices for use in systems and methods for treatment of hydrocephalus, pseudotumor cerebri, and/or intracranial hypertension.

BACKGROUND

Catheters (e.g., micro catheters) are used in a variety of medical procedures for the diagnosis and treatment of conditions and diseases occurring in remote, highly tortuous vascular sites. Typically, a catheter is introduced to the vascular system of a patient at a first location and then is advanced through the patient's vessels until the distal end of the catheter reaches a desired target location.

The process of advancing the catheter often involves applying force proximal of its distal end. Hence, as some conventional catheters advance deeper into the vascular system, it can become difficult to properly maneuver (e.g., push and pull) the distal end of the micro catheter in order to access desired regions. Additionally, advancing the catheter can involve applying torque to a proximal region of the catheter, for example by rotation, to position its distal end for a desired procedure. In this respect, it may be desirable that a catheter exhibit superior hoop strength (which can provide better kink resistance), column strength (which can provide pushability), torqueability (which can provide rotational control), and flexibility (which can provide trackability). Pushability is often understood as the ability to transmit force from the proximal end of the catheter to the distal end of the catheter while limiting kinking. Torqueability can be understood as the ability of the catheter to maintain rotational alignment between the distal and proximal ends when torque is applied to one of the ends. Trackability is often understood as the ability to navigate the catheter through tortuous vasculature.

One example medical procedure in which catheters can be used is in the endovascular treatment of hydrocephalus. Hydrocephalus is one of the most common and important neurosurgical conditions affecting both, children and adults. Hydrocephalus, meaning "water on the brain," refers to the abnormal CSF accumulation in the brain. The excessive intracranial pressure resulting from hydrocephalus can lead to a number of significant symptoms ranging from headache to neurological dysfunction, coma, and death.

Cerebrospinal fluid is a clear, physiologic fluid that bathes the entire nervous system, including the brain and spinal cord. Cells of the choroid plexus present inside the brain ventricles produce CSF. In normal patients, cells within arachnoid granulations reabsorb CSF produced in the choroid plexus. Arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm $H_2O$. This reabsorption pathway has been dubbed the "third circulation," because of its importance to the homeostasis of the central nervous system.

Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus.

A positive pressure gradient between the intracranial pressure of the subarachnoid space and the blood pressure of the venous system may contribute to the natural absorption of CSF through arachnoid granulations. For example in non-hydrocephalic individuals, intracranial pressures (ICPs) can range from about 6 cm H20 to about 20 cm H20. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

Normal pressure hydrocephalus (NPH) is one form of communicating hydrocephalus. NPH patients typically exhibit one or more symptoms of gait disturbance, dementia, and urinary incontinence, which can lead to misdiagnosis of the disease. Unlike other forms of communicating hydrocephalus, NPH patients may exhibit little or no increase in ICP. It is believed that the CSF-filled ventricles in the brain enlarge in NPH patients to accommodate the increased volume of CSF in the subarachnoid space. For example, while non-hydrocephalic patients typically have ICPs ranging from about 6 cm H20 to about 20 cm H20, ICPs in NPH patients can range from about 6 cm H20 to about 27 cm H20. It has been suggested that NPH is typically associated with normal intracranial pressures during the day and intermittently increased intracranial pressure at night.

Other conditions characterized by elevated intracranial pressure include pseudotumor cerebri (e.g., benign intracranial hypertension). The elevated ICP of pseudotumor cerebri causes symptoms similar to, but that are not, a brain tumor. Such symptoms can include headache, tinnitus, dizziness, blurred vision or vision loss, and nausea. While most common in obese women 20 to 40 years old, pseudotumor cerebri can affect patients in all age groups.

Prior art techniques for treating communicating hydrocephalus (and in some cases, pseudotumor cerebri and intracranial hypertension) rely on ventriculoperitoneal shunts ("VPS" or "VP shunt" placement), a medical device design introduced more than 60 years ago. VPS placement involves an invasive surgical procedure performed under general anesthesia, typically resulting in hospitalization ranging from two to four days. The surgical procedure typically involves placement of a silicone catheter in the frontal horn of the lateral ventricle of the brain through a burr hole in the skull. The distal portion of the catheter leading from the lateral ventricle is then connected to a pressure or flow-regulated valve, which is placed under the scalp. A separate incision is then made through the abdomen, into the peritoneal cavity, into which the proximal portion of a tubing catheter is placed. The catheter/valve assembly is then connected to the tubing catheter, which is tunneled subcutaneously from the neck to the abdomen.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage. Among these complications, infection is one of the most serious, since infection rates in adults are reported between 1.6% and 16.7%. These VPS failures require "shunt revision" surgeries to repair/replace a portion or the entirety of the VP shunt system, with each of these revision surgeries carrying the same risk of general anesthesia, post-operative infection, and associated cost of hospitalization as the initial VPS placement; provided, however that shunt infections can cost significantly more to treat (e.g., three to five times more) compared to initial VP shunt placement. Often these infections require additional hospital stays where the proximal portion of the VPS is externalized and long-term antibiotic therapy is instituted. The rate of failure is a constant consideration by clinicians as they assess patients who may be candidates for VPS placement. Age, existing co-morbidities and other patient-specific factors are weighed against the likelihood of VP shunt failure that is virtually assured during the first 4-5 years following initial VP shunt placement.

Despite significant advances in biomedical technology, instrumentation, and medical devices, there has been little change in the design of basic VPS hardware since its introduction in 1952.

SUMMARY

In some aspects, catheter devices can include: a reinforcing member having a proximal end and a distal end and defining a central opening therebetween, the reinforcing member comprising: a plurality of discrete longitudinally arranged structural regions disposed between the proximal end and the distal end comprising: a first, proximal, structural region defining a first series of wall perforations setting a first stiffness of the first structural region, the first series of wall perforations having a pitch of about 0.014 inches to about 0.018 inches and a cut frequency of about 2 to about 3 cuts per rotation; a second structural region, disposed distally relative to the first structural region, defining a second series of wall perforations setting a second stiffness of the second structural region, the second series of wall perforations having a pitch starting at about 0.014 inches to about 0.018 inches and decreasing to about 0.003 inches to about 0.007 inches and a cut frequency of about 2 to about 3 cuts per rotation; a third structural region, disposed distally relative to the second structural region, defining a third series of wall perforations setting a third stiffness of the third structural region, the third series of wall perforations having a pitch starting at about 0.008 inches to about 0.012 inches and decreasing to about 0.002 inches to about 0.006 inches and a cut frequency of about 1 to about 2 cuts per rotation; a fourth structural region, disposed distally relative to the third structural region, defining a fourth series of wall perforations setting a fourth stiffness of the fourth structural region, the fourth series of wall perforations having a pitch of about 0.002 inches to about 0.006 inches and a cut frequency of about 1 to about 2 cuts per rotation; and a distal region substantially free of perforations.

Embodiments can include one or more of the following features. A width of the perforations can be about 0.0005 inches to about 0.0015 inches. In some embodiments, the first series of wall perforations has a cut balance of about 106 degrees to about 110 degrees on and about 34 degrees to about 38 degrees off; the second series of wall perforations has a cut balance of about 106 degrees to about 110 degrees on and about 34 degrees to about 38 degrees off; the third series of wall perforations has a cut balance of about 208 degrees to about 212 degrees on and about 28 degrees to about 32 degrees off; and the fourth series of wall perforations has a cut balance of about 208 degrees to about 212 degrees on and about 28 degrees to about 32 degrees off. In some cases, the first series of wall perforations has a cut balance of about 108 degrees on and about 36 degrees off; the second series of wall perforations has a cut balance of about 108 degrees on and about 36 degrees off; the third series of wall perforations has a cut balance of about 210 degrees on and about 30 degrees off; and the fourth series of wall perforations has a cut balance of about 210 degrees on and about 30 degrees off. In some embodiments, the first series of wall perforations is formed along a substantially left-helical path; and the fourth series of wall perforations is formed along a substantially left-helical path. In some cases, the second series of wall perforations is formed along a substantially left-helical path; and the third series of wall perforations is formed along a substantially left-helical path. In some embodiments, catheter devices can also include a liner material along an inner surface of the central opening and an outer jacket material disposed along an outer surface of the reinforcing member. In some embodiments, the distal region has a length that is less than about 0.020 inches; the fourth structural region has a length that is about 6 inches to about 8 inches; the third structural region has a length that is about 4 to about 8 inches; and the second structural region has a length that is about 6 to about 9 inches. In some cases, the distal region has a length that is about 0.012 inches; the fourth structural region has a length that is about 7.862; the third structural region has a length that is about 5.906 inches; and the second structural region has a length that is about 7.874 inches. Wall perforations of one or more regions can define a seam of interruption along which uncut regions of the reinforcing member are disposed.

In some aspects, catheter devices can include: a reinforcing member having a proximal end and a distal end and defining a central lumen therebetween, the reinforcing member comprising: a plurality of discrete longitudinally arranged structural regions disposed between the proximal end and the distal end comprising: a first, proximal, structural region defining a first series of wall perforations that generate structural properties within the first structural region, the first series of wall perforations setting a first stiffness of the first structural region; and a second structural region, disposed distally relative to the first structural region, defining a second series of wall perforations that generate structural properties within the second structural region, the second series of wall perforations setting a second stiffness of the second structural region, which is less than the first stiffness, wherein the second series of wall perforations differs from the first series of wall perforations by at least one of: cut balance, cut frequency, or pitch.

Embodiments can include one or more of the following features. In some embodiments, the first series of wall perforations and the second series of wall perforations together define one or more seams of interruption along which the first and second series of wall perforations are periodically interrupted. In some cases, the seams of interruption have a width that is about 0.001 inches to about 0.020 inches. The catheter can define an inner width of about 0.014 inches to about 0.038 inches. The catheter can defines an outer width of about 0.022 inches to about 0.048 inches. In some embodiments, the plurality of discrete longitudinally arranged structural regions further comprises a third, fourth, and fifth structural region disposed distally relative to the second structural region, wherein the first series of wall perforations has a pitch of about 0.014 inches to about 0.018 inches, the second series of wall perforations has a pitch that varies from about 0.014 inches to about 0.018 inches down to about 0.003 inches to about 0.007 inches, the third structural region defines a third series of wall perforations that has a pitch that varies from about 0.008 inches to about 0.012 inches down to about 0.002 inches to about 0.005 inches, and the fourth structural region defines a fourth series of wall perforations that has a pitch of about 0.002 inches to about 0.006 inches. In some cases, the plurality of discrete longitudinally arranged structural regions further comprises a third, fourth, and fifth structural region disposed distally relative to the second structural region, wherein the first series of wall perforations has a pitch of about 0.016 inches, the second series of wall perforations has a pitch that varies from about 0.016 down to about 0.005 inches, the third structural region defines a third series of wall perforations that has a pitch that varies from about 0.010 inches down to about 0.004 inches to about 0.005 inches, and the fourth structural region defines a fourth series of wall perforations that has a pitch of about 0.004 inches. In some embodiments, a cut of the first series of wall perforations and/or the second series of wall perforations have a width that is about 0.0004 inches to about 0.002 inches. In some embodiments, the plurality of discrete longitudinally arranged structural regions further comprises a third, fourth, and fifth structural region disposed distally relative to the second structural region, wherein the second series of wall perforations has a cut frequency of about 2.5 cuts per rotation, the third structural region defines a third series of wall perforations that has a cut frequency of about 1.5 cuts per rotation, and the fourth structural region defines a fourth series of wall perforations that has a cut frequency of about 1.5 cuts per rotation. In some embodiments, catheter devices can include a radiopaque marker disposed at or near the distal end. In some embodiments, a liner material can be disposed along an inner surface of the lumen. The liner material can extend longitudinally beyond the proximal end and/or the distal end of the reinforcing member. The catheter devices can include an outer jacket material disposed about the reinforcing member. The outer jacket can extend longitudinally beyond the proximal end and/or the distal end of the reinforcing member.

In some aspects, micro catheter devices can include: a tubing core having a proximal end and a distal end and defining a lumen therebetween, the tubing core comprising: a plurality of discrete structural zones disposed between the proximal end and the distal end, each of the discrete structural zones having different stiffness properties than an adjacent zone, the stiffness properties of at least one of the zones being set by a periodically interrupted cut formed through a wall of the tubing core along a substantially helical path.

In some aspects, micro catheter devices can include: a tubing core having a first end and a second end and defining an inner opening therebetween, the tubing core comprising: multiple discrete axially distributed structural regions disposed between the first end and the second end, each of the discrete structural regions having a series of wall perforations that generate stiffness properties that are different than a stiffness property in an adjacent structural region.

In some aspects, methods of deploying a component of an endovascular shunt implantation system can include: advancing a proximal region of a micro catheter into a patient, the proximal region defining a first series of wall perforations setting a stiffness of the proximal region, the first series of wall perforations having a pitch of about 0.014 inches to about 0.018 inches and a cut frequency of about 2 to about 3 cuts per rotation; based on the advancing the proximal region of the microcatheter, maneuvering a distal section region about a deployment site defined by an anatomical feature of the patient, the distal section region being disposed distally relative to the proximal region and defining a series of wall perforations setting a stiffness of the distal section region that is less than the stiffness of the proximal region, the series of wall perforations having a pitch of about 0.002 inches to about 0.006 inches and a cut frequency of about 1 to about 2 cuts per rotation; and releasing the component for deployment.

Embodiments can include one or more of the following features.

The maneuvering the distal section region can include deflecting the distal section region. Methods can include deflecting a distal transition section region disposed between the proximal region and the distal section region to maneuver the distal section region. In some embodiments, the distal transition section region defines a series of wall perforations setting a stiffness of the distal transition region that is greater than the stiffness of the distal section region and less than the stiffness of the proximal region, the third series of wall perforations having a pitch starting at about 0.012 inches to about 0.008 inches and decreasing to about 0.002 inches to about 0.006 inches and a cut frequency of about 1 to about 2 cuts per rotation. Methods can include deflecting and/or advancing a mid transition section region disposed between the proximal region and the distal transition section region to maneuver the distal section region. In some embodiments, the mid transition section region defines a series of wall perforations setting a stiffness of the mid transition section region that is less than the stiffness of the proximal region and greater than the stiffness of distal transition section, the series of wall perforations having a pitch starting at about 0.014 inches to about 0.018 inches and decreasing to about 0.003 inches to about 0.007 inches and a cut frequency of about 2 to about 3 cuts per rotation. The advancing can include rotating the first region of the micro catheter. In some embodiments, the distal section region rotates at least about 0.5 rotations for each rotation applied to the first region. In some cases, the distal section region rotates at least about 0.65 rotations for each rotation applied to the first region. Methods can include capturing the component for removal.

In some aspects, the systems and methods described herein can include a catheter (e.g., a micro catheter) having an elongated reinforcing member having a plurality of partial or full fenestrations (e.g., perforations, recesses, material divisions, openings, cuts, etc.) therein. For example, in some embodiments, the cuts have a first pitch in a proximal portion of the reinforcing member, and a second pitch less than the first pitch in a distal portion of the reinforcing member. In some embodiments, the cuts have a first pitch in a proximal portion of the reinforcing member, a second pitch less than the first pitch in a middle portion of the reinforcing member, and a third pitch greater than the second pitch in a distal portion of the reinforcing member. The elongated reinforcing member may further comprise a strain relief element disposed in its distal portion when incorporated in a catheter embodiment (e.g., proximal of a penetrating element when incorporated in an endovascular shunt delivery catheter).

The size and orientations of the cuts around the catheter can be configured and designed to create catheter regions (e.g., zones) having different structural properties, such as torqueability and pushability at different locations along the catheter's length. As a result of creating different material properties, the catheter can have desired properties for carrying out a particular task or operation. For example, the configurations of cuts along the catheter can be designed such that the distal end can have high flexibility for navigation purposes while the proximal end can be stiffer for ease of handling and improved force transmission.

As a result of the cut configurations described herein, the catheter can provide for easier and more accurate navigation within a body and safer and more repeatable medical procedures than with some other conventional catheters. Additionally, improved column strength caused by the cut configurations described herein can help to limit procedure complications or failures in which a catheter might otherwise collapse when retracting tools (e.g., collapsible stents) into the catheter.

The micro catheters described here can be used in any of a variety of medical treatment systems or procedures. For example, in accordance with one aspect of the disclosed inventions, an endovascular shunt implantation system is provided, the system including a guide member having a distal portion configured for being deployed in an inferior petrosal sinus (IPS) of a patient via a micro catheter (the micro catheter device can be configured to deploy the guide member and include a tubing core having a first end and a second end and defining an inner opening therebetween, the tubing core can include multiple discrete axially distributed structural regions disposed between the first end and the second end, each of the discrete structural regions having a series of wall perforations that generate stiffness properties that are different than a stiffness property in an adjacent structural region); a delivery catheter movably coupled to the guide member, wherein a distal end of the delivery catheter includes a tissue penetrating element, such that the delivery catheter and tissue penetrating element are translatable relative to the distal portion of the guide member within the IPS. The system further includes a guard is at least partially disposed over, and movable relative to, the tissue penetrating element. Optionally, an open distal end portion of the guard includes an inner surface feature configured to deflect the tissue penetrating element away from the guide member when the tissue penetrating element is translated distally relative to the guard. Optionally, the system further includes a shunt delivery shuttle at least partially positioned within a lumen of, and movable relative to, the delivery catheter, the shunt delivery shuttle comprising an elongate proximal pusher coupled to a distal shuttle portion made of mesh or a cut tube and configured to collapse around an elongate shunt body to thereby transport the shunt body through the delivery catheter lumen. The distal shuttle portion preferably self-expands to release the shunt body when the distal shuttle portion is advanced out of the delivery catheter lumen through the opening of the tissue penetrating element. The micro catheter can include any of the micro catheters described herein.

In exemplary embodiments, the system further includes an expandable anchor configured for being deployed in a dural venous sinus of the patient at a location distal to a target penetration site located on a curved portion of the IPS wall via a micro catheter, wherein the elongate guide member is coupled to, and extends proximally from, the anchor. Optionally, the system further includes a guide member pusher tool configured for translating the respective guide member and anchor relative to the respective IPS and dural venous sinus (which may be the IPS), for example, through a micro catheter. In various embodiments, the pusher tool comprises a handle having a lumen extending there through, and a tubular body portion coupled to the handle, the tubular body portion having a lumen that is contiguous with or otherwise extends through the handle lumen, the respective handle and tubular body lumens being configured to receive the guide member, wherein the handle is configured to allow selective engagement and release of a portion of the guide member extending proximally through the handle lumen for thereby pushing the guide member, and thus the anchor, distally.

In various embodiments, the guard includes a tubular guard body having a first guard body lumen or recess configured to receive the penetrating element, and a plurality of pull wires, each pull wire having a distal portion fixed within or otherwise attached to the guard body, wherein the pull wires are configured to translate the guard body proximally or distally relative to the delivery catheter so as to at least partially expose or cover, respectively, the penetrating element. The open distal end portion of the guard member preferably has a beveled or tapered portion, and wherein the inner surface feature is located on the beveled or tapered portion. In various embodiments, the inner surface feature of the guard member is formed by at least a partial bead of material applied to, or molded as part of, an inner surface of the guard member.

In various embodiments, the system further comprises an endovascular shunt device, which may also be provided separately from the system. The shunt device includes an elongate shunt body made out of a flexible unreinforced polyurethane-silicone blend or other polymer, and a distal shunt anchor coupled to a distal end of the shunt body, wherein the distal shunt anchor self-expands when advanced out of the delivery catheter lumen. The shunt device further includes one or more cerebrospinal fluid (CSF) intake openings in a distal portion of the shunt that are in fluid communication with a shunt lumen extending through the shunt body, the shunt body comprising one or more longitudinal slits configured to allow egress there through of CSF in the shunt lumen if a fluid pressure within the shunt lumen exceeds a body fluid pressure external of the one or more slits, and wherein a proximal end of the shunt body is fluidly sealed. In an exemplary embodiment, the shunt device includes a tubular connector having a proximal portion secured to a distal end of the shunt body, a distal portion secured to the distal shunt anchor, and an open distal end located within the distal shunt anchor, wherein the one or more CSF intake openings comprise a single CSF intake opening located in the distal end of the tubular connector. The tubular connector may be radiopaque or otherwise have one or more radiopaque elements coupled thereto. In some embodiments, the one or more longitudinal slits in the tubular body portion are configured and dimensioned to achieve a target flow rate of 5 ml of CSF per hour to 15 ml of CSF per hour through the CSF drainage lumen under normal differential pressure conditions between the CP angle cistern and venous system of the patient. In some embodiments, the one or more longitudinal slits in the tubular body portion are configured and dimensioned to allow CSF egress out of the CSF drainage lumen at a pressure differential between the CP angle cistern and the venous system of the patient in a range of 3 mm Hg to 5 mm Hg.

In accordance with another aspect of the disclosed inventions, a pusher tool is provided for deploying an elongate member (e.g., a solid guide wire or an expandable anchor with elongate guide member) through a micro catheter and/or a body lumen. In an exemplary embodiment, the pusher tool includes a handle having a lumen extending there through; and a tubular body portion coupled to the handle, the tubular body portion comprising a lumen that is contiguous with or otherwise extends through the handle lumen, the respective handle and tubular body lumens being configured to receive an elongate member there through, wherein the handle is configured to allow selective engagement and release of a portion of the elongate member extending proximally through the handle lumen for thereby pushing the elongate member distally. In a preferred embodiment, the handle comprises a proximal facing surface configured to mate with a human thumb or finger in order to selectively engage or release the elongate member using said thumb or finger.

In accordance with yet another aspect of the disclosed inventions, a method for deploying an elongate member (e.g., a guide wire or catheter) into a micro catheter and/or body lumen of a patient using the above-described pusher tool includes the steps of (a) inserting an elongate member (e.g., a catheter (e.g., a micro catheter)) through the respective handle and tubular body portion lumens of the pusher tool (the micro catheter device can be configured to deploy the guide member and include a tubing core having a first end and a second end and defining an inner opening therebetween, the tubing core can include multiple discrete axially distributed structural regions disposed between the first end and the second end, each of the discrete structural regions having a series of wall perforations that generate stiffness properties that are different than a stiffness property in an adjacent structural region); (b) grasping the pusher tool (e.g., using a single hand); (c) pinching to thereby secure a portion of the elongate member against a proximal facing surface of the handle (e.g., using a finger or thumb of the same hand that is grasping the tool); (d) advancing the pusher tool while maintaining the pinched engagement of the elongate member against the handle surface so as to advance the elongate member distally into, or further into, the micro catheter and/or body lumen; (e) releasing the engaged portion of the elongate member from the handle surface; and (f) withdrawing the pusher tool proximally relative to the elongate member, wherein the method may further include repeatedly performing steps (c) through (f) until a distal end portion of the elongate member is positioned at a targeted location in the patient's body.

In instances in which the body lumen is a blood vessel, the elongate member is normally advanced into the blood vessel through an introducer sheath and/or micro catheter having a proximal opening outside of the patient and a distal opening within the blood vessel, in which case advancing the pusher tool may include advancing a distal portion of the tubular body into the proximal opening of the micro catheter and/or introducer sheath. The proximal opening of the micro catheter or introducer sheath is normally accessed via a proximal catheter or introducer hub, in which case the method may further include grasping to thereby stabilize the catheter or introducer hub while advancing the distal portion of the tubular body through such hub.

Other and further aspects and features of embodiments will become apparent from the ensuing detailed description in view of the accompanying figures.

BRIEF DESCRIPTION OF THE DRAWINGS

FIGS. 19A-I are perspective and cross-sectional views of a delivery assembly having a penetrating element guard, according to embodiments of the disclosed inventions;

FIG. 20 is a sidecross-sectional view of an penetrating element guard, constructed according to an alternative embodiment of the disclosed inventions;

FIGS. 21A-M are side, perspective and cross-sectional views of a delivery catheter, constructed according to alternative embodiments of the disclosed inventions;

FIGS. 24A-F are side, perspective and cross-sectional views of shunt and pusher member interface according to embodiments of the disclosed inventions;

FIGS. 30F-G are side and cross-sectional views of a reinforcing member of the shunt delivery catheter of FIGS. 30A-E, constructed according to embodiments of the disclosed inventions.

FIGS. 31A-G are perspective and side views of a marker constructed according to embodiments of the disclosed inventions;

FIG. 32 is a perspective view of an implanted shunt according to the embodiments of the disclosed invention;

FIGS. 56A-58F are perspective, side and cross-sectional views of shunts constructed according to alternative embodiments of the disclosed inventions;

FIGS. 59-62E are perspective and cross-sectional views of shunt delivery shuttles constructed according to embodiments of the disclosed inventions;

FIGS. 64A-E are perspective and cross-sectional views of a penetrating element guard constructed according to alternative embodiments of the disclosed inventions;

DETAILED DESCRIPTION OF THE ILLUSTRATED EMBODIMENTS

Figure 1:
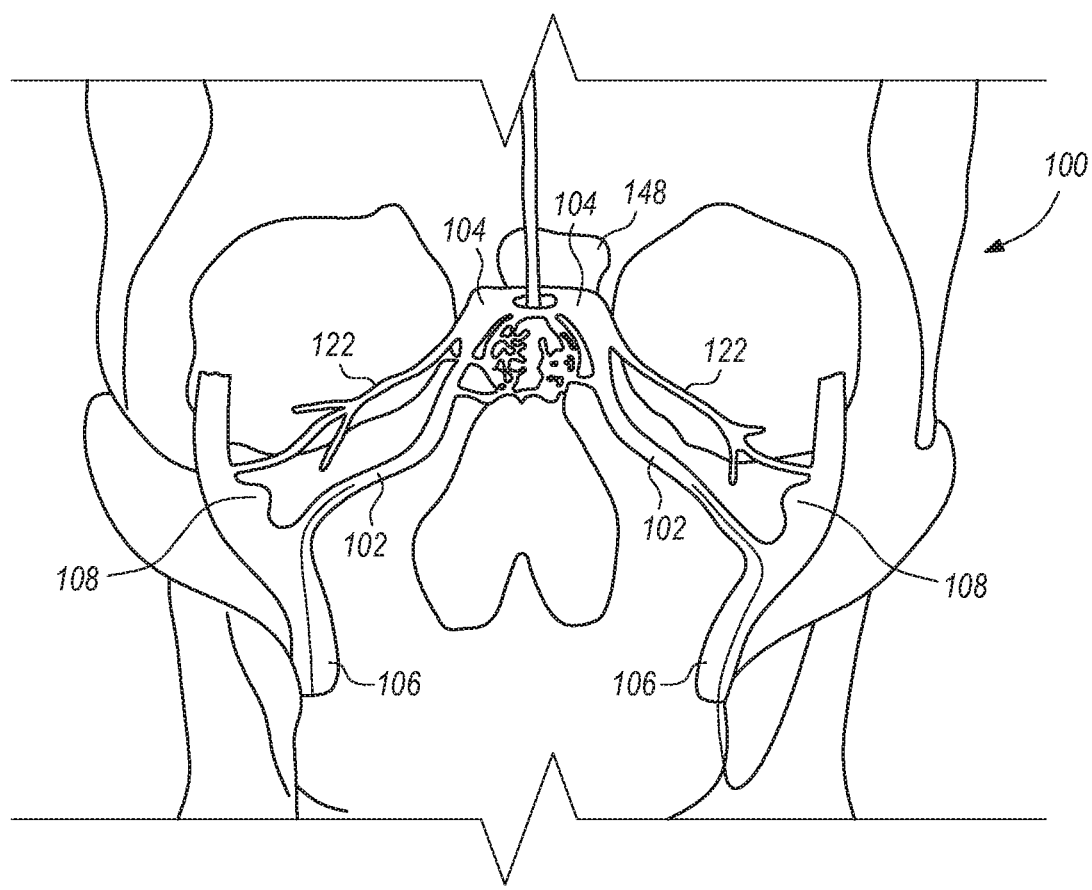
FIG. 1 is a schematic diagram of a head of a human patient.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Micro Catheter Devices

In some aspects, the micro catheters described herein can have varying structural properties along their length to exhibit different performance characteristics for carrying out any of various procedures. The varying structural properties can be defined or determined (e.g., set) by structural properties of a reinforcing member of the micro catheter. In some embodiments, a proximal region of a micro catheter (e.g., where a user handles the micro catheter) can be configured to be stronger (e.g., stiffer, higher pushability, higher torqueability, etc.) than a distal region. In some cases, the micro catheter (e.g., the reinforcing member) can include multiple structural zones, each having different structural properties, which can be set by wall perforations.

Figure 68A:
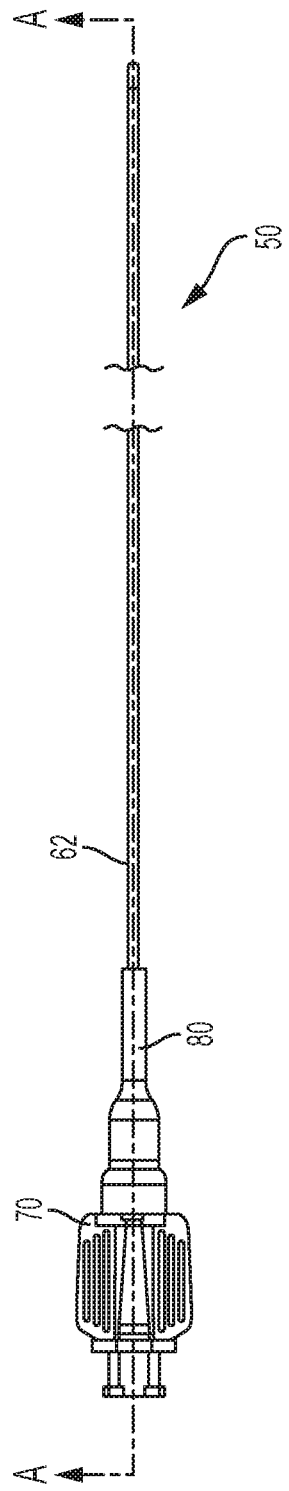
FIGS. 68A-68C are side views of an example micro catheter assembly having a structural micro catheter device with different structural properties at different regions along its length.
Figure 68B:
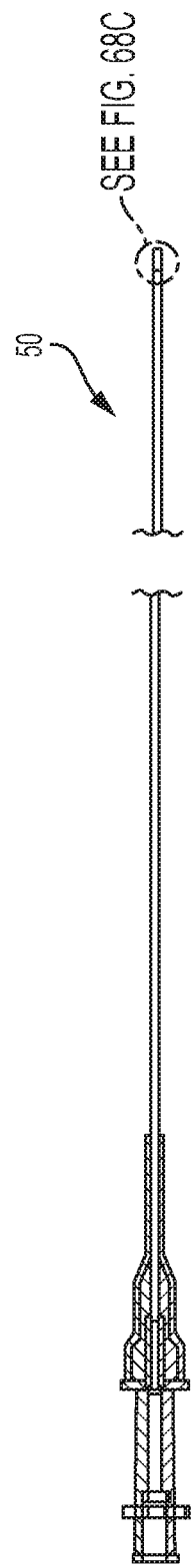
Figure 68C:
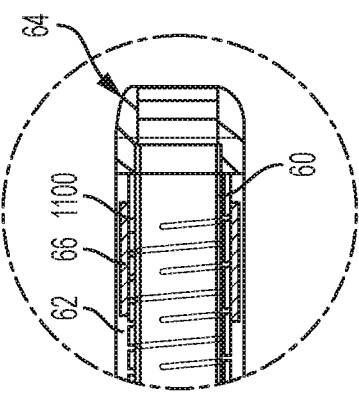

A micro catheter assembly 50, referring to FIGS. 68A-68C can include a reinforcing structural member (e.g., a reinforcing member, a catheter tube (e.g., micro catheter tube (e.g., a micro catheter tubing core (e.g., a stainless steel or Nitinol hypo tube)))) 1100 that can be lined along its inner surface with one or more liner materials 60. In some cases, the liner material 60 can include any of various flexible and smooth materials, such as a plastic (PTFE) or other material, and can form the inner or working lumen of the catheter assembly 50. The liner 60 can increase lubricity of the assembly. In some examples, the liner material 60 can be thin, for example, having a thickness that is about 0.00075 inches. The micro catheter assembly 50 can also include a jacket material (e.g., an extruded tubing or coating) 62 around the outer surface of the structural component 1100. In some embodiments, the outer jacket 62 surrounds the reinforcing member 1100, with material along its inner surface, outer surface, and inside the cuts. The jacket material can also be a flexible and smooth material, such as PEBAX 6333 or PEBAX 3533, which can be hydrophilically coated, and can define a distal tip 64, which can be tapered. Other examples can include medical grade polymers including, but not limited to, nylon, hytrel, silicone, polyurethane, siliconepolyurethane blends, or other materials. The assembly can include an identifier (e.g., a marker (e.g., a radiopaque marker)) disposed at or near the distal end.

At a proximal end of the assembly 50, the structural component 1100 can be coupled to a hub 70 for handling or connections to other devices. For example, the hub 70 can include a Luer-type connection. In some cases, a strain relief component 80 can be used to connect the structural component 1100 to the hub 70 to limit damage of the flexible structural component 1100 where it is coupled to the substantially rigid hub 70.

Figure 69:
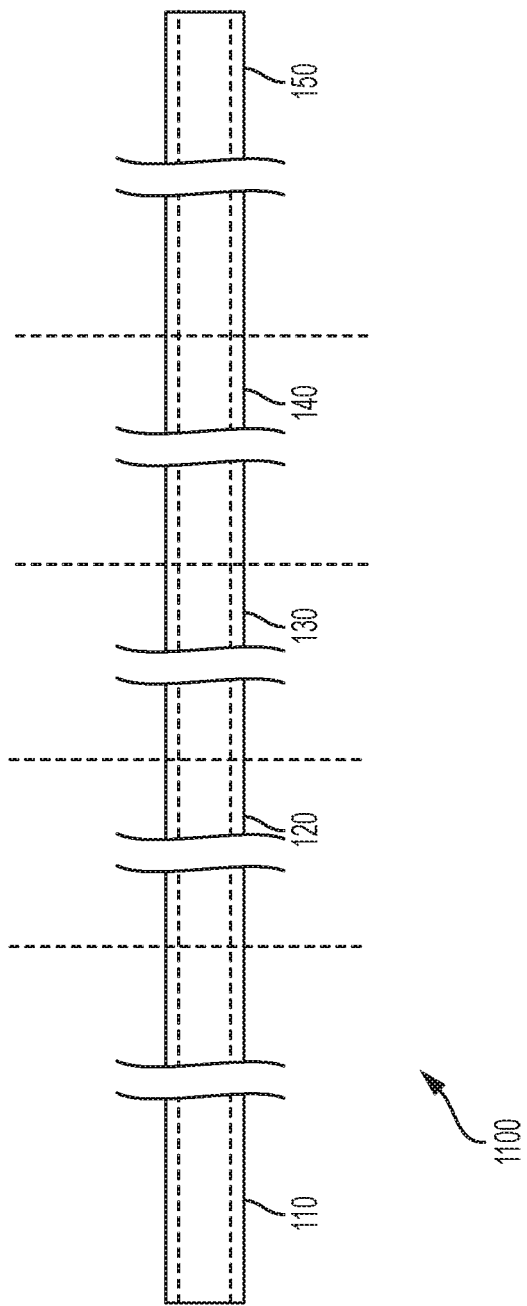
FIG. 69 is a side schematic view of an example structural micro catheter device having different structural properties at different regions along its length.

The varying structural properties of the micro catheter assembly 50 can be caused in large part by structural properties of the reinforcing member 1100. For example, referring to FIG. 69, a reinforcing structural member (e.g., a reinforcing member, a catheter tube (e.g., micro catheter tube (e.g., a micro catheter tubing core))) 1100 can include multiple structural zones 110 (e.g., at its proximal end), 120, 130, 140, 150 (e.g., at its distal end) formed along its length. In the example depicted in FIG. 69, the reinforcing member 1100 has five zones, but other configurations are possible. For example, in some embodiments, the catheter can include 2-50 zones (e.g., 2-10 zones (e.g., 4-6 zones)). The zones can be discrete zones with definite ends where the structural properties of two adjacent zones have discrete end points. However, in some embodiments, zones can be transitional where the properties of one zone transition into the properties of an adjacent zone. In some cases, the structural properties can vary (e.g., vary substantially continuously) along the length of the reinforcing member.

The various zones can be configured so that the reinforcing member 1100 has beneficial material properties for one or more medical procedures. The zones can be of various lengths with respect to the overall length of the reinforcing member. For example, the zones can have the same or different lengths. In some cases, a zone can have a length that is 50% or less (e.g., about 40% or less, about 20% or less, about 15% or less, about 10% or less, about 5% or less, about 2% or less, or about 1% or less) than the overall length of the reinforcing member. The length of the zones can vary between adjacent zones. In some embodiments, a reinforcing member 1100 can include one long zone (e.g., a single zone (e.g., a single zone along 100% of its entire length). In some cases, the reinforcing member 1100 can include a substantially continuously progressive pattern of cuts along its full length.

In some embodiments, the various lengths can be configured based upon the medical environment in which the reinforcing member 1100 and catheter will be deployed, such as having zones at or near its distal end having lengths that are configured to match or otherwise correlate to one or more parts body (e.g., particular venous or arterial locations) around which the catheter needs to be disposed. In some examples, zones closer to the distal end can be shorter than zones closer to the proximal end. In some cases, longer zones at or near the proximal end of the reinforcing member 1100 can help to increase control of the catheter where it will be handled by a user.

Additionally, having shorter zones at or near the distal end of the reinforcing member 1100 can help to create specific desired structural properties along the reinforcing member where the catheter assembly 50 is expected to be used to carry out specific procedures. For example, in some embodiments of the reinforcing member 1100, a first zone 110 can have a length that is about 5% to 50% of the overall length, a second zone 120 can have a length that is about 2% to 20% of the overall length, a third zone 130 can have a length that is about 1% to 20% of the overall length, a fourth zone 140 can have a length that is about 0.25% to 16% of the overall length, and a fifth zone 150 can have a length that is about 0.1% to 12% of the overall length. In some embodiments, a first, proximal zone can be about 36.201 inches, a second zone can be about 8.000 inches, a third zone can be about 5.000 inches, a fourth zone can be about 2.988 inches, and a fifth zone can be about 0.012 inches. In some embodiments, a first, proximal zone can be about 30.547 inches, a second zone can be about 7.874 inches, a third zone can be about 5.906 inches, a fourth zone can be about 7.862 inches, and a fifth zone can be about 0.012 inches.

In some embodiments, the reinforcing member 1100 can include an unmodified region before or after the zones. For example, in some cases, the distal most tip of the reinforcing member can include a short unmodified length. For example, the unmodified region (e.g., along the fifth zone) can include a length of about 0.012 inches of the material used to form the reinforcing member.

The reinforcing member can be made from substantially cylindrical tubing formed of any of various materials, such as metals including stainless steel or Nitinol hypotube. In some cases, the reinforcing member 1100 can also be formed of polymeric materials, such as PEEK or PET. The tubing can be formed to have various inner diameters (ID) or outer diameters (OD), for example, based on the intended size or use of the catheter assembly 50. The inner diameter of the reinforcing member 1100 can be about 0.005 inches to about 0.080 inches. In some examples, the inner diameter can be about 0.014 inches to about 0.038 inches (e.g., about 0.021 inches to about 0.027 inches). The outer diameter can be about 0.016 inches to about 0.100 inches. In some examples, the outer diameter can be about 0.022 inches to about 0.048 inches (e.g., about 0.031 inches to about 0.039 inches).

Figure 70:
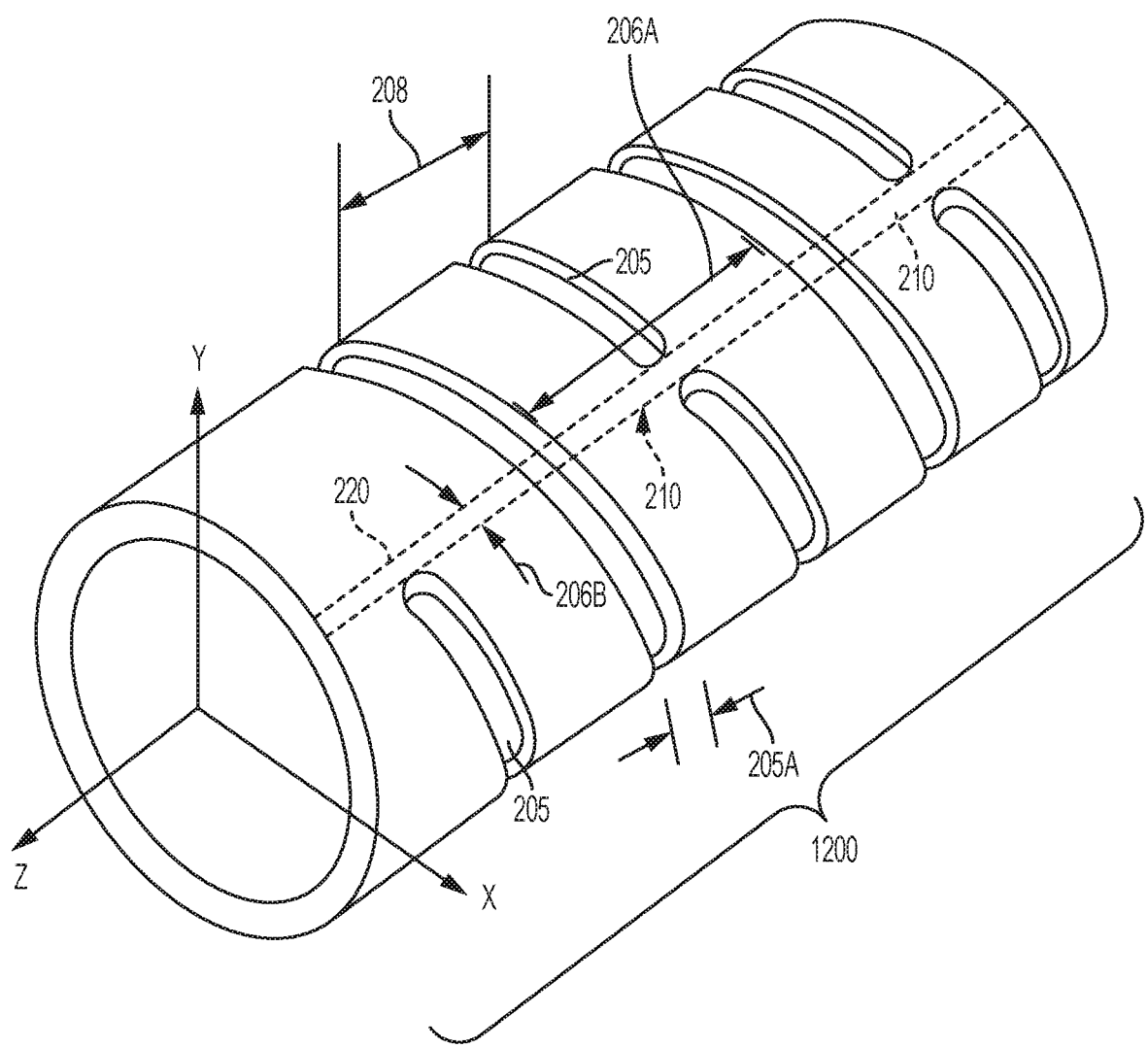
FIG. 70 is a perspective view of an example micro catheter device region having a spiral-like cut formed to alter material properties of the region.

Referring to FIG. 70, in order to set structural properties for the catheter, zones can include a series of one or more cuts (e.g., wall perforations or linear openings) 1200 through the reinforcing member 1100 to generate additional flexibility in the zone. In some examples, the cuts can include one or more spiral-like cuts along the reinforcing member's length. For example, a zone can include an interrupted cut having multiple segments 205 separated by uncut regions 210. The resulting structural properties of the zone can depend on several aspects of the cut, such as pitch of the cut, width of the cut formed, cut balance, cuts per rotation, a size of a seam of interruptions, as well as other aspects. In some embodiments, multiple zones or regions could be formed by one or more reinforcing elements disposed along the length of a catheter, for example, in examples where discrete sections of reinforcement are desired. As used herein, different regions formed of discrete reinforcing member lengths can include the various features described herein with respect to different regions. Additionally or alternatively, in some examples, reinforcing member sections can be used along only one or more portion of a catheter length, transitioning then to unreinforced or otherwise reinforced portions of a catheter.

The pitch 208 of the cut (e.g., the longitudinal length along which the cut path spans 360 degrees about the tubing) can be altered such that decreasing the pitch can decrease the stiffness of the tubing or reinforcing member (thus increasing the flexibility for use) because more cuts can be formed along a given length. The pitch of the spiral-like cut can be about 0.002 inches to about 5 inches. In some examples, the pitch of a cut can be about 0.003 inches to about 0.060 inches. For example, the pitch can be about 0.004 inches to about 0.020 inches (e.g., about 0.004 inches to about 0.010 inches or about 0.005 inches to about 0.016 inches). In some embodiments, the pitch can decrease in zones closer to the distal end of the catheter, for example, to make the distal end more flexible. For example, in some embodiments, a catheter can include a reinforcing member having a first zone 110 having a pitch that is about 0.016 inches, a second zone 120 having a pitch that is about 0.005 inches to about 0.016 inches, a third zone 130 having a pitch that is about 0.004 inches to about 0.010 inches, and a fourth zone 140 having a pitch that is about 0.004 inches. Additionally, in some embodiments, a reinforcing member having fives zones can have, a first zone 110 having a pitch that is about 0.016 inches, a second zone 120 having a pitch that is about 0.005 inches to about 0.016 inches, and a third zone 130 having a pitch that is about 0.004 inches to about 0.010 inches. While these configurations of zones have been generally described as being implemented in catheters with reinforcing members having five zones, other configurations are possible. In such cases, the term "fifth zone" is used to refer to the distal most zone and preceding zones (e.g., fourth, third, etc.) are used to refer to proximally located zones. Additionally, while the distal end is referred to herein at some points as a "fifth zone," five discrete zones are not required. That is it, the distal end can be the fourth zone in an example having four zones, or the tenth zone in an example having ten zones.

Additionally, the direction of the spiral cut along the reinforcing member 1100 can vary or be the same from zone to zone. For example, in some embodiments, all of the spiral cuts can follow a right-handed helix or a left-handed helix. Alternatively or additionally, a portion or all of the cuts can be formed along an interrupted pattern along a path aligned orthogonally relative to the catheter's longitudinal axis (e.g., the cuts can be formed along a zero degree helical path, which can form a partially circumferential cut). In some cases, the cuts can vary from zone to zone where some are right-handed and some are left-handed. In some cases, the cuts can vary from zone to zone where some are right-handed, some are left-handed, and/or some are circumferentially oriented. In some examples, the distal-most zone can have a cut that follows a left-handed helix and the proximal-most zone can have a cut that follows a right-handed helix. In some cases, adjacent zones can alternate between cuts following a left-handed helix and then a right-handed helix.

The width 205A of the cut (e.g., the width of a void formed that is generally perpendicular to the cutting path) can be altered such that increasing the width can decrease the strength of the tubing because more material is removed along a given length. The width (e.g., kerf) of the spiral-like cut can be about 0.0002 inches to about 0.04 inches. In some examples, the width of the cut can be about 0.0004 inches to about 0.002 inches. For example, the width can be about 0.0005 inches to about 0.0015 inches (e.g., about 0.0075 inches to about 0.00125 (e.g., about 0.001 inches)).

The cut balance typically refers to an amount of cut formed through a single unit structure of cut and uncut material along the cut path around the tubing of the reinforcing member 1100. For example, if a cut was formed continuously around the tubing, its cut balance would be 360 degrees on, 0 degrees off. If a cut was formed one quarter of the way around the tubing, its cut balance would be 90 degrees on, 270 degrees off. The cut balance can be adjusted to create desired pattern symmetry in concert with the cut frequency, or cuts per rotation (CPR), referring to the number of cuts present in a single 360 degree sweep along the cut path around or along the reinforcing member 1100. Assorted combinations of cut balance and CPR around or along the reinforcing member 1100 can be leveraged in adjacent zones throughout the reinforcing member to optimize the properties of pushability, torqueability, and trackability for a given zone.

For example, in some embodiments, the cut frequency can vary along the reinforcing member 1100 between 1 cut per rotation to 5.5 cuts per rotation, or more. In some cases, the cut frequency can be about 1.5 CPR (e.g., which can be formed by a cut having a cut balance of about 230 degrees on, an uncut region along about 10 degrees off, a cut along another about 220 degrees on, and an uncut region along about 20 degrees off). A cut can also be formed by a cut with about 210 degrees on, an uncut region along about 30 degrees off, a cut along another about 180 degrees on, and an uncut region along about 60 degrees off. The cut frequency can be about 2.5 CPR (e.g., which can be formed by a cut having a cut balance of about 136 degrees on, an uncut region along about 8 degrees off, a cut along another about 128 degrees on, and an uncut region along about 16 degrees off). A cut frequency of about 2.5 CPR can also be formed by a cut with about 108 degrees on, an uncut region along about 36 degrees off, a cut along another about 72 degrees on, and an uncut region along about 72 degrees off. The cut can be about 3.5 CPR (e.g., which can be formed by a cut having a cut balance of about 96 degrees on, an uncut region along about 6.8 degrees off, a cut along another about 91 degrees on, and an uncut region along about 11.9 degrees off). The cut frequency can be about 5.5 CPR (e.g., which can be formed by a cut having a cut balance of about 60 degrees on, an uncut region along about 5.5 degrees off, a cut along another about 50 degrees on, and an uncut region along about 15.5 degrees off). The cut frequency can also be about 5.5 CPR (e.g., which can be formed by a cut having a cut balance of about 61 degrees on, an uncut region along about 4.5 degrees off, a cut along another about 57 degrees on, and an uncut region along about 8.5 degrees off). While some examples have been provided, other configurations are possible for both cut balance and the particular cut sequence/pattern to achieve the cut balance.

In some embodiments, the cut frequency (cuts per rotation) can decrease in zones closer to the distal end of the reinforcing member, for example, to make the distal end more flexible. For example, in some embodiments, a catheter can have a first zone 110 having a cut frequency about 2.5 cuts per rotation, a second zone 120 having a cut frequency about 2.5 cuts per rotation, a third zone 130 having a cut frequency about 1.5 cuts per rotation, a fourth zone 140 having a cut frequency about 2.5 cuts per rotation, and fifth zone 150 substantially free of cuts. In some embodiments, a catheter can have a first zone 110 having a cut frequency about 2.5 cuts per rotation, a second zone 120 having a cut frequency about 2.5 cuts per rotation, a third zone 130 having a cut frequency about 1.5 cuts per rotation, and a fifth zone 150 being substantially free of cuts. Additionally, in some embodiments, a catheter with a reinforcing member having five zones can have a distal-most cut zone 140 having a cut frequency of about 1.5 cuts per rotation, a next distal-most zone 130 having a cut frequency of about 1.5 cuts per rotation, and a next distal-most zone 120 having a cut frequency of about 2.5 cuts per rotation, with a distal tip that can be free of cuts. While these configurations of zones have been generally described as being implemented in catheters having five zones, other configurations are possible. In such cases, the term "fifth zone" is used to refer to the distal most zone and preceding zones (e.g., fourth, third, etc.) are used to refer to proximally located zones.

The reinforcing member 1100 can also include a region around its circumference along which one or more of the uncut regions 210 can be aligned along a longitudinal path. This path can be referred to as a seam of interruption 220, for example, to denote a seam along the reinforcing member. Configuring the cut path so that uncut regions 210 are aligned along a common seam of interruption can help to create more repeatable and predictable material properties at different longitudinal regions along the reinforcing member. For example, maintaining a consistent seam of interruption can help to create consistent torsion or stiffness with respect to an x-axis and y-axis at different locations along a z-axis. Whereas, in cases where uncut regions are positioned at different positions around the circumference of the reinforcing member with respect to its length (e.g., along a spiraling path), the resulting reinforcing member, and therefore the catheter, could have different stiffness to resist deflection about its x-axis at different positions along the z-axis due to the presence or absence of uncut regions.

In some embodiments, a seam of interruption on or along the reinforcing member 1100 can have a seam width 206B that is about 0.001 inches to about 0.020 inches (e.g., about 0.004 inches to about 0.020 inches, about 0.005 inches to about 0.012 inches). Additionally, the seam can include one or more uninterrupted lengths 206A along which the reinforcing member remains uncut. In some embodiments, the length of a given uninterrupted length 206A can be about 0.001 to about 5 inches (e.g., about 0.004 inches to about 0.050 inches, about 0.005 inches to about 0.040 inches).

The configurations of the cut path as described with respect to the various parameters above can cause the different zones to exhibit different structural properties. In some cases, the configurations the pitch and cut balance of the reinforcing member 1100 can create a micro catheter that is stronger than most conventional devices while also maintaining operability that is typically not possible with most conventional devices. That is, in some cases, the reinforcing member, and therefore the catheter, can be stiffer and more resistant to torsion deflection while maintaining maneuverability within the desired procedure site.

For example, the reinforcing members, and therefore the catheters in which they are installed, herein can be made to have a stiffness (e.g., a resistance to deflection perpendicular to its longitudinal axis) that is equal to or up to 20 times greater (e.g., 15 times greater, 10 times greater, 7 times greater, 5 times greater, 2 times greater, etc.) than a stiffness of conventional reinforcing members and catheters having a similar diameter configuration.

The reinforcing members, and therefore the catheters in which they are installed, herein can be made to also have a torque resistance (e.g., a resistance to rotational deflection of one end with respect to its other end when undergoing an applied torque) that is up to 10 times greater (e.g., 7 times greater, 5 times greater, 2 times greater, etc.) than a torque resistance of conventional reinforcing members and catheters having a similar diameter configuration.

In some cases, the reinforcing members, and therefore the catheters in which they are installed, herein can be made to have a column strength (e.g., a resistance to buckling when an axial force is applied) that is up to 5 times greater (e.g., 4 times greater, 2 times greater, 1.5 times greater, etc.) than a column strength of conventional reinforcing members and catheters having a similar diameter configuration.

Additionally, the reinforcing members, and therefore the catheters in which they are installed, herein can be made to have a hoop strength (e.g., a resistance to forces inside the cylindrical wall of the microtube acting towards the circumference perpendicular to the length of the microtube) that is up to 10 times greater (e.g., 7 times greater, 5 times greater, 2 times greater, etc.) than a hoop strength of conventional reinforcing members and catheters having a similar diameter configuration.

Figure 71A:
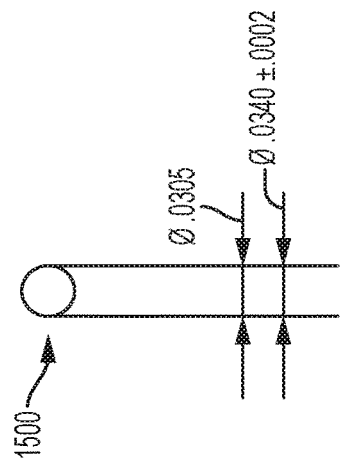
FIGS. 71A and 71B are front and side schematic views of another example micro catheter device having different cut patterns between its proximal and distal ends.
Figure 71B:
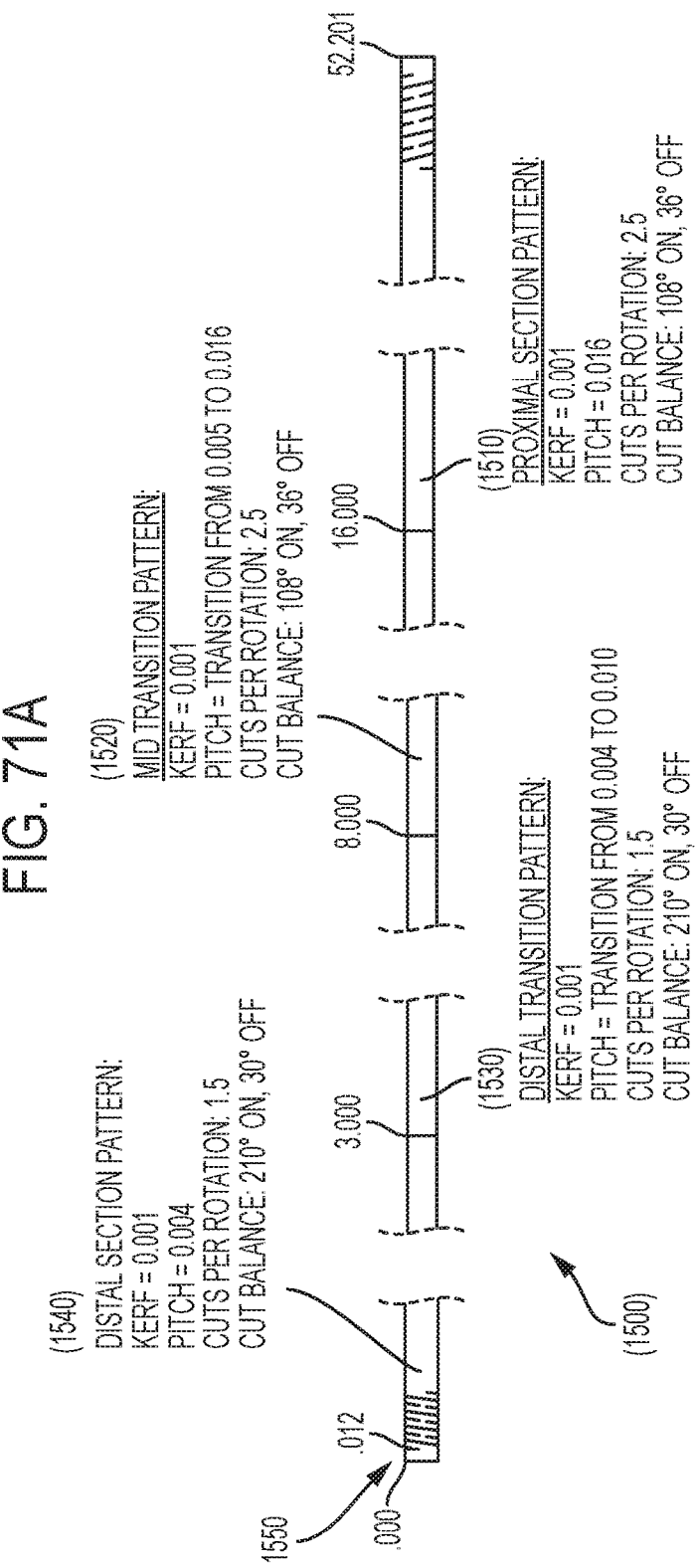

Another example reinforcing member 1500 for a micro catheter is illustrated in FIGS. 71A and 71B. As depicted in FIGS. 71A and 72B, a reinforcing member 1500 can include a first zone (e.g., proximal section) 1510 defining a proximal section pattern of cuts, a second zone (e.g., a mid-transition section) 1520 defining a mid-transition section pattern of cuts, a third zone (e.g., a distal transition section) 1530 defining a distal section pattern of cuts, a fourth zone (e.g., a distal section) 1540 defining a distal section pattern of cuts, and a fifth zone (e.g., a distal end section) 1550.

The distal end section 1550 can include a section that is substantially free of any cuts. As such, the distal end section 1550 can have material properties that substantially match the tubing from which the reinforcing member 1500 is made. Having a distal end section 1550 free of cuts (e.g., to have a solid end section) can also help to improve the structural integrity of the reinforcing member 1500 and helping to prevent the distal end of the reinforcing member from unraveling (e.g., pulling apart) during torsion or tension. The distal end section 1550 can have a length that is about 0.012 inches.

The distal section 1540 can include a distal section pattern of cuts having a width (e.g., a kerf) that is about 0.001 inches, arranged at a pitch of about 0.004 inches. The distal section pattern of cuts can have a cut frequency of about 1.5 cuts per rotation (CPR). The cuts along the distal section can follow a left-handed helix. The distal section pattern of cuts can have a cut balance of about 210 degrees on and about 30 degrees off. The distal end section 1550 can have a length that is about 0.012 inches.

The distal transition section 1530 can include a distal transition section pattern of cuts having a kerf that is about 0.001 inches, arranged at a pitch of about 0.004 inches (e.g., which can be configured to match the pitch of the distal section pattern) to about 0.010 inches. The pitch can vary from 0.004 inches to 0.010 inches along the length of the distal transition section, where the smallest pitch occurs at a distal-most end of the distal transition section and the largest pitch occurs at a proximal-most end of the distal transition section with a continually increasing or variable rate of change in pitch distance along the transition zone. As a result, the distal transition section can increase in stiffness from its distal-most end to its proximal-most end. The cuts along the distal transition section can follow a left-handed helix. In some cases, the cuts along the distal transition section can follow a right-handed helix so that the helical path can alternate between sections. In some embodiments, all of the cut patterns are formed along helical paths of the same direction (e.g., all left-handed helical paths or all right-handed helical paths). The distal transition section pattern of cuts can have a cut frequency of about 1.5 cuts per rotation (CPR). The distal transition section pattern of cuts can have a cut balance of about 210 degrees on and about 30 degrees off. Due to a larger pitch, the distal transition section 1530 can have a stiffness that is greater than that of the distal section 1540. The distal transition section 1540 can have a length that is about 2.988 inches.

The mid transition section 1520 can include a mid transition section pattern of cuts having a kerf that is about 0.001 inches, arranged at a pitch of about 0.005 inches to about 0.016 inches. The pitch can vary from 0.005 inches to 0.016 inches along the length of the mid transition section, where the smallest pitch occurs at a distal-most end of the mid transition section and the largest pitch occurs at a proximal-most end of the mid transition section with a continually increasing or variable rate of change in pitch distance along the transition zone. As a result, the mid transition section can increase in stiffness from its distal-most end to its proximal-most end. The cuts along the mid transition section can follow a left-handed helix. In some cases, the cuts along the mid transition section can follow a right-handed helix. The mid transition section pattern of cuts can have a cut frequency of about 2.5 cuts per rotation (CPR). The mid transition section pattern of cuts can have a cut balance of about 108 degrees on and about 36 degrees off. Due to a larger pitch, higher cuts per rotation (CPR), and/or lower cut balance, the mid transition section 1520 can have a stiffness that is greater than that of the distal transition section 1530. The mid transition section 1520 can have a length that is about 8.000 inches.

The proximal section 1510 can include a proximal section pattern of cuts having a kerf that is about 0.001 inches, arranged at a pitch of about 0.005 inches to about 0.016 inches (e.g., which can be configured to match the pitch of the proximal-most end of the mid transition section pattern). The cuts along the proximal section can follow a left-handed helix. In some cases, the cuts along the proximal section can follow a right-handed helix. The proximal section pattern of cuts can have a cut frequency of about 2.5 cuts per rotation (CPR). The proximal section pattern of cuts can have a cut balance of about 108 degrees on and about 36 degrees off. Due to a larger pitch, higher cuts per rotation (CPR), and/or lower cut balance, the proximal section 1510 can have a stiffness that is greater than that of the mid transition section 1520. The length of the proximal section 1510 can depend on the desired usable handling length of the reinforcing member 1500. For example, in some embodiments, the proximal section 1510 can have a length that is about 36.201 inches.

Figure 72A:
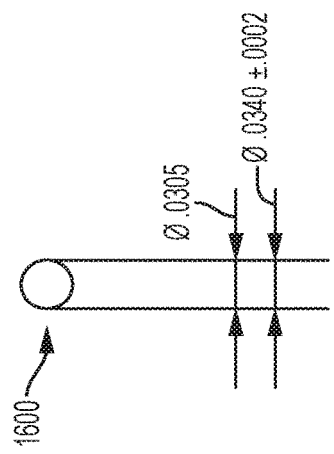
FIGS. 72A and 72B are front and side schematic views of another example micro catheter device having different cut patterns between its proximal and distal ends.
Figure 72B:
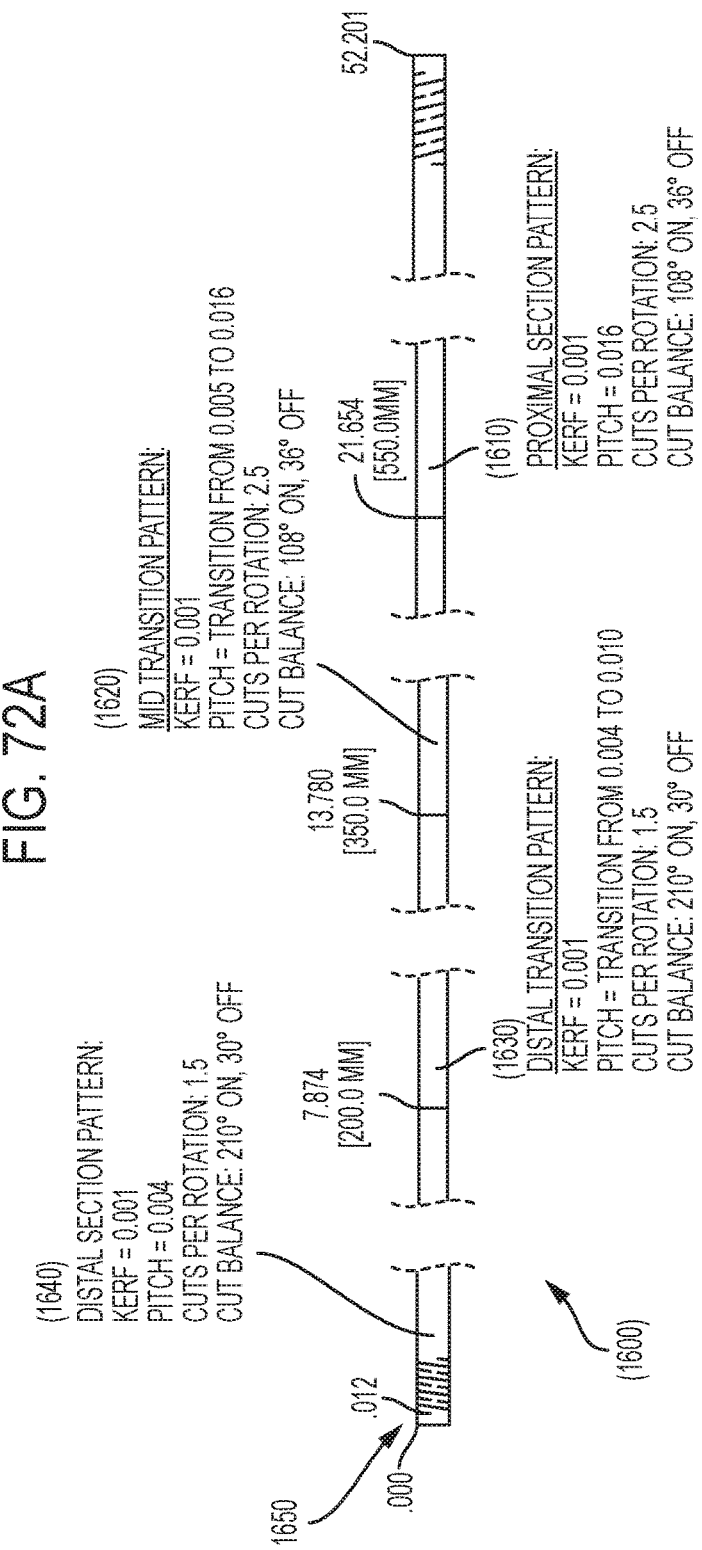

Another example reinforcing member 1600 for another micro catheter is illustrated in FIGS. 72A and 72B. Like the reinforcing member 1500, as depicted in FIGS. 72A and 72B, a reinforcing member 1600 can include a reinforcing member with a proximal section 1610 defining a proximal section pattern of cuts, a mid-transition section 1620 defining a mid-transition section pattern of cuts, a distal transition section 1630 defining a distal section pattern of cuts, a distal section 1640 defining a distal section pattern of cuts, and a distal end section 1650. Along the various sections (1610, 1620, 1630, 1640, 1650), the reinforcing member 1600 can include or define cut patterns that are similar or substantially the same as those depicted in FIGS. 71A and 72B and described above with respect to reinforcing member 1500 (i.e., section 1510, 1520, 1530, 1540, 1550, respectively). However, some specific features or implementations can vary. For example, in some embodiments, a length of the distal section 1640 can be about 7.862 inches. In some embodiments, a length of the distal transition section 1630 can be about 5.906 inches. In some embodiments, a length of the mid transition section 1620 can be about 7.874 inches. And in some embodiments, a length of the proximal section 1610 can be about 30.547 inches.

While several example configurations have been described, the individual parameters of various micro catheters (e.g., and the reinforcing members therein) described herein can be combined with one another unless otherwise stated. For example, features described with respect to the various zones of reinforcing member 1100 (or of the catheter 50) can be implemented in reinforcing member 1200, 1500, 1600 and vice versa.

Performance Testing

The micro catheter designs described herein, due to the various cut patterns and configurations described herein, have been found to perform better than some conventional micro catheter designs. For example, the micro catheter designs described herein have been found to have better column strength, tensile strength, and resistance to torsion deflection than commercially available micro catheters lacking one or more of the cut pattern configurations described herein. The improved structural properties have been revealed through several tests that have been performed.

Test 1—Push/Pull

For example, in one test, several micro catheters were inserted into a testing path formed of a polymer guide tube configured to replicate tortuous vasculature, for example, forming an "s" bend in the tube along a flat surface and then transitioning the tube into a 360-degree loop and rising perpendicularly and away from the flat surface. A distal force sensor was arranged at a distal end of the testing path to measure the force conveyed by the micro catheter as it exits the testing path. A proximal force sensor was arranged at proximal end of the testing path to measure the force provided to the micro catheter. A guide wire was fixed between the proximal and distal sensors along which the micro catheter traveled. With the proximal and distal force sensors, it was possible to measure the force driving the micro catheter into the testing and the resulting force from micro catheter. As such, the force loss (e.g., how efficiently the micro catheter could convey force to its distal tip through a series of tortuous bends) could be measured and compared.

During the test, micro catheters were advanced at 150 centimeters/minute (cm/min), along the fixed guide wire, until they made contact with the distal force sensor. Once contact was made and a consistent amount of compression applied, the micro catheter was held in place for 3 seconds and pulled back out of the testing path at 300 cm/min. Displacement, proximal force, and distal force were measured for each test specimen.

Over three different test runs, micro catheters having reinforcing members as discussed herein, for example, as depicted in FIGS. 71A and 71B were tested and found to perform better than some conventional micro catheters of similar size. For example, micro catheters depicted in FIGS. 71A and 71B were found to exhibit a greater force transmission ratio (e.g., a ratio force observed at the distal end compared to the force inputted at the proximal end) than conventional micro catheters. Force transmission ratio can describe the amount of force a user could reasonably convey to the distal end of the micro catheter during clinical use. Typically, a higher force transmission ratio can be desired, as it can make the micro catheter more responsive and allow the user to more easily perform a desired operation. In some cases, example micro catheters described herein achieved force transmission ratio of 0.21 and over 0.35, whereas conventional micro catheters achieved force transmission ratios of about 0.17, 0.3, 0.19, 0.14, and 0.18.

Test 2—Torque

In another test, micro catheters were inserted through the testing path as described above for Test 1, formed of a guide tube having two opposing u-shaped bends together forming an "s" bend along a flat surface (e.g., shown along the page) and then a perpendicular loop (e.g., shown coming out of the page). A proximal torque transducer and encoder were arranged at the proximal end of the testing path and a distal encoder was arranged at the distal end of the testing path. The transducer was configured to generate torque being applied to rotate the micro catheter at the proximal end. The encoders were configured to measure an amount of rotation (e.g., in degrees) and torque at the proximal and distal ends. For example, the encoders were coupled to the proximal and distal ends of the micro catheter, respectively. With a micro catheter disposed through the testing path, using these devices, the test was able to measure and compare the force required to rotate the proximal end of the micro catheter. Additionally, the test could determine how much the distal end of the micro catheter would rotate as the proximal end rotates. As such, the micro catheter's resistance to torsion deflection could be measured and compared.

During the test, the micro catheters were rotated at their proximal end 10 revolutions counterclockwise (e.g., with respect to facing the distal end) at 20 revolutions per minute. The micro catheters were then rotated 20 revolutions clockwise at 20 revolutions per minute. The various samples were tested to measure rotations observed at the distal end, to compare rotations inputted at the proximal end to the rotations observed at the distal end, and a number of input rotations needed to begin rotating the distal end.

The micro catheters described herein were observed to withstand the user applying more torque (since torque applied to the micro catheters described herein input values were higher) were found to have greater responses (e.g., more output revolutions) at their distal end. That is, the micro catheters described herein were able to meet or exceed rotational response compared to commercially available products). Additionally, the micro catheters described herein were found to be more durable. That is, all three of the micro catheters described herein that were tested were able to transmit torque to rotate their distal ends successfully. Whereas, 4 of the 5 conventional micro catheters tested failed to transmit torque when rotating their proximal ends in at least one direction (i.e., no rotation was detected at the distal end). In addition, multiple conventional micro catheters mechanically failed (e.g., permanent deformation of catheter wall, break through reinforcing structure and catheter wall, complete break through catheter body) during torque testing.

As result of the testing performed and described above, it was found that the micro catheters described herein, due at least to improved column strength and resistance to rotational deflection created by the cut patterns described herein, have adequate or better force transmission properties and substantially better torque transmission and rotational properties than conventional micro catheters.

The micro catheters described herein can be used in various medical procedures, for example, in treating hydrocephalus, pseudotumor cerebri, and/or intracranial hypertension, as detailed throughout this application. However, other uses of the micro catheter are possible in treating any of various other types of medical issues or carrying out various other types of procedures including, but not limited to, other interventional neurovascular, cardiovascular, or peripheral vascular procedures.

Uses of the Micro Catheters in Medical Procedures

FIG. 1 is a schematic diagram showing the head 100 of a human patient. Within each side of the patient's head, an inferior petrosal sinus (IPS) 102 connects a cavernous sinus (CS) 104 to a jugular vein 106 and/or a jugular bulb 108. For clarity, the acronym "IPS" is used herein to refer generally to the inferior petrosal sinus and more particularly to the interior space (or lumen) of the inferior petrosal sinus. The IPS 102 facilitates drainage of venous blood into the jugular veins 106. In some patients, the junction of the IPS 102 and the jugular vein 106 occurs within the jugular bulb 108. However, in other patients, this junction can occur at other locations in the jugular vein 106. Moreover, while the IPS 102 in FIG. 1 is a single sinus passageway, in some patients the IPS can be a plexus of separate channels that connect the CS to jugular vein 106 (not shown) and/or jugular bulb 108.

Embodiments of the disclosed inventions are described with respect to a target penetration site in the IPS 102 to access the CSF-filled CP angle cistern 138, which provide a conduit for CSF to flow, via an implanted shunt device, from the subarachnoid space 116 into the jugular bulb 108, jugular vein 106 (FIGS. 1, 2A-B) and/or the superior vena cava-right atrium junction (not shown). The delivery assemblies and shunts described herein can access the target penetration site in the IPS 102 through a venous access location in the patient. The delivery assemblies and shunts described herein can penetrate the dura mater IPS wall 114 and the arachnoid layer 115 to access the CP angle cistern 138 from within a superior petrosal sinus (SPS) 122 (FIG. 1) for delivery and implantation of the shunt at the target site. The dura mater IPS wall 114 is also referred to herein as the dura IPS wall 114, or simply as the IPS wall 114. The SPS is a small diameter venous sinus that connects from the sigmoid sinus (distally located to jugular bulb 108) to the cavernous sinus 104 (1). Further, the delivery assemblies and shunts described herein can be advanced through the IPS 102 and into the cavernous sinus 104, so that an anastomosis (not shown) can be created in the upper portion or roof of the cavernous sinus 104 to access the CSP-filled suprasellar cistern 148, shown in 1, for implantation of the shunt at such target site. Whether penetration to access a target site, deployment and implantation of a shunt occurs from the lumen of the SPS or cavernous sinus to access CSF in the subarachnoid space, the embodiments of the inventions described herein provide a conduit for CSF to flow from the subarachnoid space into the jugular bulb 108, jugular vein 106, and/or the superior vena cava-right atrium junction (not shown).

Figure 2A:
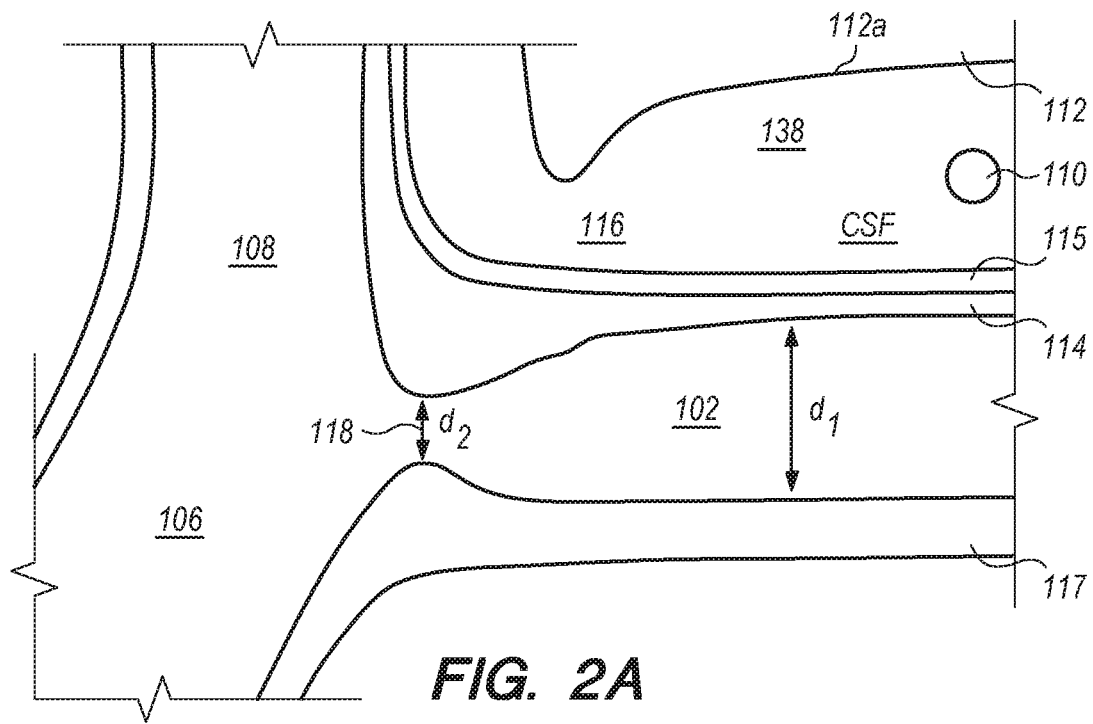
FIG. 2A-D are cross-sectional views of a portion of the head of a human patient.

FIG. 2A shows a cross-sectional view of a portion of head 100, including IPS 102, jugular vein 106, and jugular bulb 108. In addition, basilar artery 110, brain stem 112, pia 112a, and IPS wall 114 are also shown in FIG. 2A. The IPS is a relatively small diameter intracranial venous sinus that facilitates drainage of cerebral venous blood into the jugular vein; the IPS is formed by a cylindrical layer of dura mater, typically about 0.9 mm to 1.1 mm thick for the portion of IPS wall 114 shown in FIG. 2A, which creates a hollow lumen through which blood flows. In the cross-section view of FIG. 2A, the hollow lumen of the IPS resides between upper IPS wall 114 and a lower IPS wall 117, also comprised of dura mater; the IPS itself lies in a bony groove or channel in the clivus bone (not shown) beneath IPS wall 117 in FIG. 2A.

A cross-section of the IPS 102 orthogonal to the plane depicted in FIG. 2A would show that the cylindrical layer of dura mater forming IPS 102 is surrounded by bone for about 270° of its circumference with the remaining portion of the IPS circumference (i.e., IPS wall 114 in FIGS. 2A-B) covered by arachnoid matter 115 and facing CP angle cistern 138. Arachnoid mater 115 (also referred to herein as the arachnoid layer) is a delicate and avascular layer, typically about 0.05 mm to 0.15 mm thick, that lies in direct contact with the dura mater comprising the exterior of IPS wall 114; arachnoid layer 115 is separated from the pia mater surrounding brain stem 112 by the CSF-filled subarachnoid space 116 (e.g., CP angle cistern 138). The lower portion of the IPS 102, opposite to the IPS wall 114 is the IPS wall 117 formed by dura mater that sits in a channel in the clivus bone (not shown).

It should be appreciated that for the embodiments of the disclosed inventions, the methods and devices are configured to create an anastomosis via an endovascular approach by piercing or penetrating from within the hollow IPS 102 to pass through the dura of IPS wall 114, and continue penetrating through the arachnoid layer 115 until reaching the CSF-filled subarachnoid space 116 (e.g., CP angle cistern 138). For ease of illustration, it should be appreciated that the arachnoid matter 115 covering the IPS wall 114 is present, although, not shown in certain figures.

The diameter $d_1$ of IPS 102 is approximately 3 mm but can range from approximately 0.5 mm to about 6 mm. As shown in FIG. 2A, at the junction 118 between the IPS 102 and the jugular bulb 108 and/or jugular vein 106, the diameter $d_2$ of the IPS 102 can narrow. For example, $d_2$ is approximately 2 mm, but can be as small as about 0.5 mm. The length of the IPS 102 from the junction 118 with the jugular vein 106 to the cavernous sinus 104 (shown in FIG. 1) is approximately in a range between 3.5 cm to 4 cm.

Figure 2B:
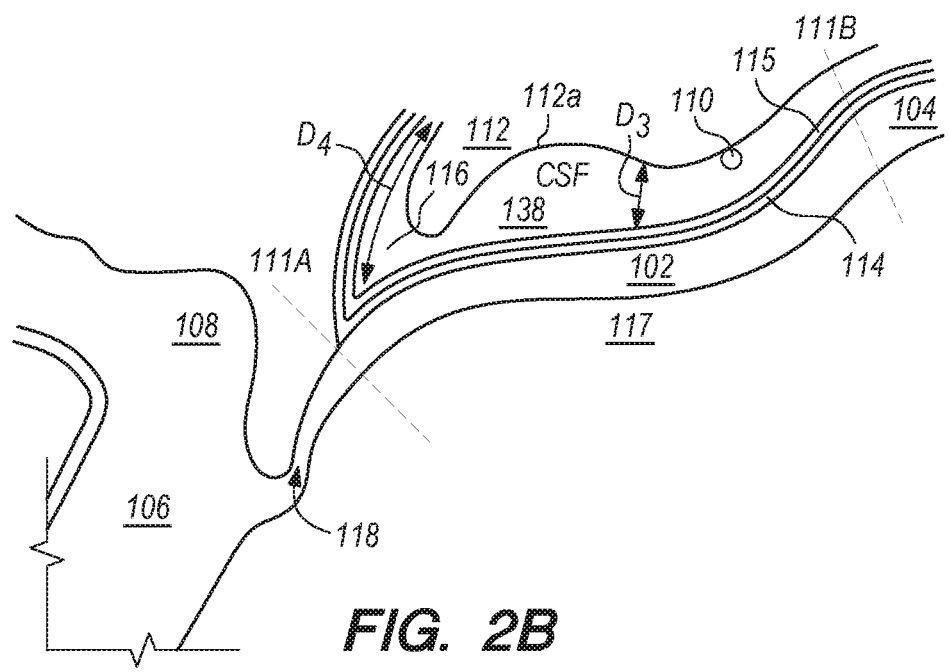

In many patients, the IPS 102 is coupled to the jugular vein 106 at a location disposed below of the jugular bulb 108, depicted as junction 118, shown in FIG. 2B. The IPS 102 extends distally from the junction 118 in the medial wall of the jugular vein 106, past the 9th cranial nerve 111A and jugular tubercle (not shown) while curving rostral-medially through a first curved portion 102A shown in FIG. 2C, and then further curving medial-superiorly through a second curved portion 102B shown in FIG. 2C before connecting at the connection point 111B with the cavernous sinus (CS) 104. The IPS 102 extends distally from the junction 118 through a curvature of approximately 45° to 100° in the first and second curved portions 102A and 102B until the IPS 102 connects with the CS 104. The CSF-filled CP angle cistern 138 lies immediately above the curved portion of the IPS 102.

Figure 2C:
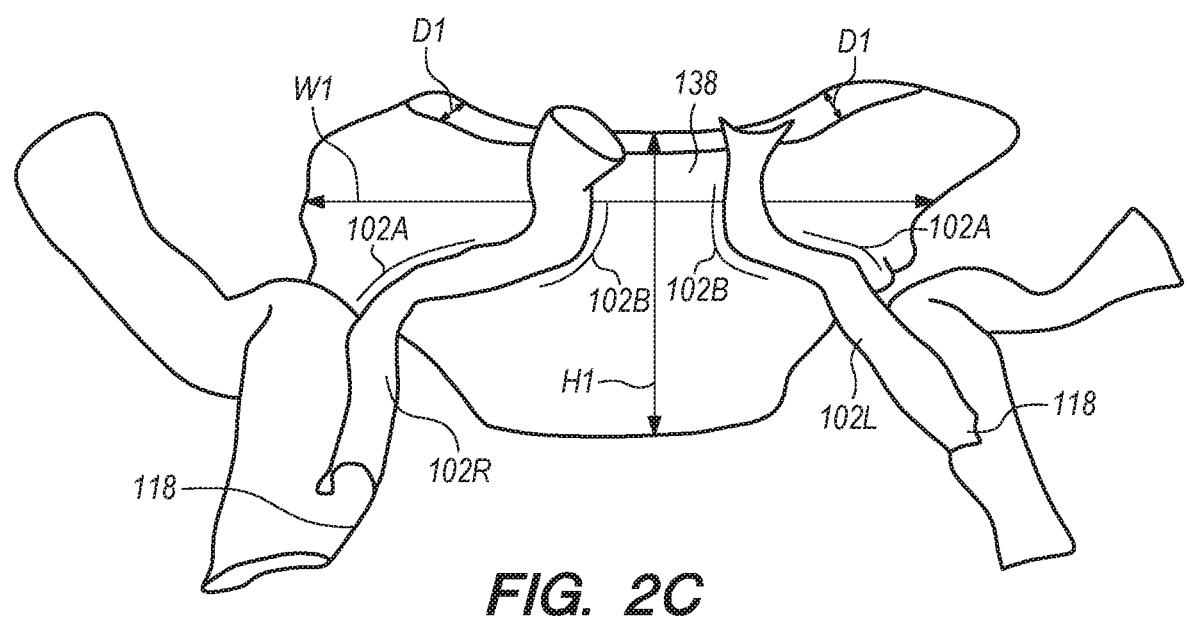
Figure 2D:
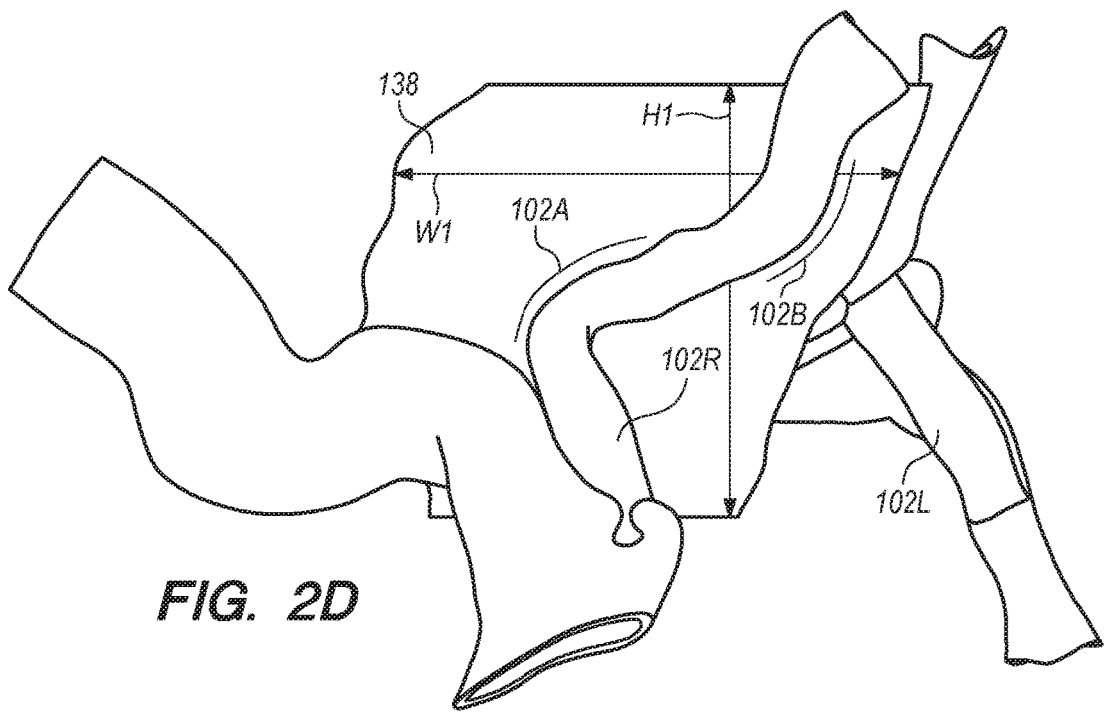

Anatomical features of CP angle cistern 138 provide a large extent of unobstructed, CSF-filled subarachnoid space to accommodate a penetrating element and shunt distal anchoring mechanism as further described herein. FIG. 2C shows a portion of CP angle cistern 138 and the relative proximity of the cistern to a patient's right IPS 102R and left IPS 102L. Beyond the lateral boundaries of the cistern depicted in the figure, the CSF filled subarachnoid space continues circumferentially around the base of the skull, albeit with a lesser extent of CSF space than in CP angle cistern 138. CP angle cistern 138 comprises a depth of free CSF space labelled D1 in FIG. 2C between the skull base and brainstem (not shown, but, e.g., between the anterior portions of the occipital and sphenoid bones and the brain stem). CP angle cistern 138 also comprises a height of free CSF space labelled H1 in FIG. 2C that extends superiorly along the base of the skull (not shown, but extending superiorly from the jugular foramen). CP angle cistern 138 further comprises a width extent of free space labelled W1 in FIG. 2C (e.g., extent of free CSF space extending laterally between the right and left jugular foramina, not depicted). CP angle cistern 138 contains a relatively large volume of CSF, as defined by the exemplary depth D1, height H1, and width W1 dimensions. FIG. 2D shows an alternative view of the same patient anatomy depicted in FIG. 2C, albeit with the D1 cistern dimension portions of left IPS 102L obscured by the view.

As shown in FIGS. 1 and 2C, most patients have two IPS 102 and two jugular veins 106 (left and right). In a very small percentage of patients (e.g., less than 1%), there is no connection between one IPS and the corresponding jugular vein. It is highly unlikely, however, that any given patient will lack connections to the corresponding jugular veins on both left and right IPS.

Subarachnoid spaces are naturally occurring separations between the pia mater and the arachnoid layer where the CSF pools. Typically, the CSF is passed into a subarachnoid space over the cerebral hemispheres and then into the venous system by arachnoid granulations. The subarachnoid space 116 in FIG. 2A corresponds to a cerebellopontine (CP) angle cistern 138, which acts as a reservoir for CSF. In patients with hydrocephalus, a build-up of CSF within the CP angle cistern 138 (in addition to other cisterns and the brain ventricles) can occur, for example, if patients lack properly functioning arachnoid granulations. If the excess CSF is not removed, the resulting excess intracranial pressure can lead to symptoms such as headache, neurological dysfunction, coma, and even death.

Figures 3A, 3B:
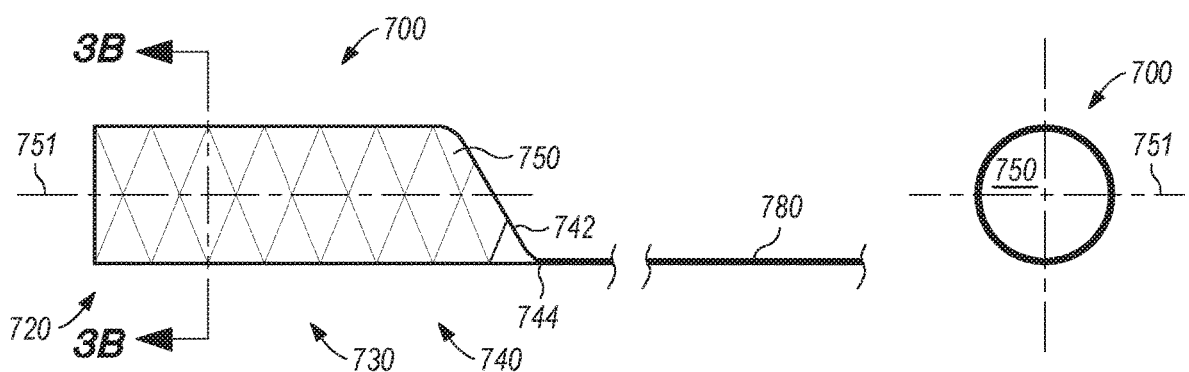
FIG. 3A-J are side, perspective and cross-sectional views of an anchor and elongate guide member, according embodiments of the disclosed inventions.
Figures 3C, 3D:
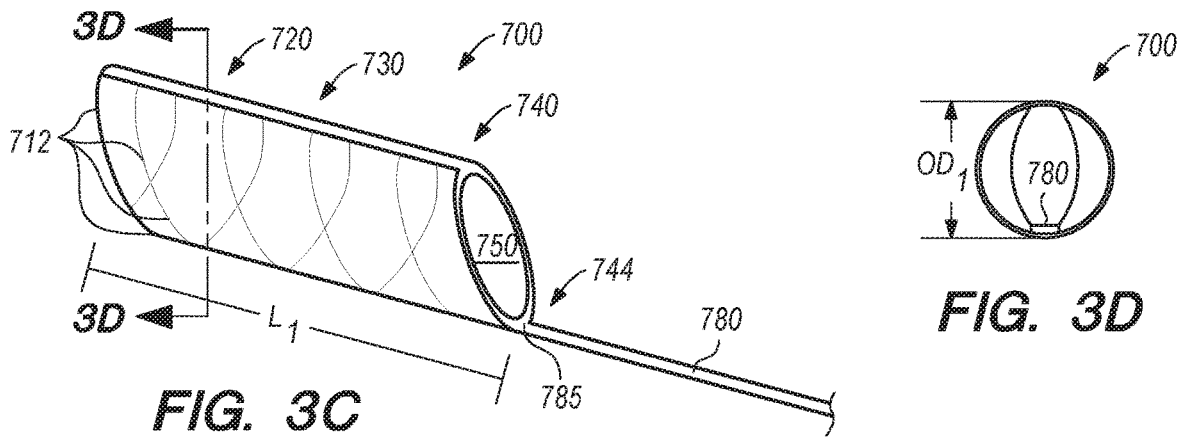
Figure 3E:
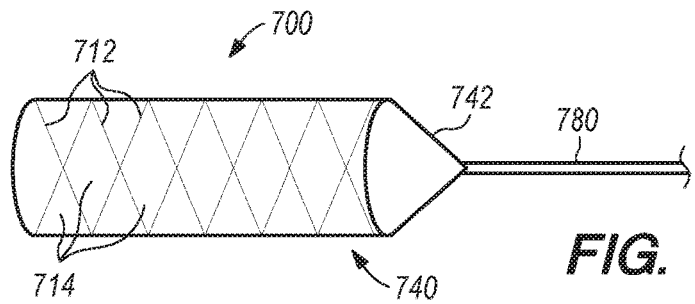
Figure 3F:
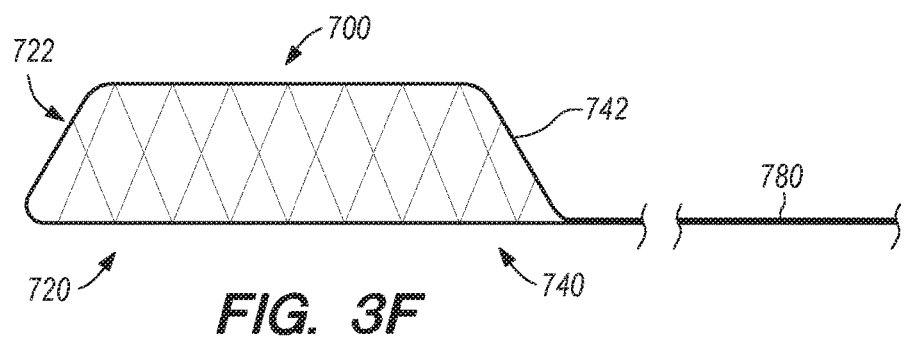
Figure 3G:
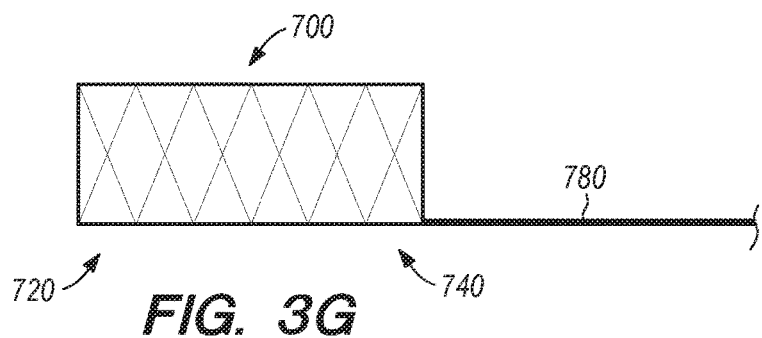
Figure 3H:
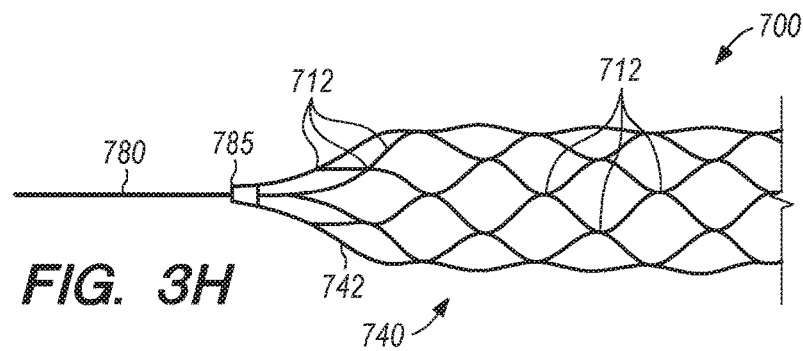

FIGS. 3A-J illustrates exemplary anchor 700, according to the embodiments of the disclosed inventions. The anchor 700 comprises a proximal portion 740, a middle or body portion 730, a distal portion 720 (FIG. 3A), and a lumen 750 extending therebetween (FIG. 3A-B). The proximal portion 740 of FIGS. 3A, 3C, 3E, 3F includes a beveled or tapered proximal section 742. The anchor 700 further comprises an elongate guide member 780 coupled to the proximal portion 740 and/or beveled/tapered proximal section 742. As shown in FIGS. 3A, 3C and 3F, the beveled/tapered proximal section 742 is offset, as the taper transitions to the bottom of proximal portion 740 and the elongate guide member 780. Alternatively, the beveled/tapered proximal section 742 may be symmetrical having the elongate guide member 780 centrally disposed, as shown in FIGS. 3E and 3H. Additionally, the distal portion 720 of the anchor 700 may include a beveled/tapered distal section 742, as shown in FIG. 3F. The proximal portion 740 and distal portion 720 of the anchor 700 may taper at a variety of suitable angles. The proximal portion 740 of the anchor 700 may comprise a strut or plurality of struts 712 directly or indirectly coupled to the elongate guide member 780 (e.g., FIG. 3E, 3H). In an alternative embodiment, the anchor 700 proximal portion 740 and distal portion 720 terminates at approximately 90° angle (i.e., without tapering), as shown in FIG. 3G.

The anchor 700 may be composed of suitable materials, such as, platinum, Nitinol®, gold or other biocompatible metal and/or polymeric materials, for example, silicon, or combinations thereof. In some embodiments, the anchor 700 may include materials that are compatible with magnetic resonance imaging and have radiopacity sufficient to allow the use of known imaging techniques. In some embodiments, the anchor 700 is composed of shape memory, self-expandable and biocompatible materials, such as Nitinol®, or other super-elastic alloys, stainless steel, or cobalt chromium, and comprises a stent-like configuration. In other embodiments, the anchor 700 may include other suitable configurations, such as tubular prosthesis, flow diverter, clot retriever, or the like. Alternatively, the anchor 700 can be composed of magnesium, zinc, or other bio-absorbable or dissolvable components.

Figure 3I:
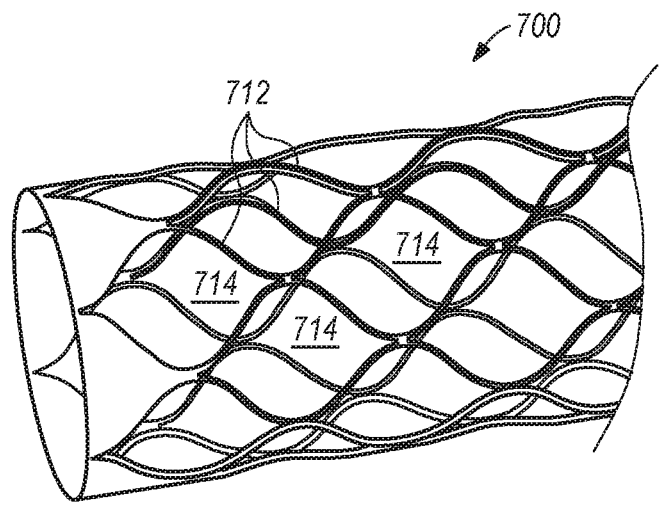
Figure 3J:
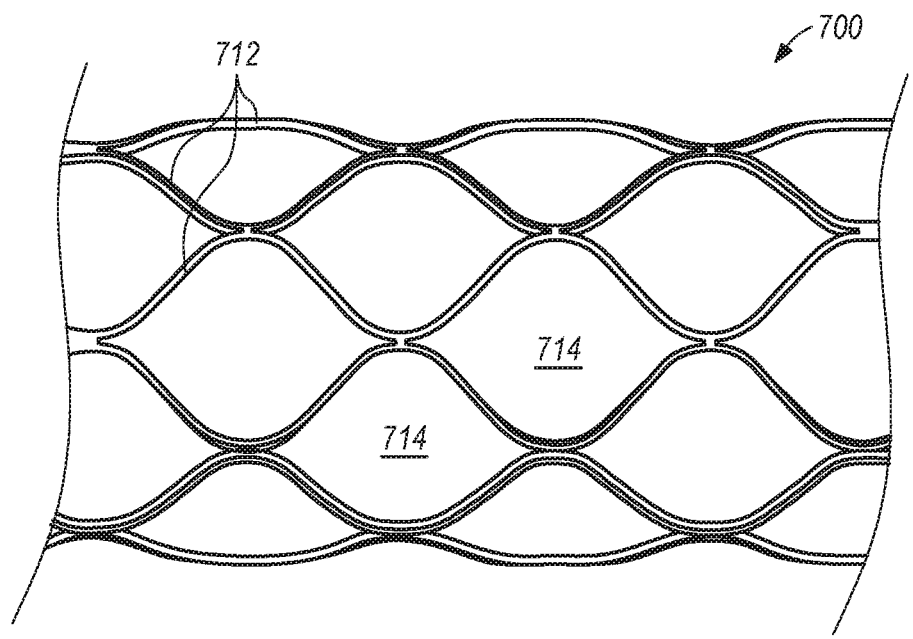

The anchor 700 may be formed by laser cutting a flat sheet, a tubular member, or other suitable configuration of the described materials into interconnected struts 712 forming an open or closed cell pattern having a plurality of cells 714, as shown by the closed cell patterns in FIGS. 3A and 3C-H. Detailed portions of exemplary closed cell patterns of the anchor 700 having the plurality of struts 712 defining the plurality of cells 714 are shown in FIGS. 3I-J. Other suitable techniques may be used to form the closed (or open) cell pattern of the anchor 700, such as etching, or having a plurality of wires braided, woven, or coupled together (not shown). The anchor 700 further comprises a radially collapsed or delivery configuration and, a radially expanded or deployed configuration. In the deployed configuration the anchor 700 is configured to radially expand and anchor itself within the IPS 102 or CS 104. The anchor 700 may include a length $L_1$ of approximately 2 mm to approximately 20 mm, in the radially expanded configuration (FIG. 3C). The anchor 700 may include an outer diameter $OD_1$ of approximately 2 mm to approximately 6 mm or larger, in the radially expanded configuration (FIG. 3D). The anchor 700 is radially compressible about the axis 751 of the lumen 750, and configured to collapse within a delivery catheter (e.g., a delivery catheter having an inner diameter of approximately 0.014" to approximately 0.040") such that a clinician can navigate the collapsed anchor 700 through one or more catheters into the IPS 102 or CS 104.

The anchor 700 and the elongate guide member 780 coupled to the proximal portion 740 of the anchor 700 can be manufactured from the same piece of material (e.g., a super-elastic alloy such as Nitinol®), or may comprise separate parts joined at a joint 744 between anchor 700 and the elongate guide member 780. As shown in FIGS. 3A, 3C, 3E-H, the elongate guide member 780 is coupled (e.g., directly or indirectly, attached, secured, joined, or their like) to the proximal portion 740 of the anchor 700. Alternatively, the elongate guide member 780 can be coupled to the distal portion 720, middle portion 730, and/or to any strut or plurality of struts 712 (FIG. 3E, 3H) of the anchor 700 (not shown). The elongate guide member 780 can have a flat, rectangular, or otherwise non-circular, cross-sectional profile, as shown for example in FIG. 3D and FIG. 11. By way of non-limiting example, the elongate guide member 780 can have a rectangular cross-sectional profile with dimensions of approximately 0.001"×0.003" to 0.008"×0.040". An elongate guide member 780 with rectangular cross-sectional profile can provide increased column strength to facilitate navigation of the anchor 700 through a delivery catheter to a target location in IPS 102 or CS 104 and, if necessary, to assist with the re-sheathing of the anchor 700 into a delivery catheter for re-deployment of the anchor 700 prior to penetration of the IPS wall 114/arachnoid layer 115 and deployment of the shunt, or when removing the anchor 700 from the patient's vasculature after the deployment of the shunt. When used with the delivery catheter 3304 including a dedicated lumen 3315 configured to conform to the rectangular cross-sectional profile of the guide member 780 (e.g., as shown in FIG. 10), the elongate guide member 780 maintains the trajectory of the delivery catheter 3304 over the guide member and at the target penetration site by limiting or preventing rotation of the delivery catheter 3304 about or around the guide member 780.

Figure 17A:
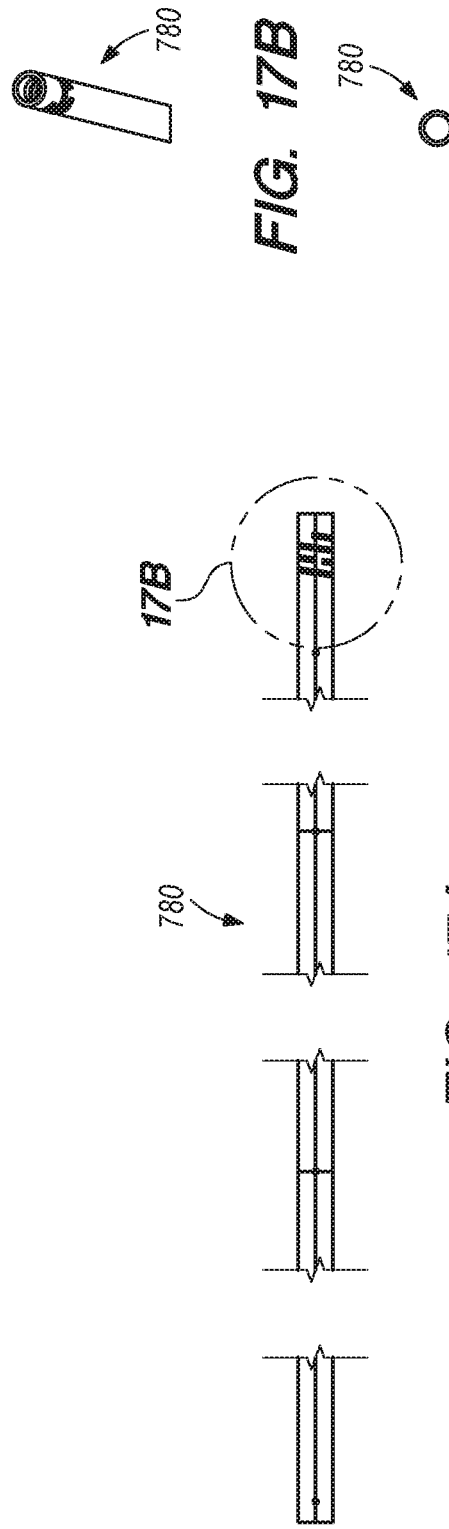
FIGS. 17A-C are side, perspective and cross-sectional views of an elongated guide member, constructed according to an alternative embodiment of the disclosed inventions.
Figure 17B:
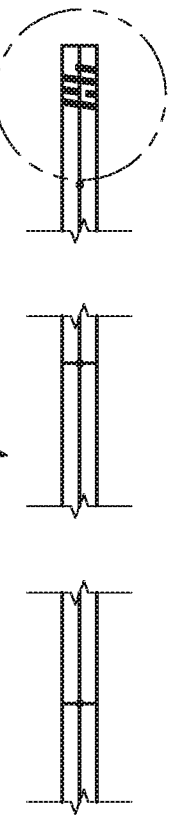
Figure 17C:
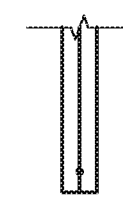

Alternatively, embodiments of elongate guide member 780 can have a circular cross-sectional profile, as shown in FIGS. 17A-C. By way of non-limiting example, an elongate guide member 780 with circular cross-sectional profile can have a diameter of about 0.005" to 0.018" or more. The elongate guide member 780 having a tubular configuration may include a plurality of cuts to increase flexibility, as shown by the exemplary spiral cut pattern of kerf, pitch, cuts per rotation and cut balance depicted in sections of FIGS. 17A-C. Such configurations of the elongate guide member can improve the "trackability" of a delivery catheter over the guide member (e.g., a delivery catheter with a dedicated lumen configured to conform to the guide member profile), and provide the ability to radially orient the delivery catheter and penetrating element about the guide member in the lumen of IPS 102 or CS 104. An elongate guide member 780 with circular cross-sectional profile can provide increased column strength to facilitate navigation of the anchor 700 through a delivery catheter to a target location in IPS 102 or CS 104 and, if necessary, to assist with the re-sheathing of the anchor 700 into a delivery catheter for re-deployment of the anchor 700 prior to penetration of the IPS wall 114/arachnoid layer 115 and deployment of the shunt, or when removing the anchor 700 from the patient's vasculature after the deployment of the shunt. Further, the ability to radially orient the delivery catheter and penetrating element about the guide member in the lumen of IPS 102 or CS 104 can be used to correct the orientation of a mis-loaded delivery catheter over the guide member.

Figure 18A:
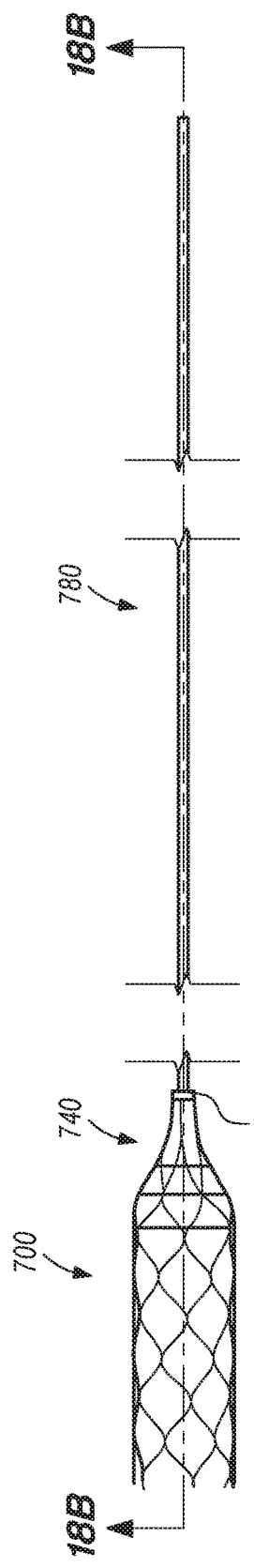
FIGS. 18A-E are side, perspective and cross-sectional views of the interface between the elongated guide member and the anchor, according to embodiments of the disclosed inventions.
Figure 18B:
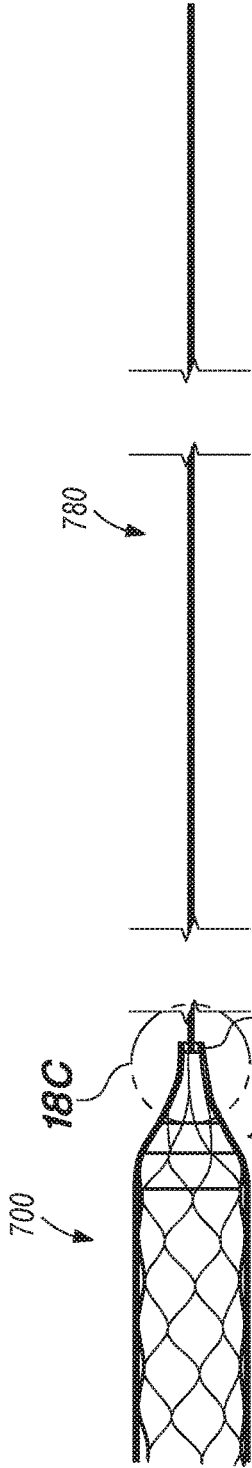
Figure 18C:
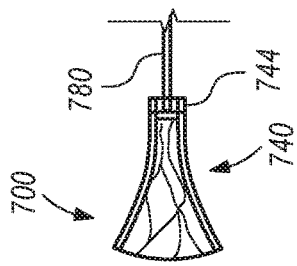

The profile, dimensions, and material for the elongate guide member 780 are configured to resist kinking along the length of the elongate guide member 780 and provide sufficient column strength for anchor deployment and re-sheathing, while still allowing sufficient flexibility for deployment through a delivery catheter by tracking through the curved portion of the IPS 102. Alternatively, the elongate guide member 780 can have a pre-curved distal portion, disposed closer to the joint 744 between anchor 700 and the elongate guide member 780, so as to bias the elongate guide member 780 towards IPS wall 114 or IPS wall 117 when the elongate guide member 780 is deployed through the curved portion of the IPS 102. Further, the joint 744 between the anchor 700 and the elongate guide member 780 may include a rotatable element (FIGS. 18E-F) allowing the elongate guide member 780 to assume a desirable orientation through the curved portion of the IPS 102.

Radiopaque markings or coatings can be incorporated into the anchor 700 and/or elongate guide member 780 to assist with navigation and deployment of the anchor 700 in a sinus lumen distal to a target penetration site on IPS wall 114. The radiopaque markings may be placed on one or more of the following locations along the anchor 700 and elongate guide member 780, as shown in FIG. 3C: in a plurality of struts 712 at the distal portion 720 of the anchor 700; along $L_1$, with or without rotationally varying marker placement along the middle or body portion 730 of the anchor 700 to further aid navigation and orientation; at the joint 744 between anchor 700 and the elongate guide member 780, and/or on or around the first full-diameter portion of anchor 700 at the proximal portion 740.

Figure 4A:
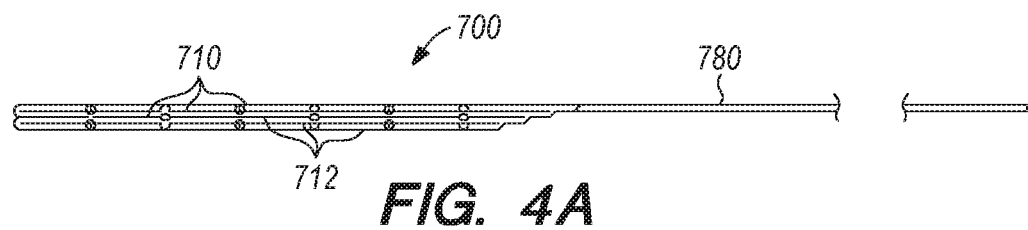
FIG. 4A-C are perspective and cross-sectional views of an anchor and elongate guide member, according another embodiment of the disclosed inventions.
Figure 4B:
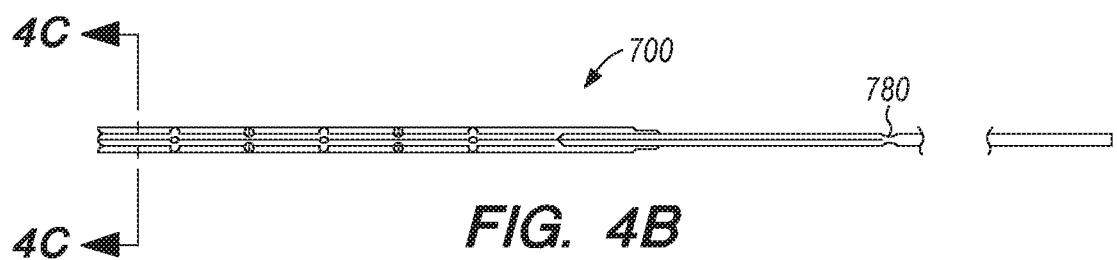
Figure 4C:
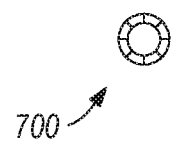
Figure 5G:
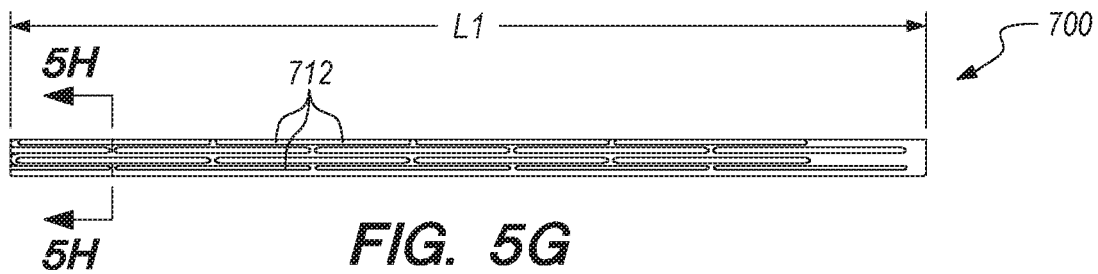
FIGS. 5A-W are perspective and cross-sectional views of an anchor, according other embodiments of the disclosed inventions.
Figure 5H:
Figure 5I:
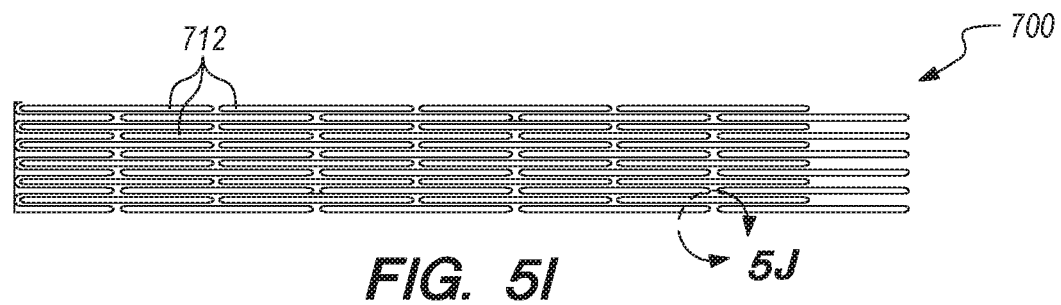
Figure 5J:
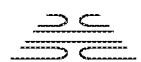
Figure 5U:
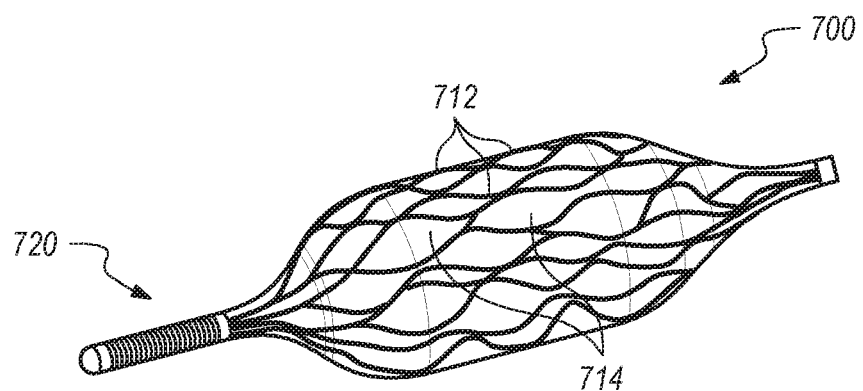
Figure 5V:
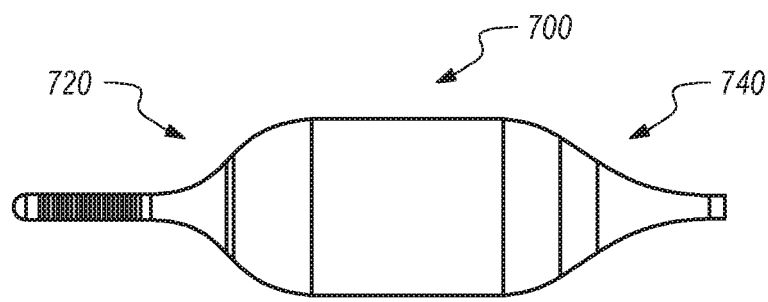
Figure 5W:
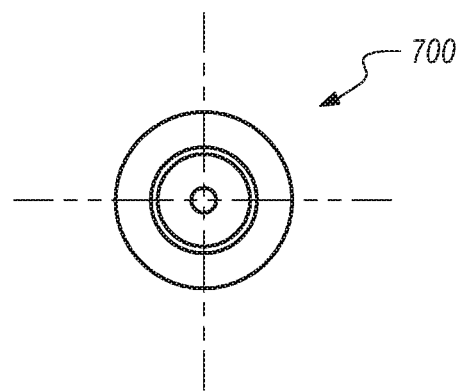

FIGS. 4A-C illustrate another exemplary anchor 700, constructed according to embodiments of the disclosed inventions. FIG. 4A-B depict respective side views, and FIG. 4C depicts a cross-sectional view of the anchor 700, comprising a plurality of cuts 710 forming a stent-like configuration, having a plurality of struts 712. The anchor 700, the elongate guide member 780, cuts 710 and/or the patterns of the cuts 710 may be manufactured by selectively cutting a tubular element using any suitable cutting method (e.g., laser cutting, etching or their like). FIGS. 5A-W depicts exemplary dimensions and cut patterns of the anchor 700, constructed according to embodiments of the disclosed inventions. The struts 712 of the anchor 700 form a plurality of spaces or cells 714 therebetween. The cells 714 include a closed cell pattern when the anchor 700 is in the radially expanded configuration, as for example shown in FIGS. 3E, 3H-J, 5O and 5U, and a closed cell pattern when the anchor 700 is in the radially compressed configuration, as for example shown in FIGS. 4A, 5G, and 5K. In one embodiment of the anchor 700, the cut pattern shown in the radially compressed configuration in FIG. 5G, is configured to form the radially expanded configuration of the anchor 700 shown in FIG. 5O. FIGS. 5P-T illustrate exemplary dimensions and properties of the anchor 700 of FIGS. 5G and 5O, such as the variations of the beveled/tapered proximal portions 740. Varying the taper in the proximal portion 740 (e.g., as described by the transition length measurements of FIG. 5T) can facilitate smooth anchor deployment and retrieval when paired with an appropriately sized catheter (e.g., catheter with 0.027" inner diameter). In an alternative embodiment of the anchor, the cut pattern shown in the radially compressed configuration in FIG. 5K, is configured to form the radially expanded configuration of the anchor 700 shown in FIG. 5U. FIGS. 5V-W illustrate exemplary dimensions and properties of another embodiment of anchor 700 of FIG. 5U, such as having beveled/tapered proximal portion 740 and distal portion 720. The beveled/tapered distal portion 720 of anchor 700 depicted in FIG. 5U, and corresponding flexibility provided by the spiral cut pattern of such distal portion shown in FIG. 5K, facilitates access to remote, narrowing, and/or tortuous regions of the intracranial venous anatomy such as IPS 102 and CS 104. For illustration purposes, FIGS. 5P-S and 5V-W are depicted without the struts 712 and cells 714 of the anchor 700 to better appreciate the dimensions and properties of the anchor 700 in said figures (in a radially expanded configuration). However, it should be appreciated that the anchor 700 of FIGS. 5P-S and 5V-W includes the struts 712 and cells 714 of their respective FIGS. 5O and 5U The struts 712 and cells 714 of the anchor 700 substantially extend along the length $L_1$, as for example shown in FIG. 3C in the radially expanded configuration, and in FIG. 5G in the radially compressed configuration. However, the struts 712 and cells 714 may extend along selected portions of the anchor 700, as for example shown in FIG. 5U at the distal portion 720. Additionally, the anchor 700 can include a mesh framework between the struts 712 to increase the friction between the anchor 700 and IPS 102 (or CS 104), further securing the anchor 700 at or about the target site when deployed. The struts 712 of anchor 700 can have flat, round, elliptical, or irregularly shaped profiles or suitable cross-sections. The width of the struts 712 can vary from approximately 0.0030" to 0.0045", or larger. Additionally, the struts 712 can be configured to exhibit a negative Poisson's ratio under strain such that, after deployment in a sinus lumen (e.g., IPS 102 or CS 104), applying a retrograde force to anchor 700 (e.g., by pulling proximally on the anchor 700 via the elongate guide member 780) further expands the struts 712 radially outward to secure the anchor 700 at the target site.

Dimensions referenced in FIGS. 5A-5W in brackets (e.g., [14.67]) are provided in millimeters, while all other dimensions referred without brackets are provided in inches. It should be appreciated that the dimensions depicted in FIGS. 4A-5W are exemplary dimensions of the anchor 700, which are not intended to limit the embodiment of the anchor 700 disclosed herein.

Figure 6:
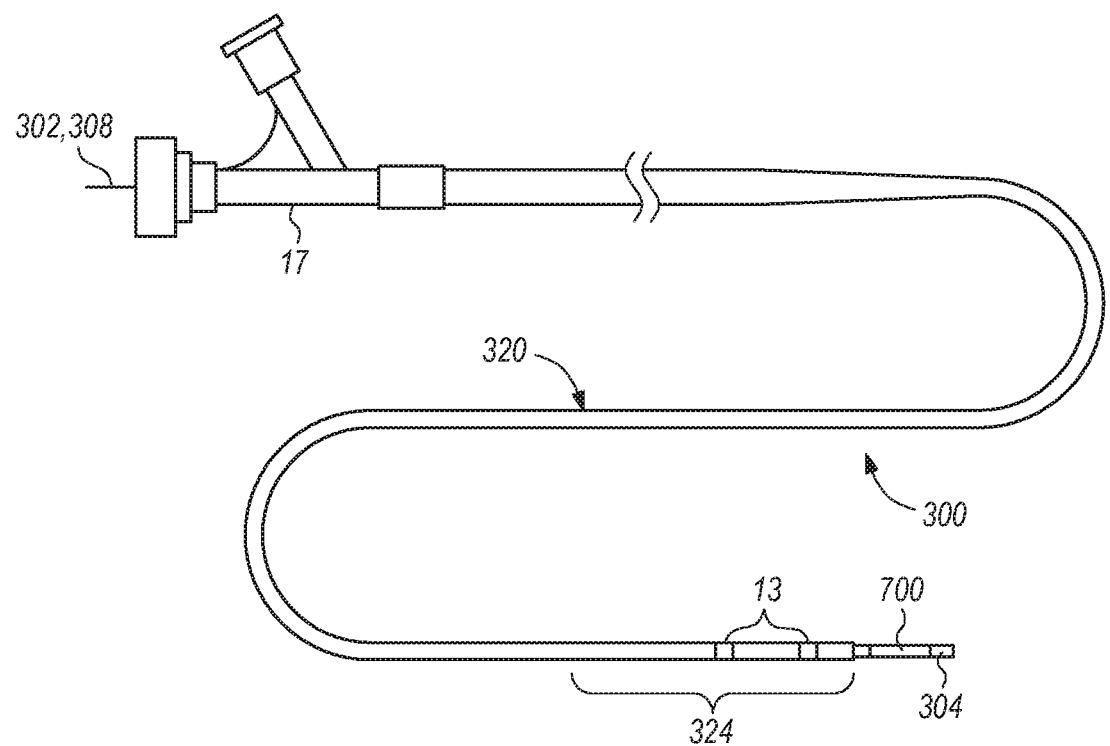
FIG. 6 is a side view of a delivery assembly according to embodiments of the disclosed inventions.

FIG. 6 is a side view of a delivery assembly 300 for delivering the anchor 700 and the shunt into a target site of a patient, constructed in accordance with embodiments of the disclosed inventions. The delivery assembly 300 includes the anchor 700 and the shunt (not shown) detachably coupled to the delivery assembly 300. The delivery assembly 300 and the shunt may be composed of suitable biocompatible materials. The delivery assembly 300 is dimensioned to reach remote locations of the vasculature and is configured to deliver the anchor 700 and the shunt percutaneously to the target location (e.g., inferior petrosal sinus). The delivery assembly 300 includes a tubular member interface having an outer tubular member 320 (i.e., guide catheter) and an inner tubular member 304 (i.e., delivery catheter/micro catheter) coaxially disposed within the outer tubular member 320 and movable relative to the outer tubular member 320. The delivery assembly 300 may include a guidewire 302 coaxially disposed within the guide catheter 320 and/or the delivery catheter 304. The guidewire 302 can be, for example, 0.035" (0.889 mm) in diameter. Additionally to the guidewire 302, the delivery assembly 300 may include a delivery guidewire 308 disposed within the delivery catheter 304. The delivery guidewire 308 has a smaller diameter (e.g., approximately 0.010" (0.254 mm) to 0.018" (0.4572 mm) or other suitable dimension to facilitate accessing intracranial venous vasculature with other components of delivery assembly 300) compared to guidewire 302.

The guide catheter 320, delivery catheter 304, and guidewires 302/308 (FIG. 6) may be formed of suitable biocompatible materials, and may include markings 13 for purposes of imaging (e.g., markers composed of radiopaque materials). Various known and often necessary accessories to the delivery assembly 300, e.g., one or more radiopaque marker bands 13 at the distal portion 324 of the guide catheter 320 to allow viewing of the position of the distal portion under fluoroscopy and a Luer assembly 17 for guidewires and/or fluids access, are shown in FIG. 6. The delivery assembly 300 and/or the shunt may include a penetrating element (not shown) configured to pierce and/or penetrate the IPS wall 114 and arachnoid layer 115 to access the CP angle cistern 138 for implantation of the shunt 200.

FIGS. 7A-F illustrate exemplary methods of delivering the anchor 700, the elongate guide member 780 and the shunt 200 at a target site, according embodiments of the disclosed inventions. The anchor 700 is configured to be deployed and disposed within the IPS 102 or the CS 104 prior to penetration of the IPS wall 114 and deployment of a shunt. In some embodiments, the anchor 700 is configured to be distally disposed to a target penetration site in IPS wall 114, as to provide support (e.g., foundation) for subsequent IPS wall 114 penetration, and shunt deployment steps of the implant procedure. The anchor 700 may be deployed in the IPS 102 or CS 104 by advancing the anchor 700 out of the distal end opening of the delivery catheter 304, or by withdrawing the delivery catheter 304, and/or by a combination of advancing the anchor 700 and withdrawing the catheter 304 for deployment of the anchor 700 in the IPS 102 or CS 104 (not shown).

When the anchor 700 is deployed into the target site (e.g., IPS 102 or CS 104), the anchor 700 transitions from its delivery configuration (e.g., radially constrained by an inner lumen of the delivery catheter 304) to its deployed configuration (e.g., expanding radially outwards, so as to engage the walls of the IPS 102 or CS lumen 131). When deployed (FIG. 7A), the struts 712 of the anchor 700 are biased to exert an outward radial force that engages and secures the anchor 700 within the IPS 102, against IPS walls 114 and 117, or against the equivalent walls of the CS 104. The ratio of the resting anchor 700 diameter (i.e., expanded, unconstrained configuration) to the reference vessel diameter (i.e., diameter of the sinus lumen where the anchor will be deployed) can range from about 1:1 up to about 2:1. In addition, the exterior surface of anchor 700 can include anchoring elements, spikes, burrs, barbs or other features to engage the dura mater of IPS walls 114 and 117 (or the walls of CS lumen 131), which further secures the anchor in IPS 102 or CS 104.

The delivery catheter 304, with or without a delivery guide wire, facilitates navigation and delivery of the anchor 700 within the patient's vasculature through the junction 118 and into the IPS 102 and/or CS 104. The compressible nature of the anchor 700 allows the clinician to deploy the anchor 700 from the delivery catheter 304 within the IPS 102 (or CS 104), re-sheath the anchor 700 into the delivery catheter 304 (when needed), and redeploy the anchor 700 within the applicable sinus lumen (e.g. IPS 102 and/or CS 104) until the clinician is satisfied with the deployment location and orientation of the anchor 700 and/or elongate guide member 780 in the patient.

Figure 7A:
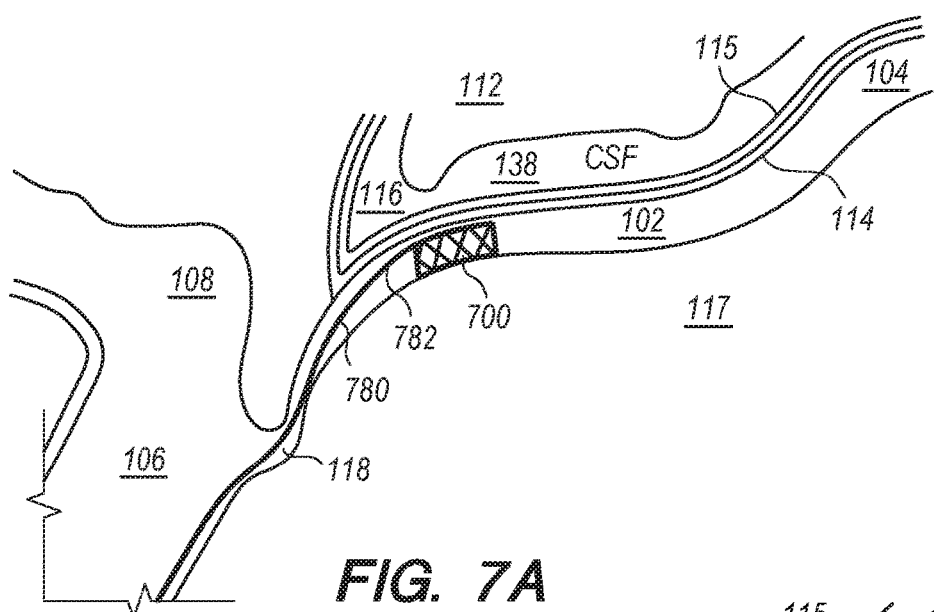
FIGS. 7A-F are cross-sectional views of exemplary methods of delivering the anchor, the elongate guide member and the shunt at a target site, according embodiments of the disclosed inventions.

As shown in FIG. 7A, the anchor 700 is deployed in the IPS 102. The anchor 700 is disposed in the IPS 102 distal to a target penetration site in IPS wall 114. The elongate guide member 780 coupled to the anchor 700 extends from the IPS 102 through the curved portion of IPS 102 into the junction 118. The elongate guide member 780 further extends into the jugular vein 106, and can extend further through venous vasculature and out of the patient's body at the peripheral access site (e.g., femoral vein). The delivery catheter 304 used to deploy the anchor 700 may be withdrawn from the patient to allow for other delivery system components to access the IPS 102 after deployment of the anchor. Alternatively, the delivery catheter 304 used to deploy the anchor 700 may allow further deployment of other components (e.g., piercing or penetrating elements, shunts, or their like) into the IPS 102 without needing withdrawal of the delivery catheter 304 for other delivery systems. As previously disclosed, the anchor 700 can be deployed in a more distal location, such as CS 104.

The shunt 200 capitalizes on a favorable pressure gradient between the subarachnoid space 116 (e.g., CP angle cistern 138) and venous system (e.g., IPS 102, jugular vein 106, and/or a jugular bulb 108) to drive CSF through the shunt 200 (i.e., inner lumen). In patients without hydrocephalus, the normal differential pressure between the intracranial pressure of the subarachnoid space 116 and blood pressure of the venous system is about 5 to 12 cm $H_2O$; this differential pressure between the subarachnoid space and venous system can be significantly higher in hydrocephalic patients. Once deployed and implanted, the shunt 200 facilitates one-way flow of CSF from the subarachnoid space 116 into the jugular the bulb 108 and/or jugular vein 106 where CSF is carried away by venous circulation, similar to the way that normally functioning arachnoid granulations drain CSF into the venous system. The shunt 200 prevents backflow of venous blood into subarachnoid space 116 via one or more one-way valves or any other flow regulating mechanisms. The shunt 200 allows for a more physiologic drainage of CSF by directing CSF into the cerebral venous system, a process that occurs naturally in people without hydrocephalus. In this manner, the pressure created by the excess CSF in the subarachnoid space 116 is relieved, and patient symptoms due to hydrocephalus can thereby be ameliorated or even eliminated. The shunt 200 of FIGS. 7E-F includes a valve 209 as the flow regulating mechanism configured to regulate fluid flow through the shunt 200 into the venous system.

In embodiments of the inventions, a target flow rate of CSF (e.g., in a range of about 5 ml per hour to about 15 ml per hour) through the shunt 200 at a normal differential pressure is defined as being in a range between about 5 cm $H_2O$ to about 12 cm $H_2O$ between the subarachnoid space 116 and venous system (e.g., jugular vein 106 and/or a jugular bulb 108).

In some embodiments, a target flow rate of CSF through the shunt 200 and/or valve 209 is approximately 10 ml per hour at a range of differential pressure between the subarachnoid space 116 and venous system ("ΔP") between 3 to 5 mmHg. A maximum flow rate of CSF through the shunt 200 and/or valve 209 can exceed 20 ml per hour and typically occurs immediately after shunt implantation in a patient with elevated ICP (e.g., ICP greater than 20 cm $H_2O$). The valve 209, as the flow regulating mechanism of the shunt 200, comprises a normal operating range (CSF flow direction) of 0.5 to 8 mmHg ΔP, having a valve opening pressure (CSF flow direction) of approximately 0.5 mmHg ΔP, and a reverse opening pressure (backflow prevention) of at least −115 mmHg ΔP. Additionally, the valve 209 may comprise an allowable CSF leakage (flow direction) of less or equal to 0.5 ml per hour, and/or an allowable blood backflow (reverse direction) of less or equal to 0.25 ml per hour.

A positive pressure gradient between the intracranial pressure (ICP) of the subarachnoid space and the blood pressure of the venous system may contribute to the natural absorption of CSF through arachnoid granulations. ICP greater than 20 cm H20 is considered pathological of hydrocephalus, although ICP in some forms of the disease can be lower than 20 cm H20. Venous blood pressure in the intracranial sinuses and jugular bulb and vein can range from about 4 cm H20 to about 11 cm H20 in non-hydrocephalic patients, and can be slightly elevated in diseased patients. While posture changes in patients, e.g., from supine to upright, affect ICP and venous pressures, the positive pressure gradient between ICP and venous pressure remains relatively constant. Momentary increases in venous pressure greater than ICP, however, can temporarily disturb this gradient, for example, during episodes of coughing, straining, or valsalva.

The shunt 200 and/or the valve 209 are configured to handle expected acute and chronic differential pressures between the subarachnoid space 116 and venous system ("ΔP") when implanted in a patient. A maximum, acute negative ΔP occurs, for example, between a maximum venous pressure (VP) and a minimum intracranial pressure (ICP), such as, if the patient coughs while moving from a supine to upright position. Embodiments of the valve 209 are configured to seal, shut and/or close under the negative ΔP conditions (i.e., when venous pressure exceeds intracranial pressure), preventing venous blood from flowing back through the shunt 200 into the subarachnoid space 116. A maximum, acute positive ΔP occurs, for example, between a maximum ICP and a minimum VP, such as the acute positive ΔP caused by coughing when the patient transitions from an upright to supine position. Additionally, the shunt 200 and/or the valve 209 are configured to handle chronic elevated, positive ΔP conditions (e.g., approximately two or more minutes of elevated positive ΔP, such as between maximum hydrocephalus ICP and normal VP [e.g., hydrocephalus with low expected VP]); and to handle chronic, elevated negative ΔP conditions (e.g., approximately two or more minutes of negative ΔP, such as between minimum ICP and maximum VP [e.g., supine→upright posture change with minimal VP adjustment]).

Figure 7B:
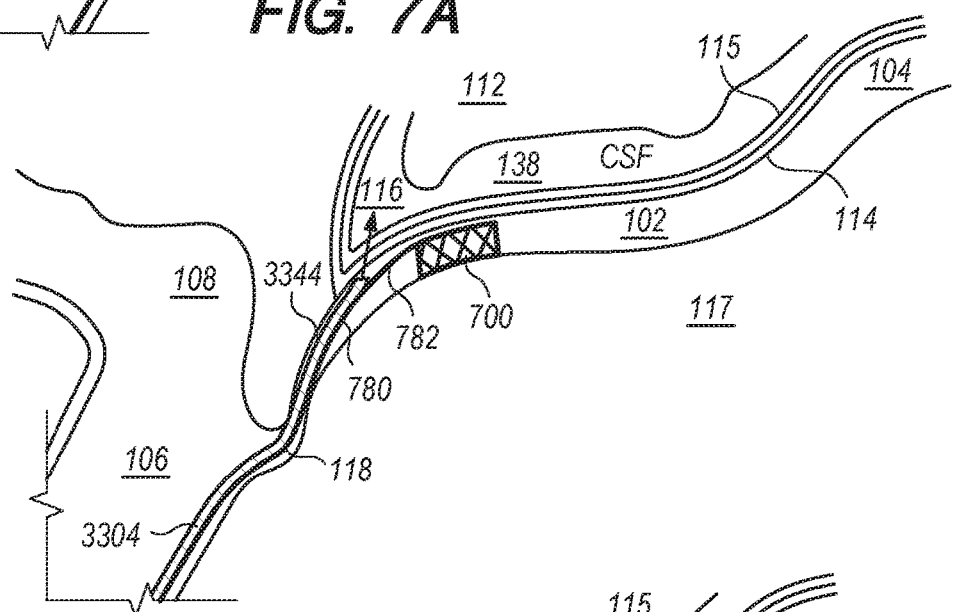
Figure 7C:
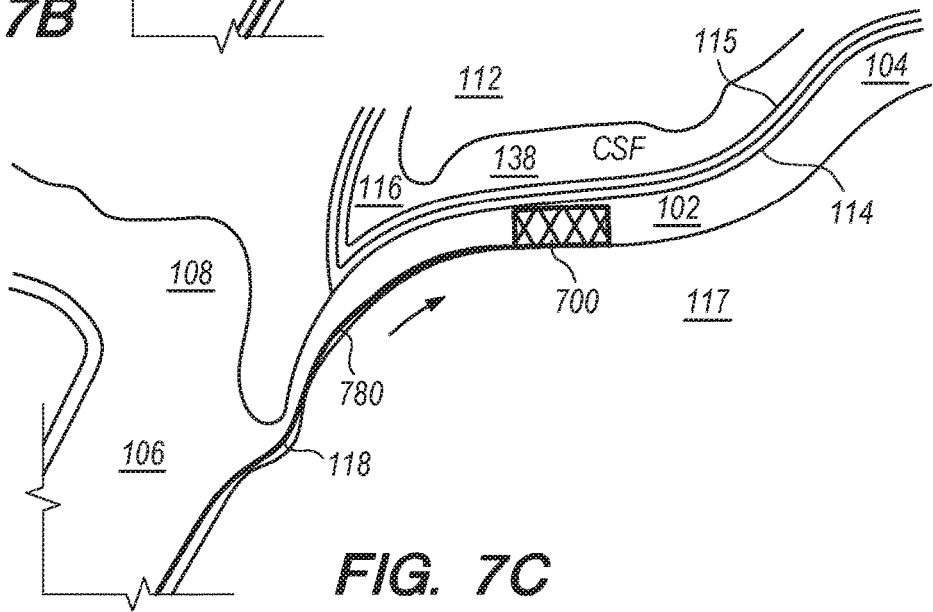
Figure 7D:
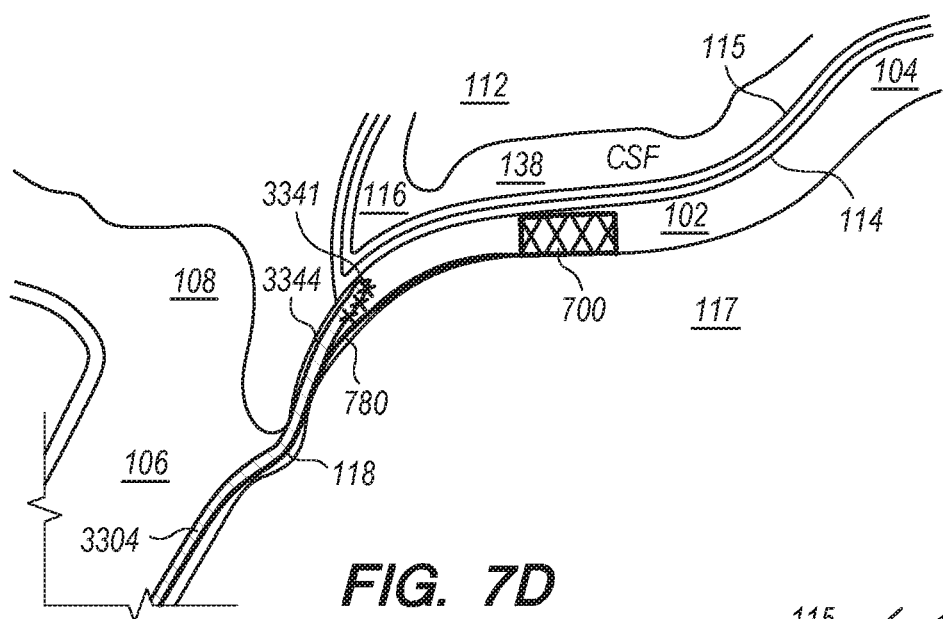
Figure 8A:
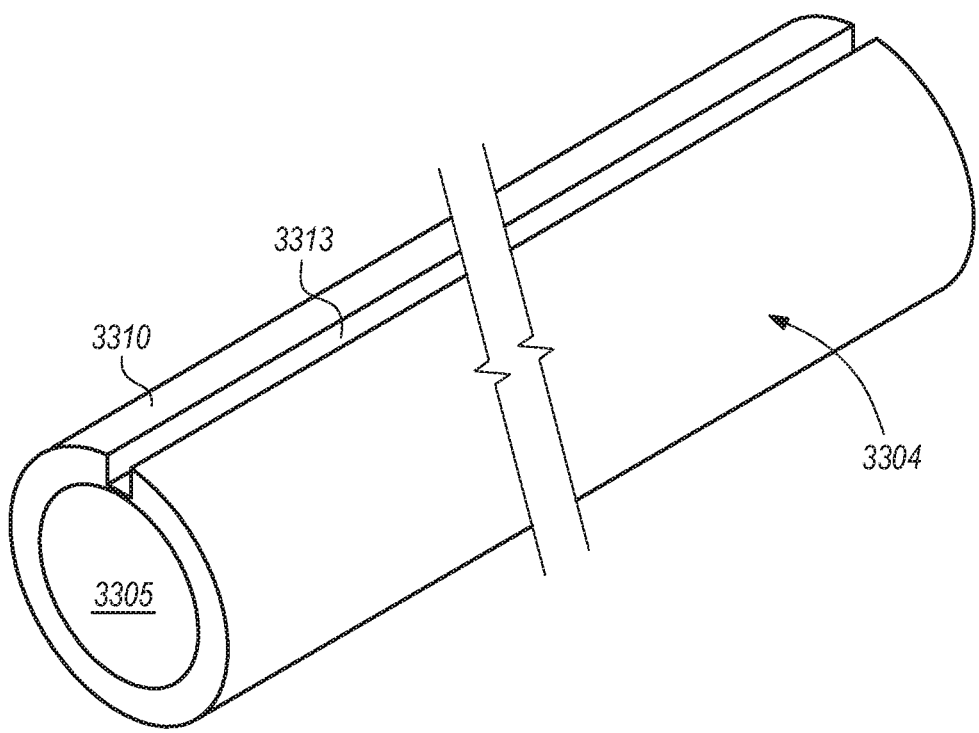
FIGS. 8A-B are perspective and cross-sectional views of a delivery catheter, constructed according to embodiments of the disclosed inventions.
Figure 8B:
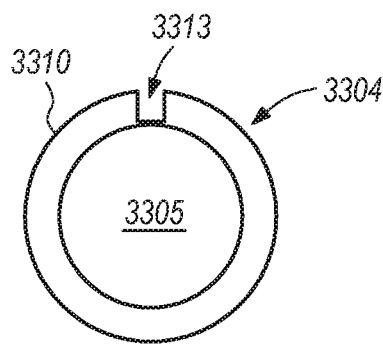

In some embodiments, a delivery catheter 3304 can include one or more features that allow for accurate guidance, navigation and/or control of the deployment of the penetrating element and/or the shunt, particularly when passing through the junction 118 into the IPS 102. FIGS. 8A-B illustrate perspective and cross-sectional views of the delivery catheter 3304, according to one embodiment of the disclosed inventions. The delivery catheter 3304 comprises a recess 3313 formed in the outer surface 3310 of the catheter. The recess 3313 is configured to slidably engage the elongate guide member 780 of the anchor 700, so that the delivery catheter 3304 rides on the elongate guide member 780 of the previously deployed anchor 700 (e.g., "side car" configuration), allowing the catheter 3304 to be guided in a desired orientation and location within the target site in the IPS 102, as shown in FIG. 7B. The elongate guide member 780 is dimensioned and configured to engage the recess 3313 in the delivery catheter 3304. The elongate guide member 780 is further configured to guide the delivery catheter 3304 into the target penetration site, as shown in FIGS. 7B and 7D. The embodiment shown in FIGS. 8A-B is an exemplary control feature that can be implemented in connection with the catheter 3304. In some embodiments, the catheter 3304 and anchor 700 can include a plurality of such features (e.g., a plurality of elongate guide members that engage with a plurality of recesses).

Figure 9:
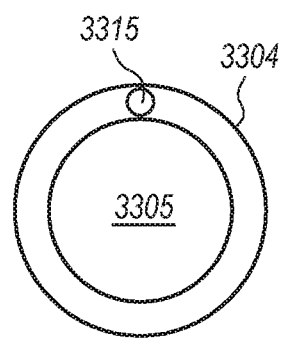
FIG. 9 is cross-sectional view of another delivery catheter, constructed according to another embodiment of the disclosed inventions.

As shown in FIG. 7B, the delivery catheter 3304 has been advanced over, in or on the elongate guide member 780 of the previously deployed anchor 700. Alternatively to the recess 3313 disclosed above, the delivery catheter 3304 can have a dedicated lumen 3315 extending between the delivery catheter proximal and distal portions configured to accommodate the elongate guide member 780 of the anchor 700. Alternatively, the delivery catheter 3304 can include a broken or incomplete lumen extending between the proximal and distal portions of the catheter that captures the elongate guide member 780 against IPS wall 117 and allows the catheter to travel over the elongate guide member 780. At least one other lumen 3305 of delivery catheter 3304 extends between the proximal and distal portions of the catheter 3304 (FIGS. 8A-B, and FIG. 9), which allows for navigation and delivery of the penetrating elements (e.g., surgical tool, needles, RF stylets, or the like) and shunt devices, with or without penetrating distal tip disclosed herein, and in the related application previously incorporated by reference herewith. The distal portion 3344 of the delivery catheter 3304 intersects the IPS wall 114 at an angle of approximately 75° (or any other suitable angle) at the target penetration site, as shown in FIG. 7B.

FIGS. 10A-K depict additional embodiments of a dual lumen delivery catheter 3304. As shown in FIGS. 10A-E, a distal portion 3344 of the delivery catheter includes a penetrating element 3350. Each catheter of FIG. 10 includes a first lumen 3315 extending between the ends of the catheter, which is configured to receive the elongate guide member 780 and, optionally, conforms to the profile of the elongate guide member. A second lumen 3305 of the foregoing catheter embodiments extends between the ends of the catheter, which allows for navigation and delivery of the penetrating elements (e.g., surgical tool, needles, RF stylets, or their like) and shunt devices with or without penetrating distal tip disclosed herein, and in the related application previously incorporated by reference herewith. Further, one or both lumens of delivery catheter 3304 shown in FIGS. 10A-K can include a liner and/or can be coated with a hydrophilic agent to increase the lubricity of such lumens with respect to other delivery assembly components as described in the related application previously incorporated by reference herewith. FIGS. 10B, 10D, and 10E-J show elongate guide member 780 disposed within first lumen 3315, and FIGS. 10B, 10E-J show the shunt 200 with a hollow inner lumen 207 disposed within second lumen 3305 for the exemplary delivery catheter 3304 embodiments. It should be appreciated that the dimensions depicted in 10A-K are exemplary dimensions of the delivery catheter 3304, first lumen 3315, second lumen 3305, penetrating element 3350, shunt 200, and shunt lumen 207, which are not intended to limit the scope of embodiments disclosed herein. For example, embodiments of delivery catheter 3304 can have a second lumen 3305 with an inner diameter in a range of about 0.012" (0.3048 mm) to 0.040" (1.016 mm) or more.

The anchor 700 and the elongate guide member 780 can be optimized to orient the penetrating element or shunt advancing via the catheter 3304 over the elongate guide member 780 towards a target penetration site on the IPS wall 114 along the curved portion of IPS 102. For example, the elongate guide member 780 coupled to the anchor 700 at a location along the top edge of anchor 700, is configured to orient a distal portion 782 of the elongate guide member 780 proximate or adjacent to the IPS wall 114, as shown in FIGS. 7A-B. Alternatively, the anchor 700 and the elongate guide member 780 can be configured such that the elongate guide member 780 orients (e.g., "hugs") nearest the IPS wall 117 through the curved portion of IPS 102, as shown in FIGS. 7C-D, when the anchor 700 is deployed distally to a target penetration site along the IPS wall 114.

Additionally, the deployment location of the anchor 700 in the sinus lumen can vary the path of the elongate guide member 780 through the curved portion of IPS 102, regardless of how the elongate guide member 780 is oriented with respect to the top, midline, or bottom portions of the anchor 700. For example, deploying the anchor 700 more distally than the deployment location shown in FIGS. 7A-B will orient the elongate guide member 780 more proximate to the IPS wall 117 than IPS wall 114.

Additionally, embodiments of the delivery catheter 3304 (or a shunt if delivered over the elongate guide member 780 without a delivery catheter) can be optimized to orient a penetrating element and/or shunt advancing through or over the elongate guide member 780 towards a target penetration site in the IPS wall 114 along the curved portion of IPS 102. The distal portion 3344 of the delivery catheter 3304 can have multiple interface points to accommodate the elongate guide member 780, as denoted by the "×" markings in FIG. 7D. The interface point on the distal portion 3344 of delivery catheter 3304 for the elongate guide member 780 provides a penetration stop to limit the distance the penetrating element 3350 can travel through IPS wall 114 and into CP angle cistern 138 (e.g., the maximum penetration depth corresponds to the distance between the distal tip of penetrating element 3350 and the interface point on delivery catheter 3304 for receiving elongate guide member 780). Introducing the elongate guide member 780 into or along the delivery catheter 3304 at a more proximal location on the catheter 3304 allows for more separation between the penetrating element 3350 and/or a distal open end 3341 of the delivery catheter 3304 and the elongate guide member 780. The greater extent of separation between the penetrating element 3350 and elongate guide member 780 provides a relatively longer depth of penetration through IPS wall 114 and arachnoid layer 115 along the curved portion of IPS 102. Conversely, a more distal entrance point or connection along the delivery catheter 3304 and the elongate guide member 780 decreases the separation between the elongate guide member 780 and the penetrating element 3350 and/or distal open end 3341 of delivery catheter 3304. The lesser extent of separation between the penetrating element 3350 and elongate guide member 780 provides a relatively shorter depth of penetration through IPS wall 114 and arachnoid layer 115 along the curved portion of IPS 102. A clinician can adjust the interface point between the elongate guide member 780 and delivery catheter 3304 to optimize the trajectory of a penetrating element from the delivery catheter 3304 and penetration depth at a target penetration site along the IPS 114. The interface point between the elongate guide member 780 and delivery catheter 3304 can range from the distal end 3341 of delivery catheter 3304 (e.g., where the distal end of the delivery catheter includes a distal opening to a dedicated rail lumen) to an interface point about 10 cm proximal from the distal end of delivery catheter 3304.

Once deployed, the anchor 700 and the elongate guide member 780 provide a stable, intra-sinus platform that creates an off-axis trajectory for the penetrating element during shunt implantation. The deployed anchor 700 and elongate guide member 780, along with other aspects of the delivery system, afford clinicians controlled access to the greatest extent of CSF-filled space in the CP angle cistern 138 during shunt deployment. The elongate guide member 780 extending through the curved portion of IPS 102 advantageously orients the penetrating element 3350 (i.e., advancing via the guide member) toward IPS wall 114 into CP angle cistern 138. As shown in FIG. 7D, the portion of delivery catheter 3304 distal of the interface point separates from the axis of the elongate guide member 780 as the delivery catheter advances over the guide member through the curved portion of the IPS; that is, the distal most portion of delivery catheter 3304 including penetrating element 3350 travel off-axis from elongate guide member 780 to puncture IPS wall 114 and access the CSF-filled CP angle cistern 138. This orienting feature of the elongate guide member with respect to delivery catheter 3304 ensures that advancement of the penetrating element will: (a) intersect the IPS wall 114 at a target penetration site along the curved portion of IPS 102 at an angle of approximately 90° (i.e., oriented orthogonal to IPS wall 114) to approximately 30° (although, other suitable angles may be provided), and (b) continue on a trajectory through the dura mater of the IPS wall 114 and through the arachnoid layer 115 to access at least 2-3 mm of unobstructed, CSF-filled space of CP angle cistern 138 as measured distally from the penetration point on the IPS wall 114. Features of anchor 700 and the elongate guide member 780 disclosed herein allow clinicians to access and deploy a shunt in a relatively larger extent of free CSF-filled space in the cistern, often more than 3 mm to 5 mm of unobstructed CSF-filled space, compared to other endovascular shunt delivery techniques.

After the anchor 700 and the elongate guide member 780 have been deployed at a desired location in the sinus lumen and the penetrating element has been advanced over the elongate guide member 780 to a target penetration site along the IPS wall 114, the clinician can proceed by creating anastomosis between the IPS 102 and the CP angle cistern 138, followed by the shunt delivery and implantation steps of procedure. The clinician can penetrate the IPS wall 114 to access the CP angle cistern 138 with the penetrating element (e.g., penetrating element advanced via the catheter, on the shunt, or carried by the catheter distal end) by pulling the elongate guide member 780 in the proximal direction (or locking the elongate guide member 780 in place relative to other delivery system components) while advancing the penetrating element over the elongate guide member 780, toward the IPS wall 114. The retrograde force on the elongate guide member 780 during the penetration step further secures the guide member and anchor 700 in the sinus lumen, thereby stabilizing the elongate guide member 780 in the curved portion of the IPS 102 while it orients a penetrating element towards IPS wall 114 and off-axis from the trajectory of elongate guide member 780 in the curved portion of the IPS lumen. And by simultaneously advancing the penetrating element and/or shunt 200 (as previously disclosed) through the IPS wall 114 and arachnoid layer 115 until a distal anchoring mechanism 229 of the shunt 200 is deployed in the CP angle cistern 138 (i.e., without an exchange of delivery system components between the penetration and shunt deployment steps) eliminates the risk of bleeding from the sinus lumen into the subarachnoid space.

Radiopaque markings or coatings can be incorporated on the penetrating element 3350 (e.g., penetrating element advanced via the catheter, on the shunt, or carried by the distal end of the delivery catheter) and/or the delivery catheter to assist the clinician visualize the orientation of delivery system elements in the sinus lumen and the trajectory of such elements prior to or during the penetration step of the shunt implant procedure. For example, a semi-circle piece or half-band of radiopaque material can be coupled to or incorporated within the penetrating element 3350 and/or in the distal portion 3344 of the delivery catheter 3304. Depending on the location of the marker in the penetrating element 3350 and/or distal portion 3344 of the delivery catheter 3304 (e.g., distal section or proximal section of the penetrating element to assist with the visualization of the respective section of the inner diameter or lumen), the clinician can confirm whether the penetrating element 3350 is properly oriented toward the IPS wall 114 and/or improperly oriented toward the IPS wall 117.

After the distal anchoring mechanism 229 of the shunt 200 has been deployed in the CP angle cistern 138, the delivery catheter 3304 can be withdrawn (i.e., pull in the proximal direction) from the curved portion of IPS 102. The distally anchored shunt 200 emerges from the distal end opening 3341 of the delivery catheter 3304 as the catheter is withdrawn through the IPS 102 into the junction 118; the distal anchoring mechanism of the shunt disposed within the CP angle cistern 138 retains, secures and/or anchors the shunt in its deployed location within the subarachnoid space 116 as the delivery catheter 3304 is withdrawn from the IPS 102. Thereafter, the delivery catheter 3304 can be further withdrawn through the junction 118 to allow the proximal anchoring mechanism 227 of shunt 200 to be deployed in the jugular vein 106, as shown in FIG. 7E.

After the shunt 200 has been fully deployed and/or secured at the target site by the shunt 200 respective anchoring mechanisms 227, 229, the clinician can advance the delivery catheter 3304 and/or a micro catheter (e.g., catheter having an inner diameter of 0.027" or 0.021") over the elongate guide member 780 to re-sheath the anchor 700, and then withdraw the catheter 3304 containing anchor 700 and elongate guide member 780 from the patient (e.g., via a femoral access point). Alternatively, the elongate guide member 780 can include an electrolytic detachment element 785 in or around the joint 744 with anchor 700 (FIGS. 3C, 3H) or at any other suitable portion of the elongate guide member 780 (e.g., FIG. 7F), so as to detach the elongate guide member 780 from the anchor 700. After detachment of the elongate guide member 780 from the anchor 700, the elongate guide member 780 can be withdrawn from the patient while anchor 700 remains deployed in the IPS 102 or CS 104. This configuration can be advantageous to avoid accidental pullout of an implanted shunt from CP angle cistern 138 while retrieving the anchor 700 from its distal deployment location by snagging the anchor 700 on a portion of the deployed shunt, as the anchor 700 is withdrawn through the IPS 102 and the junction 118.

Figure 7E:
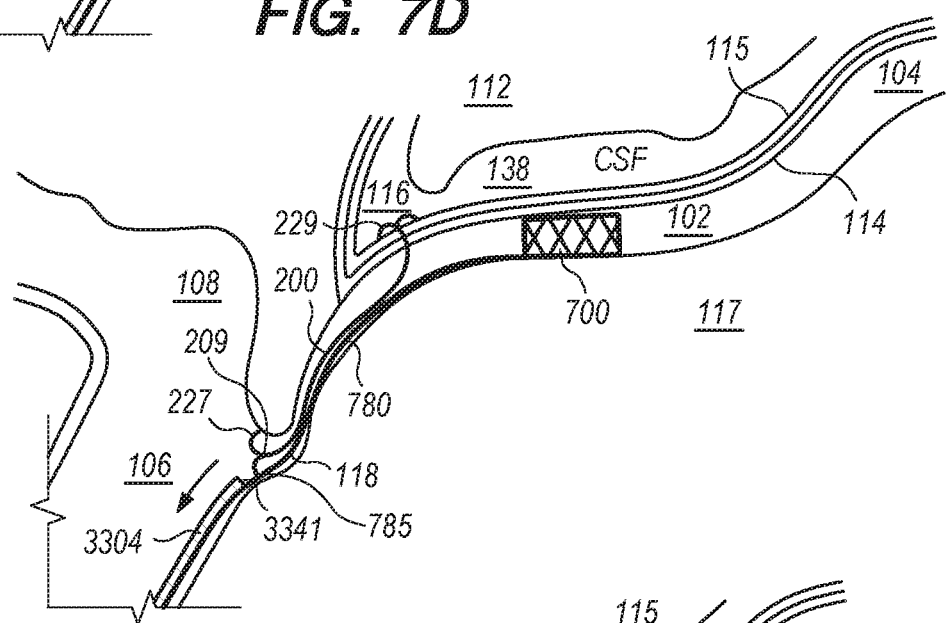
Figure 7F:
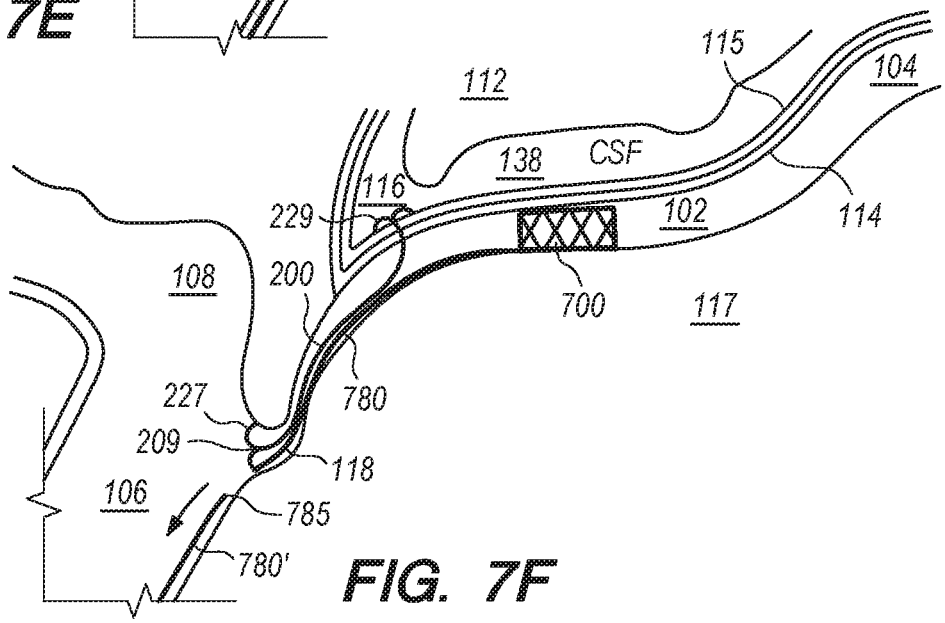

In further alternative embodiments, the electrolytic detachment element 785 can be proximately disposed from the joint 744 (e.g., at the elongate guide member 780 portion configured to be disposed around the junction 118), as shown in FIGS. 7E and 7F. The anchor 700 and a portion of the elongate guide member 780 can be part of the implanted shunting system where a deployed shunt includes one or more connection points or interfaces with the elongate guide member 780, allowing the deployed anchor 700 and portion of the elongate guide member 780 to further anchor the shunt at its deployed location. In such embodiments, the elongate guide member 780 can include the electrolytic detachment element 785 at a portion of the elongate guide member 780 configured to be disposed around the junction 118. So that, a proximal portion 780' (i.e., proximately to the electrolytic detachment element 785) of the elongate guide member 780 is withdrawn from the patient after deployment of the shunt, while the distal portion of the elongate guide member 780 remains coupled to the anchor 700. In this embodiment, the anchor 700 may further provide a scaffold support for the deployed shunt 200, as shown in FIG. 7F.

The anchor 700 and the elongate guide member 780 system can have the following advantages over other endovascular shunt delivery systems and techniques:

Separate anchor 700 and shunt 200 deployment steps preserve critical working and deployment space in the IPS 102 and/or CS 104 around the target penetration site to accommodate delivery system components such as delivery catheter 3304 and shunt 200 compared to a delivery system configured for a single anchor and shunt 200 deployment step comprising multiple, concentric elements (e.g., a delivery catheter, delivery system anchor and/or guide wire, a shunt, and a penetrating element).

The anchor 700 and the elongate guide member 780 system provides a stable platform to secure delivery system components during (a) penetration through the dura mater IPS wall 114 and arachnoid layer 115 into CP angle cistern 138, and (b) deployment of the shunt distal anchoring mechanism 229 in the cistern compared to a conventional delivery catheter and guide wire system.

The anchor 700 and the elongate guide member 780 system resists "kickout" of delivery system components (e.g., delivery catheter 3304) from the IPS 102 and/or CS 104 into the jugular vein 106 resulting from tortuous anatomy during critical procedure steps such as penetrating dura mater IPS wall 114 and arachnoid layer 115 and deploying the shunt and its distal anchoring mechanism 229.

In some embodiments of anchor 700, for example when the anchor is left behind in the sinus lumen (IPS 102 or CS 104) to secure that the implanted shunt 200, the anchor can be configured for hydraulic expansion using stainless steel or cobalt chromium materials, thereby simplifying system design and reducing product manufacturing costs.

The elongate guide member 780 extending proximally from a deployed anchor 700 along the IPS wall 117 eliminates or decreases the risk that an uncovered or unprotected penetrating element inadvertently snags a portion of the IPS wall 114 as the penetrating element is delivery to the target penetration site.

FIGS. 12A-F illustrate an alternative delivery catheter 1304 for delivering a shunt into a target site of a patient, constructed in accordance with embodiments of the disclosed inventions. For ease in illustration, the features, functions, and configurations of the delivery catheter 1304 that are the same as in the delivery catheters 304 and 3304 of the present disclosure and the delivery catheters 304, 304' in the related application previously incorporated by reference herewith, are given the same reference numerals. The delivery catheter 1304 comprises an elongated configuration having a proximal portion 1342, a distal portion 1344 and a lumen 1341 extending therebetween. The delivery catheter 1304 is dimensioned to reach remote locations of the vasculature and is configured to deliver the shunt percutaneously to the target site (e.g., IPS, CS, CP angle cistern, or the like). The delivery catheter 1304 comprises variable stiffness sections (e.g., varying ratio of material, including selective reinforcement, varying the properties or distribution of the materials used and/or varying the durometer or thickness of the materials during the process of manufacturing) suitable to provide sufficient "pushability" (e.g., exhibits sufficient column strength to enable delivery to target locations such as IPS 102 or CS 104; in embodiments comprising a tissue penetrating element 1350, provides sufficient column strength to transmit about 0.1 N to 2.0 N force or more for the penetrating or piercing element to penetrate dura of IPS wall 114 and arachnoid layer 115) and "torqueability" (e.g., in the vasculature exhibits a torque response of about 1:1 such that a single clockwise turn of the catheter at the patient's groin or proximal portion results in approximately single clockwise turn of the distal portion of the catheter at a target location such as IPS 102 or CS 104) to allow the catheter 1304 to be inserted, advanced and/or rotated in the vasculature to position the distal portion 1344 of the catheter at the target site within the IPS 102 or CS 104. Further, the distal portion 1344 has sufficient flexibility so that it can track and maneuver into the target site, particularly in tortuous anatomy.

Known components, such as embedded coils or braids, are often used to provide selective reinforcement to delivery catheters. Delivery catheters including embedded coils can provide suitable flexibility, however, the embedded coils usually fail to provide the necessary column strength for the catheter, particularly at the distal portion of micro-catheters. Delivery catheters including embedded braids can provide with suitable column strength, while sacrificing flexibility, particularly if the embedded braids are disposed at the distal portion of the catheter.

Figure 12A:
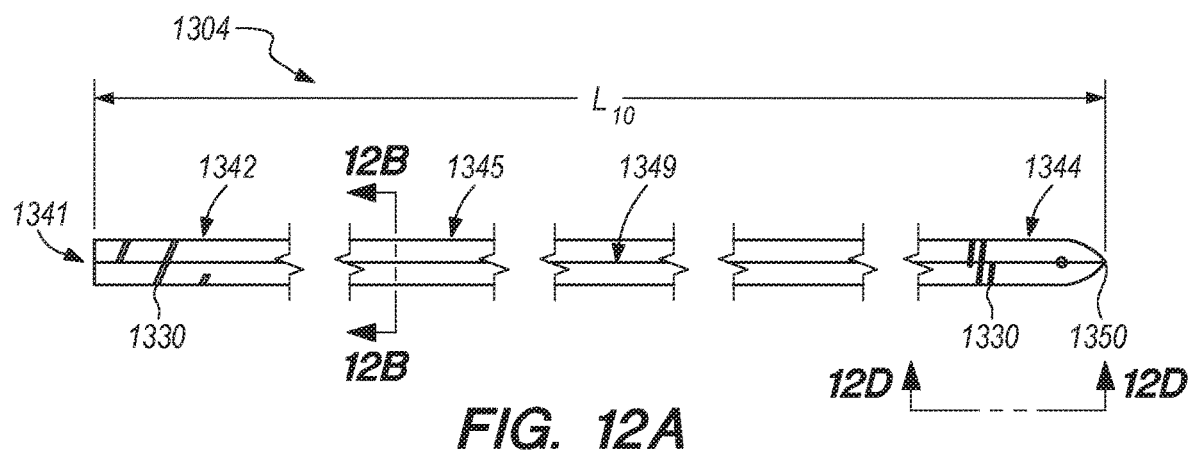
FIGS. 12A-E are side, perspective and cross-sectional views of an elongated member of the delivery catheter, constructed according to other embodiments of the disclosed inventions.
Figure 12B:
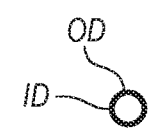
Figure 12C:
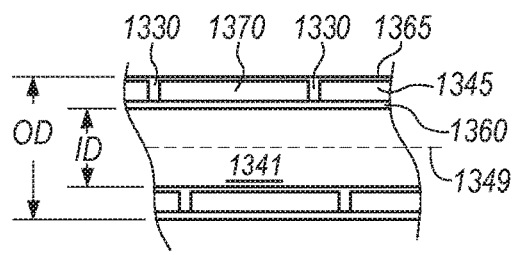

In the embodiments of FIGS. 12A-C, the delivery catheter 1304 comprises an reinforcing member 1345 configured to reinforce the catheter 1304 while providing a suitable balance between column strength and flexibility (e.g., "pushability" and "torqueability"). The reinforcing member 1345 is composed of suitable biocompatible and elastomeric materials such as, stainless steel, Nitinol® or the like. In some embodiments, the reinforcing member 1345 comprises a stainless steel or Nitinol hypotube providing suitable column strength, the hypotube further comprises selective cuts 1330, which provides suitable flexibility.

The reinforcing member 1345 may extend along a substantial length of the catheter 1304 (e.g., the reinforcing member 1345 extends from the proximal portion 1342 to the distal portion 1344 of the catheter 1304). In the embodiment of FIG. 12A, length $L_{10}$, measured along a central axis 1349 of the reinforcing member 1345 is approximately 59" (150 cm). Alternatively, the reinforcing member 1345 can extend along a section of the catheter 1304 (e.g., the reinforcing member 1345 extends along the distal portion 1344 without extending to the proximal portion 1342 of the catheter 1304). For example, $L_{10}$ can range between 1.9" (5 cm) to 6" (15.2 cm), or any other suitable length.

Further, in the embodiment of FIGS. 12A-C, the inner diameter (ID) of the reinforcing member 1345 (e.g., lumen 1341) measured in a direction orthogonal to axis 1349 can range between 0.0205" (0.5207 mm) to 0.024" (0.6096 mm), and the outer diameter (OD) of the reinforcing member 1345 measured in the same direction (i.e., orthogonal to axis 1349) can range between 0.026" (0.6604 mm) to 0.03" (0.762 mm). It should be appreciated that the ID, OD and/or the $L_{10}$ and any other length, width, or thickness of the reinforcing member 1345 of the delivery catheter 1304 may have any suitable dimension for delivering the shunt in the target site (e.g., IPS, CP angle cistern, or the like). Exemplary dimensions (in inches) and properties of the reinforcing member 1345 are shown in FIG. 12G, which are not intended to limit the embodiment of FIGS. 12A-C.

In the embodiments of FIGS. 12A and 12C, the reinforcing member 1345 comprises one or more cuts 1330 (e.g., kerfs, slots, key-ways, recesses, or the like) selectively disposed at the proximal portion 1342 and the distal portion 1344 of the reinforcing member 1345. Additionally, the one or more cuts 1330 can be disposed in sections of the reinforcing member 1345 along $L_{10}$, as shown by the exemplary spiral cut pattern of kerf, pitch, cuts per rotation and cut balance depicted in sections of FIG. 12A. Alternatively, the cuts 1330 can be continuously disposed substantially along $L_{10}$ (not shown), and the continuously disposed cuts 1330 can have variable spiral cut patterns of kerf, pitch, cuts per rotation and cut balance along $L_{10}$ or combinations thereof.

The cuts 1330 of the reinforcing member 1345 can have a variety of suitable patterns, and can be manufactured by laser cutting the reinforcing member 1345 of the delivery catheter 1304. Alternatively, the cuts 1330 and their patterns can be manufactured by etching or other suitable techniques. FIGS. 12E-F depict an exemplary cut pattern of the reinforcing member 1345 of FIGS. 12A-C. In these embodiments, the laser cutting of the reinforcing member 1345 creates between 1.5 to 2.5 cuts 1330 per rotation of the reinforcing member 1345, having a cut balance of between 100° to 202° of rotation with laser on, and then 34° to 38° of rotation with laser off.

As shown in FIG. 12A, the cuts 1330 of the reinforcing member 1345 that are disposed at the proximal portion 1342 comprise a larger pitch (e.g., 0.015) than the pitch (e.g., 0.006) of the cuts 1330 disposed at the distal portion 1344 of the reinforcing member 1345. The smaller the pitch of the cuts 1330 (i.e., smaller separation between cuts) provides for an increase in flexibility of the reinforcing member 1345, such as at the distal portion 1344 of the delivery catheter 1304. The transition between the larger pitch to the smaller pitch cuts 1330 can be subtle, providing for a progressively more flexible delivery catheter towards the distal portion. By way of non-limiting examples, the spiral cut pattern to create the cuts 1330 disposed at the proximal portion 1342 of the reinforcing member 1345 comprise a kerf of 0.001, a pitch of 0.015, creating 2.5 cuts per rotation, having a cut balance of 100° of rotation with laser on, and then 34° rotation with laser off. The spiral cut pattern applied to create the cuts 1330 disposed between the proximal portion 1342 and the distal portion 1344 of the reinforcing member 1345 comprises a kerf of 0.001, a pitch transition from 0.006 to 0.015, creating 1.5 cuts per rotation, having a cut balance of 202° of rotation with laser on, and then 38° rotation with laser off. The spiral cut pattern applied to create the cuts 1330 disposed at the distal portion 1344 of the reinforcing member 1345 comprises a kerf of 0.001, a pitch of 0.004, creating 1.5 cuts per rotation, having a cut balance of 202° of rotation with laser on, and then 38° rotation with laser off. The cuts 1330 may have a width that ranges between 0.0005" (0.0127 mm) to 0.002" (0.0508 mm), or any other suitable width. It should be appreciated that the width, length and depth of the cuts 1330 and patterns of the cuts 1330 in the reinforcing member 1345 of the delivery catheter 1304, can comprise any suitable dimensions. By way of non-limiting example, the pattern of cuts 1330 can transition to a larger pitch (e.g., greater than 0.004) in the distal portion 1344 of reinforcing member 1345 to increase column strength and provide support to a delivery catheter during the penetration step of the shunt implant procedure.

Additionally, the reinforcing member 1345 comprises an inner liner 1360 and an outer jacket 1365, as better seen in FIG. 12C. The inner liner 1360 and outer jacket 1365 are composed of suitable implantable polymeric materials, such as polytetrafluoroethylene "PTFE", polyethyleneterephthalate "PET", High Density Polyethylene "HDPE", expanded polytetrafluoroethylene "ePTFE", urethane, silicone, or the like. The inner liner 1360 and outer jacket 1365 are configured to cover—completely or partially—the cuts 1330 of the reinforcing member 1345, from within lumen 1341 and over the elongated member outer surface 1370, respectively. In such configuration, the reinforcing member 1345 becomes an impermeable tubular element having the cuts 1330 covered by the respective inner liner 1360 and outer jacket 1365, while maintaining the flexibility provided by the selective cuts 1330 and column strength afforded, in part, by the reinforcing member 1345.

The inner liner 1360 provides a smooth inner surface in the lumen 1341 of the reinforcing member 1345 that facilities translation and delivery of the shunt (or other delivery systems or devices delivered through the lumen). Further, the inner liner 1360 can be configured to line the interior reinforcing member 1345 using an extrusion process. Alternatively, the liner material can be deposited (e.g., using a dispersion technique) on a mandrel (e.g., nickel coated copper); thereafter, the liner-coated mandrel can be placed within the reinforcing member 1345 for application of outer jacket 1365 and adhering the inner liner 1360 to the reinforcing member 1345, after which the mandrel can be withdrawn from the reinforcing member 1345 leaving inner liner 1360 in place within the lumen 1341 of the reinforcing member 1345.

The outer jacket 1365 provides a smooth outer surface to the reinforcing member 1345, which facilitates the navigation of the delivery catheter 1304 through tortuous vasculature. As noted above, the outer jacket 1365 can comprise one or more implant-grade polymers including, but not limited to, polyurethane or silicone-polyurethane blends. In some embodiments, a gas or liquid dispersion of polymer is applied to the reinforcing member 1345 and inner liner 1360, which forms the outer jacket 1365 and bonds the inner liner 1360, the reinforcing member 1345, and outer jacket 1365 together in an integrated configuration of the delivery catheter 1304.

The outer jacket 214 can substantially cover the entire outer surface of the reinforcing member 1345; however, in some embodiments, the outer jacket can be placed selectively along sections of reinforcing member 1345 to adhere the inner liner 1360 to the reinforcing member 1345. By way of non-limiting example, a liquid dispersion of polymer or an epoxy-based adhesive can be placed at discrete locations along $L_{10}$. Alternatively, the outer surface of inner liner 1360 can be coated with polymer or adhesive, and then placed within reinforcing member 1345; the polymer or adhesive can seep into the cuts 1330, completely or partially filling some or all of the cuts 1330 along $L_{10}$.

In the embodiment of FIG. 12C, the inner liner 1360 can have a thickness of 0.0005" (0.0127 mm); though the thickness of inner liner 1360 can range from 0.0005" (0.0127 mm) to 0.0015"(0.0381 mm) in other embodiments. In the embodiment of FIG. 12C, the outer jacket 1365 can have a thickness of 0.001" (0.0254 mm); though the thickness of outer jacket 1365 can range from 0.0001" (0.00254 mm) to 0.001" (0.0254 mm) in other embodiments. It should be appreciated that the inner liner 1360, and the outer jacket 1365 of the reinforcing member 1345 may comprise any suitable dimensions.

Figure 12D:
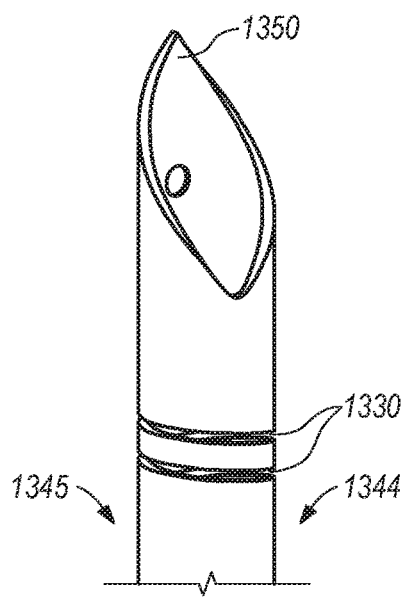
Figure 12E:
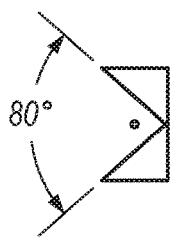

Referring back to FIG. 12A, the reinforcing member 1345 further comprises a penetrating element 1350 (e.g., sharp, tapered, cannula-like end, bevel, pencil, or Quincke tip needle, or the like) extending or disposed at the distal portion 1344 of the elongated member, as also depicted in FIG. 12D. The penetrating element 1350 is configured to penetrate the dura mater of the IPS wall 114 and the arachnoid layer 115 creating an anastomosis between the IPS 102 and the CSF-filled CP angle cistern 138 for deployment of the shunt, as previously disclosed herein, and in the related application previously incorporated by reference herewith. The cuts 1330 proximately disposed to the penetrating element 1350 are configured to provide suitable flexibility to the distal portion 1344 of the delivery catheter 1304, allowing the distal portion 1344 to bend, curve and/or orient the penetrating element 1350 towards the IPS wall 114, while maintaining suitable column strength to support the penetrating element 1350 at the distal portion 1344 as it penetrates through the IPS wall 114 and arachnoid layer 115. The penetrating element 1350 extending from, integrated with and/or incorporated to the distal portion 1344 of the reinforcing member 1345 allows for a secure withdrawal of the penetrating element 1350 when the delivery catheter 1304 is withdrawn from the patient.

Figure 13:
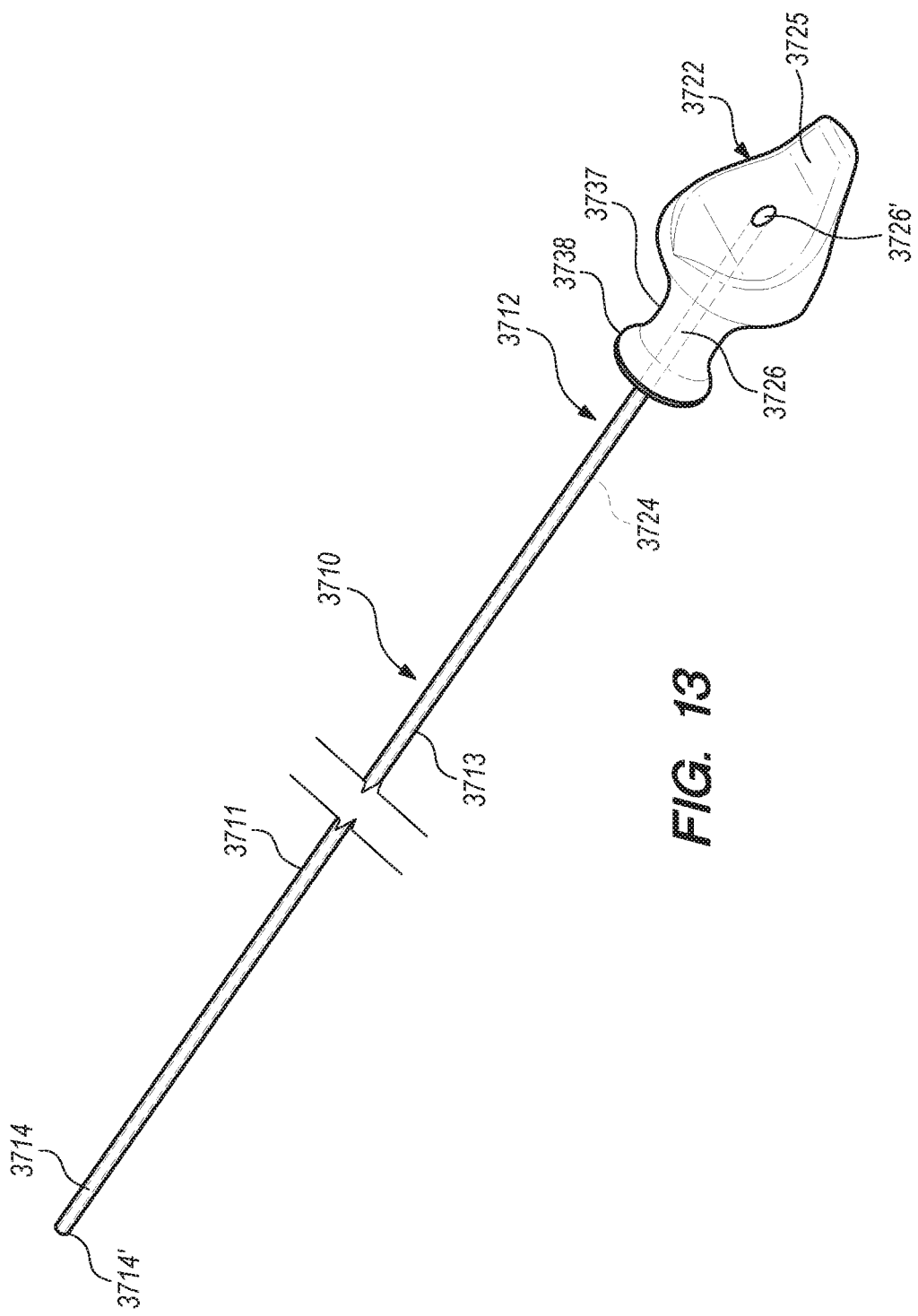
FIG. 13 is a perspective view of an elongated pusher constructed according to embodiments of the disclosed inventions.

FIG. 13 illustrates an elongated pusher 3710, constructed in accordance with embodiments of the disclosed inventions. The elongated pusher 3710 comprises a support tubular member 3711, having a proximal portion 3712, a middle portion 3713 and a distal portion 3714, and a lumen 3724 extending therebetween. The proximal portion 3712 of the support tubular member 3711 is coupled to a handle 3722, which will be described in further detail below. The pusher 3710 provides telescoping support to a guidewire or other interventional devices as a clinician translates such guidewire or device through a catheter to a target site.

The elongated pusher 3710 is configured to translate (e.g., advance, push) interventional access/treatment devices (e.g., stent anchor 700, guide member 780, guidewires, thrombectomy devices, or the like) into the IPS 102 or any other target site, through a catheter (e.g., delivery catheter 304/3304, or the like) disposed in a patient's vasculature. The pusher 3710 is further configured to receive the elongated guide member 780, and the handle 3722 is configured to assist the clinician hold a portion of the guidewire or interventional devices extending proximally through the handle lumen 3724 thereby advancing the guidewire and/or interventional devices through a catheter.

The length of the support tubular member 3711 can range from about 1" (2.54 cm) to about 60"(152.4 cm) or larger. The support tubular member 3711 comprises an inner wall defining the lumen 3724, the inner wall can include an annular, circular or any other suitable shape or dimension suitable for advancing guidewires and/or interventional devices therebetween. The inner diameter of the support tubular member 3711 can range from about 0.010" (0.254 mm) to about 0.024" (0.6096 mm). In some embodiments, the inner diameter of the of the support tubular member 3711 is larger than 0.024" (0.6096 mm), such that the pusher 3710 is configured to receive and translate larger guidewires and/or other interventional devices (e.g., 2-24 Fr). The outer diameter of the support tubular member 3711 is configured to be received into the proximal hub 3377 of a catheter or hemostasis valve through which guidewires and/or other interventional devices will be advanced into the patient's target site. The support tubular member 3711 can have a thin-walled configuration, comprising a wall thickness that ranges from about 0.001" (0.0254 mm) to about 0.005" (0.127 mm), which allows the support tubular member 3711 to fit within the catheter hub while maintaining maximum clearance within the tubular member lumen 3724 for receiving guidewires and/or interventional devices. By way of non-limiting example, an embodiment of the pusher 3710 configured for translating embodiments of anchor 700 and guide member 780 through an 0.027" micro catheter into a distal portion of the IPS can have a support tubular member 3711 that is 6" to 8" (15.25 to 20.32 cm) long, with an outer diameter of 0.025" (0.635 mm) and inner diameter of 0.020" (0.508 mm). Alternative embodiments can be configured for translating larger or smaller interventional devices through larger or smaller catheters; for example, embodiments of the pusher can be configured for translating neuro-interventional devices such as 0.010", 0.014", or 0.018" guidewires through 0.014", 0.018", or 0.021" micro catheters.

The support tubular member 3711 of the elongated pusher 3710 can be composed of metal (e.g., stainless steel, titanium, Nitinol) or plastic (e.g., polyamide, polyimide, PTFE, PEEK, polyester), or combinations thereof. The support tubular member 3711 can have a multi-layered construction, for example, stainless steel exterior with an HDPE inner layer. In embodiments of the support tubular member 3711 composed by metal, the tubular member 3711 can include progressive spiral cut or articulated construction, where cut pattern or articulations are configured to create stiffness that transitions along the length of the support tubular member 3711 (e.g., stiffness transitions over its length and becomes stiffer nearer to the handle 3722. In such embodiments, the distal portion 3714 of the support tubular member 3711 is more flexible than the proximal portion 3712 (e.g., stiffer near the handle 3722). Further, the inner wall of the support tubular member 3711 can include a PTFE liner or a lubricious coating such as PTFE, parylene, or other suitable hydrophilic coatings, configured to reduce friction or facilitate smooth translation of the guidewires and/or interventional devices through the tubular member lumen 3724.

Referring back to the handle 3722 coupled to the proximal portion 3712 of the support tubular member 3711, the handle 3722 comprises an outer surface 3725, and a lumen 3726 in fluid communication with the lumen 3724 of the support tubular member 3711 of the pusher 3710. The handle lumen 3726 is configured for receiving a proximal end 3712' of the proximal portion 3712 of the support tubular member 3711. The handle 3722 can be coupled to the proximal end 3712' of the tubular member 3711 by an adhesive (e.g., an ultraviolet light-cured adhesive, cyanoacrylate, or epoxy), using a press-fit connection, or any other suitable techniques. In alternate embodiments, the proximal end 3712' of the tubular member 3711 can be radially flared (e.g., outwardly flared, flared out, funnel-like configuration, or the like) with the handle 3722 molded around the flared proximal end 3712' of the tubular member 3711. The handle 3722 can be composed of polyethylene, HDPE, PTFE, PEEK, ABS, polycarbonate, ABS-polycarbonate, thermoplastic polyamide, or polyoxymethylene, or the like. In alternative embodiments of the pusher 3710, the handle can comprise PEEK, polyvinylidene difluoride, or other thermoplastic polymers or materials suitable for autoclaving treatments that can be used with a metal tubular member 3711.

The handle 3722 further comprises a lumen opening 3726' configured for receiving the guidewire and/or interventional devices for advancement into a target site in a patient through the support tubular member lumen 3724. In some embodiments, the handle 3722 can range in diameter (at its widest portion) from about 0.75" to 1.5" (0.75 mm to 38.1 mm) or more, and have a length of about 0.5" to 1.5" (12.7 mm to 38.1 mm) or more. The handle lumen 3726 defines an annular, circular or any other shaped space suitable for advancing the guidewire and/or interventional devices therebetween. The handle 3722 can comprise an ergonomic configuration, as shown in FIG. 13. The ergonomic configuration of the handle 3722 is suitable for providing a resting portion (i.e., surface 3725) for the clinician's fingers, typically sized for the clinician's thumb or finger, while using the pusher 3710. The resting surface 3725 is configured to be contoured for resting a human thumb or finger, such that the clinician can use the surface 3725 to hold, pinch, press or maintain a portion of the guidewire and/or the interventional devices extending out from the handle 3722 while using the pusher 3710, with one hand only. By pinching the guidewire and/or interventional device against the resting surface 3725 of the handle 3722, the clinician can advance the pusher 3710, the guidewire or the interventional devices into the catheter. Then, the clinician can release the pinch and withdraw the pusher 3710 over the guidewire. The clinician may perform a sequence of pinching the guidewire, advancing the pusher and pinched guidewire, releasing the pinch and withdrawing the pusher over the guidewire (as shown in FIGS. 14C-E), which sequence can be repeated until the guidewire and/or the interventional devices translates through the catheter and reach their target site. The handle 3722 may include other contour shapes or configurations (e.g., scallop, ramp, slopes or the like) that allow the clinician to hold, pinch, press or maintain the guidewire and/or the interventional devices against the surface 3725 of the handle 3722. The surface 3725 can include a traction pad (e.g., a thin strip of silicone, swallow ribs or the like) configured to increase the friction coefficient between the handle and the clinician, to assist with the holding of the guidewire and/or the interventional devices against the handle 3722. The traction pad may comprise a single silicone pad disposed on the surface 3725 of the handle 3722 or a silicone tab that folds over and sandwiches the guidewire and/or interventional devices pinched against the surface 3725 of the handle 3722.

The handle 3722 can further comprise features that facilitate use of the pusher 3710. In the embodiment of FIG. 13, the handle 3722 comprises a neck 3737 (e.g., annular indentation, or the like) configured to be held or gripped by the clinician's fingers during use of the pusher 3710, as shown in FIGS. 14C-D. The handle 3722 further comprises a flange 3738 (e.g., annular outward rim, protruding collar, or the like) distally disposed from the neck 3737 of handle 3722. The neck 3737, either alone or in combination with the flange 3738, is configured to assist the clinician's hold of the pusher 3710 and to control the push and pull motions of the pusher 3710 relative to the guidewire, interventional devices and/or catheter, while maintaining the position of the pusher 3710 at a desired location. Additionally, the handle 3722 can include a scalloped or tapered lead in to lumen opening 3726' for additional support for guidewire and/or interventional devices used with the pusher 3710. In alternative embodiments, a portion of the handle 3722 can include a guidewire torque features (e.g., rotating collet to lock wire or device in place).

During advancement of the guidewire and/or interventional devices into a target site of a patient using the elongated pusher 3710 of FIG. 13, the clinician introduces the guidewire and/or interventional devices through the lumen opening 3726' of the handle 3722. Then, the clinician distally translates the guidewire and/or interventional devices into the pusher 3710 (i.e., handle lumen 3726 and tubular member lumen 3724) while maintaining the proximal portion of the guidewire or interventional devices extending out of the handle 3722.

FIGS. 14A-F illustrate a method of use an elongated pusher according with embodiments of the disclosed inventions. By way of non-limiting example, FIGS. 14A-E illustrate the pusher 3710 of FIG. 13 to translate a guide member 780 through a catheter 3307 (e.g., micro catheter, introducer sheath or the like). In some cases, the catheter 3307 can include a reinforcing member that is, or otherwise includes any of the various features or properties of, the catheter reinforcing members 1100, 1200, 1500, or 1600 described above. In these embodiments, the catheter 3307 has been advanced into the vasculature (e.g., the IPS) from a femoral vein access point in the patient. It should be appreciated that the elongated pusher 3710 constructed according to embodiments of the disclosed inventions may be used in other interventional procedures including, but not limited to, stent retriever delivery, distal protection device delivery, foreign body retrieval, delivery loops and snares, pacemaker implantation, and any other suitable medical procedure.

Figure 14A:
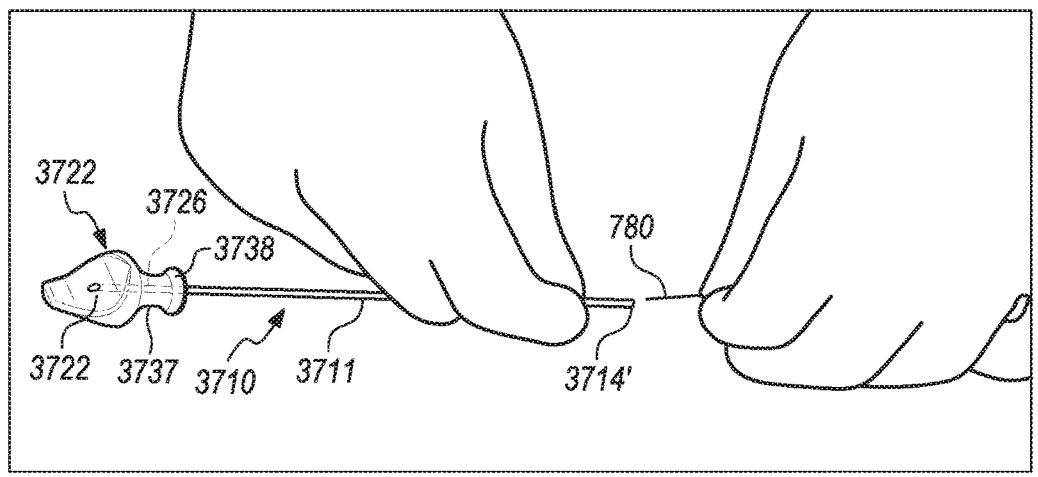
FIGS. 14A-F are perspective views of exemplary methods for the elongated pusher of FIG. 13 use, according to embodiments of the disclosed inventions.
Figure 14B:
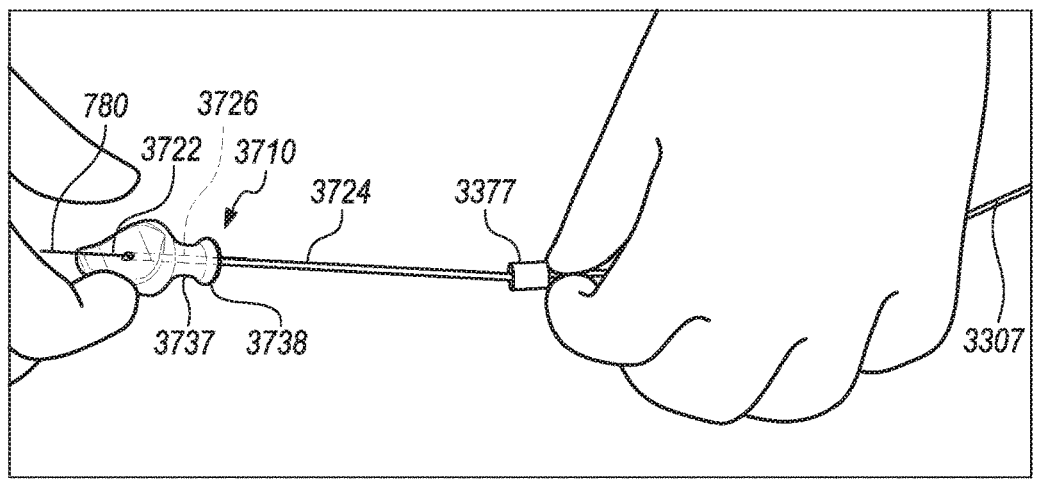
Figure 14C:
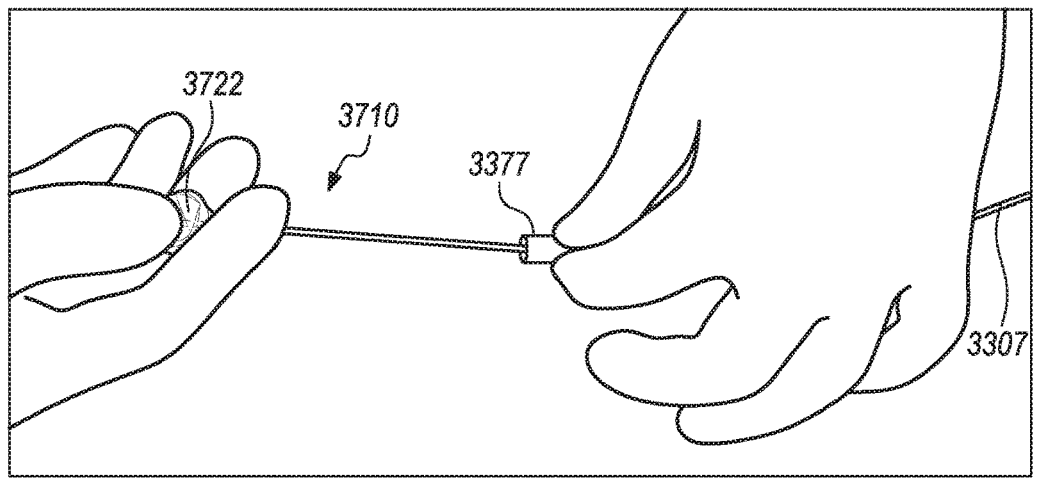
Figure 14D:
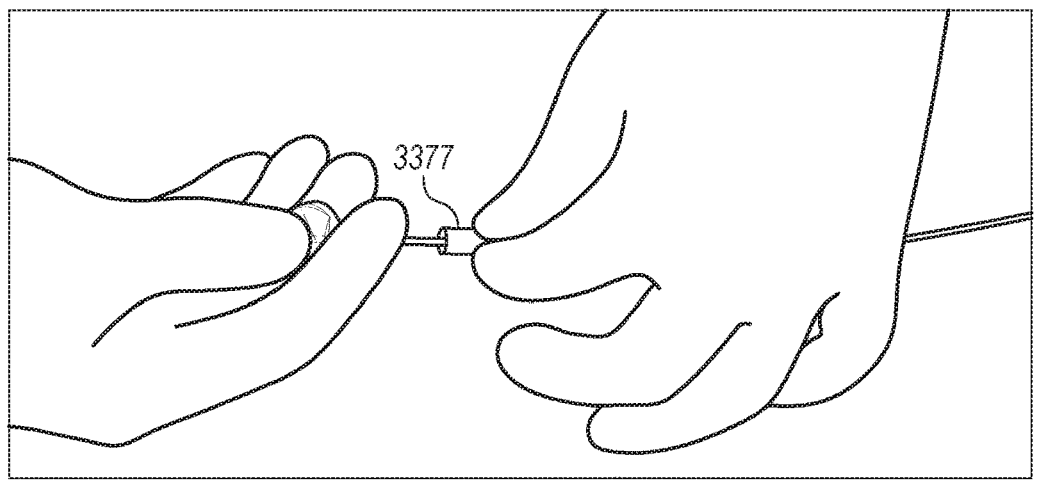
Figure 14E:
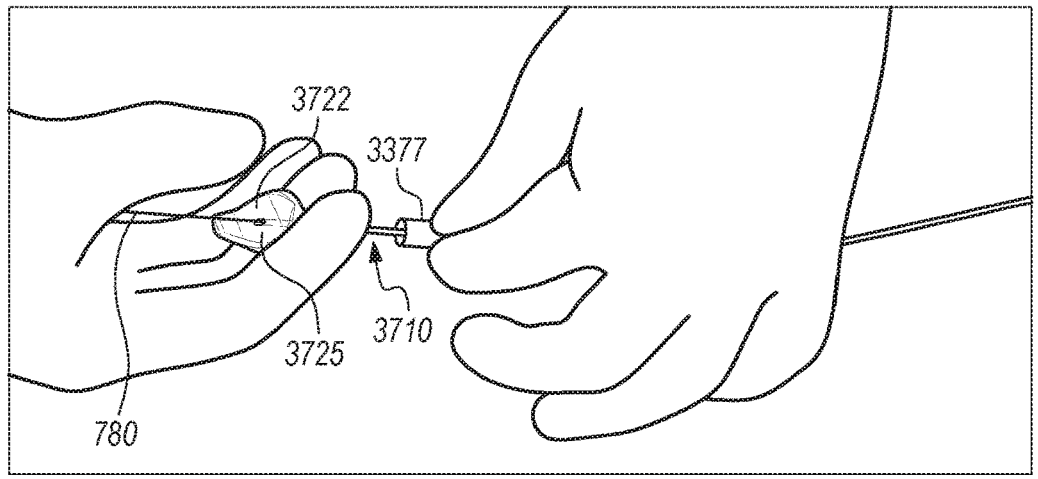
Figure 14F:
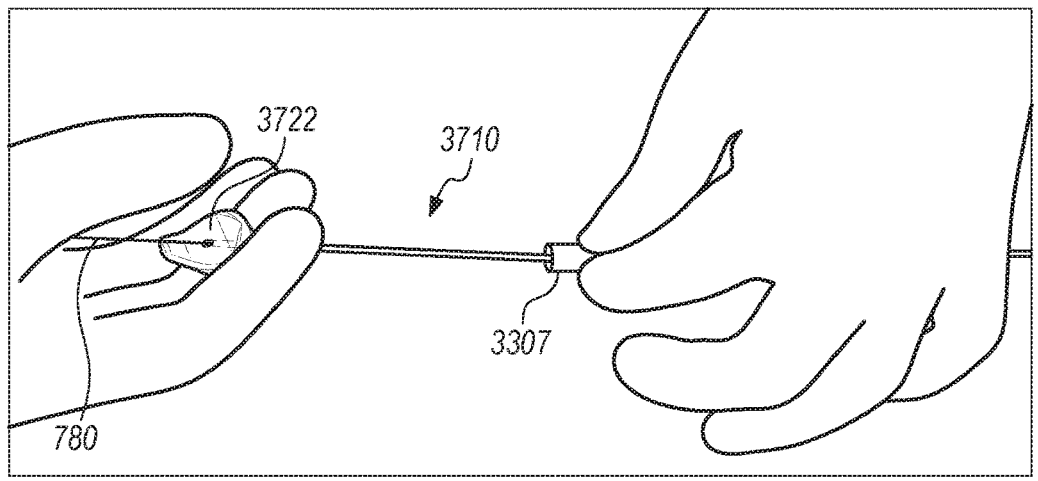

FIG. 14A depicts the guide member 780 being advanced into the distal opening 3714' of the support tubular member 3711. It should be appreciated that anchor 700 coupled to the guide member 780 has already been inserted and translated through the catheter hub 3377 into the proximal portion of the catheter 3307 (not shown). Alternatively, the pusher 3710 and guide member 780 can be introduced simultaneously into the catheter hub 3377. As shown, the clinician feeds the guide member 780 through pusher 3710, via the distal opening 3714' of the support tubular member 3711, through tubular member lumen 3724 and handle lumen 3726, such that the guide member 780 emerges from the opening 3726' of the handle 3722. Alternatively, the clinician may feed the guide member 780 through pusher 3710, via the opening 3726' of the handle 3722, through the handle lumen 3726, into the tubular member lumen 3724. Then, the clinician advances the pusher 3710 over guide member 780 until distal portion 3714 of support tubular member 3710 accesses the catheter hub 3377 of catheter 3307 (FIG. 14B).

In instances in which the body lumen is a blood vessel, the elongate guide member 780 is normally advanced into the blood vessel through a catheter (e.g., micro catheter or an introducer sheath) 3307 having a proximal opening outside of the patient and a distal opening (not shown) within the blood vessel, in which case advancing the pusher tool 3710 may include advancing the distal portion 3714 of the tubular body 3711 into the proximal opening of the introducer sheath 3307. As discussed herein, the catheter 3307 can include a reinforcing member that is, or otherwise includes any of the various features or properties of, the catheter reinforcing members 1100, 1200, 1500, or 1600 described above. The proximal opening of the introducer sheath is normally accessed via the proximal introducer hub 3377, in which case the method may further include grasping to thereby stabilize the introducer hub 3377 while advancing the distal portion 3714 of the tubular body 3711 through the hub 3377.

The clinician then holds, pinches, or presses the guide member 780 against the handle 3722, as described above, and further advances the pusher 3710 and guide member 780 into catheter hub 3377 of catheter 3307. (FIGS. 14C-14D). By pinching the guide member 780 against the resting surface 3725 of the handle 3722, the clinician can advance the pusher 3710 and guide member into the catheter 3307. Then, the clinician can release the pinch and withdraw the pusher 3710 over the guide member 780, preferably while maintaining the distal portion 3714 of the support tubular member 3711 within the catheter hub 3377. The clinician may perform a sequence of pinching the guide member 780, advancing the pusher 3710, releasing the pinch and withdrawing the pusher 3710 over the guide member 780 (as shown in FIGS. 14C-F), which sequence can be repeated until the guide member 780 translates through the catheter 3307, with the support tubular member 3711 telescoping into the catheter hub 3377 and guide member 780 reaching the target site. The clinician releases the pinch of the guide member 780 against the handle 3722 and withdraws the pusher 3710 over the guide member 780 after the guide member reaches the target site.

Figure 15A:
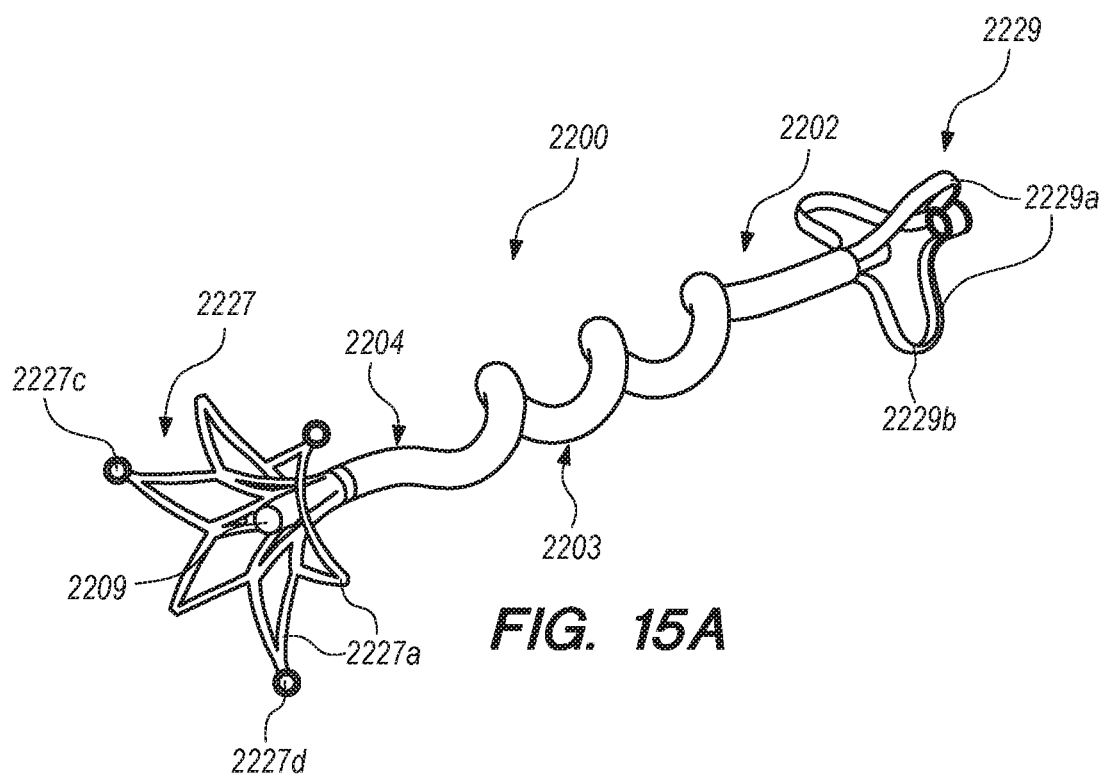
FIGS. 15A-J are side, perspective and cross-sectional views of a shunt, constructed according to another embodiments of the disclosed inventions.

FIGS. 15A-K illustrate another exemplary shunt 2200 constructed and implanted according to embodiments of the disclosed inventions. A proximal portion 2204 of the shunt 2200 includes an anchoring mechanism 2227 (i.e., proximal anchor), and a valve 2209 (e.g., duck-bill, cross cut, elastic vales, molded silicone valves as disclosed herein, or other suitable one-way valves). A distal portion 2202 of the shunt 2200 includes an anchoring mechanism 2229. The shunt 2200 further comprises an elongate body 2203 extending between the proximal 2204 and distal 2202 portions. The anchoring mechanisms 2227 and 2229 include a plurality of respective deformable elements 2227a and 2229a (e.g., arms) that are disposed radially outward in the deployed configuration of the shunt 2200 (FIG. 15A). Anchoring mechanisms 2227 and 2229 may have a preformed expanded or deployed configuration, for example, when constructed from super-elastic materials such as Nitinol®. The deployed anchoring mechanism 2227 engages the jugular bulb 108, the jugular vein 106, the IPS wall 117, and/or another portion of the IPS 102, anchoring the proximal portion 2204 of the shunt 2200 within the jugular vein 106, so that the valve 2209 is disposed within the jugular vein 106 or at least facing the blood flowing through the jugular vein (e.g., transversally disposed towards the vein), as shown, for example in FIGS. 7E-F. Alternatively, the anchoring mechanism 2227 may engage the IPS walls 114 and 117 at the junction 118 (not-shown). The deployed anchoring mechanism 2229 secures the distal portion 2202 of the shunt 2200 within the CP angle cistern 138, so that CSF flows through the implanted shunt 2200 into the jugular vein 106 (e.g., FIGS. 7E-F).

Figure 15B:
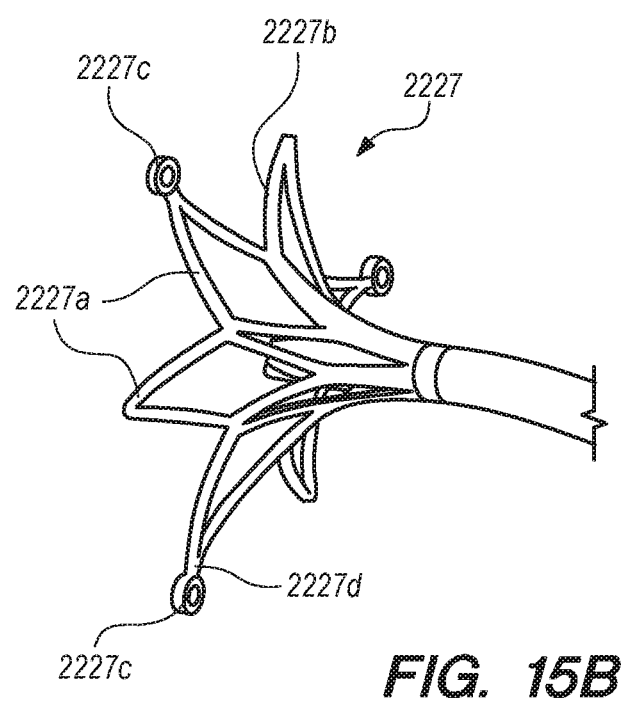
Figures 1, 15C:
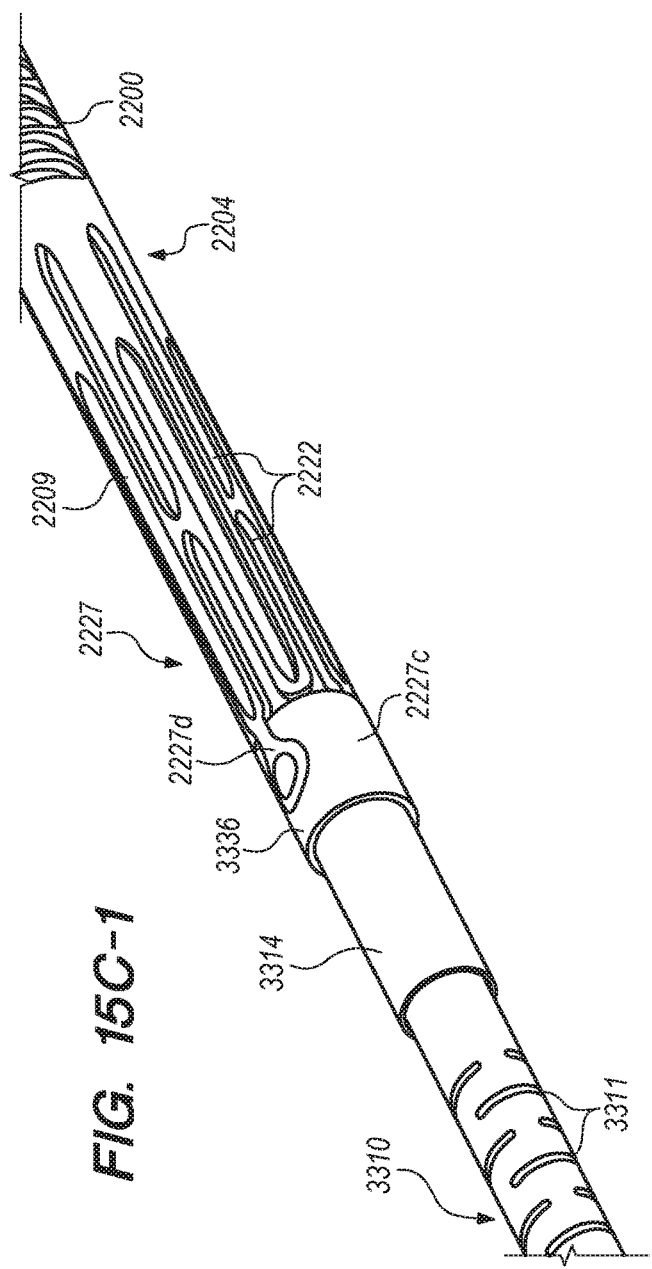
Figures 2, 15C:
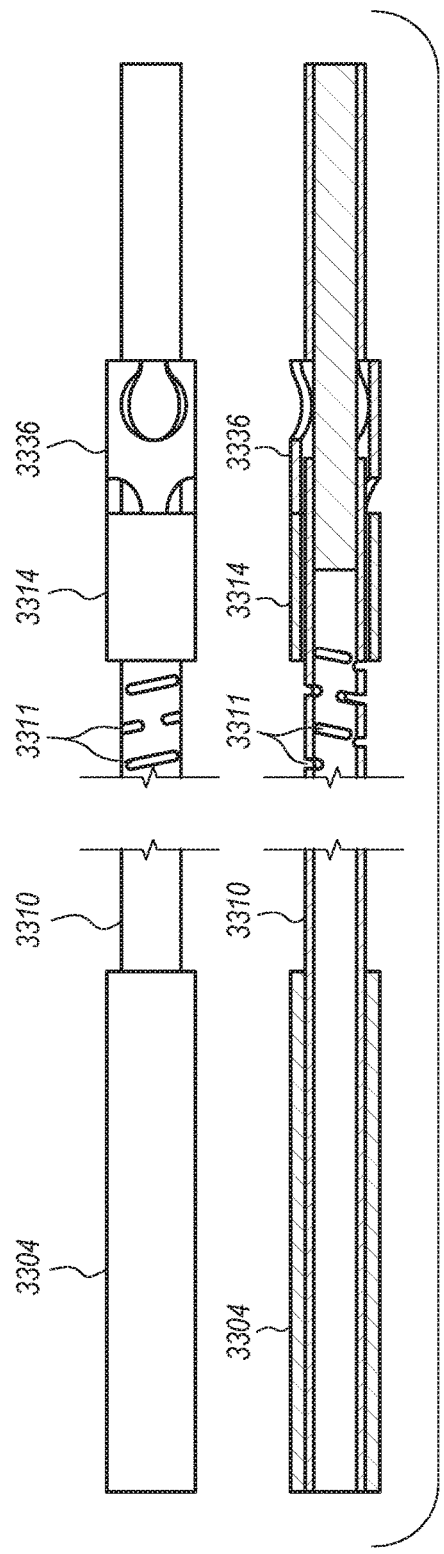
Figure 15D:
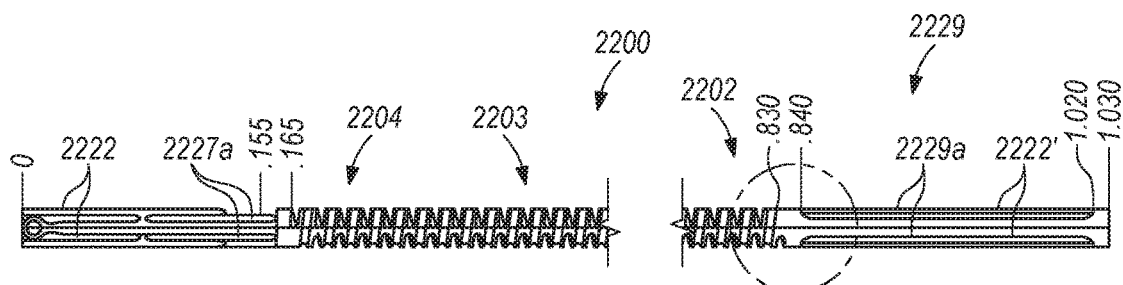
Figure 15E:
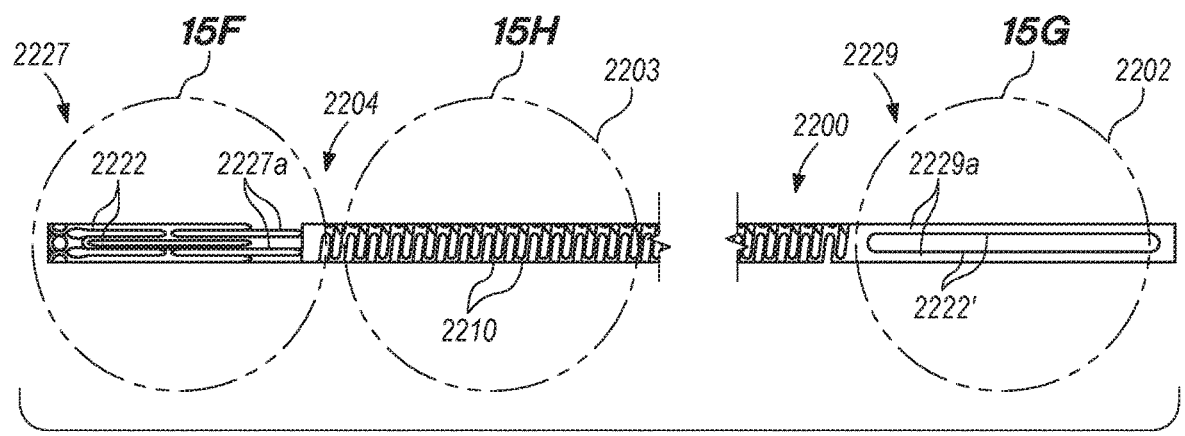
Figure 15F:
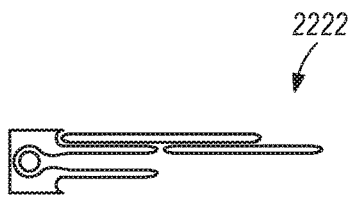

The anchoring mechanism 2227 and 2229 are formed by series of cuts 2222 and 2222' (e.g., kerfs, slots, key-ways, recesses, or the like) along the length of the respective proximal 2204 and distal 2202 portions of the shunt 2200 (FIGS. 15C1-G), forming the deformable elements 2227a (FIGS. 15A-E) and 2229a (FIGS. 15A, 15D-E, 15G, 15J). The cuts 2222 and 2222' and their patterns are preferably manufactured by laser cutting, etching or other suitable techniques. FIGS. 15D-F illustrate exemplary patterns and dimensions of the cuts 2222 in the proximal portion 2204 of the shunt 2200, the cuts 2222 forming the deformable elements 2227a configured to a flared open (e.g., funnel, flower-petal, or the like) deployed configuration (FIGS. 15A-B and 15I). The deformable elements 2227a in the flared-open deployed configuration of the anchoring mechanism 2227, as shown in detail in the perspective view of FIG. 15B, combined with a malecot distal anchor 2229 configuration, provides a "flarecot" shunt configuration as shown in FIG. 15A. Further, FIG. 15I illustrates another perspective view of the flared anchoring mechanism 2227. The deformable element 2227a may comprise hinge-like points 2227b (e.g., living hinge, joint, or the like) to assist with the deployment of the anchor 2227 into the flared configuration. Each of the deformable elements 2227a is coupled to one or more adjacent deformable element 2227a defining a plurality of closed cells 2227g, as shown in FIG. 15I. The anchoring mechanism 2227 having the plurality of closed cells 2227g is configured to minimize disruption and allow passage of fluids (e.g., blood, CSF) through the anchor 2227 when anchoring the proximal portion 2204 of the shunt 2200 within the jugular vein 106.

Referring back to the anchoring mechanism or proximal anchor 2227 of FIGS. 15A-B and 15I, the deformable elements 2227a may include one or more radiopaque markers 2227c (e.g., gold, or other suitable radiopaque materials) for imaging purposes during the delivery of the shunt 2200. The markers 2227c assist with the deployment and/or placement of the anchoring mechanism 2227 at the target site within the patient. Further, suitable markers 2227c can be included (e.g., embedded, attached, coupled) or applied (e.g., coatings) in/on the deformable elements 2227a. The radiopaque marking scheme on the proximal anchoring mechanism 2227 depicted in FIGS. 15A-B and 15I allows the clinician to visualize deployment of the proximal anchoring mechanism about the jugular vein 106, as the anchor transitions from a radially compressed to a flared, deployed configuration. In the embodiments of FIGS. 15A-B and 15I, each of deformable elements 2227a include a first end portion 2227a' and a second end portion 2227a", wherein at least two deformable elements 2227a are coupled at their respective first end portions 2227a' having an interlocking element 2227d therein. The anchoring mechanism 2227 includes one or more interlocking elements 2227d having a respective marker 2227c. The interlocking elements 2227d of the anchoring mechanism 2227 are sized and dimensioned to detachably engage the shunt 2200 to the delivery system (e.g., pusher member or the like), described in FIG. 15C-1 in further detail. Each interlocking element 2227d includes a substantially round shape, as shown in FIGS. 15A-B, 15I, and 15K, configured to arcuate in the delivery configuration to conform to the delivery system, as shown in FIGS. 15C-1, 15C-2 and 15L. The interlocking elements 2227d may include any other suitable shape, such as spherical, rectangular, or the like. Further, each interlocking element 2227d have a recess 2227e (e.g., hole, eyelet, cavity, or the like) configured for receiving a respective marker 2227c. As shown in FIGS. 15A-B and 15I, the markers 2227c are formed as rivets by pressing a respective marker 2227c into the corresponding recess 2227e. The markers 2227c may extend or protrude out of the interlocking elements 2227d (e.g., riveted), as shown in FIGS. 15A-B and 15I, or may be flushed with the interlocking elements 2227d (e.g., welded), or may be coupled to the interlocking elements 2227d with any other suitable techniques or combinations thereof.

The interlocking elements 2227d of the proximal anchor 2227 are shaped and dimensioned to detachably engage (i.e., engage and disengage) an interlocking element 3336 coupled to the distal portion 3314 of a pusher member 3310, as shown in FIGS. 15C-1 and 15C-2. The pusher member 3310 (e.g., hypotube, such as a stainless steel hypotube (FIGS. 15C-1 and 15C-2) comprises a plurality cuts 3311 to increase flexibility, a radiopaque marker 3314 (FIGS. 15C-1 and 15C-2) for imaging purposes, and a distal interlocking element 3336 (FIGS. 15C-1 and 15C-2) configured to interlock with corresponding interlocking elements 2227d of the anchoring mechanism 2227. FIGS. 15C-1 and 15C-2 illustrate the interface between the pusher member 3310 and anchoring mechanism 2227 of the shunt 2200, having the interlocking elements 2227d of the proximal anchor 2227 engaged with the interlocking element 3336 of the pusher member 3310. FIG. 15C-1 further depicts the valve 2209 disposed on the proximal portion 2204 of the shunt 2200 within the compressed anchoring mechanism 2227. The pusher member 3310 is configured to deliver the shunt 2200 through a delivery catheter while avoiding contact, bumping or interfering with the valve 2209. While the interlocked anchoring mechanism remains compressed within lumen 3305 of the delivery catheter 3304, the clinician can advance and retract the shunt 2200 within the delivery catheter prior to shunt deployment via pusher member 3310 (e.g., advancing shunt slightly proximal of the penetrating element 3350 to provide additional column strength to the delivery catheter 3304 during the penetration step of the shunt implant procedure, or alternatingly advancing the delivery catheter 3304 and then shunt 2200 through lumen 3305 to maintain the flexibility of the delivery assembly while accessing and navigating through tortuous anatomy).

In the embodiment of FIGS. 15A-J, the proximal anchor 2227 is composed of super-elastic materials (e.g., Nitinol®) having a preformed, flared configuration. When the proximal portion 2204 of the shunt 2200 is advanced out of the delivery catheter by translating the pusher member 3310 and/or withdrawing the delivery catheter, with or without holding pusher member 3310 member in place, the anchor interlocking elements 2227d disengage from the interlocking element 3336 of the pusher member 3310 by the anchor 2227 assuming the flared configuration, shown in FIGS. 15A-B and 15I. In some embodiments, the flared configuration of the proximal anchor 2227 and/or disengaging of the anchor interlocking elements 2227d from the interlocking element 3336 of the pusher member 3310 may be actuated and controlled by the clinician.

Figure 15G:

Referring back to the anchoring mechanism or distal anchor 2229 of the shunt 2200, FIG. 15G illustrates exemplary patterns and dimensions of the cuts 2222' in the distal portion 2202 of the shunt 2200 (FIGS. 15A, 15D-E, and 15G). The cuts 2222' are parallel and radially spaced to form the deformable elements 2227a configured to extend radially outward when deployed assuming a malecot configuration (FIGS. 15A and 15J). Each of the deformable elements 2229a has a respective hinge-like point 2229b (e.g., living hinge, joint, or the like) configured to move radially outward from the axis of the shunt 2200 in a hinge-like fashion, allowing the deformable elements 2229a to be outwardly disposed when deployed. The cuts 2222' forming the deformable elements 2227a of the distal anchor 2229 are substantially longitudinal along the axis of the shunt 2200 allowing the distal anchor 2229 and/or distal portion 2202 of the shunt 2200 to maintain a suitable column strength and pushability through tissue during deployment at a target site.

Figure 15H:
Figure 15I:
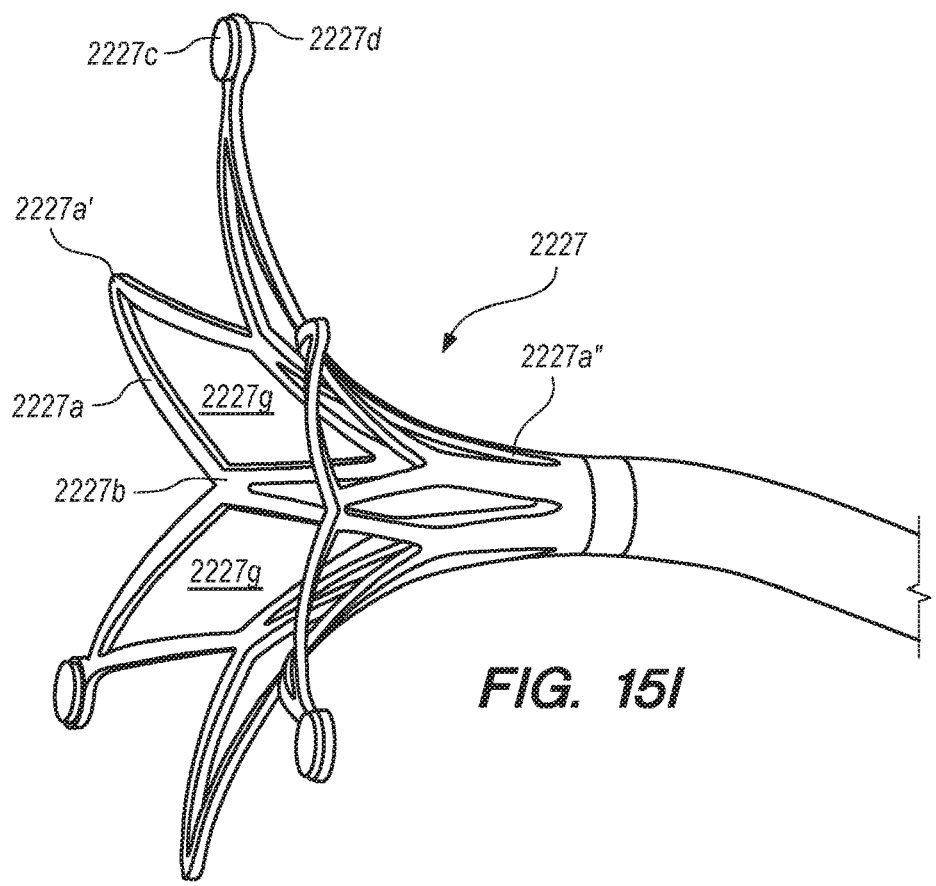
Figure 15J:
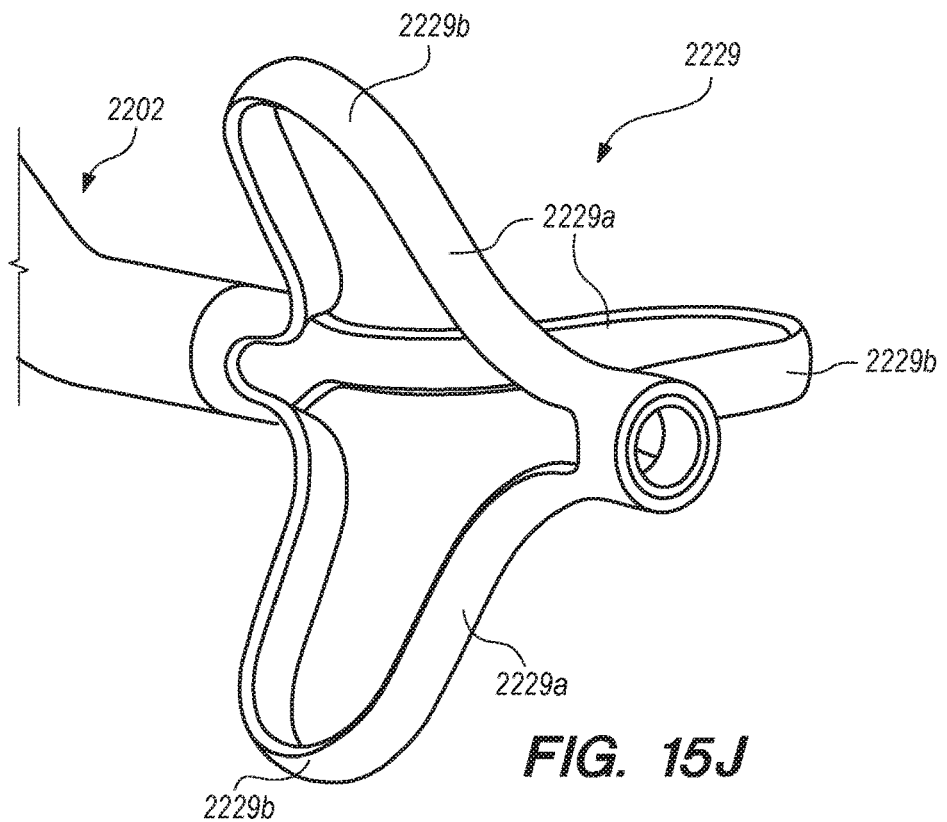

FIG. 15H illustrates exemplary patterns and dimensions of the cuts 2210 along the elongated body 2203 of the shunt 2200. The cuts 2210 of the elongated body 2203 may have a variety of suitable patterns. The cuts 2210 and their patterns are preferably manufactured by laser cutting the elongated body 2203 of the shunt 2200. Alternatively, the cuts 2210 and their patterns may be manufactured by etching or other suitable techniques. For example, with a laser oriented orthogonal to the longitudinal axis of the body 2203 and with a laser capable of holding body 2203 while rotating and advancing the body relative to the fixture, the laser can be activated and deactivated to form specific cut patterns in shunt body 2203. The laser cutting of the elongated body 2203 creates 1.5 cuts 2210 per rotation of the body, having a cut balance of about 210° of rotation with laser on, and then 30° of rotation with laser off. Further, while the pitch of the cut pattern is approximately 0.0070"(0.1778 mm) in the embodiments of FIG. 15H, each cut 2210 may have a variety of widths; for example 0.005"(0.12446 mm). Additionally, the pitch of the cut pattern may be varied. For example, the pitch of the cut pattern of the body 2203 proximately disposed to the proximal portion 2204 and/or to the distal portion 2202 of the shunt 2200 may be larger/ wider than the pitch of the cut pattern along the middle section of the body 2203, as shown in FIGS. 15D-E . . . .

It should be appreciated that the above disclosed units are exemplary dimensions, angles and properties of the shunt 2200, which are not intended to limit the embodiment of FIGS. 15A-K.

As previously disclosed, embodiments of the disclosed shunts can include an anti-thrombotic coating on all or a portion of the exterior of the device, to minimize clotting in the IPS after shunt deployment. Such anti-thrombotic coatings may comprise phosphorylcholine (e.g., Lipidure® products available from NOF Corporation) or Heparin-based compositions (e.g., CBAS® Heparin Surface available from Carmdea AB). Anti-thrombotic coatings can also be applied to anchor 700 and/or elongate guide member 780 to further minimize the risk of clotting in the IPS during the shunt implant procedure.

Figure 16:
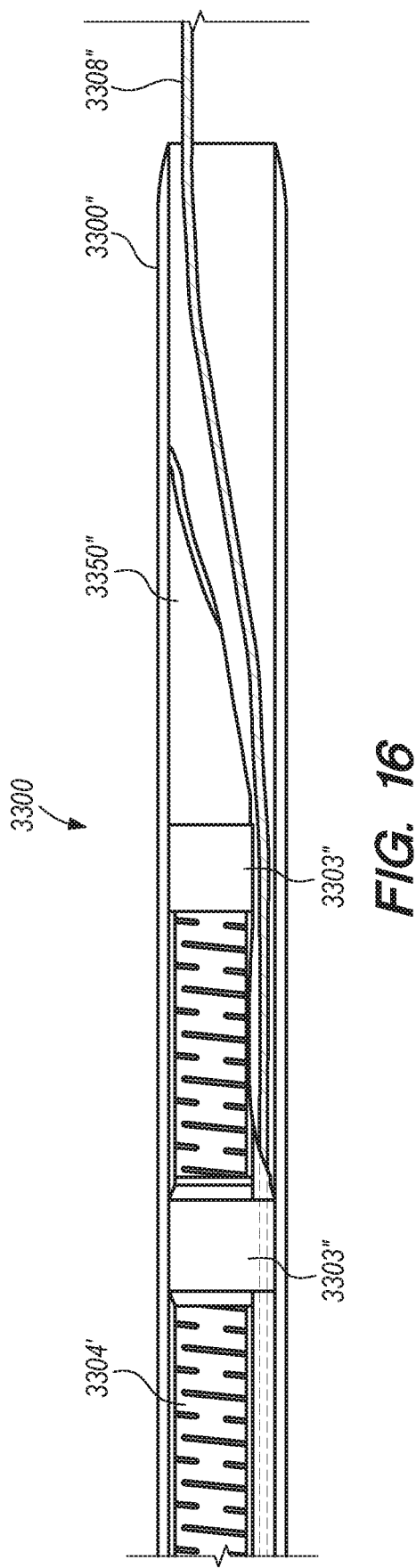
FIG. 16 is a cross-sectional views of an alternative delivery catheter, constructed according to embodiments of the disclosed inventions.

FIG. 16 illustrates a delivery catheter 3300, constructed according to embodiments of the invention. The delivery catheter 3300 (or distal most portion of the delivery catheter) can include an oversheath member 3300" (e.g., a larger, concentric sheath that covers the outer diameter of the delivery catheter and/or the penetrating element). The oversheath 3300" can translate longitudinally about the delivery catheter, and can be retracted proximally to expose the needle tip 3350" for the penetration step of the procedure. The oversheath 3300" of FIG. 16 is disposed over a delivery catheter 3304 and penetrating element advanced over a guide member 3308"; the bands 3303" located proximal of the penetrating element comprise radiopaque markings to confirm orientation of the penetrating element and assess penetration trajectory during a shunt deployment procedure. The oversheath member covers the penetrating element as the delivery system navigates through the patient's vasculature, thereby preventing inadvertent vessel punctures. The operator can position the distal portion of the oversheath adjacent or abutting the target site penetration along IPS wall 114 until the operator is ready to expose the penetrating element or advance the penetrating element through the tissue into the CP angle cistern 138.

Figure 18D:
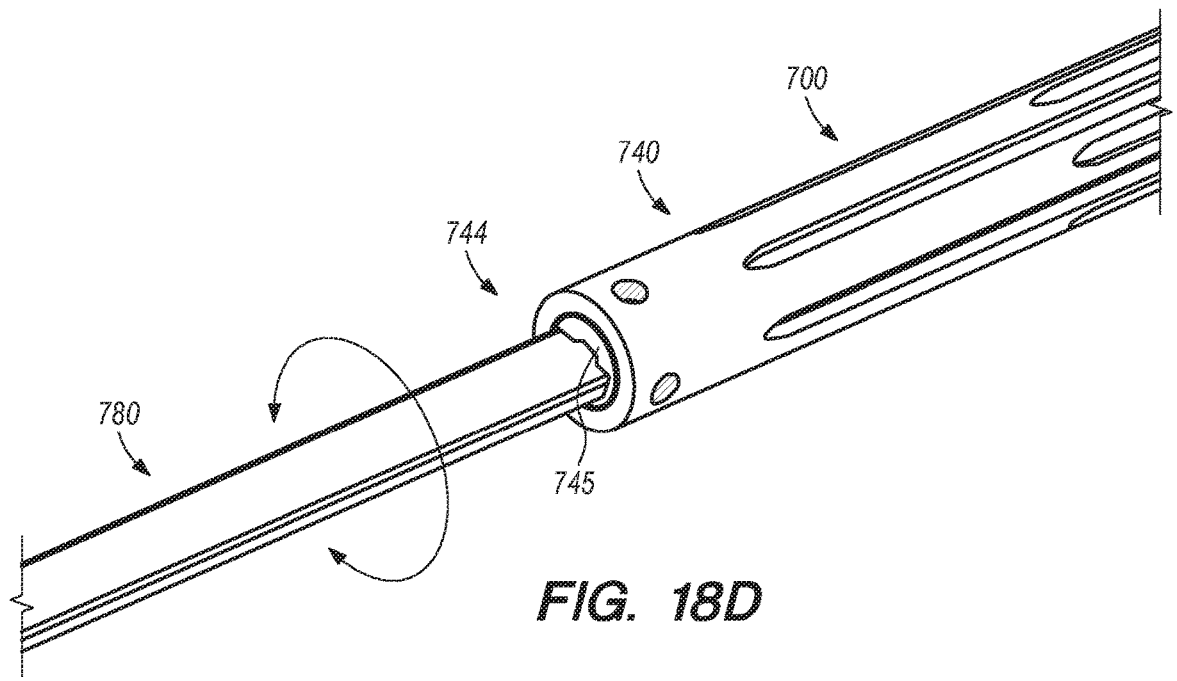
Figure 18E:
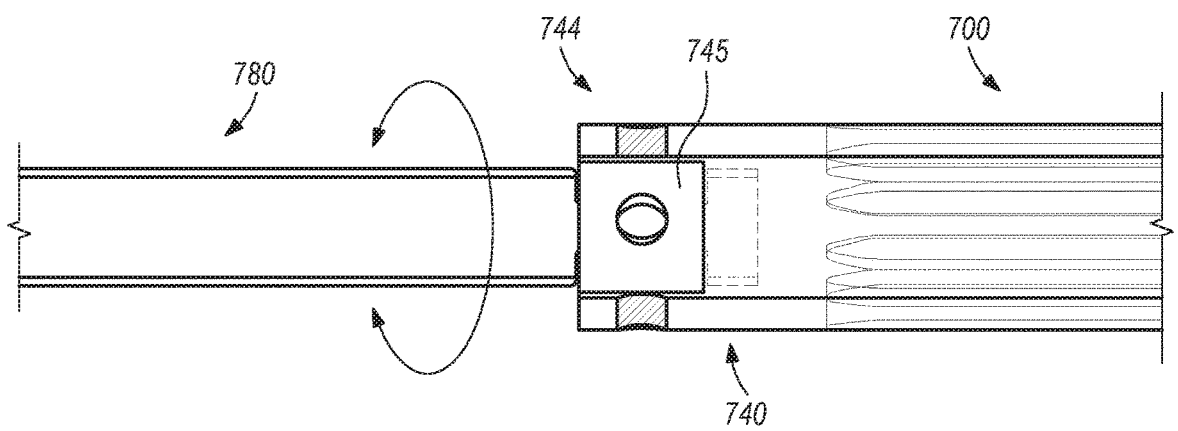

As described above, FIGS. 17A-B illustrate an exemplary elongate guide member 780 for delivering of the anchor 700 at a target site, constructed according to the disclosed inventions. FIGS. 18A-E illustrate another exemplary elongate guide member 780 for delivering of the anchor at a target site, constructed according to the disclosed inventions. The elongate guide member 780 of FIGS. 18A-E includes a flat, rectangular cross-sectional profile, as described in FIG. 3D and FIG. 11. As shown in FIGS. 18A-E, the elongate guide member 780 is coupled to the proximal portion 740 of anchor 700 via joint 744, as previously described (e.g., directly or indirectly, fixedly or detachably coupled or the like). FIGS. 18A-E illustrate exemplary dimensions and properties of the interface of the elongate guide member 780 with the anchor 700, which are not intended to limit the embodiment of the interface disclosed herein. In the embodiments of FIGS. 18D-E, the joint 744 between the anchor 700 and the elongate guide member 780 includes a rotatable element 745 configured to allow the elongate guide member 780 to rotate clockwise and/or counter-clockwise with respect to the anchor 700. The independent rotation of the elongate guide member 780 relative to the anchor 700 via the rotatable element 745 at the joint 744 allows for the elongate guide member 780 to assume a desirable orientation through the curved portion of the IPS 102 during delivery and/or after deployment of the anchor 700. For example, the anchor 700 may be delivered at a random orientation at the IPS 102, yet the elongate guide member 780 would assume a desirable orientation by rotating (if needed).

FIGS. 19A-I depict an embodiment of a delivery assembly 300 comprising delivery catheter 3304 and penetrating element guard or guard member 4000. The guard member 4000 covers the penetrating element 3350 during navigation of the delivery catheter 3304 (FIG. 19A) through the patient's vasculature to the target penetration site on IPS wall 114 and during withdrawal of delivery catheter 3304 after shunt deployment, thereby preventing inadvertent puncture or damage to other components of delivery assembly (e.g., guide catheter) and the patient's vasculature. As will be further described below, the clinician can actuate a pull wire 4010 to retract guard 4000 proximally and expose the penetrating element 3350 to the dura of IPS wall 114 prior to the penetration step of the shunt implant procedure and, optionally, then re-cover the penetrating element 3350 after the penetration step (e.g., after distal anchoring mechanism 229 of the shunt has been deployed). Radiopaque markers located on the guard 4000 and delivery catheter 3304 provide an indication of whether the guard has been retracted and penetrating element 3350 is exposed or the guard remains in a delivery configuration, covering the penetrating element 3350 for navigation through the patient's vasculature, as will be further described below.

Figure 19A:
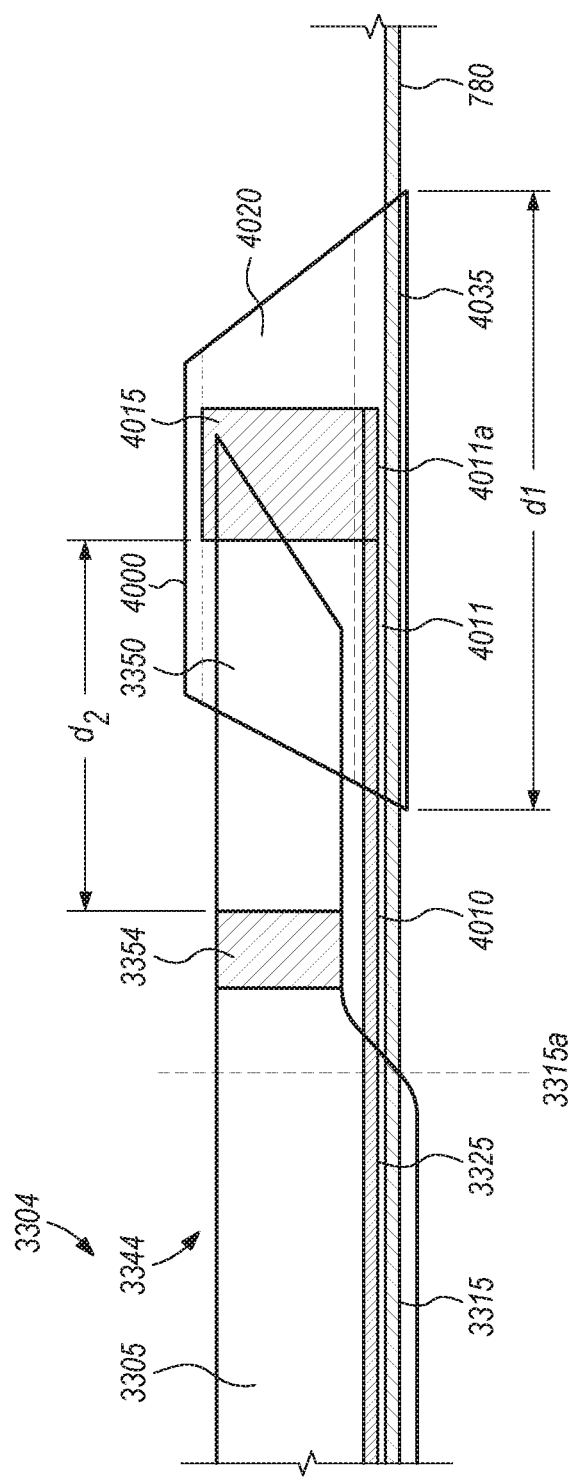

With reference to FIG. 19A, the distal portion 3344 of delivery catheter 3304 comprises penetrating element 3350 and a radiopaque marker 3354. As previously described, delivery catheter 3304 includes a first lumen 3315 to accommodate elongate guide member 780 and a second lumen 3305 to accommodate a shunt 2200 (not shown). The guard member 4000 comprises a pull wire 4010, the pull wire 4010 having a distal portion 4011 attached to a guard body 4000, where the pull wire 4010 is configured to translate the guard body 4000 proximally or distally relative to the shunt delivery catheter 3304 so as to at least partially expose or cover, respectively, the penetrating element 3350. The distal portion 4011 of pull wire 4010 is embedded or encased within guard 4000 (as will be further described below) and includes an attachment point 4011a (e.g., a weld) to radiopaque marker 4015 also embedded within guard 4000 (as will be further described below). The guard 4000 further comprises a first lumen 4020 configured to receive the penetrating element 3350 and allows the guard 4000 to retract proximally (direction of left-hand arrow d2 in FIG. 19A) over the penetrating element 3350 and distal portion of 3344 of delivery catheter and distally (e.g., to re-cover penetrating element 3350, direction of right-hand arrow d2 in FIG. 19A) via pull wire 4010. The enlarged circumference in the distal portion 3344 of delivery catheter 3304 at interface point 3315a where the elongate guide member 780 enters the first lumen 3315 of the delivery catheter prevents guard 4000 from retracting further proximally over the delivery catheter. Guard 4000 can advance distally, via pull wire 4010 and as will be further described below, to re-cover penetrating element 3350. As shown in FIG. 19A, the shunt delivery catheter 3304 includes a third lumen 3325 that extends throughout the length of the delivery catheter, from the distal portion 3344 to the proximal portion 3342; third lumen 3325 accommodates pull wire 4010 of guard 4000.

FIGS. 19B and 19C show cross section and perspective views, respectively, of penetrating element guard or guard member 4000. FIG. 19B depicts a guard member 4000 in a delivery configuration with respect to the distal portion 3344 of delivery catheter 3304 (represented by dashed lines in the figure), covering penetrating element 3350. Penetrating element 3350 is positioned within lumen 4020 of the guard 400 and inside of radiopaque marker 4015 embedded or encapsulated within the walls of guard 4000 (as will be further described below). The guard member 4000 can be approximately 0.5" (1.27 cm) long or other suitable dimensions sufficient to cover penetrating element 3350 on the distal portion 3344 of the delivery catheter. The guard lumen 4020 is sized to allow guard 4000 to retract proximally over the penetrating element 3350 and distal portion 3344 of the delivery catheter, indicated by the direction of the left-hand arrow d2 shown in FIG. 19A. For example, the inner diameter of guard lumen 4020 can be approximately 0.0385" (0.09779 cm).

Marker 4015 comprises a cylindrical profile (as can be seen in FIGS. 19B-D and 19G) such that penetrating element 3350 can reside inside of marker 4015 and the guard first lumen 4020 as depicted in FIG. 19A; the alloy material of marker 4015 shields the concentrically disposed penetrating element 3350 and can prevent the penetrating element from inadvertently puncturing through the guard 4000 when the distal portion of 3344 of delivery catheter 3304 bends as the clinician navigates the delivery assembly 300 through tortuous anatomy to the target penetration site along IPS wall 114. The distal portion 4004 of the guard 4000 has a beveled/tapered edge, as shown in FIGS. 19B and 19C. The bevel/taper facilitates access to narrow or tortuous vasculature as the clinician navigates the delivery assembly distally beyond the inferior vena cava (e.g., to access and navigate through junction 118 of jugular vein 106 and IPS 102). The guard 4000 may comprise a second lumen 4035 to accommodate elongate guide member 780 as shown in FIG. 19C. The delivery assembly 300 comprising delivery catheter 3304 and guard 4000 can advance along the elongate guide member 780 distally, toward the target penetration site; that is, the guide member 780 passes through second lumen 4035 of the guard 4000 and lumen 3315 of delivery catheter 3304 to assist delivery catheter navigation through the patient's vasculature.

FIG. 19D depicts the pull wire 4010 and radiopaque marker 4015 subassembly of guard 4000. Pull wire 4010 can comprise PFTE-coated stainless steel or other suitable materials. The diameter of pull wire 4010 can range from about 0.003" to 0.012" (0.0762 mm to 0.3048 mm). While pull wire 4010 depicted in FIG. 19B-D has a circular cross-sectional profile, other pull wire embodiments can include non-circular cross-sectional profiles (e.g., rectangular, crescent). The PTFE coating on pull wire 4010 increases the lubricity of the wire within the third lumen 3325 of delivery catheter 3304, thereby facilitating smooth proximal and distal actuation of guard 4000 to expose and re-cover penetrating element 3350 (not shown in FIG. 19D). Radiopaque marker 4015 can comprise platinum-iridium 90/10 alloy or other suitable materials that provide sufficient radiopacity and allow for a connection point 4011a between the marker and distal portion 4011 of pull wire 4010. The inner diameter of marker 4015 can be 0.0385' or other suitable dimensions compatible with a guard lumen 4020 sufficient to accommodate the distal portion of delivery catheter 3344 and penetrating element 3350. As shown in FIG. 19D, the distal portion 4011 of pull wire 4010 does not include the PTFE coating depicted on the body portion of pull wire 4010; the uncoated stainless steel distal portion 4011 of pull wire allows for a weld or other connection point 4011a to radiopaque marker.

Figure 19E:
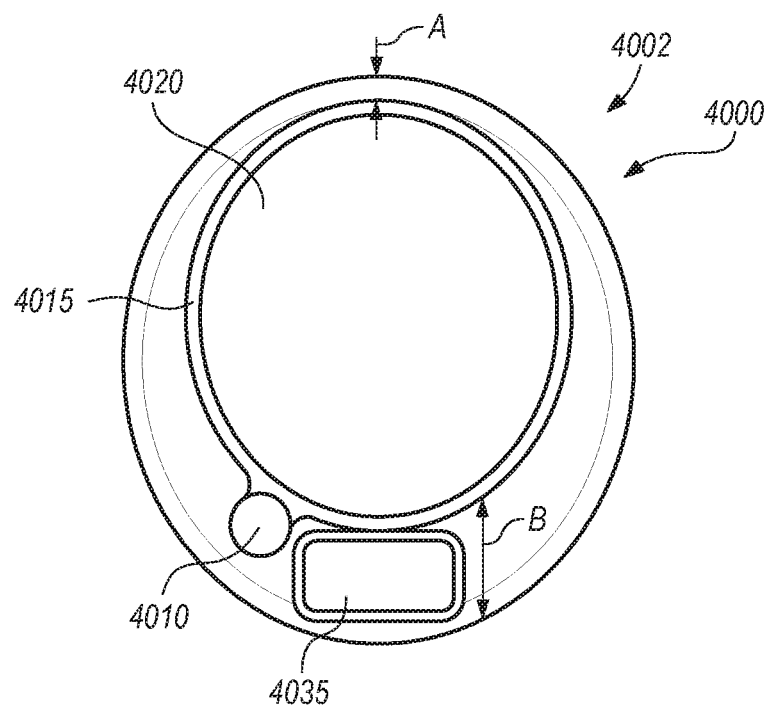
Figure 19F:
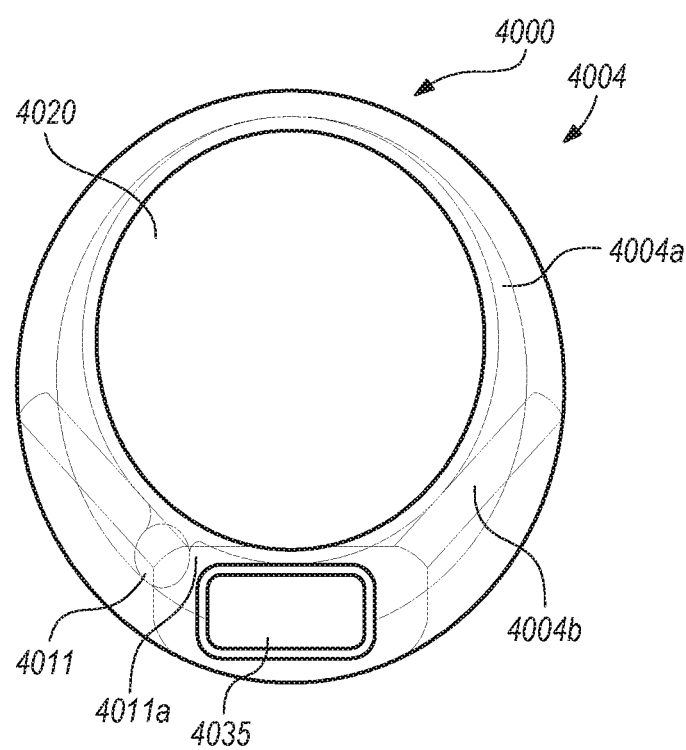

FIGS. 19E and 19F show cross section views of the proximal portion 4002 and distal portion 4004, respectively, of the guard member 4000. As depicted in FIG. 19E, marker 4015 and pull wire 4010 are embedded or encapsulated within the wall of guard 4000. Guard 4000 can comprise polymeric materials such as polyether block amide (Pebax®) available from Arkema Group), HTPE, PTFE, urethanes or the like. Pebax embodiments of guard 4000 can range from 27D to 70D hardness (e.g., Pebax 63D). The wall thickness of guard 4000 can vary depending on top-to-bottom orientation of the guard. The top portion of guard 4000 (represented by line A in FIG. 19E) can range from about 0.002" to 0.006" (0.0508 mm to 0.1524 mm) or larger. The bottom portion of guard 4000 (represented by line B in FIG. 19E) can range from about 0.008" to 0.014" (0.2032 mm to 0.3556 mm) or larger.

As previously disclosed and during the shunt implant procedure, an clinician can deploy an anchor 700 distal to a target penetration site along IPS wall 114. Thereafter, the clinician advances a delivery assembly 300 comprising delivery catheter 3304 and penetrating element guard 4000 via elongate member 780 to the target penetration site. The radiopaque marking 3354 on the distal portion 3344 of the delivery catheter 3304 and radiopaque marking 4015 within guard 4000 provide reference points for the clinician to visualize the location of the delivery assembly and penetrating element 3350 at the target penetration site. When the clinician is prepared to penetrate IPS wall 114, the clinician can pull the proximal end of pull wire 4010 proximally, which retracts guard 4000 proximally over the distal portion 3344 of delivery catheter (indicated by the direction of the left-hand arrow d2 shown in FIG. 19A) and exposes penetrating element 3350 from the delivery assembly 300. Observing the transition of marker 4015 in guard 4000 proximally towards and/or until it abuts marker 3354 on the distal portion 3344 of the delivery catheter (e.g., in the direction of arrow d2 shown in FIG. 19A) confirms that guard 4000 actuated properly and penetrating element 3350 is exposed from the delivery assembly in the patient's vasculature. Conversely, after shunt implantation, the clinician can advance pull wire 4010 distally to re-cover penetrating element 3350 and confirm that the guard 4000 is in a delivery or withdrawal configuration (e.g., penetrating element not exposed in IPS 102 or jugular vein 106 lumens).

FIG. 20 depicts an alternate embodiment of penetrating element guard 4000. For ease in illustration, like features of the penetrating element guard 4000 and delivery catheter 3304 shown in FIG. 20 have been given the same reference numerals from FIGS. 19A-F. Guard 4000 comprises a guard 4000 having a full-length, "oversheath" configuration; that is, guard 4000 is a sheath that extends along the length of and over the delivery catheter 3304 disposed concentrically within guard lumen 4020. Guard 4000 can be retracted proximally (direction of left-hand arrow D2 in FIG. 20), e.g., by a clinician pulling on the proximal portion of guard 4000 to uncover and expose a protected penetrating element 3350. Optionally, guard 4000 can include a scored or weakened portion (e.g., indicated by dotted line d1 in FIG. 20) that splits or tears (e.g., along the longitudinal axis of the guard) to facilitate guard retraction.

Guard 4000 includes a second lumen 4035 that accommodates elongate guide member 780. Lumen 4035 can extend from the distal portion or end of guard 4000 and include an exit port 4035a located in the distal portion of guard 4000, as shown in FIG. 20. As compared to the guard configuration described in connection with FIGS. 19A-F, the guard configuration shown in FIG. 20 simplifies the design of the delivery assembly 300 by eliminating pull wire 4010 and a corresponding pull wire lumen 3325 in the delivery catheter 3304.

FIGS. 21A-M depict an alternate embodiment of delivery catheter 3304. FIGS. 21C and D show longitudinal side and cross section views, respectively, of delivery catheter 3304. FIGS. 21A and B show cross section views of delivery catheter 3304 at reference lines in FIG. 21C, respectively, looking from the distal portion 3344 of the catheter towards the proximal portion. FIG. 21I shows another longitudinal side view of the delivery catheter of FIGS. 21A-M. FIGS. 21F-M depict cross section views of delivery catheter 3304 at various points along the longitudinal axis corresponding to the reference line designations in FIG. 21I.

With respect to FIGS. 21C, D, and I, the depicted delivery catheter 3304 includes a beveled-needle penetrating element 3350 on the distal portion 3344 of the delivery catheter. The penetrating element 3350 can be fixed to the delivery catheter and, as depicted, is welded to reinforcing member 1345 (further described below). Delivery catheter includes three distinct radiopaque marker bands: a distal most marker 3354 located about the proximal portion of penetrating element 3350, an intermediate marker 3354a, and proximal most marker 3345b. A first lumen 3315 in the delivery catheter accommodates elongate guide member 780 and lumen 3315 can include a polymeric liner 3306 material such as PTFE (FIG. 21B) to increase the lubricity of the lumen and facilitate smooth motion of the delivery catheter 3304 over guide member 780.

As depicted, first lumen 3315 has a rapid-exchange configuration and does not span the entire longitudinal axis of deliver catheter 3304, although such a configuration is possible in other embodiments. Marker bands 3354a and 3354b reinforce the distal 3315a and proximal 3315b openings of lumen 3315, as shown in FIGS. 21A and 21K-L. FIG. 21D includes longitudinal dimensions along the length of delivery catheter 3304, measured from the proximal portion of penetrating element 3350 to the distal opening 3315a of first lumen 3315 (0.16"/0.4064 cm), to the distal edge of marker band 3354a (0.17"/0.4318 cm), to the distal edge of marker band 3354b (7.95"/20.193 cm), to the proximal opening 3315b of first lumen 3315 (8"/20.32 cm), and to the proximal portion of delivery catheter 3304 (39.37"/100 cm). Further, delivery catheter 3304 includes a second lumen 3305 to accommodate a shunt and shunt pusher delivery assembly as disclosed herein. Second lumen 3305 includes a polymeric liner material 3306 as indicated in FIGS. 21E, 21E-1, 21E-2 to FIG. 21M, such as PTFE.

The outer diameter of delivery catheter 3304 of FIGS. 21A-M varies along the longitudinal axis. The cross section views of FIGS. 21F-M, working from the distal most cross-section to the proximal most cross-section along the axis of delivery catheter 3304, correspond to the reference lines shown in FIG. 21I as follows: FIG. 21J at reference line E-E in FIG. 21I; FIG. 21F at reference line F-F in FIG. 21I; FIG. 21K at reference line G-G in FIG. 21I; FIG. 21G at reference line H-H in FIG. 21I; FIG. 21L at reference line I-I in FIG. 21I; FIG. 21H at reference line J-J in FIG. 21I; and FIG. 21M at reference line K-K in FIG. 21I. Each of FIGS. 21A-B and F-M specify the maximum outer diameter along the longitudinal axis of the delivery catheter 3304 at the location of the particular cross section depicted, which varies depending on the longitudinal location of the cross section along the axis of the catheter (e.g., ranging from 0.036" to 0.046"/0.09144 cm to 0.11684 cm). FIGS. 21K, 21F, and 21J depict a gradually tapering outer diameter in the distal portion of the delivery catheter 3304, moving in the distal direction along the axis of the catheter (i.e., from 0.046" to 0.036"/0.11684 to 0.09144 cm), which facilitates access to tortuous anatomy and narrowings in the vasculature (e.g., junction 118 of jugular vein 106 and IPS 102).

While FIGS. 21A-M and the foregoing description reference a two-lumen delivery catheter 3304, additional embodiments of the delivery catheter can include a third lumen (e.g., lumen 3325 of 19A, FIGS. 29A-D to accommodate, for example, a pull wire of a penetrating element guard 4000, as further described below) and fourth lumen (e.g., lumen of to accommodate, for example, a second pull wire of a penetrating element guard 4000, as further described below and shown in FIGS. 64D-E).

Criteria for selecting a particular needle as the penetrating element 3350 of a delivery assembly 300 include bevel length, force required to penetrate IPS wall 114, and needle wall thickness. Bevel length is inversely related to the puncture force required to penetrate IPS wall, though longer bevels can make navigation of delivery assembly 300 more difficult as compared to shorter bevels, particularly in tortuous anatomy, given that needles do not flex as the distal portion 3344 of the delivery catheter 3304 navigates through the vasculature. Lower puncture forces facilitate a smooth penetration step of the shunt implant procedure, as the penetrating element passes through IPS wall 114 into the subarachnoid space. Puncture force for candidate penetrating element embodiments can be assessed in vitro using a dura surrogate, e.g., DuraGuard® Dural Repair Patch available from Synovis Surgical Innovations, and force gauge as further described in U.S. patent application Ser. No. 14/929, 066 filed on Oct. 30, 2015. Penetrating element embodiments comprising a needle configuration can have a puncture force of about 0.1 pounds-force or less. A thinner needle wall minimizes the gap between the anastomosis through IPS wall 114 and the outer surface of deployed shunt 2200. Reducing this gap is clinically significant to minimize or eliminate venous blood from leaking from the IPS 102 or CS 104 through the anastomosis (e.g., between the penetration tract through IPS wall 114 and the outer surface of implanted shunt 2200) into the subarachnoid space and, conversely, CSF leaking from the subarachnoid space into the IPS lumen.

Figure 22A:
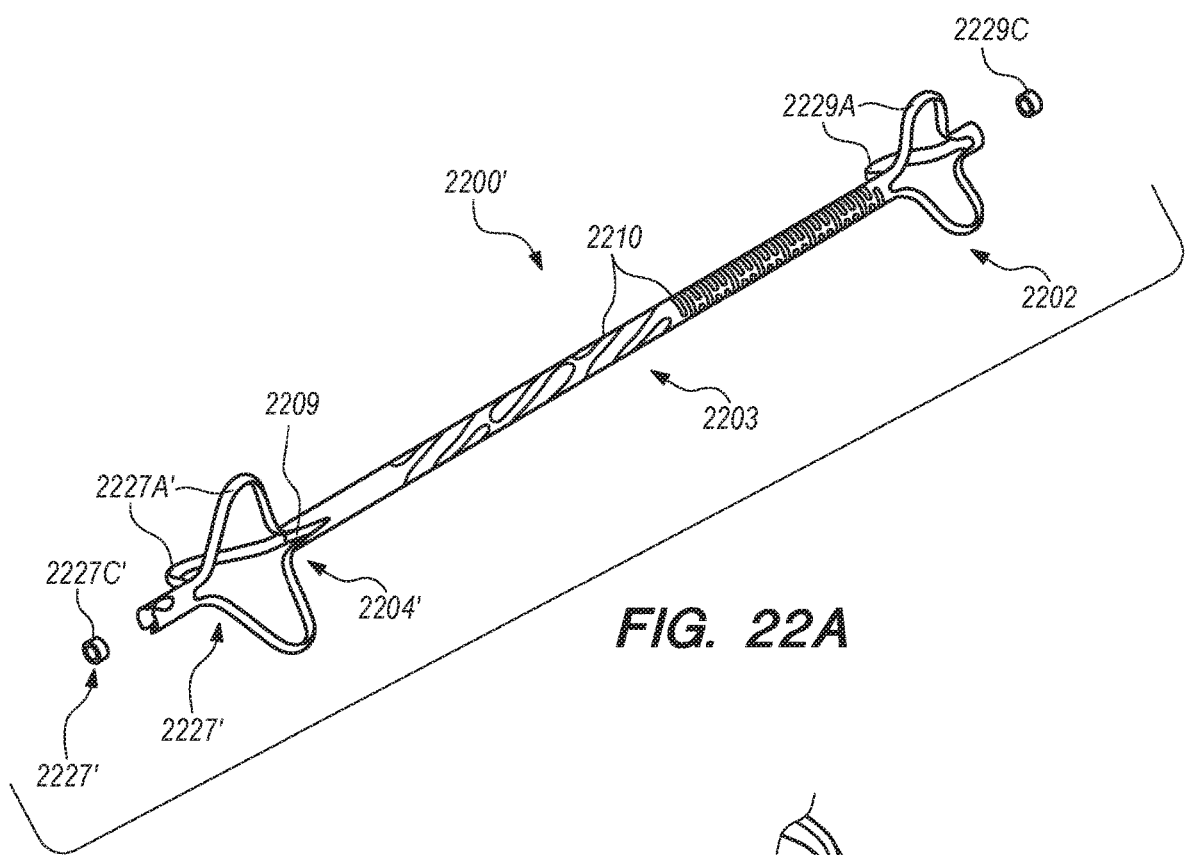
FIGS. 22A-F are side, perspective and cross-sectional views of a shunt constructed according to embodiments of the disclosed inventions.
Figure 22B:
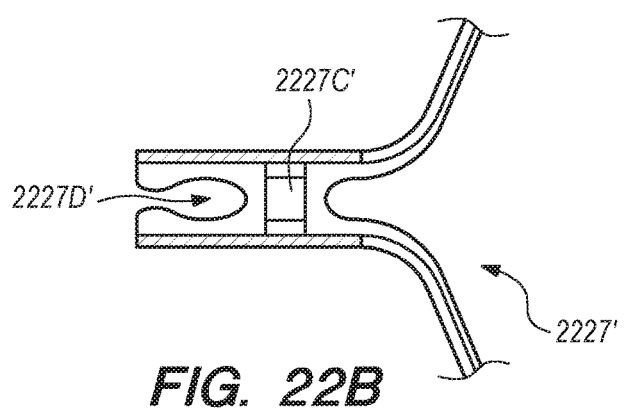
Figure 22C:
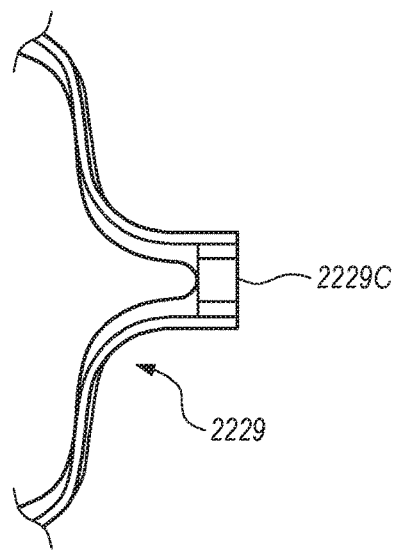
Figure 22D:
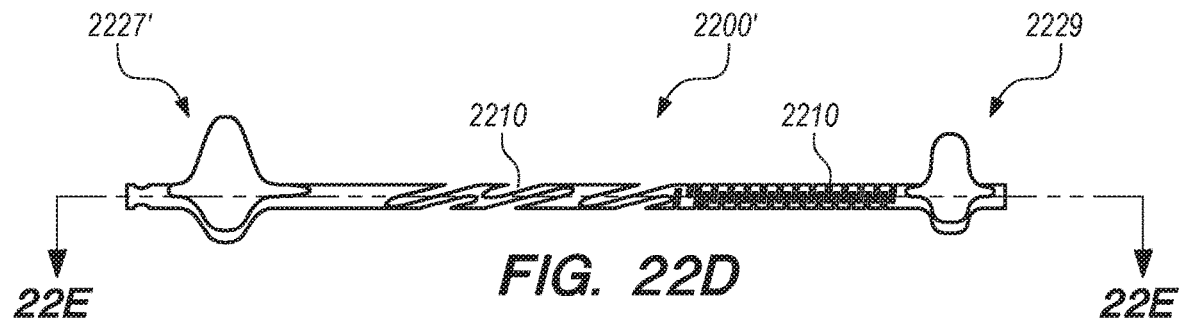
Figure 22E:
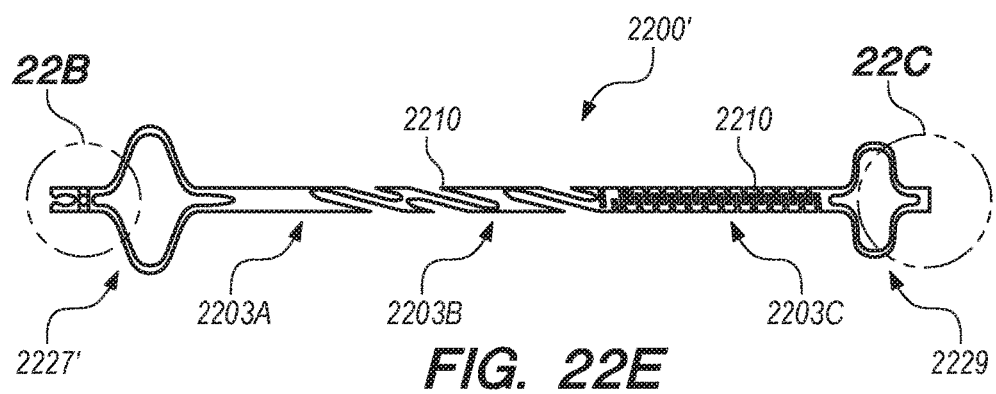
Figure 22F:
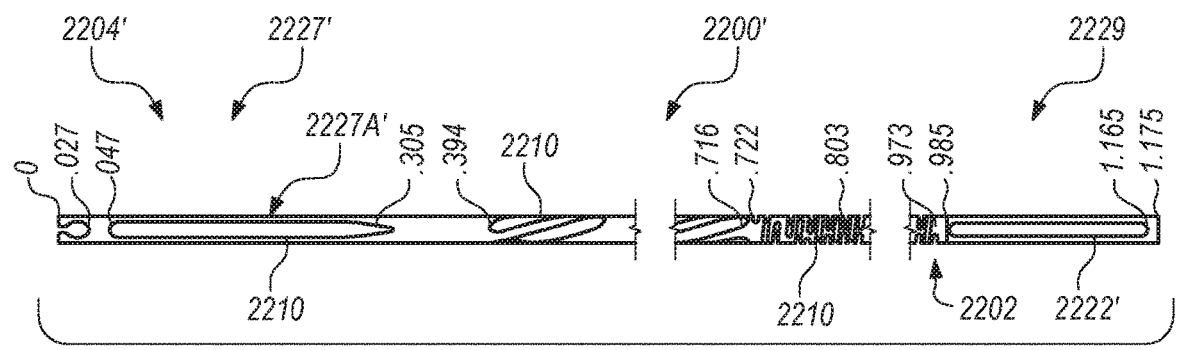

FIGS. 22A-F illustrate yet another exemplary shunt 2200' constructed and implanted according to embodiments of the disclosed inventions. For ease in illustration and disclosure, the features, functions, and configurations of the shunt 2200' that are the same as in the shunt of the present disclosure (e.g., FIGS. 15A-J) and in the related application, are incorporated by reference herewith; the differences will be described in further detail below. The shunt includes an elongate body 2203 extending between the proximal 2204' and distal 2202 portions and having a lumen. The body 2203 of the shunt includes selective cuts 2210 (e.g., kerfs, slots, key-ways, recesses, or the like) forming transition areas configured to vary the flexibility of the shunt 2200', such as, from the proximal portion 2203a (less flexible) to the distal portion 2203c (more flexible), as shown in FIGS. 22A and 22D-E. As better appreciated in the embodiment of FIG. 22E, the proximal portion of the shunt further includes an anchoring mechanism 2227' (i.e., proximal anchor), similar to the distal anchoring mechanism 2229 of the shunt 2200' and previously described distal anchoring mechanism 2229. The anchoring mechanisms 2227' and 2229 include a plurality of respective deformable elements 2227a' and 2229a (e.g., arms) that are disposed radially outward in the deployed configuration of the shunt. As shown in FIGS. 22A-B and 22D-E, the proximal anchoring mechanism 2227' further includes a proximal interlocking element 2227d' (e.g., eyelet, slot, groove, or the like) configured to interlock with corresponding interlocking elements 3336'/3336b of a pusher member. The proximal interlocking element is better appreciated in FIGS. 22B, and 22F. The anchoring mechanisms 2227' and 2229 include radiopaque markers 2227c' and 2229c (e.g. annular, ring, angled-arrow marker or the like), which are shown as press flush in FIGS. 22A-B.

FIGS. 22A-G discloses exemplary dimensions, cut patterns, angles, configurations and/or properties of the shunt 2200', pusher member 3310', radiopaque markers 2227c', and the interlocking elements 2227d' and 3336'. It should be appreciated that the disclosed dimensions, cut patterns, angles, configurations and/or properties are exemplary and not intended to limit these embodiments.

Figure 23A:
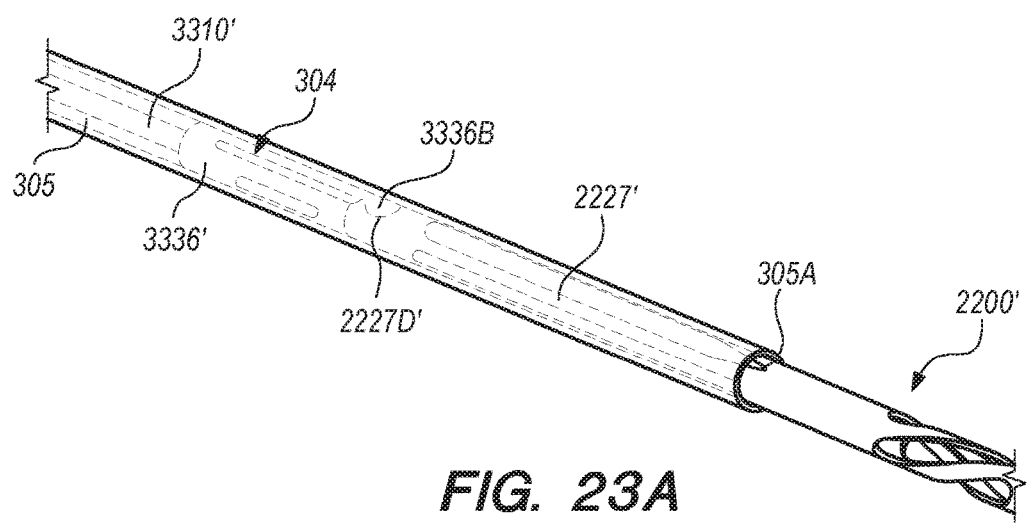
FIGS. 23A-B are side, perspective and cross-sectional views of shunt, pusher member and catheter interface according to embodiments of the disclosed inventions.
Figure 23B:
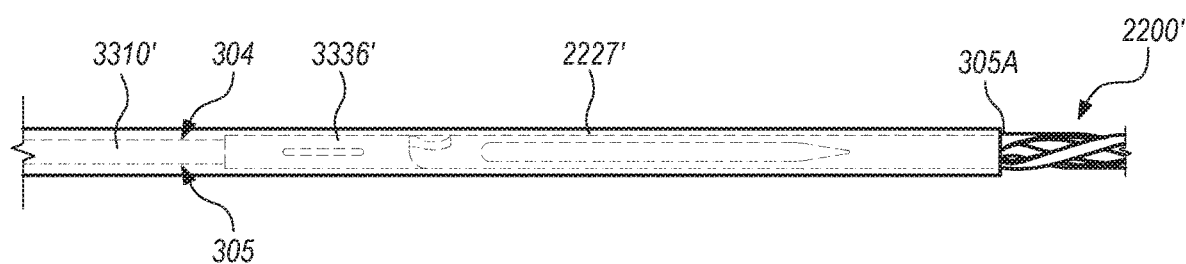

FIGS. 23A-B and 24A-F illustrate exemplary interfaces of the delivery catheter 304, pusher member 3310' and shunt 2200', according to embodiments of the disclosed inventions (e.g., FIG. 6). The delivery catheter 304 may further comprise a hypotube providing suitable column strength and flexibility, as previously described in 12A-C. FIGS. 23A-B, the pusher member 3310' and shunt are disposed within the delivery catheter lumen 305 and having their respective interlocking members 3336'/3336b and 2227d' engaged, as shown in FIGS. 23A-B and FIGS. 24A-B.

FIGS. 23A-B illustrate the pusher member and shunt interface constrained within a delivery catheter 304 and/or the pusher member and shunt interface as if advanced out of the distal end opening of the delivery catheter and before the respective interlocking elements separate to release the shunt 2200' from the pusher member 3310'. Although, the respective interlocking members of the pusher member 3310' and the shunt 2200' are engaged in FIGS. 24A-B, it should be appreciated that pusher member 3310' and shunt 2200' interface will disengage (e.g., pusher interlocking member 3336'/3336a-b outwardly expands or flares out) when the interface is no longer disposed within the delivery catheter lumen 305, as shown in FIGS. 24C-D.

Figure 24C:
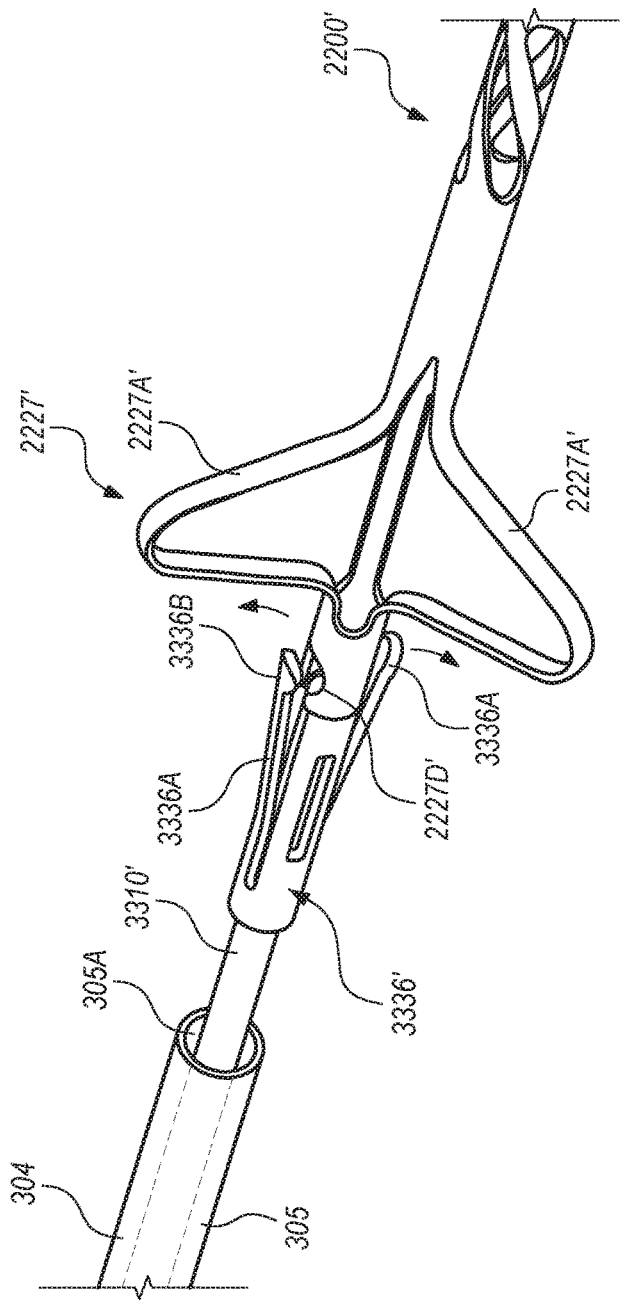
Figure 24D:
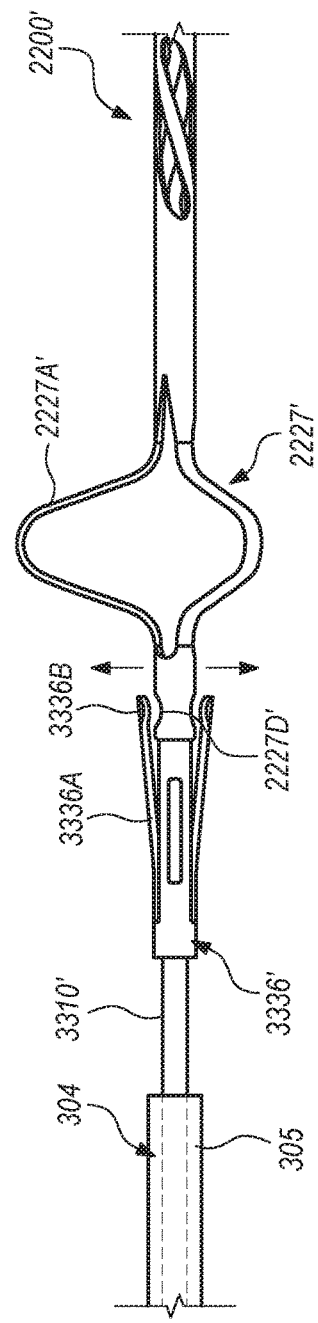

FIGS. 24E-F illustrate the pusher member 3310' and shunt 2200' interface where the interlocking members 3336'/3336a-b of the pusher member 3310' outwardly expanded (e.g., flared out) and the shunt 2200' is disengaged from the pusher member 3310'. Further, the proximal anchoring mechanism 2227' of the shunt 2200' transitions from the delivery configuration (FIGS. 22A-B and FIGS. 24A-B) to the deployed expanded configuration (FIGS. 24C-F).

FIGS. 25A-O illustrate embodiments of the valve 2209" constructed according to embodiments of the disclosed inventions. The shunt 2200 includes at least one valve 2209", as shown, for example, in FIGS. 15A-B. The valve 2209" regulates the rate of CSF flow through the shunt 2200, while allowing flow of CSF only in one direction, i.e., from the distal portion 2202 located in the subarachnoid space to the proximal portion 2204 of the shunt 2200 located in the venous anatomy. The valve 2209 may be disposed at any suitable location within the body 2203 of the shunt 2200, for example, proximate to or at the proximal portion 2204, as shown in FIG. 15A, to the distal portion 2202, and/or in between said portions 2202, 2204 (not shown). In certain embodiments, multiple valves can be disposed at different locations within the shunt 2200.

The valve 2209" can include a specific cracking pressure that, when met or exceeded by the positive pressure gradient between the subarachnoid space and venous system, opens the valve thereby facilitating CSF flow from the CP angle cistern into the jugular vein. For example, the cracking pressure of valve 2209 can be configured from about 3 mm Hg to about 5 mm Hg and/or when the differential pressure between the subarachnoid space and venous system reaches from about 3 mm Hg to about 5 mm Hg; however, other cracking pressures can be configured in valve 2209" depending on the particular clinical needs of the patient and as low as about 0.5 mm Hg. Further, a desired rate of flow is in a range between 5 ml per hour to 20 ml per hour and more desirable between 10 ml per hour to 18 ml per hour under normal differential pressure conditions between the subarachnoid space and venous system. In some embodiments, the desired flow rate of CSF is approximately 10 ml per hour. In a 24-hour period, the flow of CSF through shunt 200 can be between 200 ml to 300 ml (e.g., 200, 225, 250, 275, or 300 cm³).

Figure 25E:
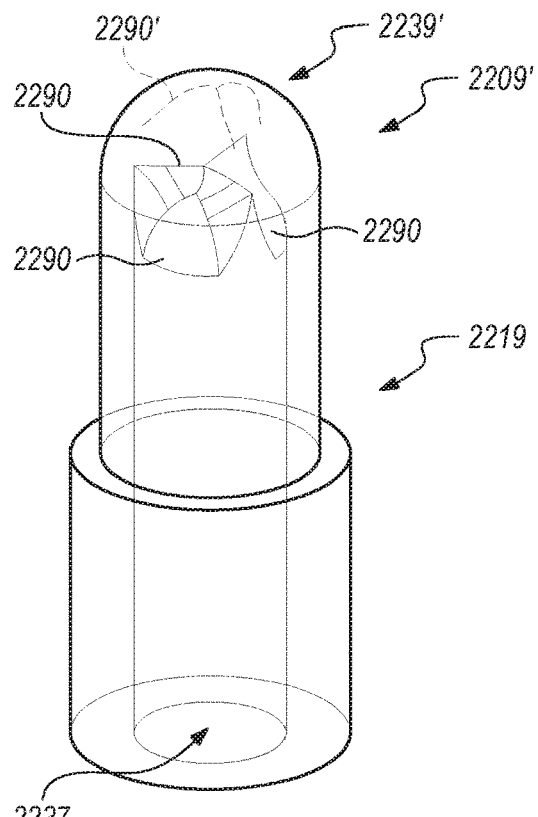
FIGS. 25A-O are side, perspective and cross-sectional views of valves constructed according to embodiments of the disclosed inventions.

The valve 2209 may have a variety of suitable features, and comprises a molded silicone element configured to be coupled to the shunt 2200 in fluid communication with the shunt lumen 2207 and/or liner 2212. For example, the valve 2209' of FIG. 25E is a one-way valve 2209' having a cylindrical body 2219 comprising a lumen 2237 and an end portion dome 2239. The dome 2239' comprises two or more leaflets 2290' on the outer portion of the dome (FIG. 25E) formed from cutting or slitting the part, and two or more leaflets 2290 on the inner portion of the dome 2239' (FIG. 30H) formed through the silicone molding process. The leaflets 2290 and 2290' are configured to open the valve 2209' facilitating CSF flow through the lumen 2237 into the jugular vein 106. The outer leaflets 2290' may be formed by creating cuts or slits in the molded silicone element of the valve 2209'. As shown in FIGS. 25E and 25H, the valve 2209' includes three inner leaflets 2290, similar to a heart valve, molded into the valve. In addition, as shown in FIGS. 25E and 25H, the inner surface of the dome 2239 of valve 2209' can include various tiling patterns to increase the available surface area that fluid flowing through the valve contacts to crack or open the valve from its resting or closed state. Other tiling patterns on the interior portion of the valve dome are possible to accommodate specific valve cracking pressures.

Figure 25F:
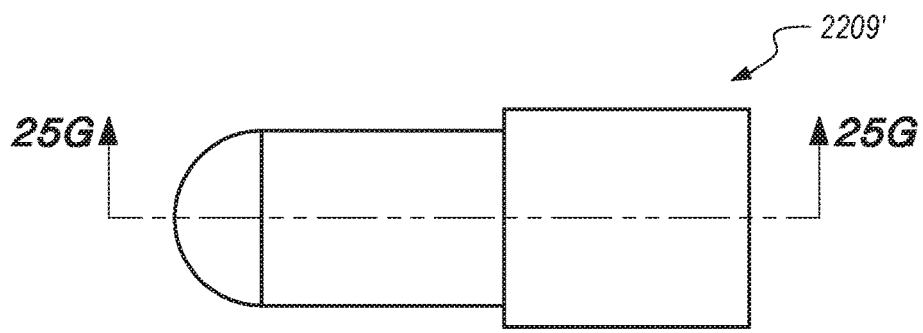
Figure 25G:
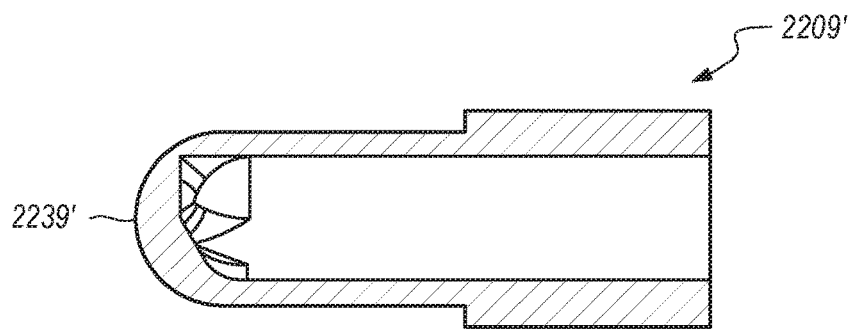
Figure 26A:
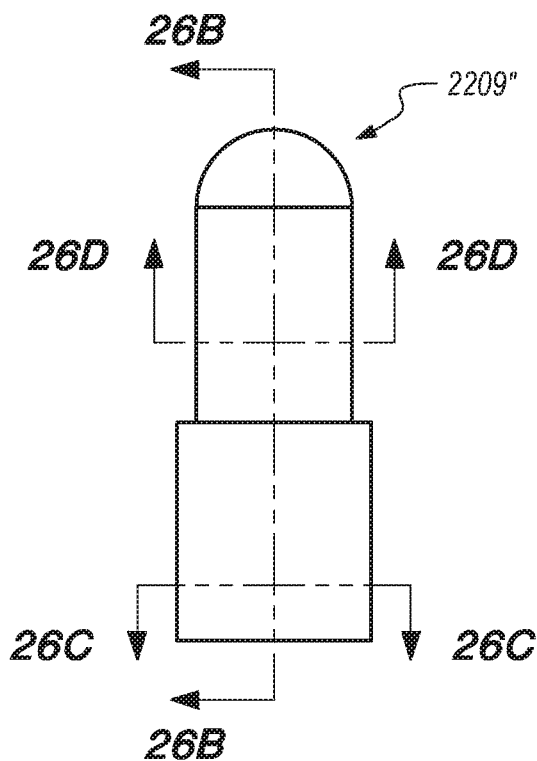
FIGS. 26A-D are side, perspective and cross-sectional views of another valve constructed according to embodiments of the disclosed inventions.
Figure 26B:
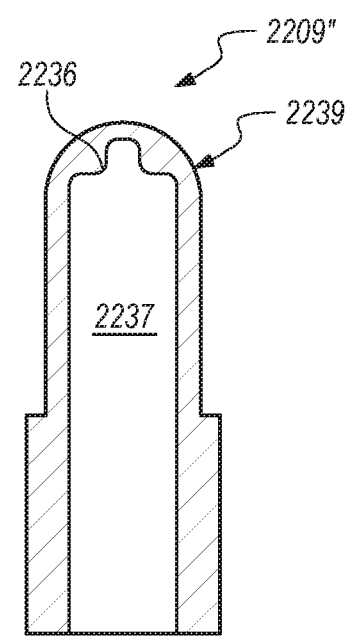
Figure 26C:
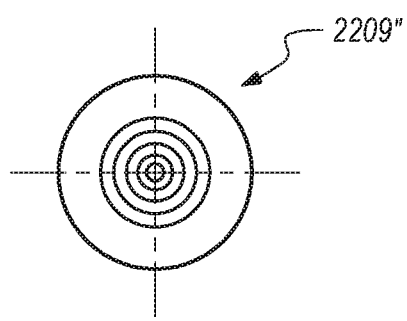
Figure 26D:
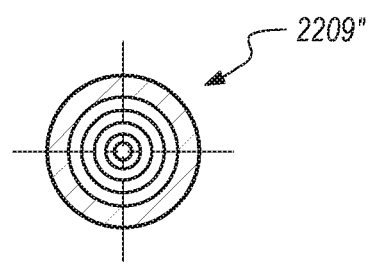
Figure 27A:
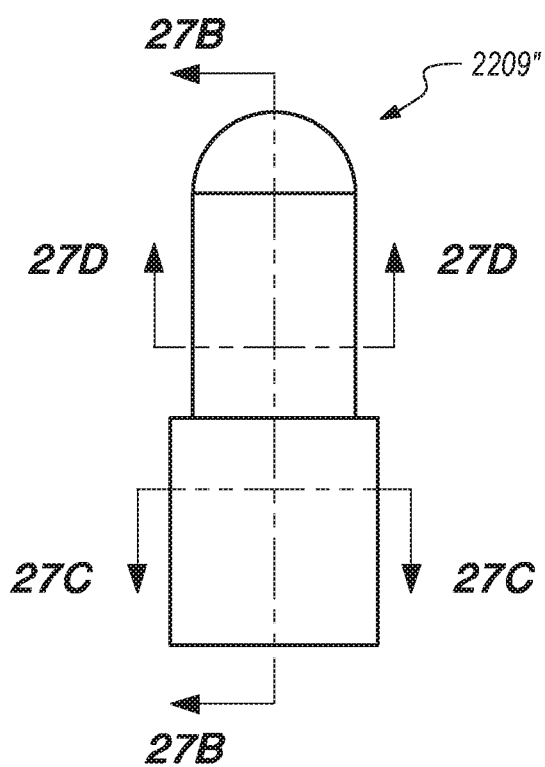
FIGS. 27A-D are side, perspective and cross-sectional views of yet another valve constructed according to embodiments of the disclosed inventions.
Figure 27B:
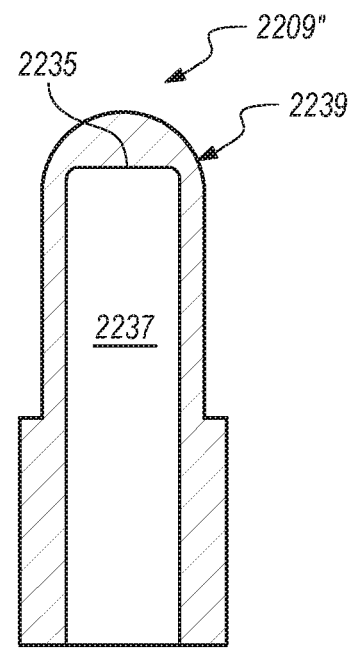
Figure 27C:
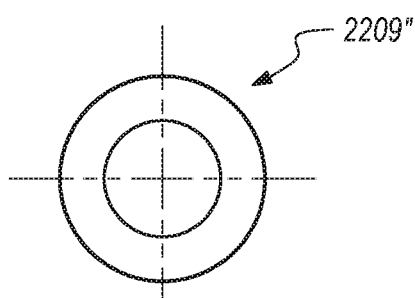
Figure 27D:
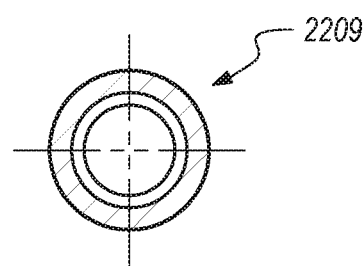

FIG. 25A illustrates an alternate embodiment of valve 2209" comprising a simple dome 2239". Two or more leaflets (not shown) can be created in the dome 2239" in FIG. 25A (e.g., by cutting or slitting with a trocar or blade, using an excimer laser, etc.) to achieve the desired cracking pressure of the valve (e.g., varying the extent of slitting across the surface of the valve dome and/or along the wall of valve 2209"). FIGS. 25B-D illustrate exemplary dimensions (in inches) of the valve 2209"; exemplary dimensions of the dome thickness for molded silicone valves can also range from about 0.001" to 0.004" (0.0254 mm to 0.1016 mm). As shown in FIG. 25B, the cylindrical body 2219 of embodiments of the valve 2209" comprises at least two portions 2219a and 2219b with variable wall thickness, the portion 2219a comprises a larger wall thickness of approximately 0.006" (0.1524 mm) that the portion 2219b having a wall thickness of approximately 0.003" (0.0762 mm), as shown in FIGS. 25B and 25G for valve 2209'. The thicker portion of the valve wall thickness can be used for handing the part during manufacturing or assembly steps, or can be an intended feature of the design (e.g., to allow incorporation into the shunt frame). The length of the portions 2219a of the valve 2209'/2209" is approximately 0.030" (0.762 mm), while the length of the portions 2219b including the dome 223972239" is approximately to 0.040" (1.016 mm), as shown in FIGS. 25B and 25F. The dome 2239' comprises a wall thickness with variable ranges shown in FIGS. 25G and 25I.

FIGS. 25J-O illustrate alternative embodiments of valve 2209 including exemplary dimensions (in inches) having outer leaflets 2290'. As shown in FIGS. 25J-L, the valve 2209''' includes three inner leaflets 2290 (FIG. 25M) and three outer leaflets 2290' (FIG. 25N). FIG. 25J illustrates a perspective view of an embodiment of the valve 2209''' including the three sets of inner and outer leaflets 2290 and 2290', respectively. In addition, the exterior portion of the valve dome 2239'' includes three ribs 2293 as shown in FIGS. 25J and 25N; the outer ribs 2293 can increase the outer surface area of the valve 2209''' to provide more robust backflow prevention of fluid through the valve (e.g., preventing backflow of venous blood through the valve into the subarachnoid space). FIGS. 25K-O illustrate exemplary dimensions (in inches) of embodiments of the valve 2209''' depicted in FIG. 25J. Similarly to FIG. 25C, the cylindrical body 2219 of the valve 2209''' of FIG. 25L comprises at least two portions 2219a and 2219b with variable wall thickness, the portion 2219a comprises a larger wall thickness that the wall thickness of the portion 2219b. For example, the wall thickness of portion 2219a can range from approximately 0.006" (0.1524 mm) to 0.001" (0.0254 mm), and the wall thickness of portion 2219b can range from approximately 0.003" (0.0762 mm) to 0.0003" (0.00762 mm). The length of the portions 2219a of the valve 2209 can range from approximately 0.030" (0.762 mm) to 0.005" (0.127 mm), while the length of the portions 2219b including the dome 2239 can range from approximately to 0.040" (1.016 mm) 0.003" (0.0762 mm), as shown in FIG. 25K. The dome 2239''' comprises a wall thickness with variable ranges shown in FIG. 25O, though alternate embodiments can include thinner or thicker wall thicknesses, e.g., in the dome portion of the valve.

FIGS. 26A-28Q illustrate alternative embodiments of the valve constructed according to embodiments of the disclosed inventions. The shunt includes at least one valve, as shown, for example, in FIGS. 15A-C. The valve regulates the rate of CSF flow through the shunt, while allowing flow of CSF only in one direction, i.e., from the distal portion of the shunt located in the subarachnoid space to the proximal portion of the shunt located in the venous anatomy. Features, functions, and configurations of the valve of FIGS. 26A-28Q that are the same as in the valve of the present disclosure (e.g., FIGS. 25A-O) and in the related application, are incorporated by reference herewith, the differences will be described in further detail below. The valve may have a variety of suitable features, such as comprising a molded silicone element configured to be coupled to the shunt in fluid communication with the shunt lumen. For example, the valve 2209'' of FIGS. 26A-D is a one-way valve having a cylindrical body comprising a valve lumen 2237 and an end portion dome 2239. The valve 2209'' includes a transitional core 2236 (e.g., inner tapered surface of the dome 2239), as better appreciated in the cross-sectional portion of the dome (FIG. 26B). By contrast, the valve 2209'' of FIGS. 27A-D include a non-transitional core 2235 (e.g., inner square or flat inner surface of the dome 2239), as better appreciated in the cross-sectional portion of the dome 2239 (FIG. 27B). Either valve 2239'', having transitional (FIGS. 26A-D) or non-transitional (FIGS. 27A-D) cores 2236 or 2235, respectively, include cuts, slits, holes, perforations or the like (FIGS. 28A-Q) configured to open the valve 2209'' and allow for fluid communication facilitating CSF flow through the shunt when deployed in the target site.

Figure 28A:
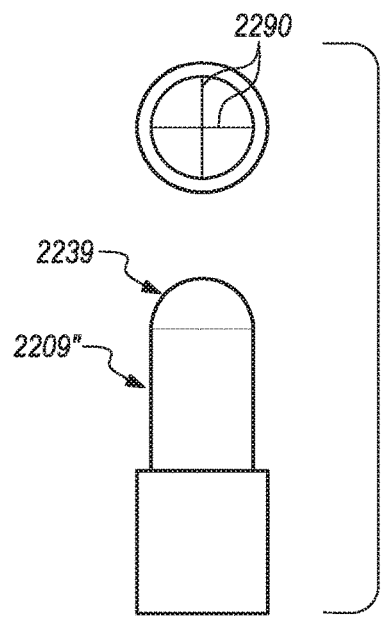
FIGS. 28A-Q are side, perspective and cross-sectional views of valves constructed according to further embodiments of the disclosed inventions.
Figure 28B:
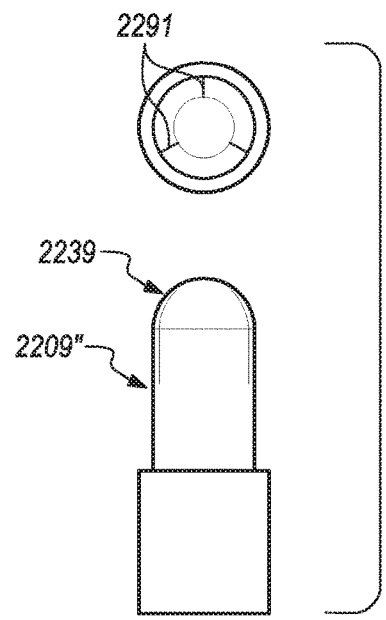
Figure 28C:
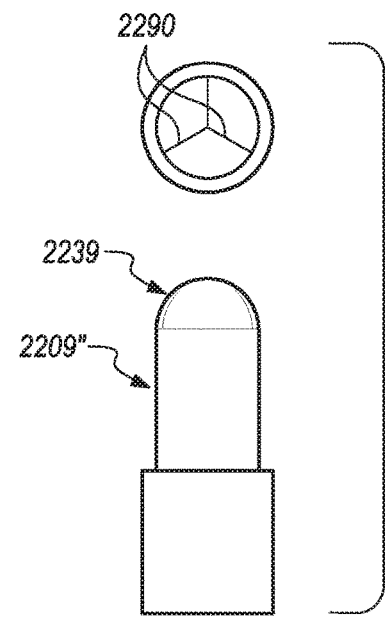
Figure 28D:
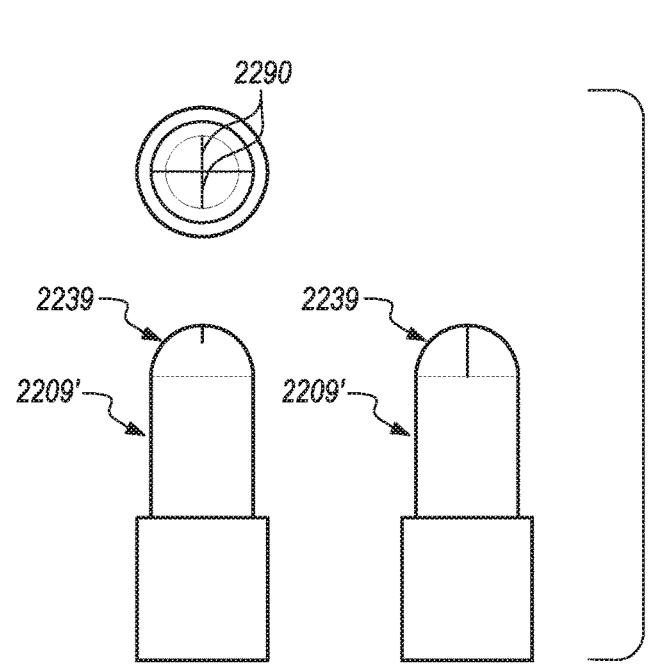
Figure 28E:
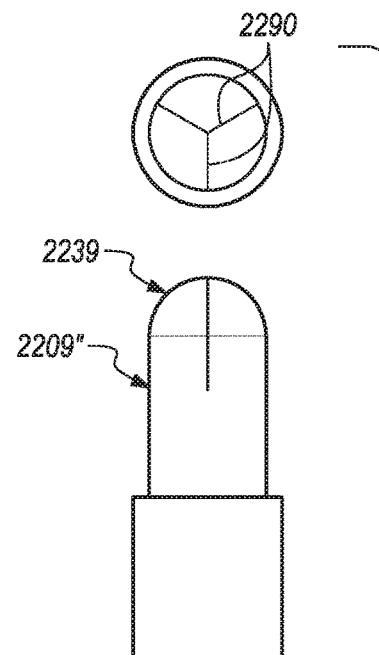
Figure 28F:
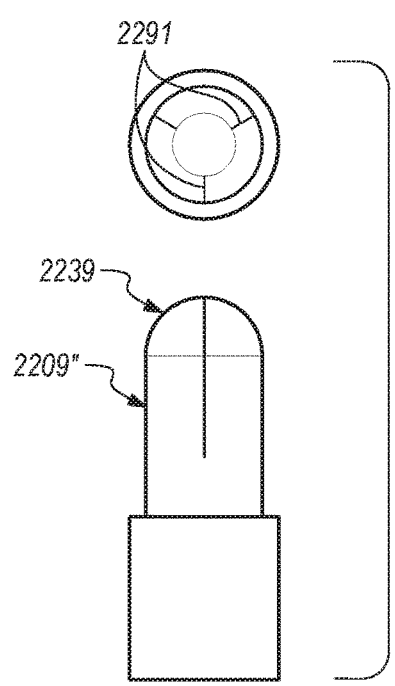
Figure 28G:
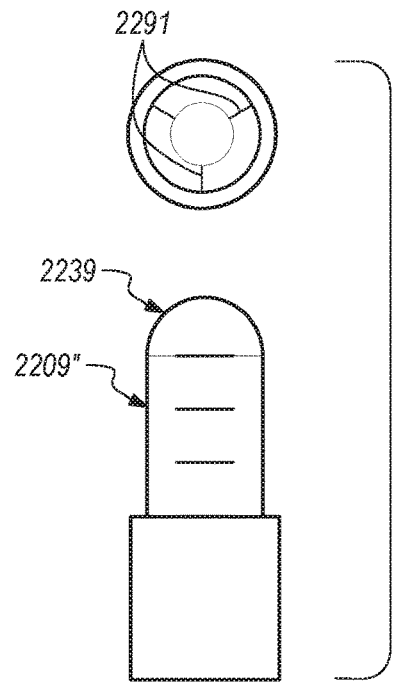
Figure 28H:
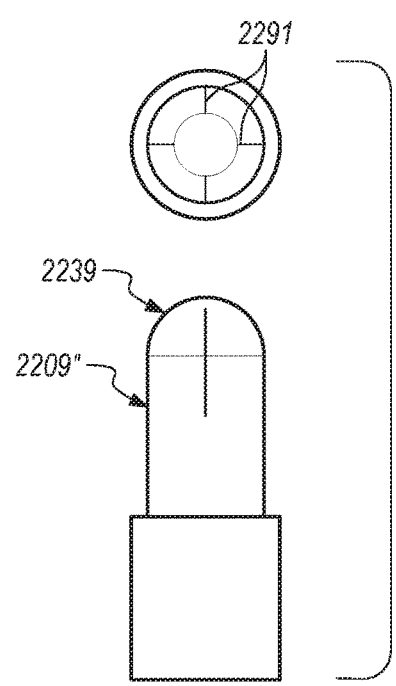
Figure 28I:
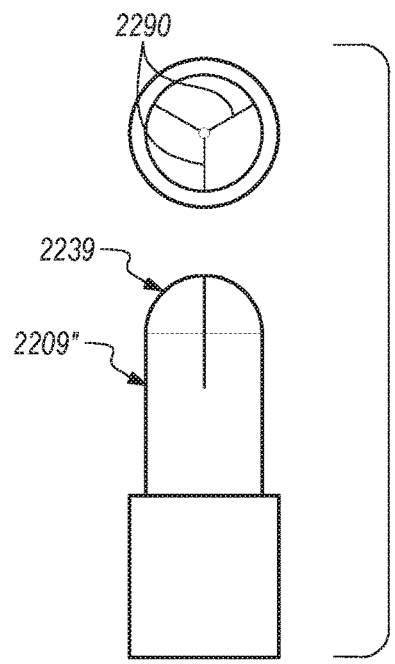
Figure 28J:
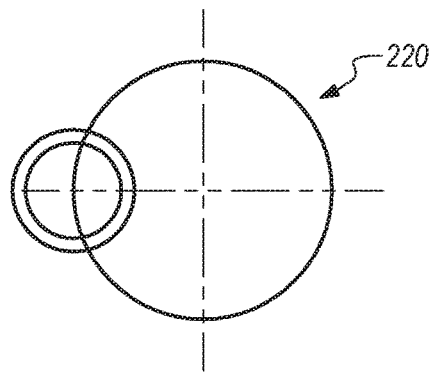
Figure 28K:
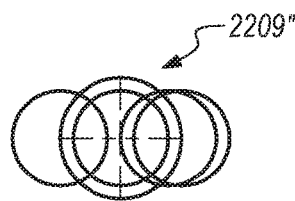
Figure 28L:
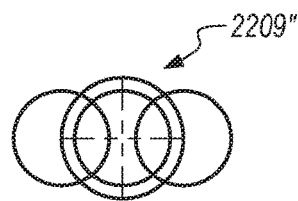
Figure 28M:
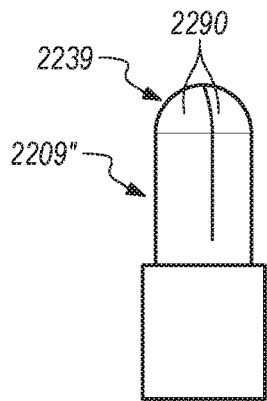
Figure 28N:
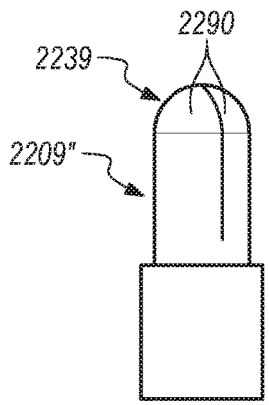
Figure 28O:
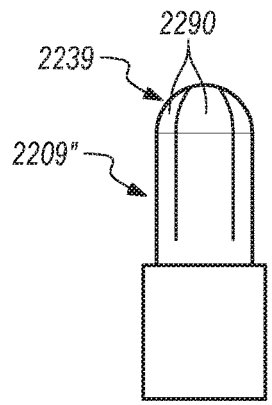
Figure 28P:
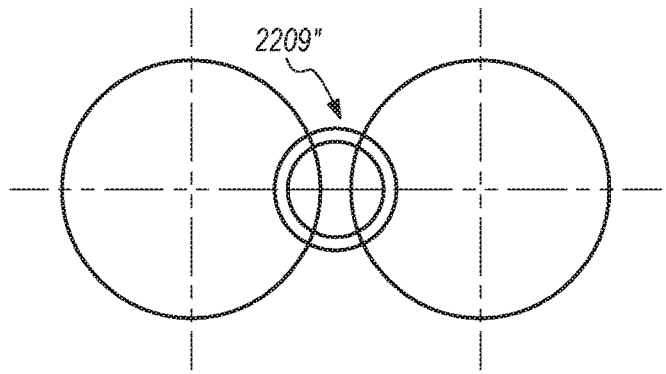
Figure 28Q:
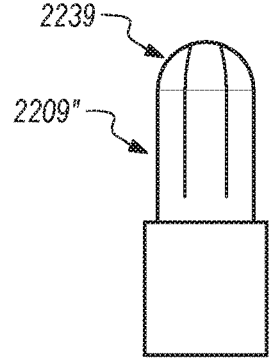

FIGS. 28A-Q illustrate exemplary valve cuts at the end portion dome 2239 of the valves 2209'' constructed according to embodiments of the disclosed inventions. The dome 2239 may be cut to include two or more leaflets 2290 formed from cutting or slitting, as shown in FIGS. 28A, 28C-E and 28I. The leaflets 2290 may be similar to a heart valve, as shown in FIGS. 25E and 25H. Alternative the cuts at the end portion dome 2239 may not form leaflets, such as when linear cuts do not intersect 2291, as better appreciated in FIGS. 28B and 28F-H. These non-intersecting cuts 2291 of the dome 2239 allow for opening of the valve 2209'' while also allowing the valve 2209'' to fully close.

FIG. 28J-Q illustrate further exemplary valve cuts at the end portion dome 2239. In contrast with the linear cuts of FIGS. 28A-I, FIGS. 28J-Q shows arcuate, circular-shaped, concave and convex cuts or the like, that may extend along the cylindrical body of the valve 2209'' forming two or more leaflets 2290.

Figure 29:
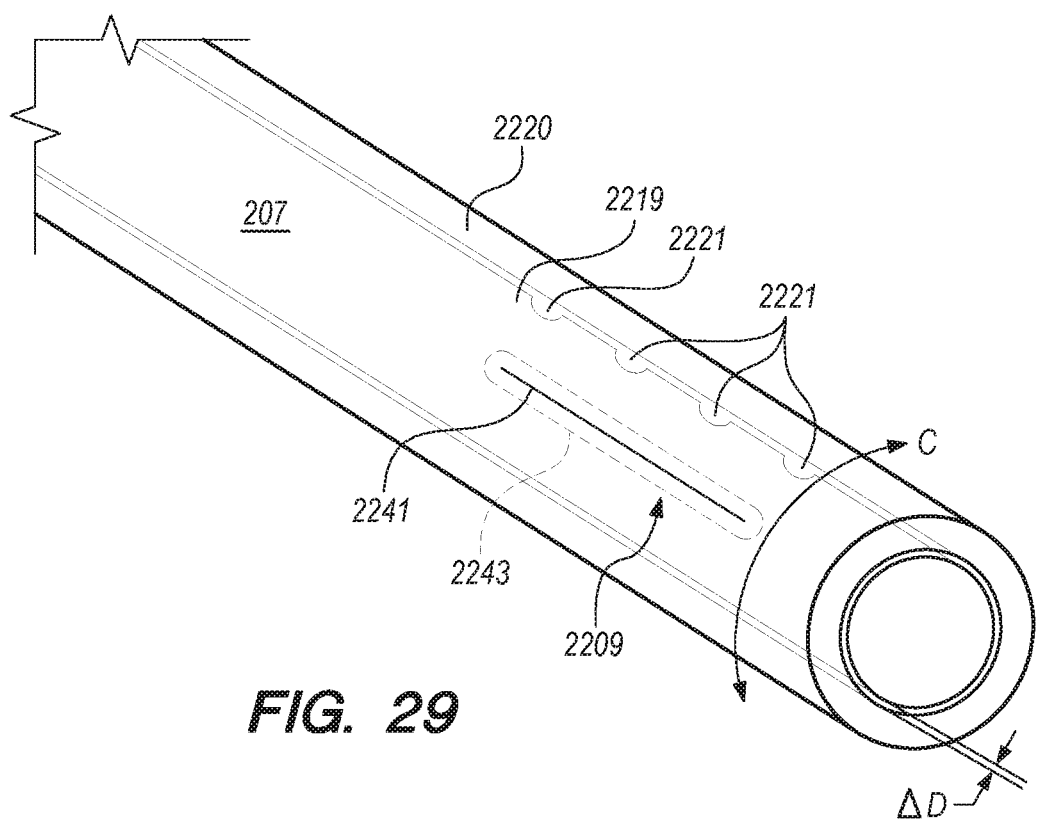
FIG. 29 is a perspective of another valve constructed according to embodiments of the disclosed inventions.

FIG. 29 illustrates valve embodiments that include an internal support member and exterior layer. For example, valve 2209 can include a relatively rigid internal support member 2219 comprising a gold (or other radiopaque metal or alloy), Nitinol, stainless steel, or polymeric hypotube (e.g., any of the polymers previously described herein or disclosed in the applications incorporated by reference). The internal lumen of the support member 2219 provides the shunt lumen 207 for a proximal portion of the shunt and can comprise the entire length of the shunt lumen in other embodiments. As shown in FIG. 29, the support member 2219 can include one or more apertures (e.g., four apertures 2221 as shown in the figure). Exterior layer 2220 can include a silicone, polyurethane, or other suitable polymeric material hypotube or layer disposed concentrically over the internal support member 2219. The proximal ends of internal support member 2219 and the exterior layer 2220 can be closed as depicted in the FIG. 29. Exterior layer 2220 can include one or more slits 2241 (e.g., slit created by a blade or trocar) or apertures 2243 (e.g., apertures created by a laser that removes a portion of the layer material between the opposing edges of the aperture). The rotational or clocking orientation of the exterior layer 2220 and slits or apertures 2243 can be varied with respect to the location of the apertures 2241 of the internal support member 2219 (e.g., indicated by the "C" arrows in the FIG. 29) to achieve a target cracking pressure in these alternate valve 2209. As will be further described below, aspects of the valve 2209 of FIG. 29 allow CSF within shunt lumen 207 to flow through the apertures 2221 of the internal support member 2219, between the respective outer surface of the internal support member and inner surface of the exterior layer, and out of the slit 2241 or aperture 2243 of exterior layer 2220.

Where exterior layer comprises one or more slits 2241, the opposing edges of the slit(s) provide a sealing interface to maintain the valve 2209 closed below a target opening or cracking pressure. When the shunt lumen 207 and/or internal support fill with CSF and meet or exceed the cracking or opening pressure of the valve 2209, the one or more slits 2241 of the exterior layer 2220 open to allow CSF to flow from shunt lumen 207 and out from the valve 2209. In backpressure conditions (e.g., venous blood pressure exceeds intracranial pressure), the slits 2241 seal to prevent blood from entering the shunt lumen 207. Support member 2219 resists compression or collapse of the exterior layer in such backpressure conditions.

The relative sizing between internal support member 2219 and exterior layer 2220 (e.g., referenced as "ΔD" in FIG. 29) can be optimized to target a valve cracking pressure, facilitate CSF flow from within internal support member 2219/ shunt lumen 207 and through the exterior layer 2220 and out of the valve 209, and prevent backflow. For example, in embodiments where exterior layer 2220 includes one or more slits 2241, the difference between the outer diameter of internal support member 2219 and the inner diameter of exterior layer 2220 can be about 0.0001" to 0.005" (0.00254 mm to 0.127 mm). In embodiments where exterior layer 2220 includes one or more apertures 2243, the outer diameter of the internal support member 2219 can be sized more closely to or slightly exceed the inner diameter of exterior layer 2220. In such embodiments, the external and internal diameters of the internal support and exterior layer, respectively, can provide a sealing interface to prevent fluid flow below a target cracking pressure and in backpressure conditions; once CSF pressure within shunt lumen 207 and/or internal support member 2219 meet or exceed a target cracking pressure, CSF flows through the one or more apertures 2243 of the internal support and out through the one or more apertures 2243 of the exterior layer 2220. In further embodiments comprising one or more slits in the exterior layer 2220, the inner diameter of such exterior layer 2220 can match the outer diameter of the internal support member 2219; in such embodiments, the exterior layer 2220 will seal against the internal support at the points where the respective inner and outer diameters touch below a target cracking pressure. Where the target cracking pressure is met or exceeded, CSF flows through the one or more apertures of the internal support 2219 and out through the one or more slits 2241 of the exterior layer 2220.

Figure 30A:
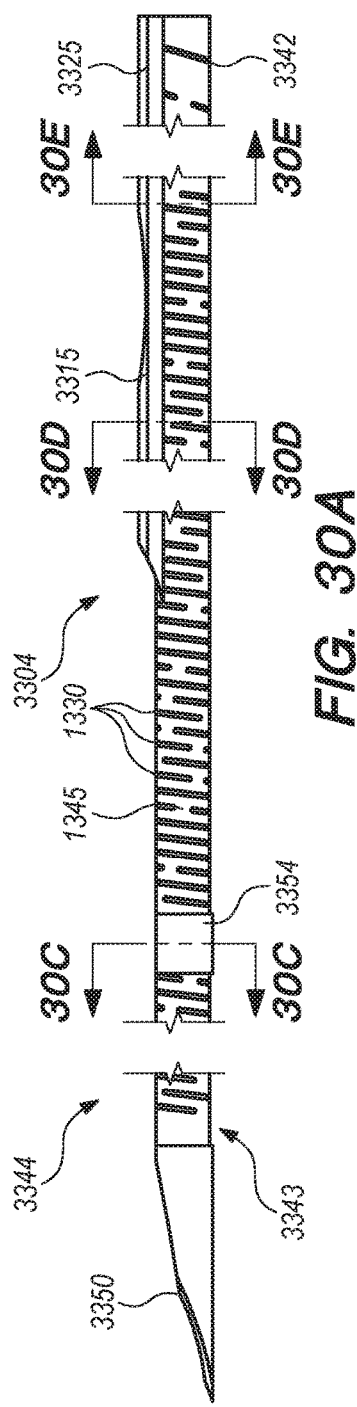
FIGS. 30A-E are side, perspective and cross-sectional views of another shunt delivery catheter, constructed according to alternative embodiments of the disclosed inventions.
Figure 30B:
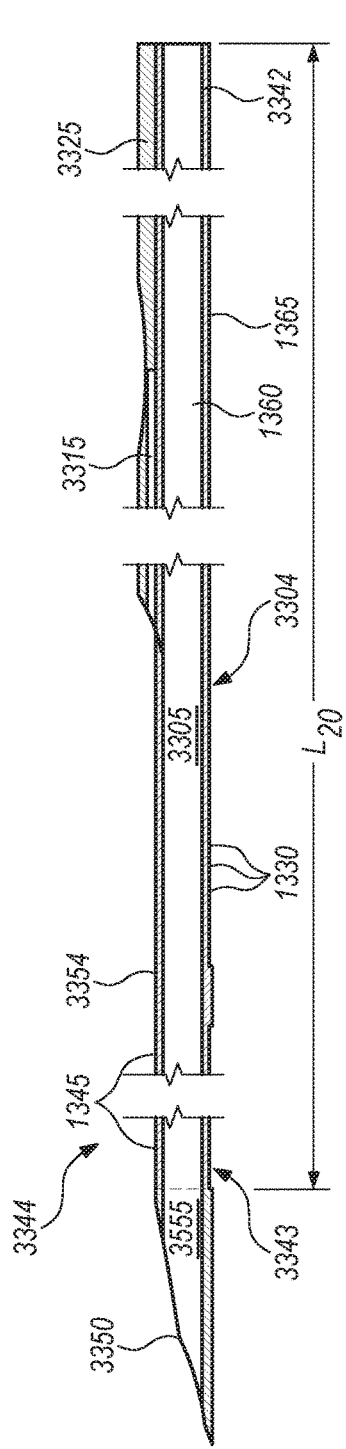
Figure 30E:
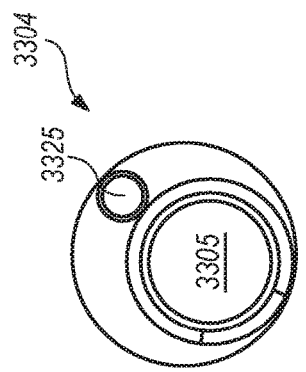
Figure 30D:
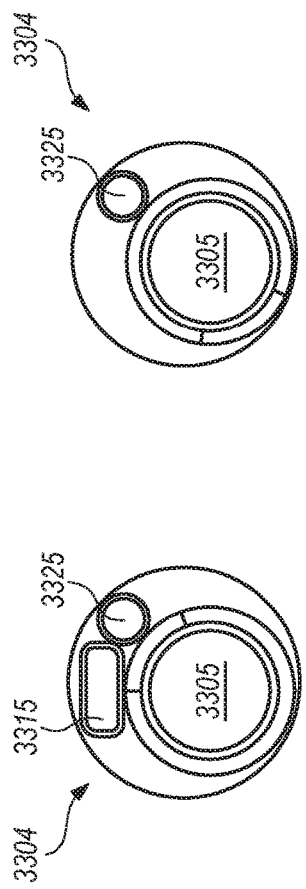

FIGS. 30A-G illustrate an alternative delivery catheter for delivering the shunt into a target site of a patient, constructed in accordance with embodiments of the disclosed inventions. For ease in illustration and disclosure, the features, functions, and configurations of the delivery catheter that are the same as in the catheter of FIGS. 10A-K and in the related application, are incorporated by reference herewith; the differences will be described in further detail below. FIG. 30A show perspective longitudinal side views at various points along the longitudinal axis of the delivery catheter. FIG. 30B shows another perspective longitudinal cross-sectional views of the delivery catheter. The delivery catheter 3304 of FIGS. 30A-E includes a penetrating element 3350 on the distal portion and a distinct radiopaque marker band 3354 proximately disposed to the penetrating element 3350. The radiopaque marker band 3354 may be disposed in an angle with respect to the longitudinal axis of the catheter 3304 to indicate direction/orientation of the catheter distal portion 3344 during delivery of the shunt at the target site. The angled marker 3354 may further include directional features, such as arrow heads, or the like, as shown in FIGS. 31A-G.

Figure 10A:
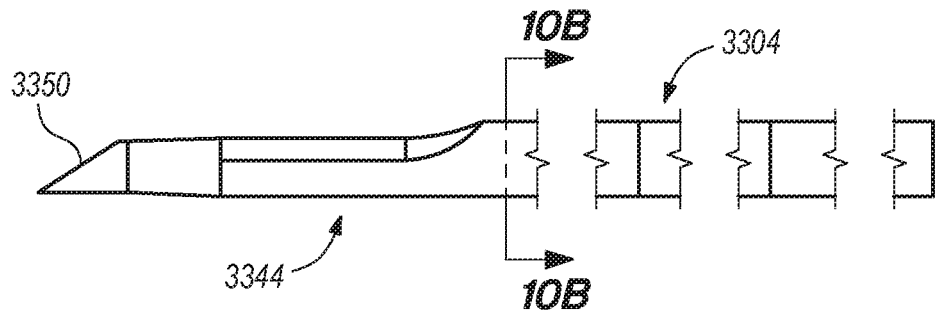
FIGS. 10A-J are perspective, side and cross-sectional views of a delivery catheter, according to another embodiment of the disclosed inventions.
Figure 10B:
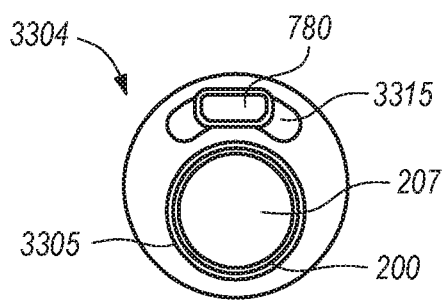
Figure 10C:
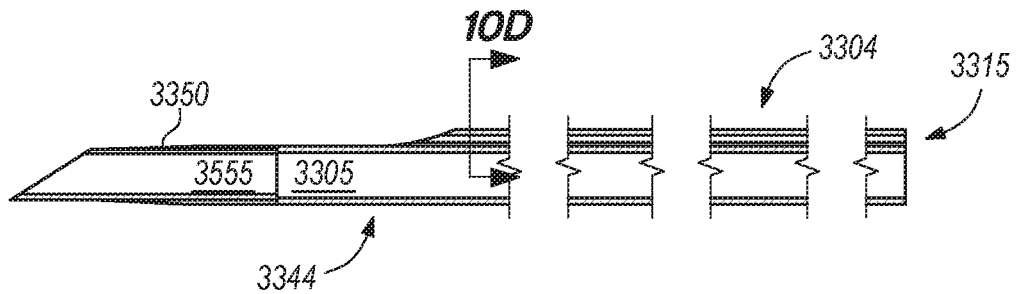
Figure 10D:
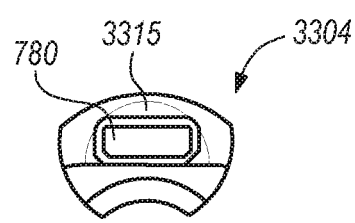
Figure 10E:
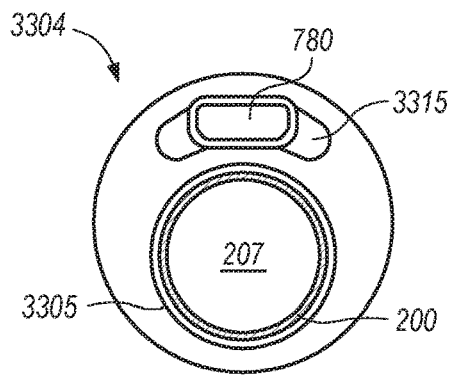
Figure 10F:
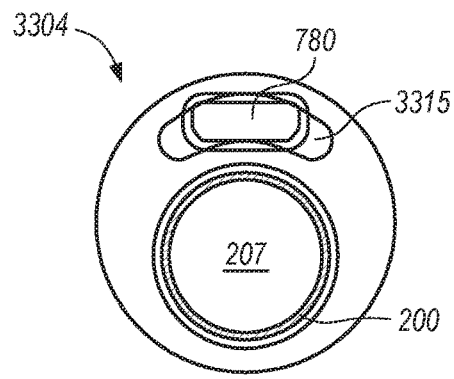
Figure 10G:
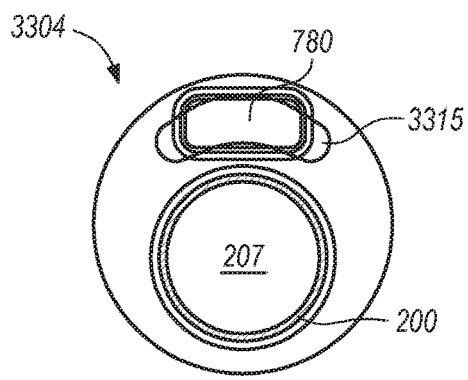
Figure 10H:
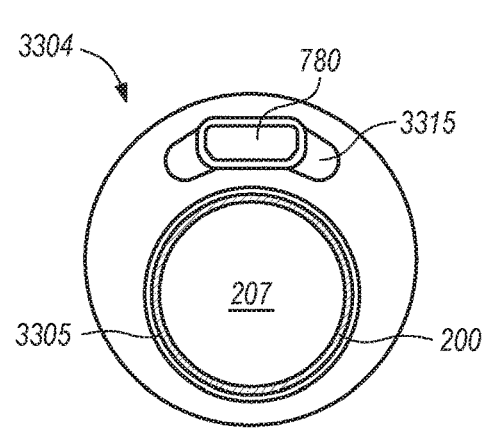
Figure 10I:
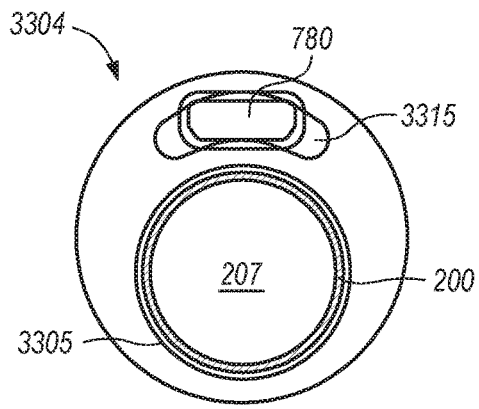
Figure 10J:
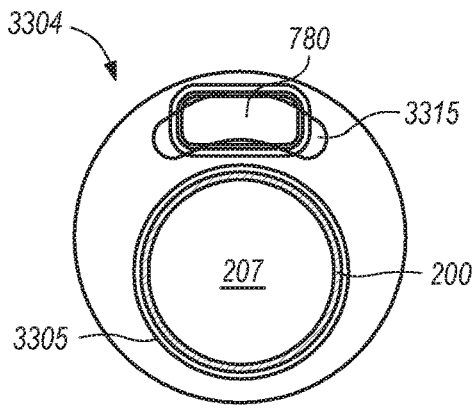
Figure 11:
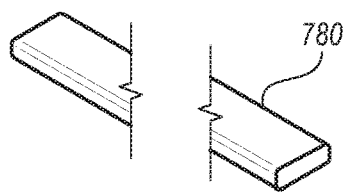
FIG. 11 is a perspective view of an elongated member of the delivery catheter, constructed according to embodiments of the disclosed inventions

Further to the shunt lumen and the elongated guide member lumen, as shown in FIG. 10C as 3305 and 3315 respectively, the delivery catheter of FIG. 30A includes an additional lumen (FIGS. 30D and 30E) adjacently disposed to the shunt lumen. The additional lumen is configured to allow passage of the guard pull wire, the penetrating element guard, an additional penetrating element, tool, or any other suitable element.

The shunt delivery catheter 3304 includes a reinforcing member 1345 (FIGS. 30A-B, FIGS. 30F-G) configured to reinforce the catheter 3304 while providing a suitable balance between column strength and flexibility (e.g., "pushability" and "torqueability"). The reinforcing member 1345 is composed of suitable biocompatible and/or elastomeric materials such as, stainless steel, Nitinol® or the like. The reinforcing member 1345 includes a plurality of cuts 1330 (e.g., kerfs, slots, key-ways, recesses, or the like) selectively disposed in sections of the reinforcing member 1345 along length $L_{20}$ of the delivery catheter 3304, as shown in FIGS. 30A-B, and FIG. 30F. Alternatively, the cuts 1330 can be continuously disposed substantially along $L_{20}$ (not shown). It should be appreciated that the cuts 1330 can have variable spiral cut patterns of kerf, pitch, cuts per rotation and cut balance along $L_{20}$ or combinations thereof. Additionally, the reinforcing member 1345 of FIGS. 30A-G includes an inner liner 1360 and an outer jacket 1365 (FIG. 30B), as previously described and better appreciated in detail in FIG. 12C. The inner liner 1360 and outer jacket 1365 are configured to cover—substantially completely or partially—the cuts 1330 of the reinforcing member 1345, while maintaining the flexibility provided by the selective cuts 1330 and column strength afforded, in part, by the reinforcing member 1345.

Figure 30C:
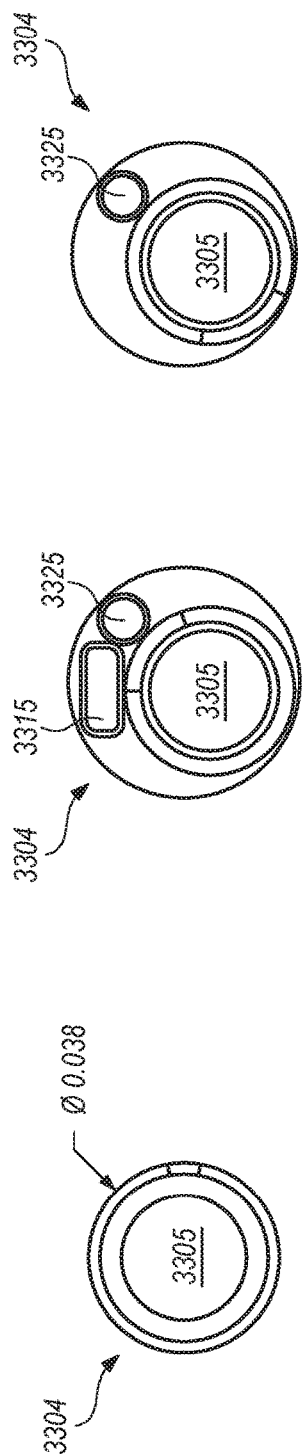

The distal portion of the delivery catheter 3344 of FIGS. 30A-B and FIG. 30F, further includes a stain-relief portion 3343 element proximately disposed to the penetrating element 3350 to avoid, minimize and/or resist kinking of the catheter 3304 at the transition area from the flexible portion of the catheter to the penetrating element, during penetration of the IPS wall and delivery of the shunt. Further, the selective cuts along the length of the delivery catheter are configured to provide a balance between column strength and flexibility of the catheter, such as, having a more rigid proximal portion to a more flexible distal portion (FIGS. 30A-C).

FIGS. 31A-G illustrate an alternative marker, constructed in accordance with embodiments of the disclosed inventions. The marker 3354 is composed of radiopaque material and may be formed by cutting a tubular element in an angle, as shown for example in angle $A_{30}$ of FIG. 31A. Additionally, the marker 3354 may include any other relative size, geometry or configurations (e.g., arrow head, different width of the band, asymmetric band, or the like) suitable to indicate direction and/or orientation of the element where the marker is disposed, such as for example, when the marker is disposed on the delivery catheter to indicate the direction of the penetrating element. FIGS. 31D-E are detailed views of respective edges 3354' and 3354" of the marker of FIG. 31C.

FIG. 32 illustrates a shunt constructed and implanted according to embodiments of the disclosed inventions. FIG. 32 illustrates yet another exemplary shunt 2200 constructed and implanted according to embodiments of the disclosed inventions. For ease in illustration and disclosure, the features, functions, and configurations of the shunt 2200 that are the same as in the shunt of the present disclosure (e.g., FIGS. 15A-J, 22A-24F) and in the related application, are incorporated by reference herewith; the differences will be described in further detail below. The implanted shunt 2200 of FIG. 32 shows three distinct zones; zone I (Distal) depicts the distal portion 2202 of the shunt having the distal anchoring mechanism 2229 engaging the dura mater IPS wall 114, the arachnoid layer 115 and/or securing the shunt 2200 at the target site (e.g., subarachnoid space, CP angle cistern 138), zone II (Mid) depicts the middle or body portion 2203 of the shunt disposed within the IPS 102 and zone III (Proximal) depicts the proximal portion 2204 of the shunt having the proximal anchoring mechanism 2227 engaging and/or securing the shunt in the venous system (e.g., IPS 102, jugular vein 106, and/or a jugular bulb 108). In some shunt embodiments (e.g., FIGS. 53, 54A, 56A-58F), zone III (Proximal) does not include an anchoring mechanism and the proximal portion 2204 of the implanted shunt is disposed in the IPS 102, jugular vein 106, and/or a jugular bulb 108. The zone I (Distal) is configured to maintain a patent fluid inlet, zone II (Mid) is configured to accommodate a variety of IPS anatomies (e.g., length, curvature, width, or the like), maintain a patent fluid lumen (e.g., kink-resistant, non-thrombogenic, protein resistant, or the like), or alternatively function as an anchor within the IPS. Zone III is configured to minimize or prevent thrombus formation on the implanted shunt, maintain valve patency, and/or further maintain the valve 2209 separated from the vessel wall to prevent encapsulation (e.g., 2-3 mm away from the wall). FIGS. 33A-40C illustrate exemplary embodiments of zones I-III of the shunt 2200 according to the disclosed inventions. It should be appreciated that the shunt 2200 constructed according to embodiments of the disclosed inventions may include any variety or combinations of zones I-III as disclosed herein and/or in the related application that are incorporated by reference herewith.

Figure 33C:
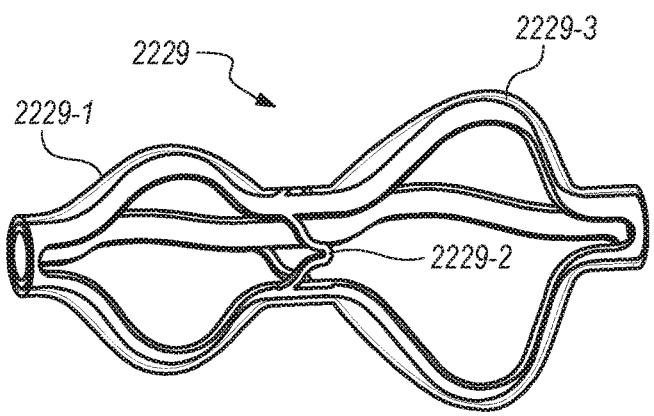
FIGS. 33A-40C are perspective and cross-sectional views of various embodiments of distal anchoring mechanisms of the shunt, constructed according to the embodiments of the disclosed invention.

FIGS. 33A-40C illustrate exemplary embodiments of zone I (Distal) of the shunt, according to the disclosed inventions. FIGS. 33A-C illustrates a distal portion 2202 of the shunt 2200 including a double-malecot anchoring mechanism 2229 in a deployed expanded configuration. The double-malecot includes a proximal malecot 2229-1, a distal malecot 2229-3 and a joint element 2229-2 (e.g., collar, band—FIGS. 33A-B—, struts with hinge members—FIG. 33C—or the like) disposed therebetween. The double-malecot is configured to expand into the deployed configuration engaging the arachnoid layer 115 at the CP angle cistern 138 and the dura layer 114 at the IPS 102. The double-malecot configuration of the distal anchoring mechanism 2229 further secures the distal portion 2202 of the implanted shunt 2200, while avoiding or minimizing distal or proximal migration/translation of the shunt 2200. Additionally, the double-malecot distal anchoring mechanism 2229 may further include a liner 2229-4 (e.g., membrane, mesh, braid or other suitable permeable material or combinations thereof), as shown in FIGS. 33B-C, configured to avoid or minimize the formation of thrombus.

Figure 34:
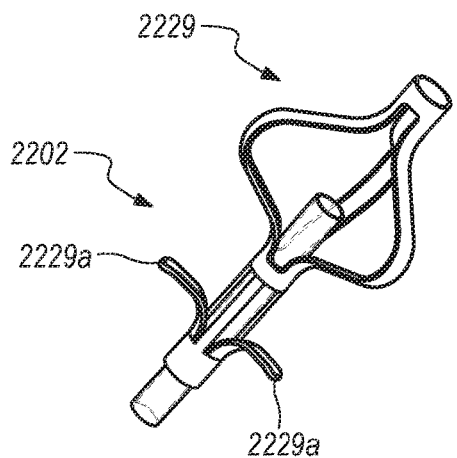
Figure 35:
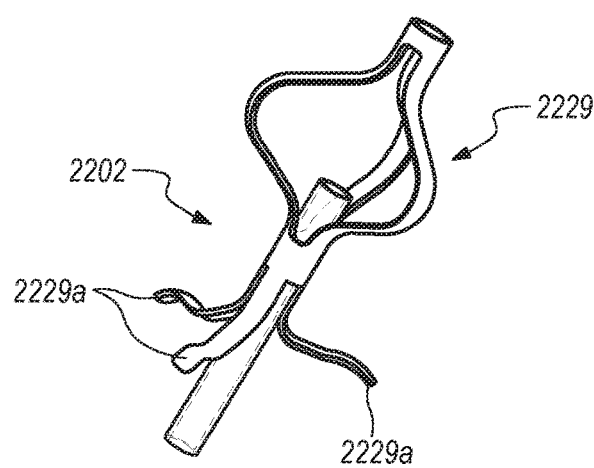

FIGS. 34-35 illustrate distal portions 2202 of the shunt including a malecot-flarecot anchoring mechanism 2229 in a deployed expanded configuration. The malecot portion is configured to expand into the deployed configuration engaging the arachnoid layer 115 at the CP angle cistern 138 and the flarecot is configured to engage the dura mater 114 at the IPS 102. The flarecot arms 2229a of the malecot-flarecot anchoring mechanism 2229 can flare out in the distal direction (e.g., towards the dura mater 114 in the implanted shunt), as shown in FIG. 34 or the flarecot arms 2229a can flare out in the proximal direction (e.g., towards the IPS 102 in the implanted shunt), as shown in FIG. 35, or the flarecot arms 2229a may comprise a combination of the arms 2229a of FIGS. 34 and 35. Similar to the double-malecot configuration, the zone I (Distal) embodiments of FIGS. 34-35 further secure the distal portion 2202 of the implanted shunt 2200, while avoiding or minimizing distal or proximal migration/translation of the shunt.

Figure 36:
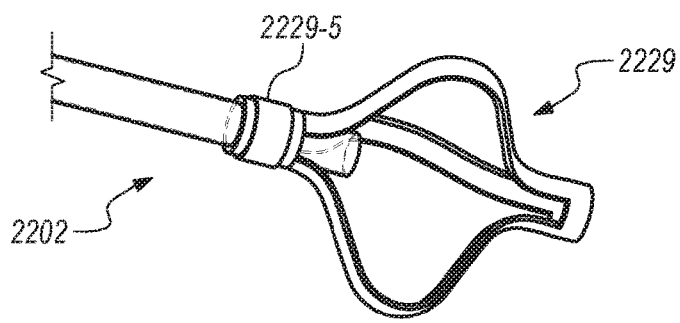

FIG. 36 illustrates a distal portion 2202 of the shunt 2200 including a malecot anchoring mechanism 2229 in a deployed expanded configuration. The malecot anchoring mechanism further includes an annular element 2229-5 composed of expandable material (e.g., foam, swellable or the like). The annular element 2229-5 is configured to expand when disposed within an anastomosis channel formed by piercing the IPS wall 114 and arachnoid layer 115, and further secure the shunt 2200 at the target site.

Figure 37:
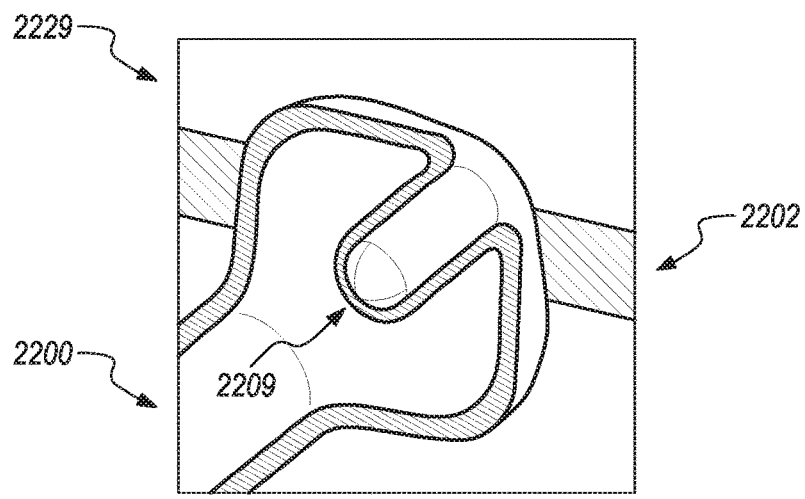
Figure 38:
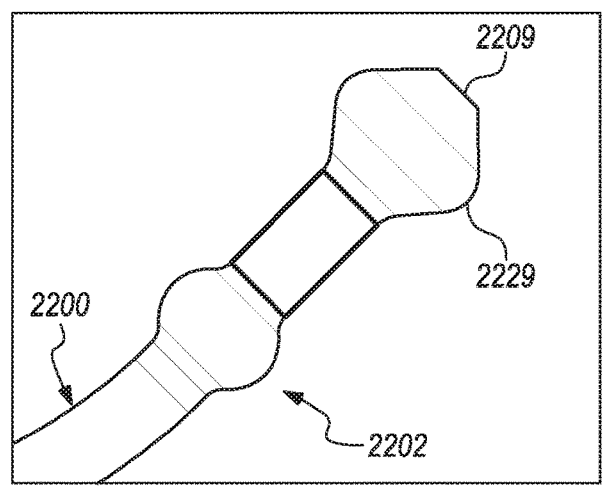
Figure 39A:
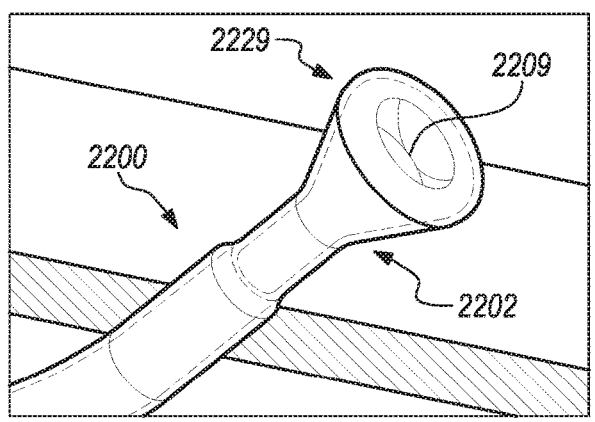
Figure 39B:
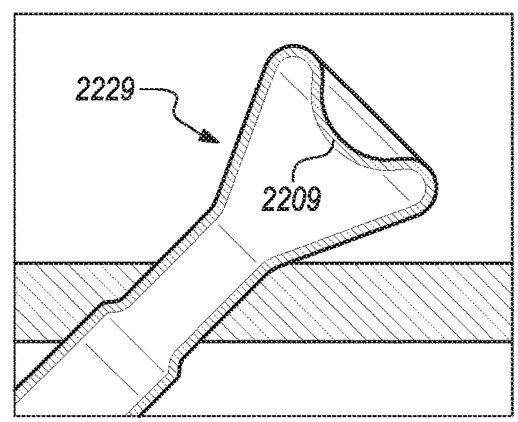

FIGS. 37-39B illustrate distal portions of embodiments of the shunt 2200 including anchoring mechanisms 2229 in a deployed expanded configuration. The anchoring mechanism 2229 is composed of polymeric material, such as silicone, or any other suitable biocompatible non-metallic materials. The anchoring mechanism 2229 includes an expandable element that may have a spheroid, ellipsoid, obloid, diamond-like (FIGS. 37-38), funnel-like (FIGS. 39A-B) or any other suitable shape and dimension configured to anchor the shunt 2200 at the target site when expanded. In some embodiments, the distal anchoring mechanism 2229 includes one expandable element, as shown in FIGS. 37 and 39A-B. In other embodiments, the distal anchoring mechanism includes at least two expandable elements and a portion therebetween, as shown in FIG. 38. The distal anchoring mechanisms 2229 of FIGS. 37-39B further include a one-way valve 2209, which functions as the valves previously described herein (e.g., FIGS. 25A-28Q).

Figure 40A:
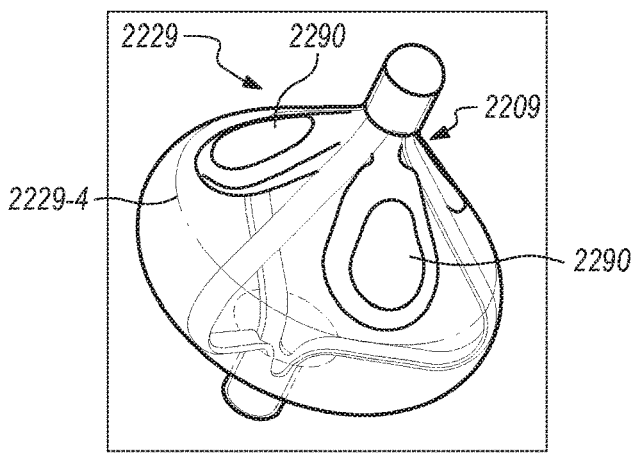
Figure 40B:
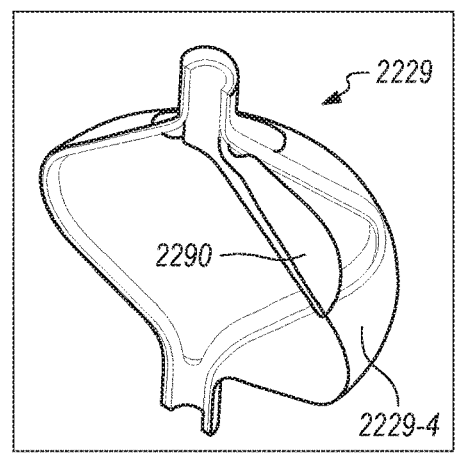
Figure 40C:
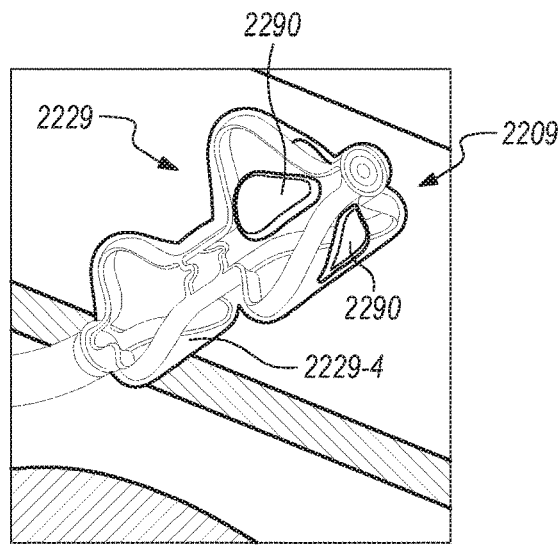

FIGS. 40A-C illustrate another embodiment of the distal portion of the shunt having an anchoring mechanism 2229 in a deployed expanded configuration. The anchoring mechanism 2229 of FIGS. 40A-B includes a malecot and polymeric cover 2229-4; the polymeric cover 2229-4 further includes a plurality of leaflets 2290. In one embodiment, the polymeric cover 2229-4 is composed of urethane, and the leaflets 2290 are composed of silicone. It should be appreciated that any other suitable biocompatible materials may be used in the distal anchoring mechanisms 2229. The leaflets 2290 are configured as one-way valve, and function as the valves previously described. The leaflets 2290 may further increase the functional valve area, as shown in FIGS. 40A-B. The anchoring mechanism of FIG. 40C includes a double-malecot and polymeric cover 2229-4 having a plurality of leaflets 2290 acting as one-way valve 2209.

Figure 41A:
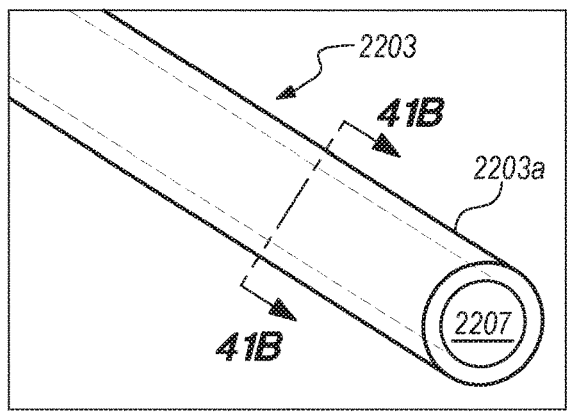
FIGS. 41A-48B are perspective and cross-sectional views of various embodiments of shunt bodies, constructed according to the embodiments of the disclosed invention.

FIGS. 41A-48B illustrate exemplary embodiments of zone II (Mid) of the shunt, according to the disclosed inventions. FIG. 41A illustrates an elongated tubular member 2203 having a proximal portion (not shown), a distal portion 2203a, and a lumen 2207 (FIGS. 41A-B) extending therebetween. FIG. 41B is a cross-sectional view of FIG. 41A. The elongated tubular member 2203 of FIGS. 41A-B is configured to be compressed and/or stretch during delivery of the shunt 2200. The elongated tubular member 2203 of FIGS. 41A-B is composed of silicone and is formed by extrusion. In other embodiments, the elongated tubular member 2203 of zone II (Mid) of the shunt 2200 can be composed of any other suitable biocompatible polymeric material including, for example, polyurethane or silicone-polyurethane blend, and can be formed by any suitable technique.

Figure 41B:
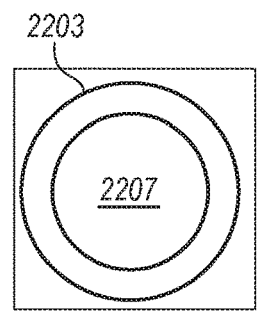
Figure 42A:
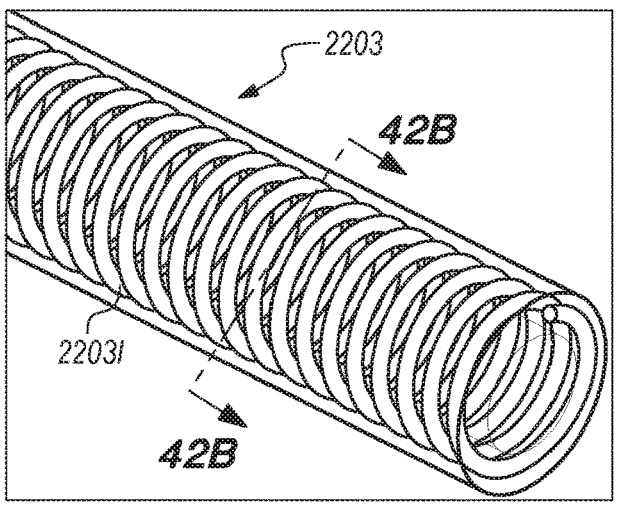
Figure 42B:
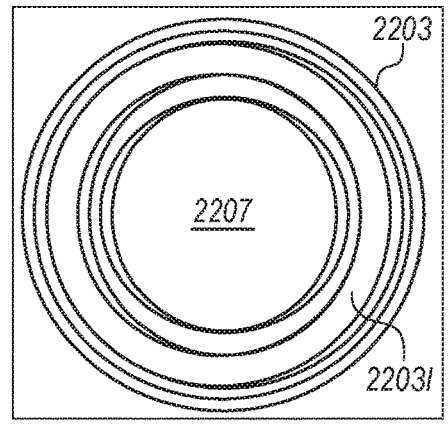

FIG. 42A illustrates the elongated tubular member 2203 of FIGS. 41A-B having an embedded coil element 22031. The coil element 22031 can be composed of any suitable polymeric, metallic material or combination thereof. The coil element 22031 provides reinforcement (e.g., increased column strength) and kink resistance to the zone II (Mid) of the shunt. FIG. 42B is a cross-sectional view of FIG. 42A.

Figure 43A:
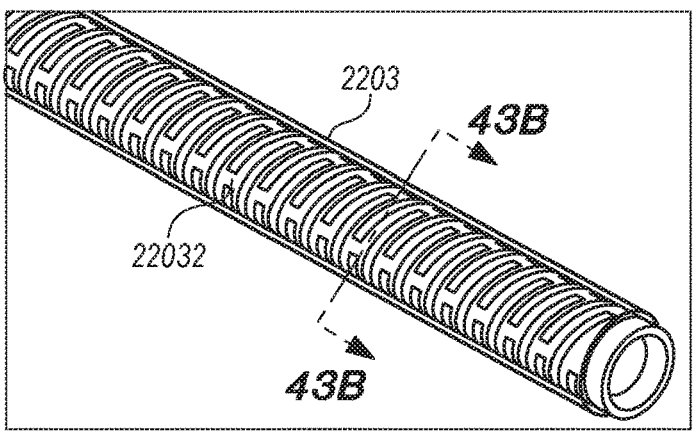
Figure 43B:
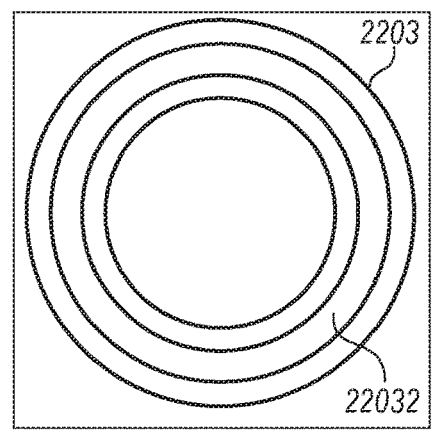

FIG. 43A illustrates the elongated tubular member 2203 of FIGS. 41A-B having an embedded tubular element 22032. The embedded tubular element 22032 can be composed of any suitable materials, such as, platinum, Nitinol®, gold or other biocompatible materials. The embedded tubular element 22032 provides reinforcement (e.g., increased column strength) and kink resistance to the zone II (Mid) of the shunt. Further, the embedded tubular element 22032 includes a plurality of cuts along the length configured to increase flexibility of the element. FIG. 43B is a cross-sectional view of FIG. 43A.

Figure 44A:
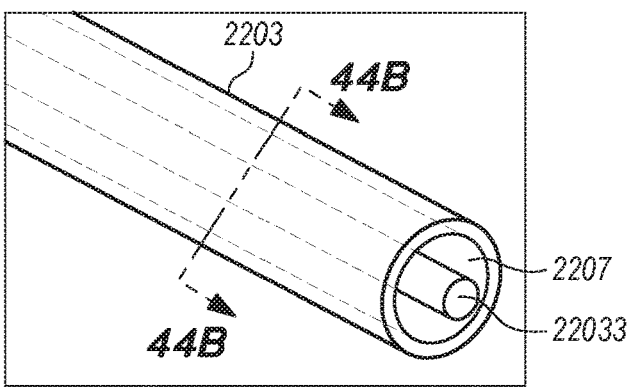
Figure 44B:
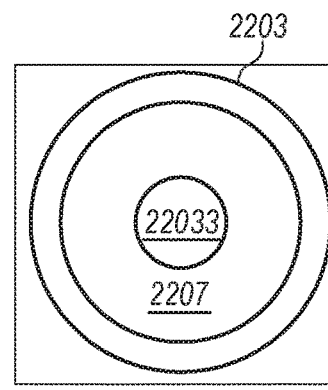
Figure 45A:
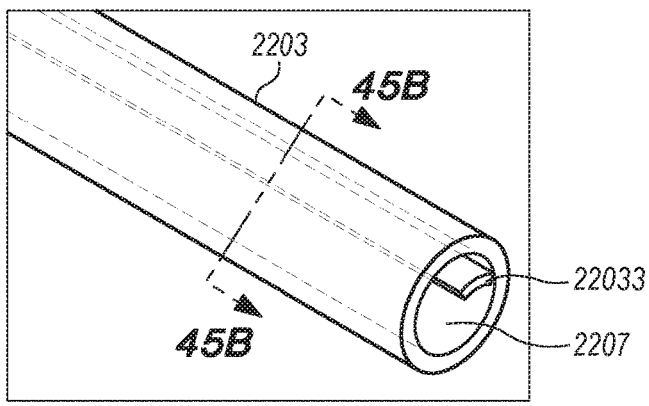
Figure 45B:
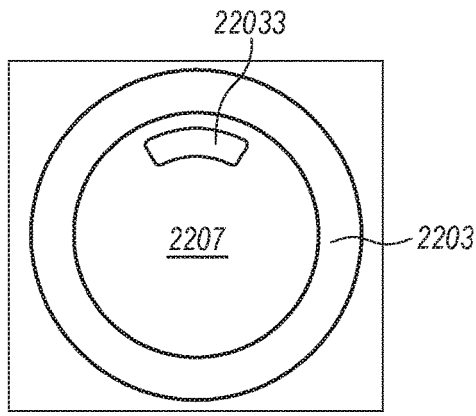
Figure 46A:
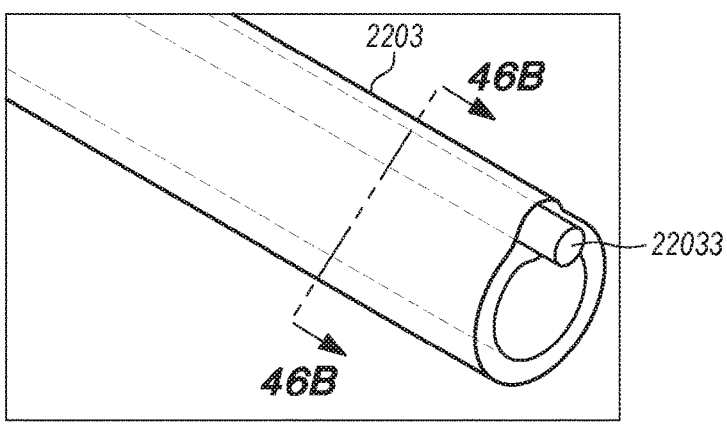
Figure 46B:
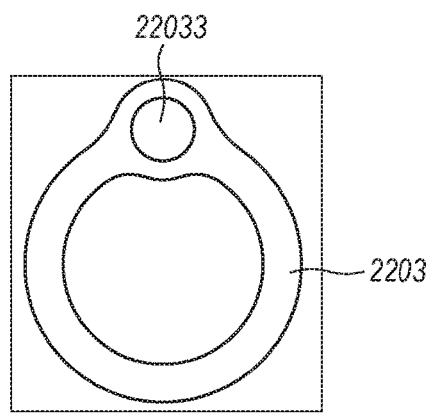
Figure 47A:
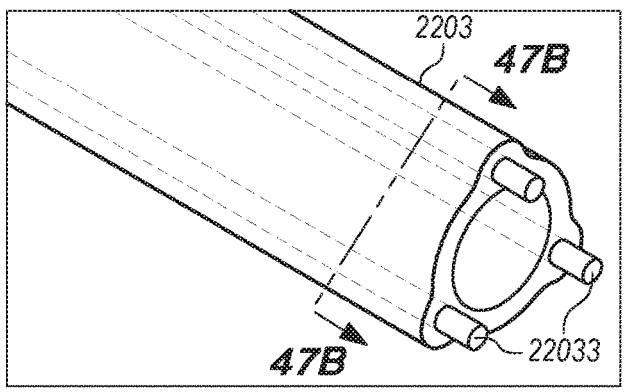
Figure 47B:
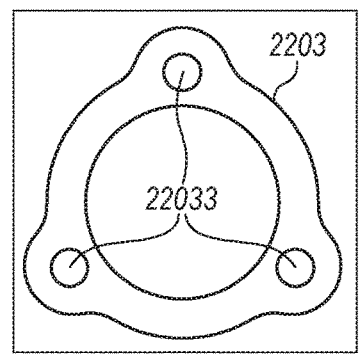
Figure 48A:
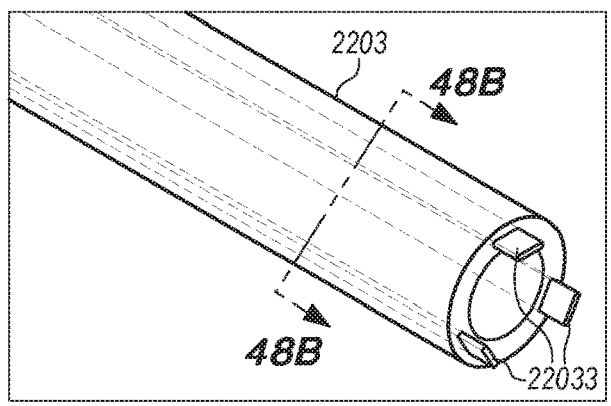
Figure 48B:
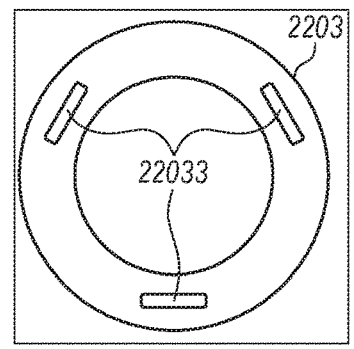

FIGS. 44A-48B illustrate the elongated tubular member 2203 of FIGS. 41A-B having one or more spine elements 22033. The spine element 22033 can be composed of any suitable materials, such as, platinum, Nitinol®, gold or other biocompatible materials. The spine element 22033 is configured to provide reinforcement (e.g., increased column strength) and kink resistance to the zone II (Mid) of the shunt. In some embodiments, the spine element 22033 can be used as shunt shaping stylets. The spine element 22033 can be an elongated rod or cylindrical member (FIGS. 44A-B, 46A-B), an arcuate elongated member (FIGS. 45A-B), a flat elongated member (FIGS. 48A-B), or can have any other suitable configuration. In the embodiments of FIGS. 44A-B, the spine element 22033 is disposed in the lumen 2207 of the tubular element, such as concentrically disposed (FIGS. 44A-B) or laterally disposed (FIGS. 45A-B). In the embodiments of FIGS. 46A-48B, a plurality of spine elements 22033 is embedded in the tubular element 2203. FIGS. 44B-48B are a cross-sectional view of the respective FIGS. 44A-48A.

Figure 49A:
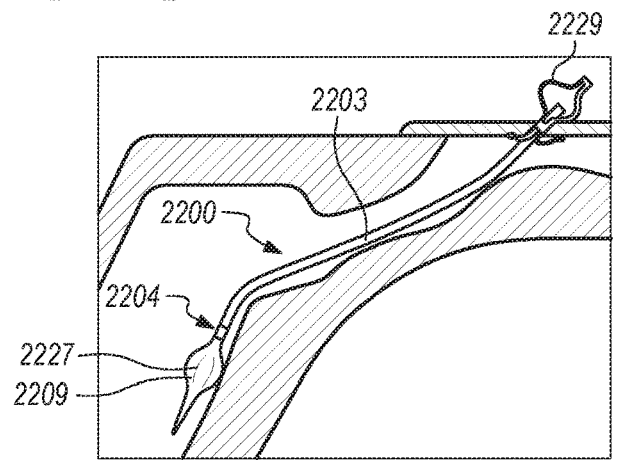
FIGS. 49A-54B are perspective and cross-sectional views of various embodiments of implanted shunts according to the embodiments of the disclosed invention.
Figure 49B:
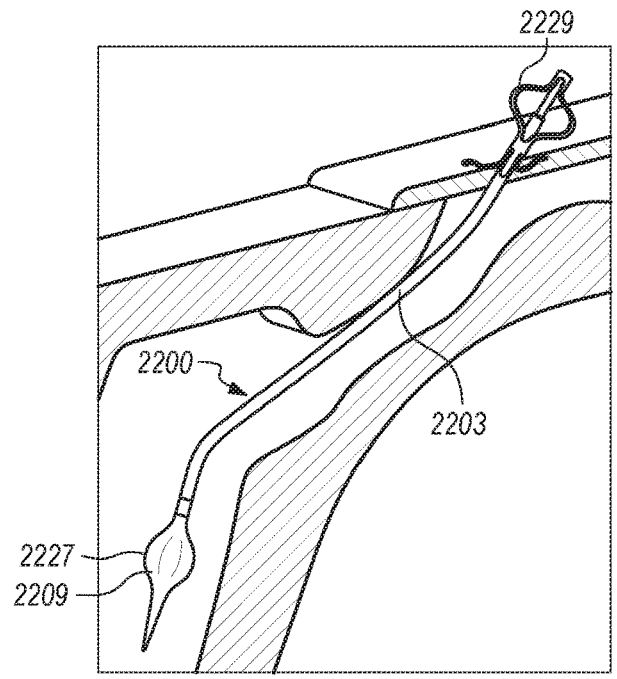

FIGS. 49A-B illustrate exemplary embodiments of zone III (Proximal) of the shunt according to the disclosed inventions. Additionally, FIGS. 49A-B illustrate deployed shunts 2200 having previously disclosed zones I and II, in combination with zone III of the shunt that will be described below. As shown in FIGS. 49A-B, the proximal anchoring mechanism 2227 includes an expandable member and having a bulb-like configuration. The proximal portion 2204 of the shunt further includes a valve 2209 proximally disposed to the anchoring mechanism 2227 (e.g., at the tip of the conical proximal end and/or the valve being formed by slits on the bulb-like anchoring mechanism). FIGS. 49A-B are perspective views of the shunt; the shunt further having the elongated tubular member 2203 of FIGS. 41A-B in zone II, and the malecot-flarecot anchoring mechanism 2229 of FIG. 35 in zone I.

Figure 50A:
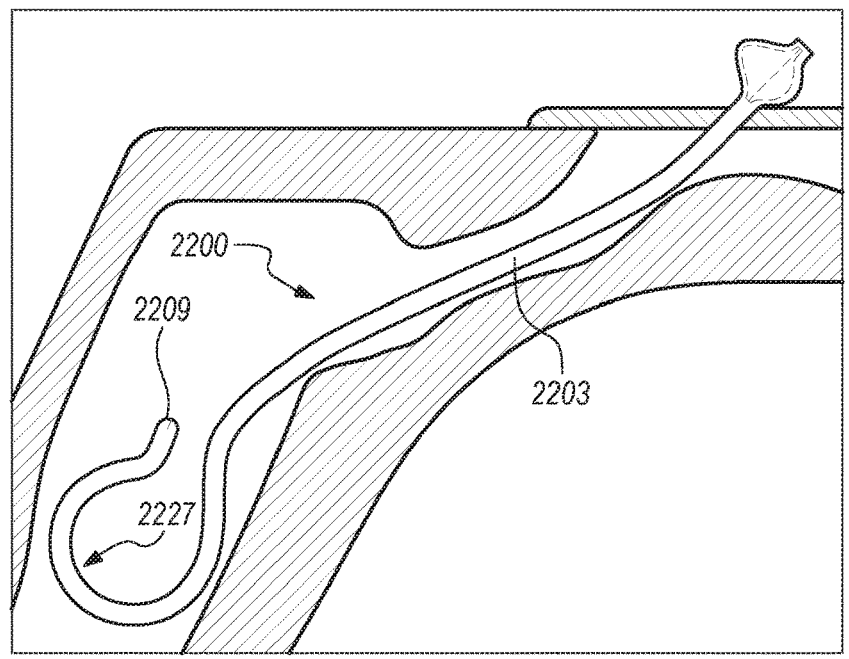
Figure 50B:
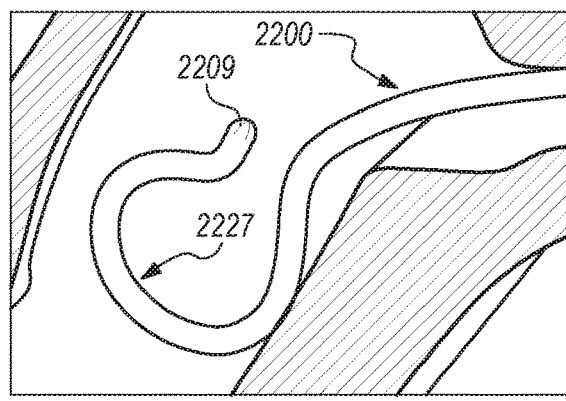
Figure 50C:
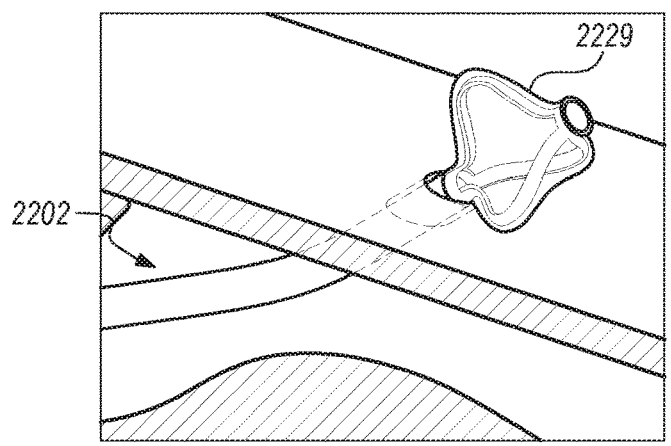

FIGS. 50A-C illustrate another exemplary embodiment of zone III (Proximal) of the shunt having a proximal anchoring mechanism 2227. As shown in FIGS. 50A-B, the proximal anchoring mechanism 2227 includes a spine composed of shape memory material, such as Nitinol®, or other super-elastic alloys, configured to form a loop when the shunt is deployed. The spine can be configured to adjust the direction of CSF outflow from the deployed shunt device. For example, as shown in FIG. 50B, the spine is configured to form a coil in zone III (Proximal) of the shunt with CSF outflow antegrade to the venous blood flow of the IJV; the valve 2209 shown in the FIG. 50B faces the direction of blood flow in the IJV. The proximal anchoring mechanism 2227 of FIGS. 50A-B is configured to maintain valve patency and further maintain the valve 2209 separated from the vessel wall to prevent encapsulation. FIGS. 50A-C are perspective views of the shunt 2200; the shunt further having the elongated tubular member of FIGS. 45A-B or 46A-B in zone II, and a single malecot-liner distal anchoring mechanism in zone I, as better appreciated in FIG. 50C.

Figure 51A:
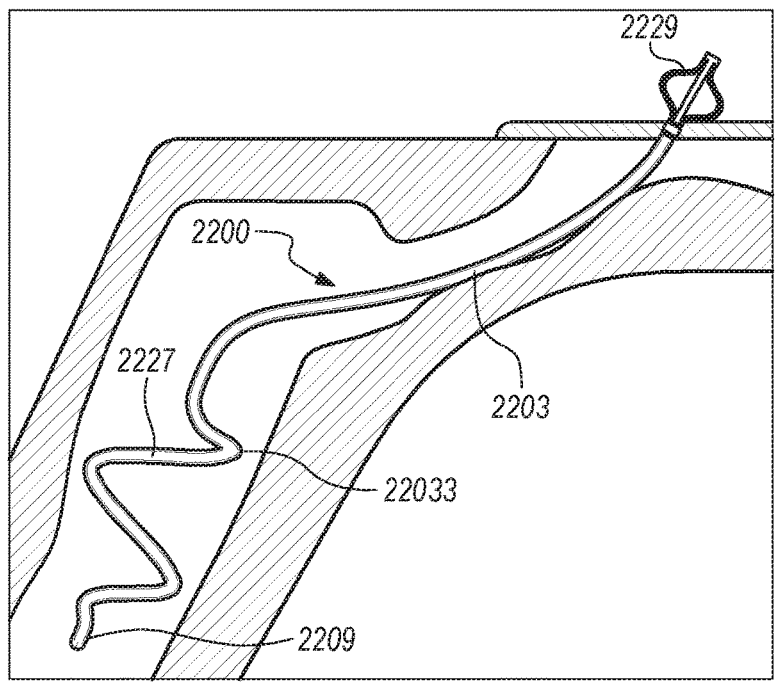
Figure 51B:
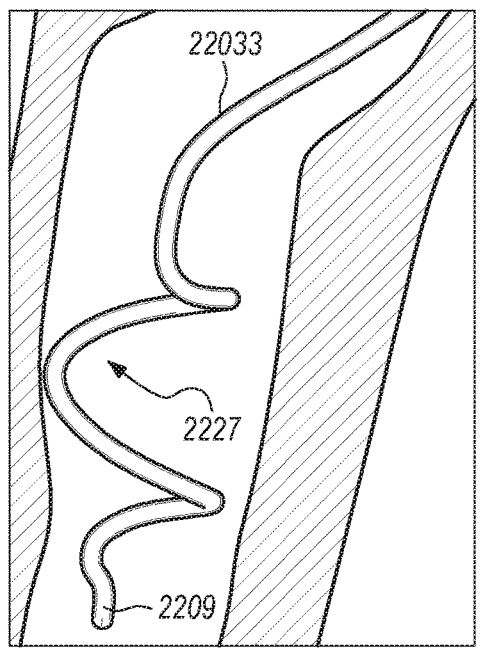
Figure 51C:
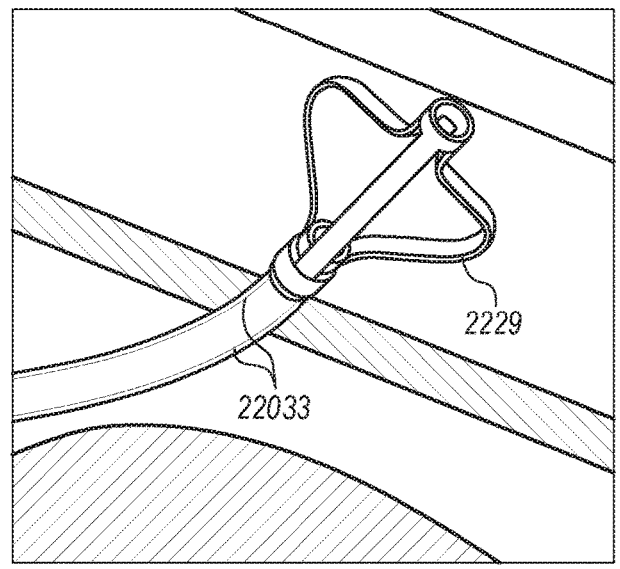

FIGS. 51A-C illustrate yet another exemplary embodiment of zone III (Proximal) of the shunt having a proximal anchoring mechanism 2227. As shown in FIGS. 51A-B, the proximal anchoring mechanism 2227 includes a plurality of spine elements 22033 composed of shape memory material, such as Nitinol®, or other super-elastic alloys, configured to form a coil when the shunt is deployed. Similar to the embodiments of FIGS. 50A-B, the proximal anchoring mechanism 2227 of FIGS. 51A-B is configured to maintain valve patency and maintain the valve 2209 separated from the vessel wall to prevent encapsulation. FIGS. 51A-C are perspective views of the shunt; the shunt further having the elongated tubular member 2203 of FIGS. 46A-B or 47A-B in zone II, and the malecot distal anchoring mechanism 2229 of FIG. 36 in zone I.

Figure 52A:
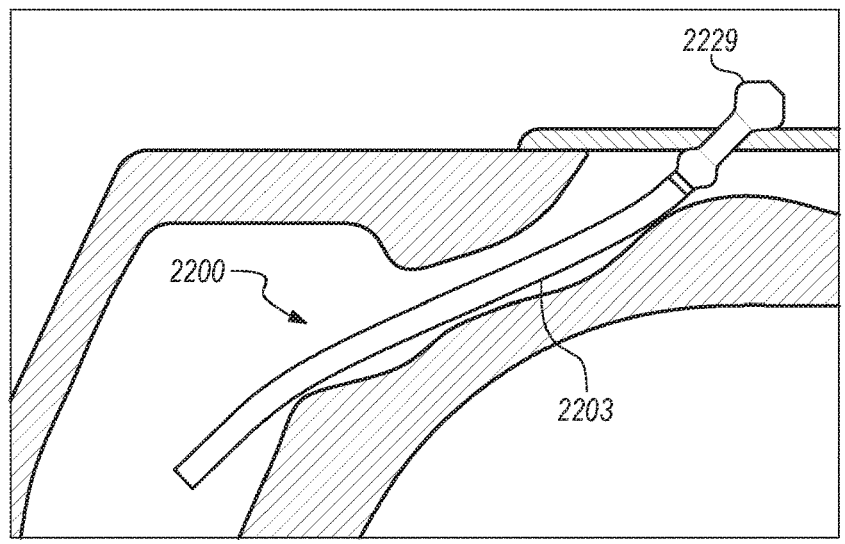
Figure 52B:
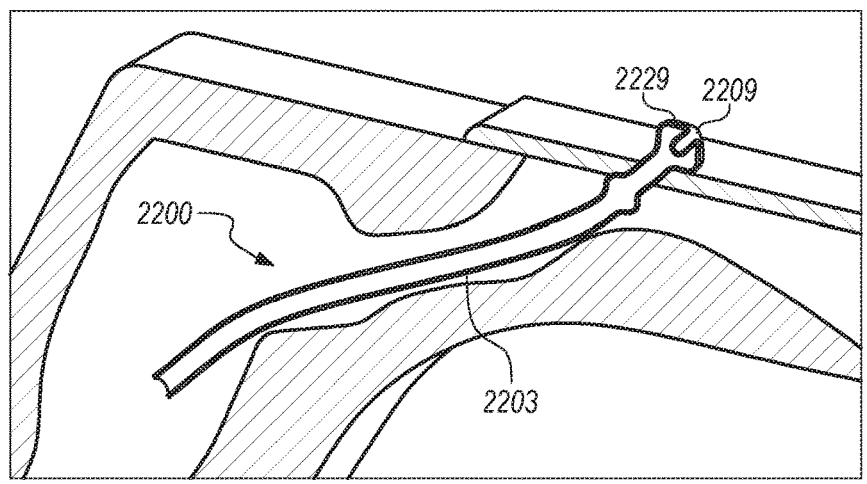
Figure 52C:
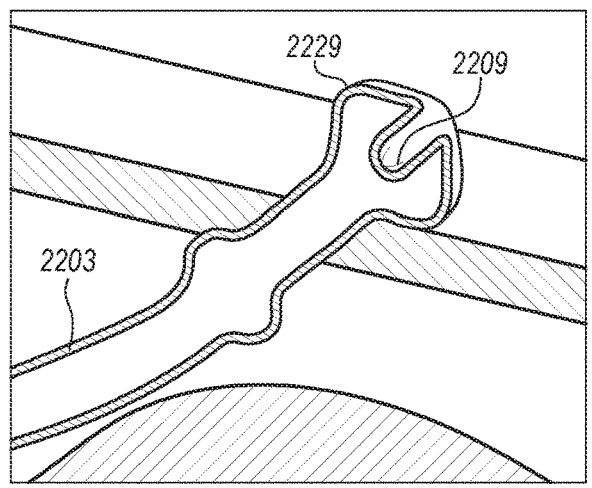

FIGS. 52A-C illustrate another exemplary embodiment of zone III (Proximal) of the shunt 2200. As shown in FIGS. 52A-B, the zone III (Proximal) includes the configuration of the elongated tubular element 2203 of zone II (Mid) of FIG. 41A-B. FIGS. 52A-C are perspective views of the shunt 2200; the shunt having the elongated tubular member 2203 of FIGS. 41A-B in zone 2, and the anchoring mechanism 2229 of FIG. 38 in zone 1. In the embodiments of FIGS. 52A-C the one-way valve 2209 is disposed in the distal anchoring mechanism 2229.

Figure 53:
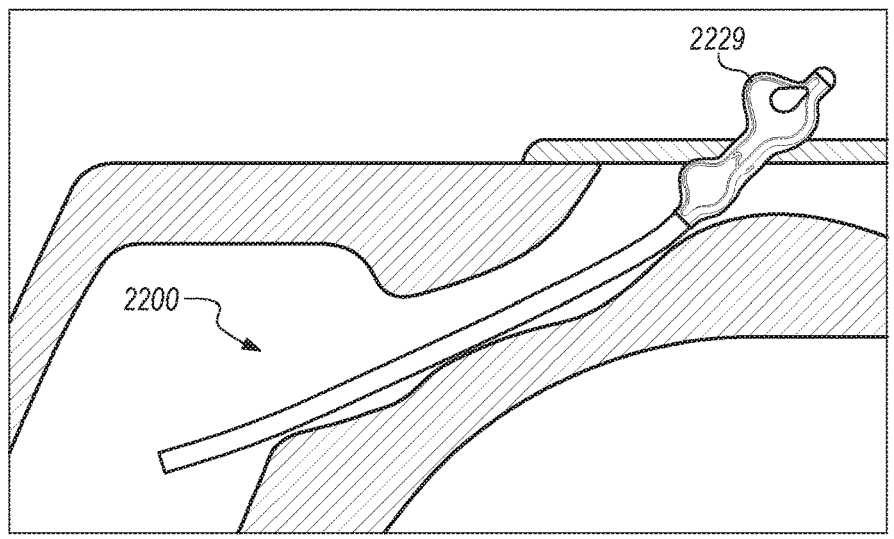

FIG. 53 illustrates the embodiment of zone III (Proximal) of the shunt 2200 of FIGS. 52A-B having the distal anchoring mechanism 2229 of FIG. 40C.

Figure 54A:
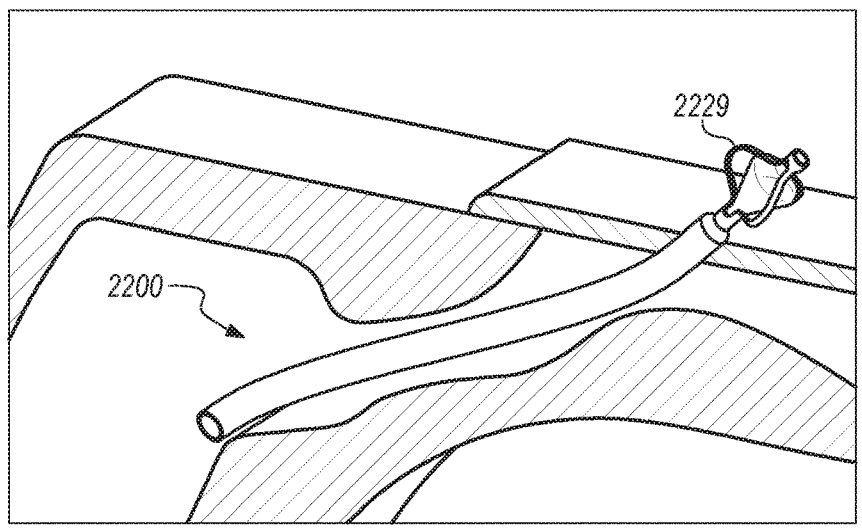
Figure 54B:
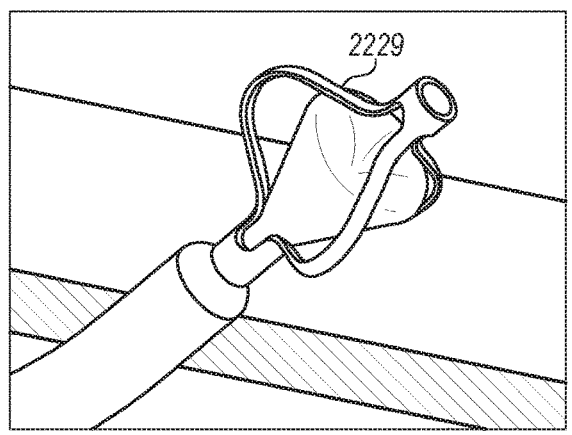

FIGS. 54A-B illustrates the embodiment of zone III (Proximal) of FIGS. 52A-B having the distal anchoring mechanism 2229 of combined FIG. 36 with 39A-B.

Figure 55A:
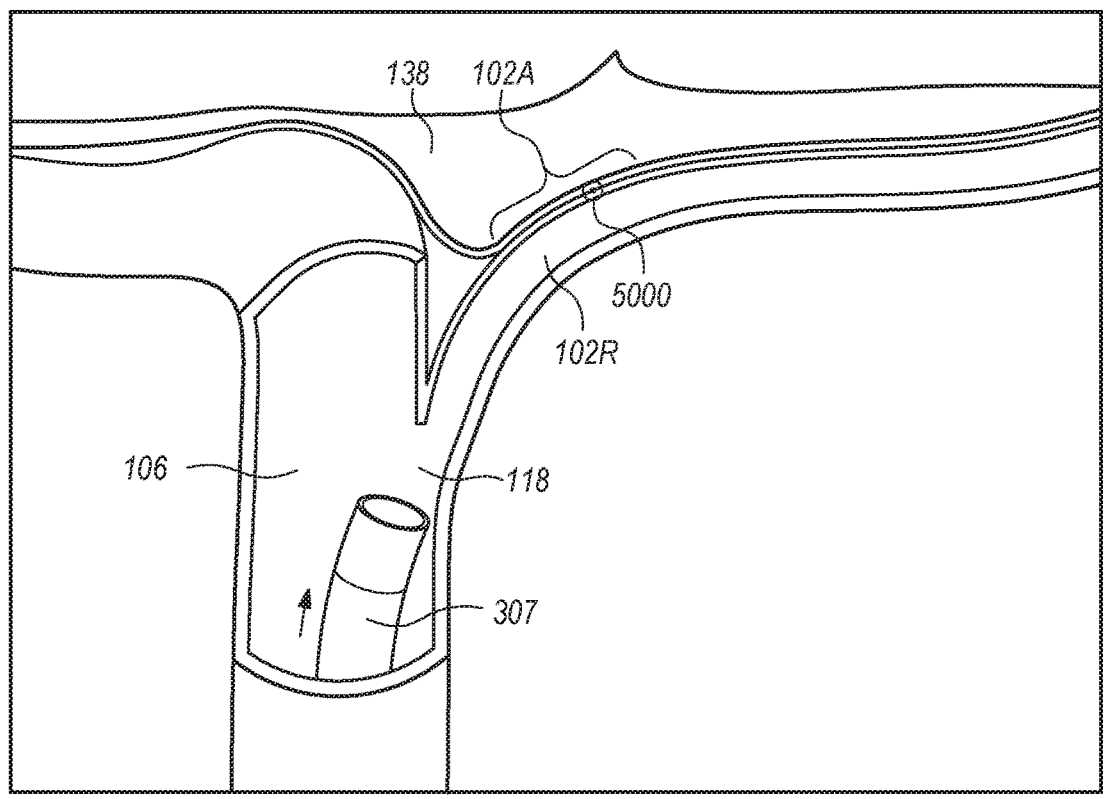
FIGS. 55A-O are perspective and cross-sectional views of exemplary methods for anchor delivery and shunt implantation procedures, according embodiments of the disclosed inventions.
Figure 55B:
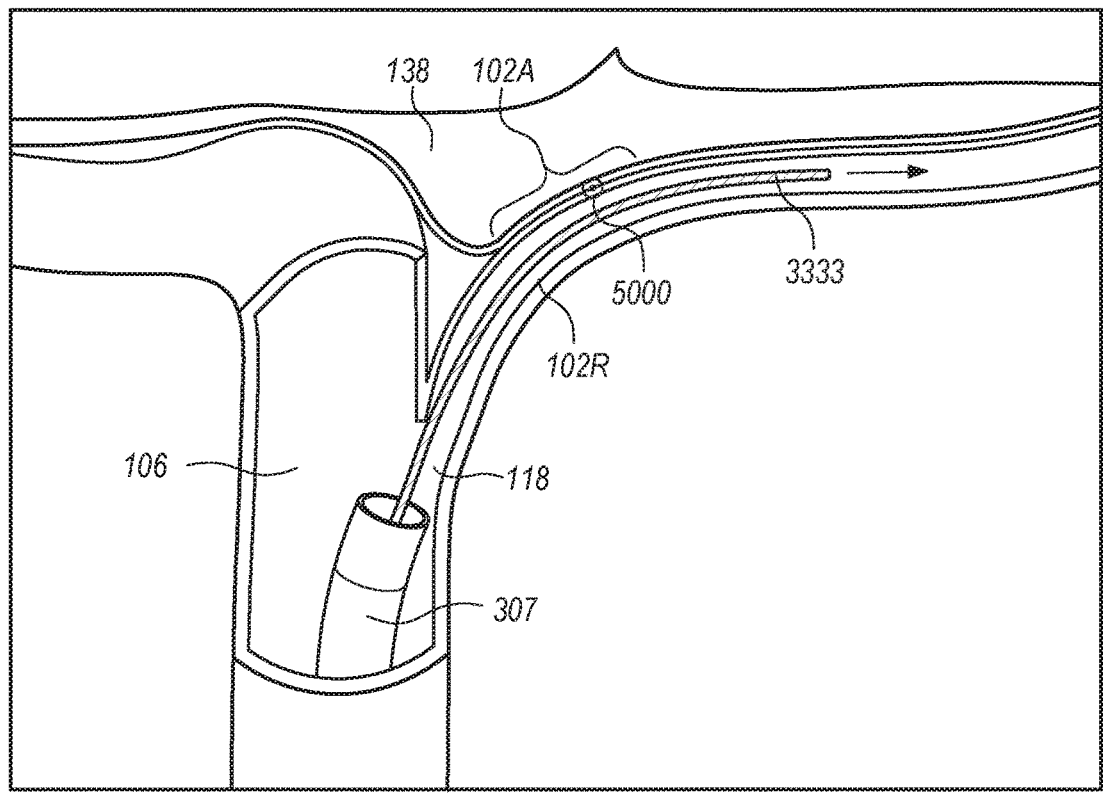
Figure 55C:
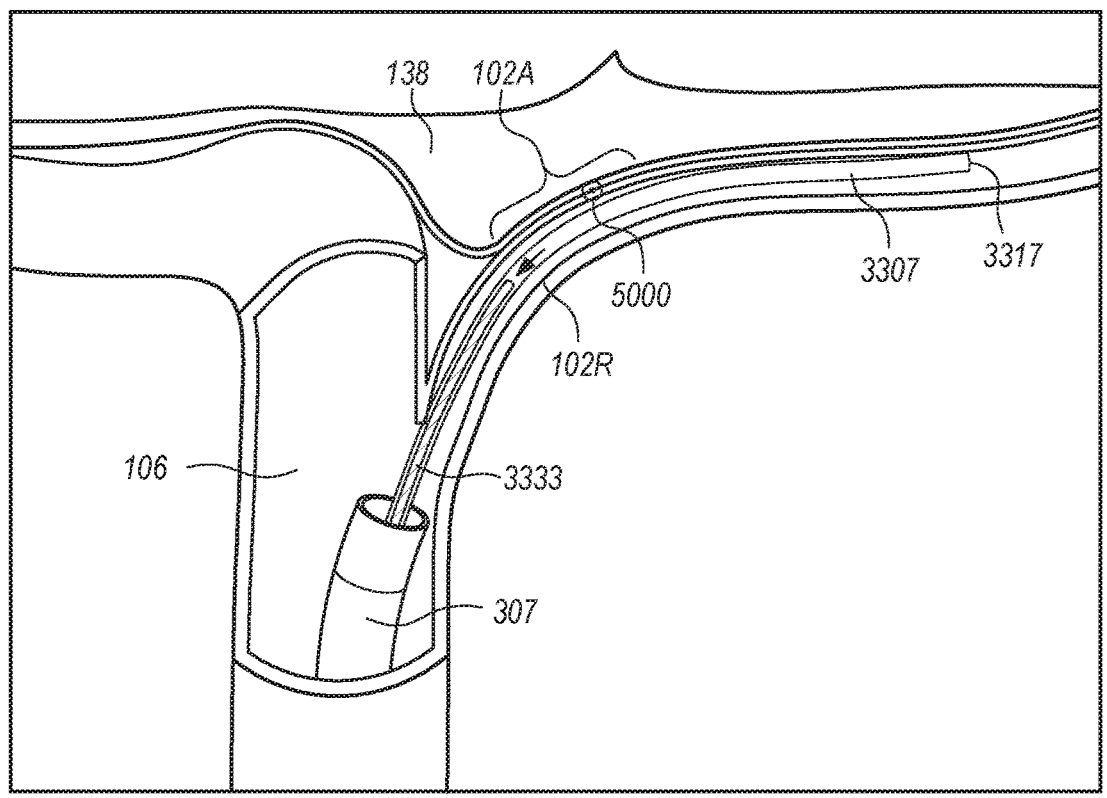
Figure 55D:
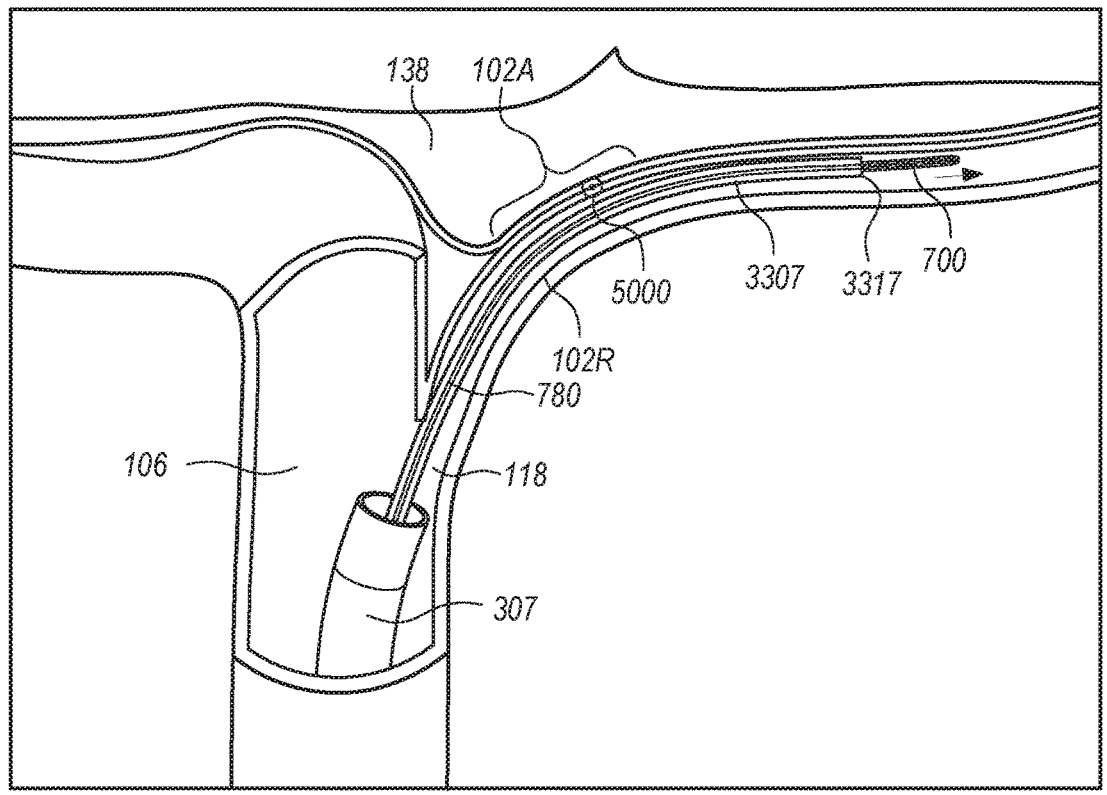
Figure 55E:
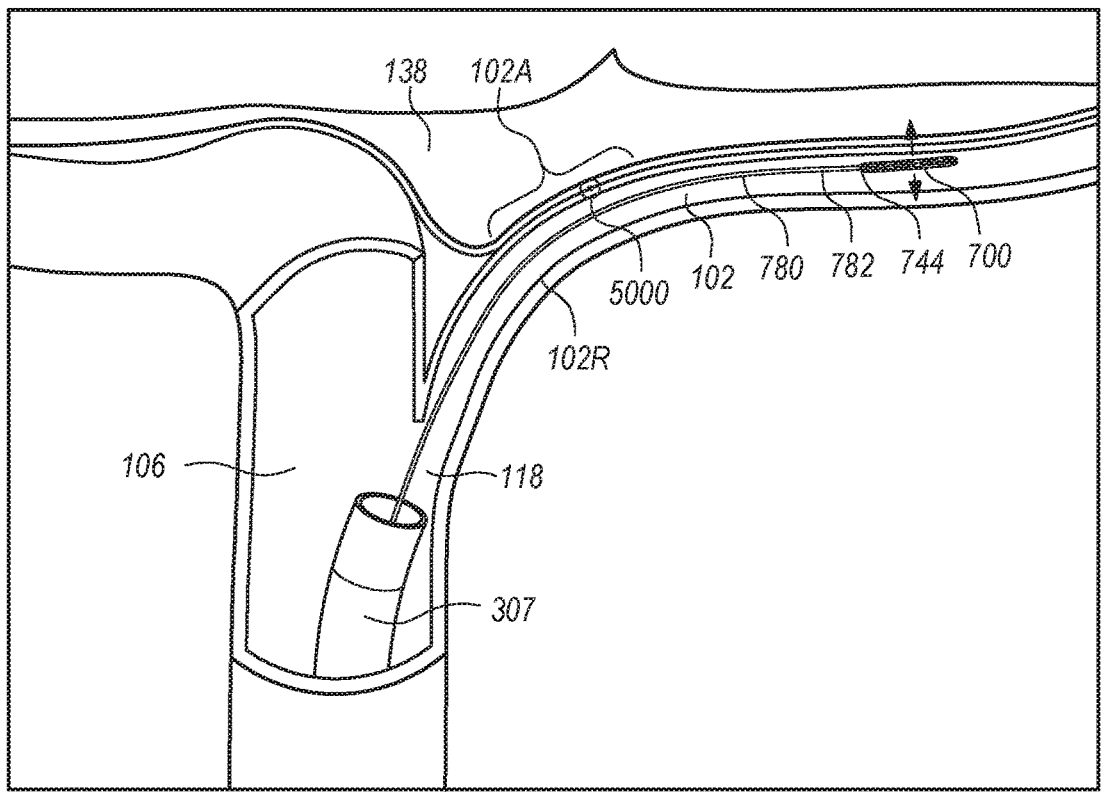
Figure 55F:
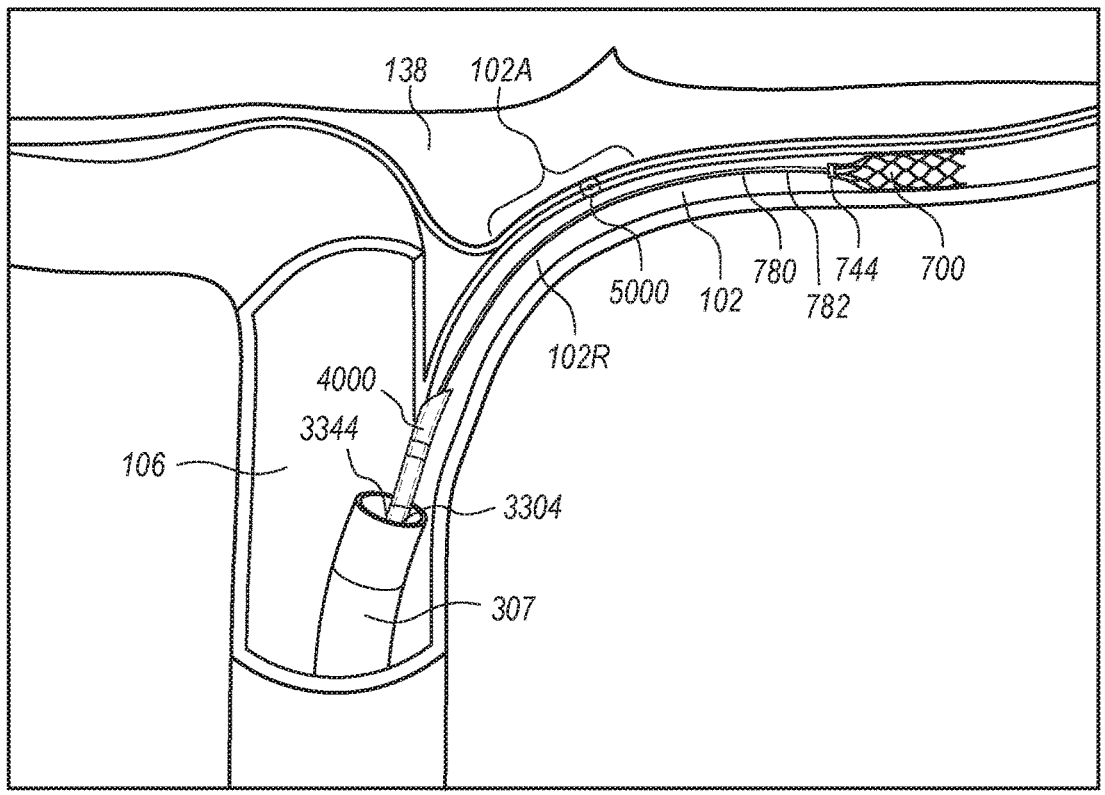
Figure 55G:
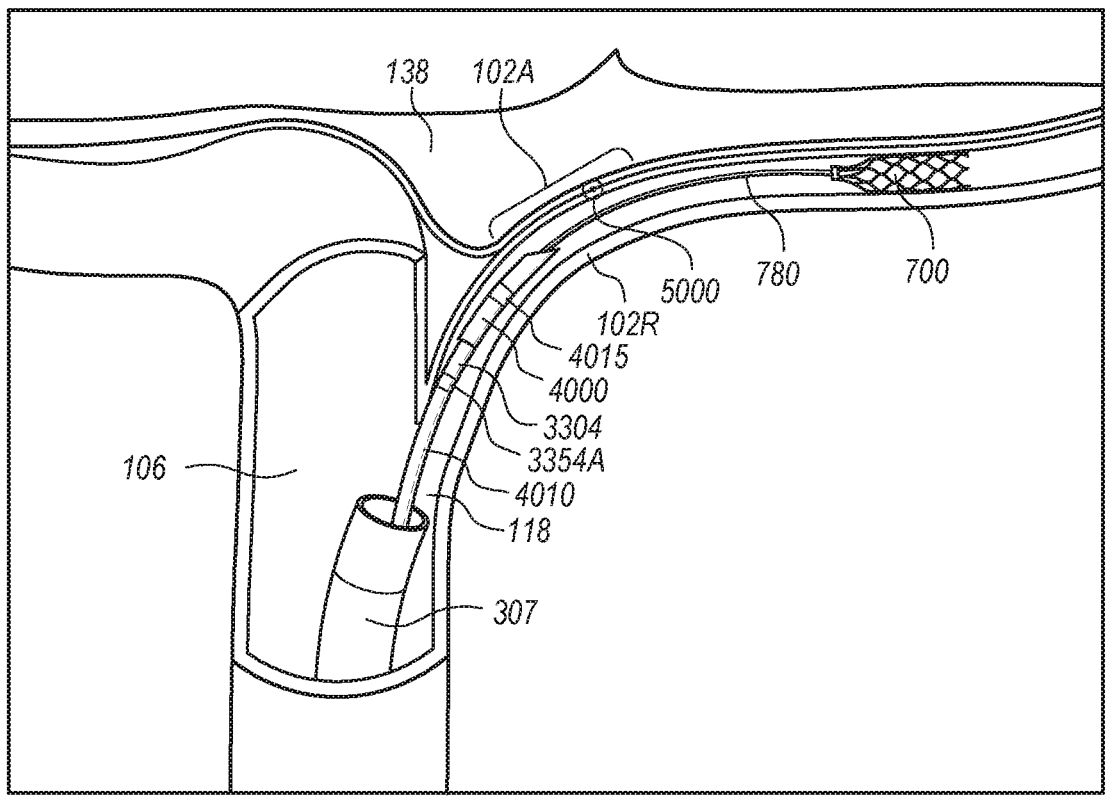
Figure 55H:
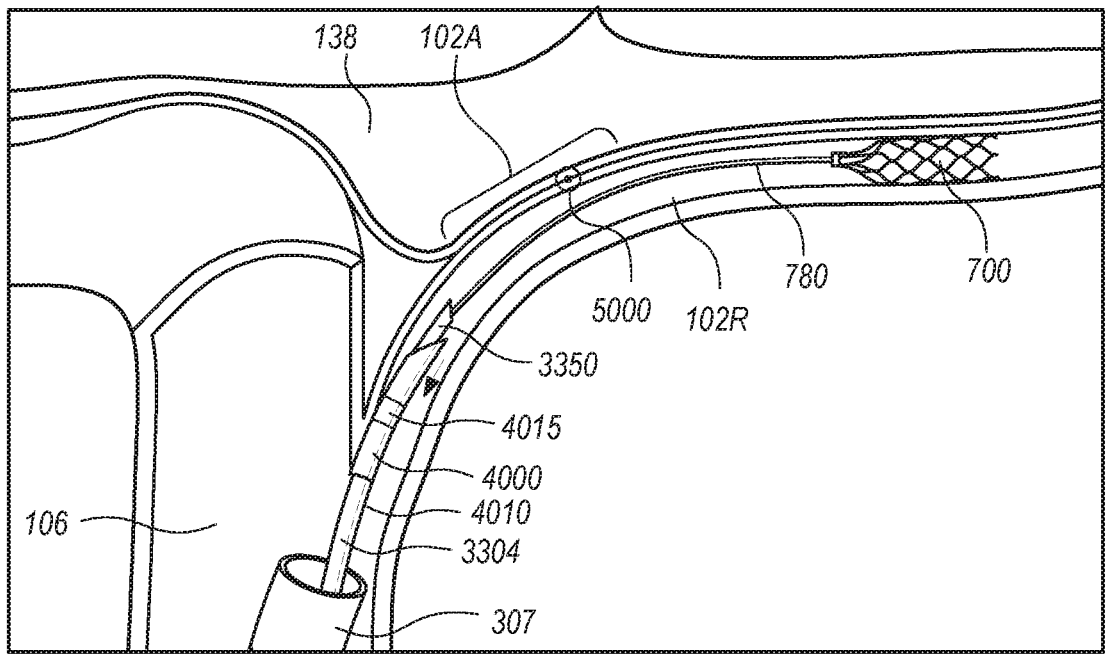
Figure 55I:
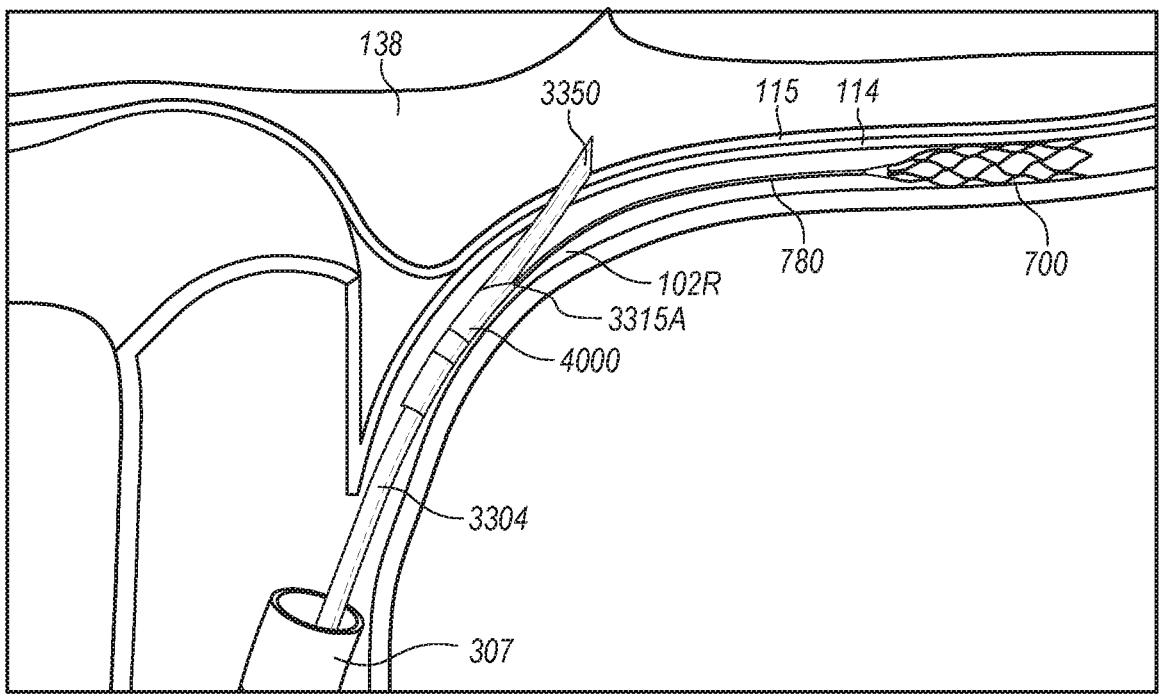
Figure 55J:
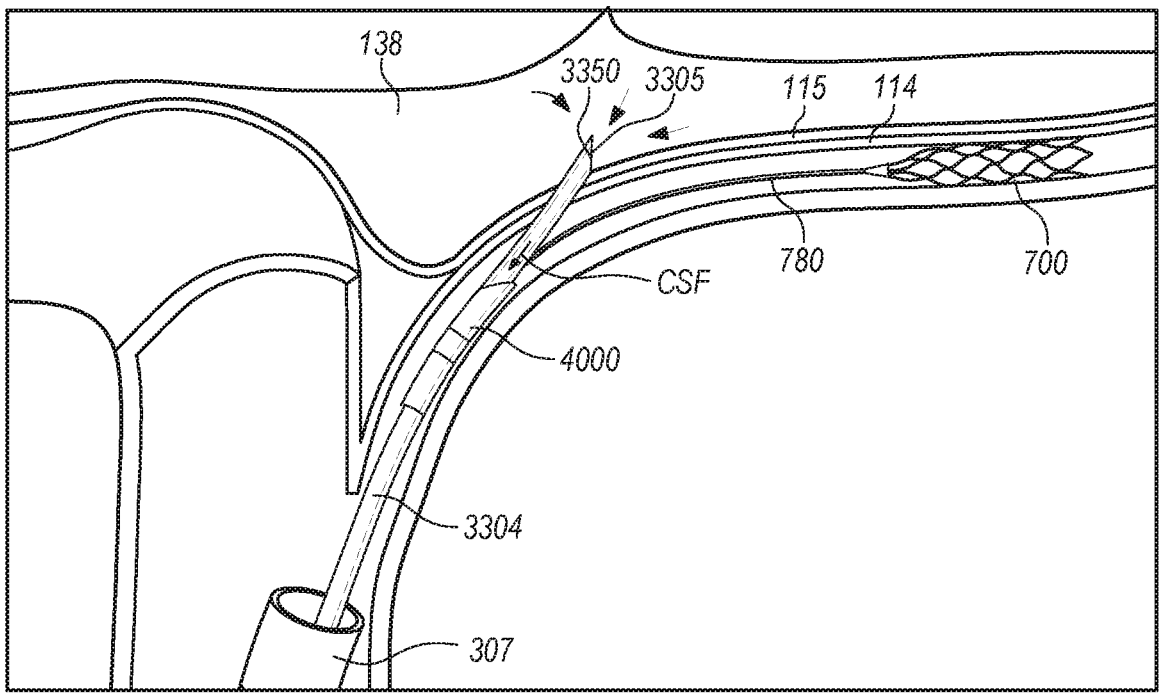
Figure 55K:
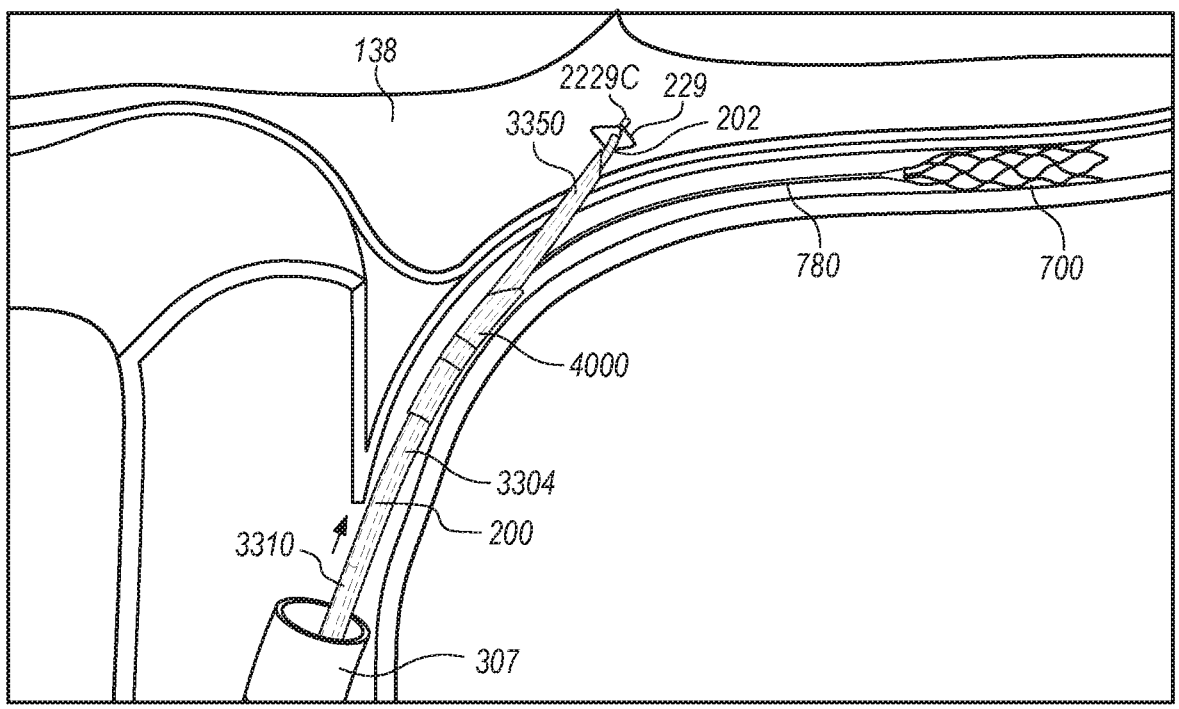
Figure 55L:
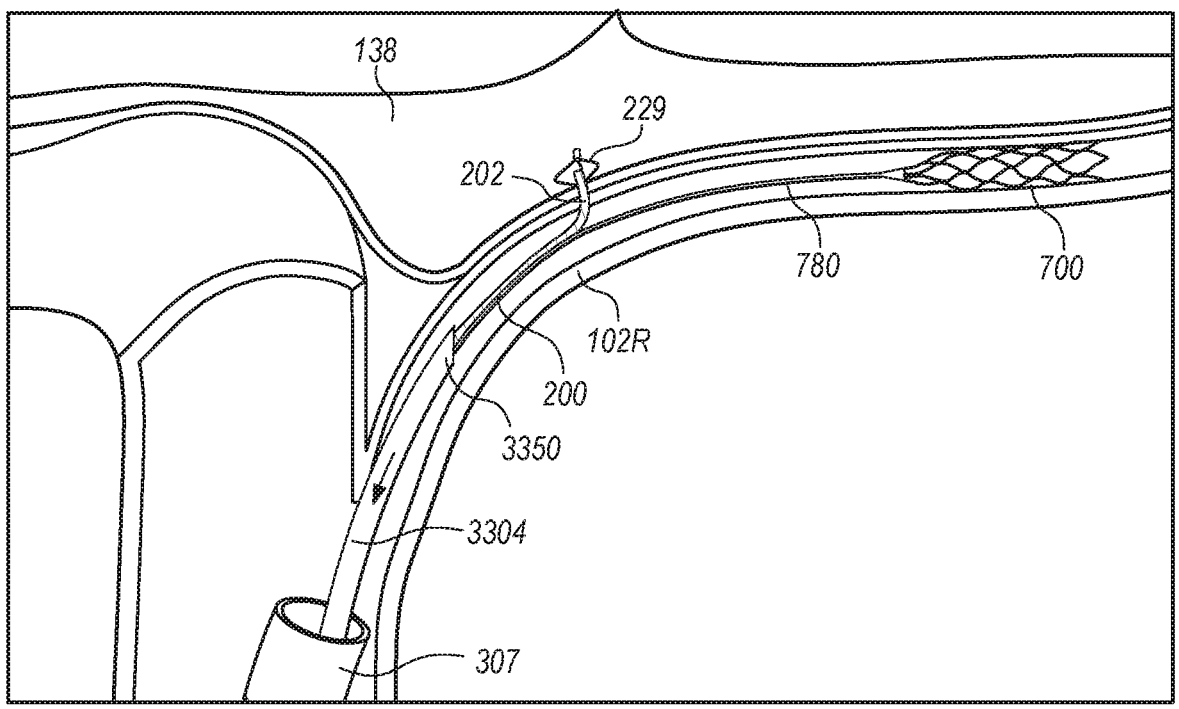
Figure 55M:
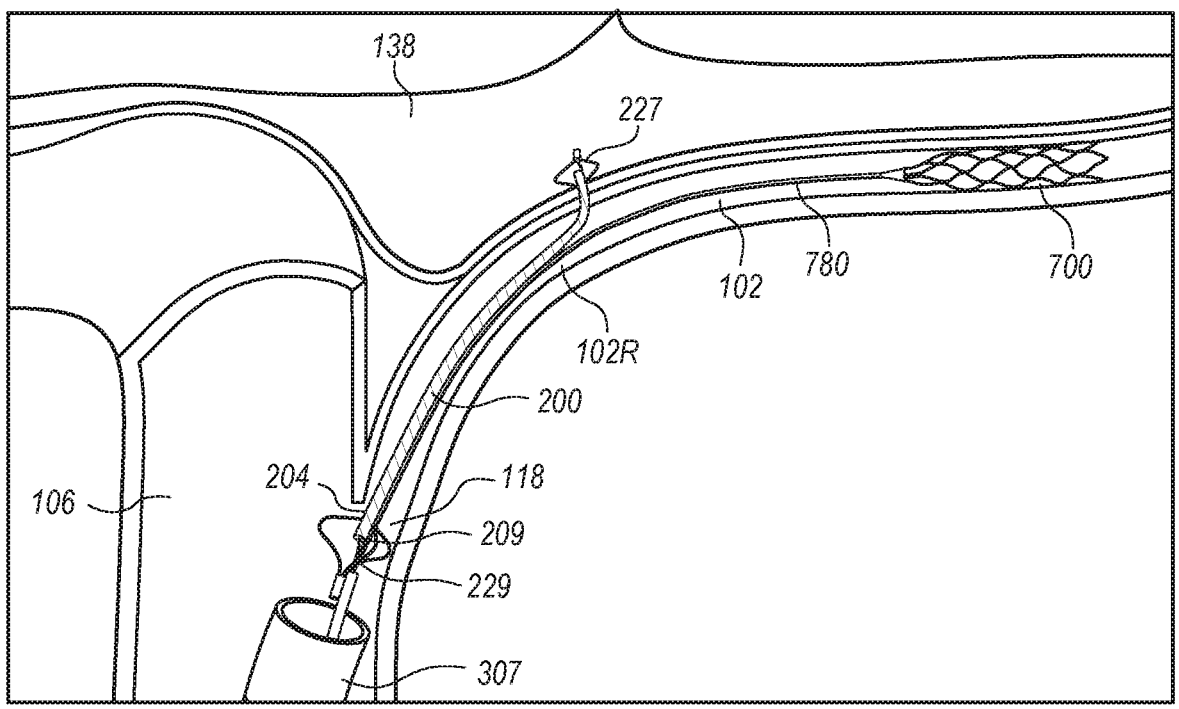
Figure 55N:
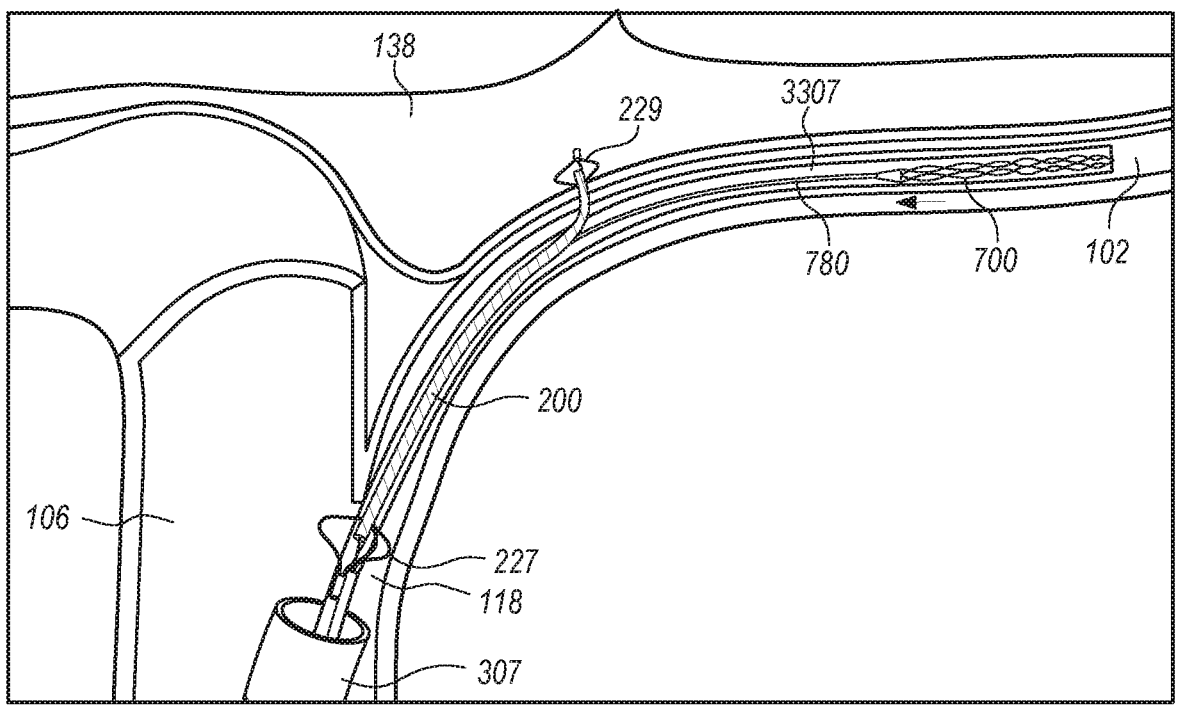
Figure 55O:
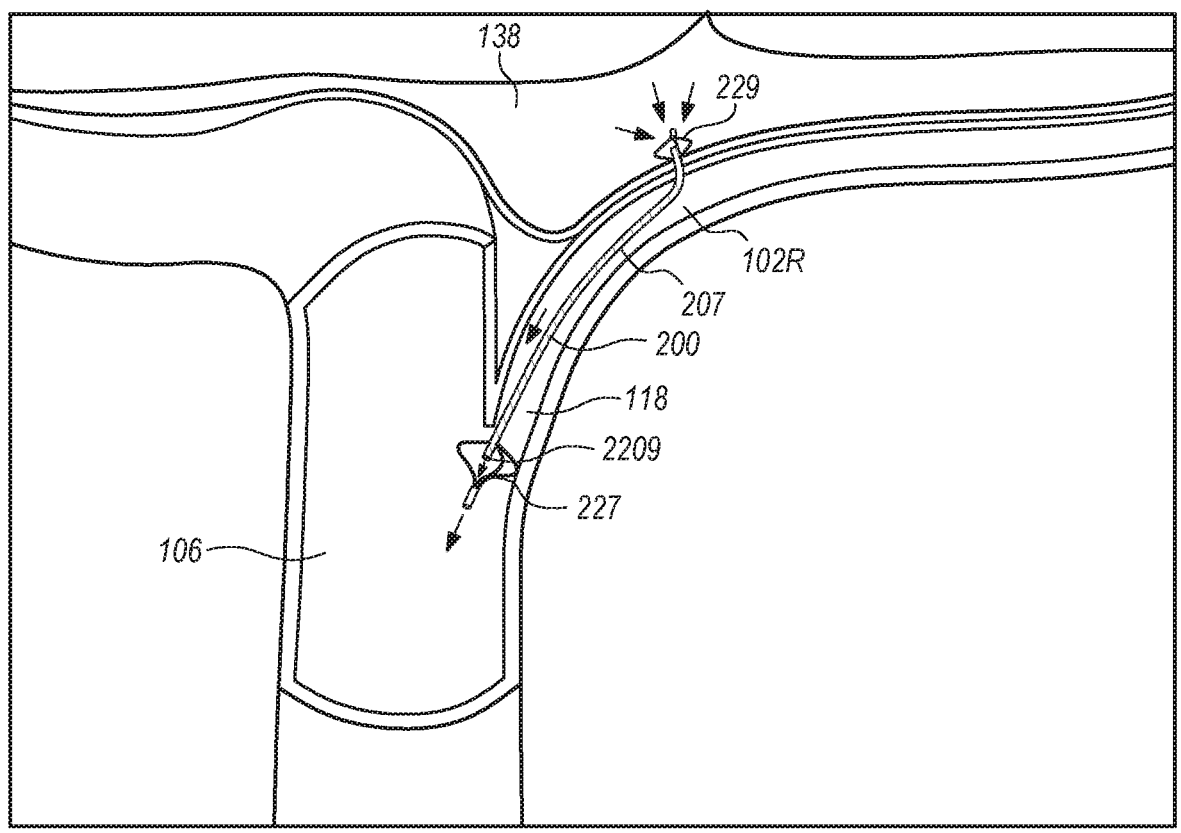

FIGS. 55A-O illustrate an exemplary shunt implant procedure in a patient suffering from elevated intracranial pressure. Any of the foregoing shunt and delivery system embodiments described herein can be used in the following exemplary procedure. The clinician can obtain CT and/or MRI imaging (e.g., coronal, T2, thin cut MRI images with gadolinium contrast) studies of the patient's intracranial anatomy to ascertain the sizing and relative proximity between the patient's right IPS 102R and left IPS 102L, CP angle cistern 138, arterial structures (e.g., basilar artery), and surrounding bony anatomy; such imaging can also be used to assess the volume of unobstructed CSF space of CP angle cistern 138 surrounding the left and right IPS channels relative to a target penetration site 5000 in an IPS 102 where an anastomosis will be made during the shunt implant procedure. The clinician can use this pre-procedure imaging to select one or more preferred shunt deployment locations along the first curved portion 102A and/or second curved portion 102B in the patient's right IPS 102R and/or left IPS 102L. To further illustrate the following exemplary procedure, the clinician selects the patient's right IPS 102R and a target penetration site 5000 along the first curve 102A of the IPS based on the pre-procedure MRI imaging study, as shown in FIG. 55A.

The clinician gains access to the patient's venous vasculature through the patient's right femoral vein using an introducer kit (e.g., Micropuncture Introducer Set from Cook Medical of Bloomington, Ind.) and the Seldinger technique. The clinician then navigates a guide wire (e.g., 0.035" guide wire such as an 0.035" GLIDEWIRE from Terumo Interventional Systems of Somerset, N.J.) and a guide catheter 307 (e.g., 6 Fr catheter such as 6 Fr ENVOY Guiding Catheter from Codman Neuro of Raynham, Mass.) through the femoral vein access point, distally through the vena cava and into the right jugular vein. The clinician can position the distal end of the guide catheter 307 about the JV-IPS junction 118 as shown in FIG. 55A, and in certain patient anatomies, the distal end of the guide catheter can access the proximal portion of the IPS 102. Optionally, a shuttle sheath (e.g., 7 Fr Flexor Shuttle Guiding Sheath from Cook Medical of Bloomington, Ind.) may be advanced through the patient's venous vasculature, prior to advancing the guide catheter 307; the guide catheter 307 can then be advanced through the shuttle sheath lumen to the jugular vein or JV-IPS junction 118. The shuttle sheath can provide additional support to the guide catheter, other catheter and guide wire components navigated to IPS 102 during the shunt procedure.

Then, the clinician accesses the right IPS 102R and/or cavernous sinus 104 with a micro catheter 3307 and micro wire 3333 (FIGS. 55B and 55C). The micro catheter is omitted from FIG. 55B for clarity of the micro wire 3333. The micro catheter 3307 described as being used in the medical procedures herein can include the micro catheter reinforcing members 1100, 1200, 1500, or 1600 described above and can include any of the various parameters or features discussed herein to achieve improved performance characteristics such as better maneuverability and reliability. The micro catheter 3307 advances through the guide catheter lumen, and the micro wire (e.g., an 0.010", 0.014", or 0.018" guide wire such as a Synchro2 Guidewire from Stryker Neurovascular of Fremont, Calif.) can pass through the micro catheter lumen. The clinician advances the micro wire 3333 and micro catheter 3307 through the JV-IPS junction 118 into the right IPS 102R (e.g., the micro wire 3333 may be advanced distally and incrementally, followed by the micro catheter 3307 advancing distally and incrementally over the micro wire 3333, repeating the wire and catheter advancement steps in serial fashion; the micro wire may be advanced to its distal location first with the micro catheter following thereafter in two separate advancements; or the micro wire and micro catheter can be advanced distally, simultaneously through the JV-IPS junction 118 and into the right IPS 102R). The clinician can position the distal end of the micro catheter 3307 at a location distal to the target penetration site 5000 in IPS wall 114 along first curve 102A of the right IPS 102R as shown in FIG. 55C. As discussed herein, the catheter, the reinforcing member therein, can be formed to have structural features to improve maneuverability as the clinician positions the distal tip of the catheter. For example, improved column strength and better responsiveness to torque and rotational inputs can help make it easier for the clinician, for example, to access and maneuver within the IPS and other venous sinuses. The clinician withdraws the micro wire 3333 from the micro catheter 3307, leaving the distal opening 3317 of the micro catheter 3307 distal to the target penetration site 5000 in IPS wall 114 along first curve 102A of the right IPS 102R, as shown in FIG. 55C.

The clinician then deploys an anchor 700 and guide member 780 in the distal portion of the right IPS 102R in step 5020 of the procedure, which results in the anchor 700 secured in IPS 102R, distal to the target penetration site along IPS wall 114 of the first curved portion 102A of the right IPS 102R as shown in FIG. 55E. The clinician can load the anchor 700 and elongate guide member 780 into the proximal opening (not show) of the micro catheter 3307. Using elongated pusher of FIGS. 13, 14A-E and by loading the proximal portion 784 of guide member 780 through the pusher lumen 3724 as previously disclosed, the clinician advances anchor 700 and guide member 780 distally through the micro catheter lumen until the anchor 700 reaches the distal opening 3317 of the micro catheter lumen as shown in FIG. 55D. The elongated guide member 780 may be disposed within the lumen 3724 of the elongated pusher 3710 (FIGS. 13, 14A-E) for delivering the anchor 700 into the IPS 102, while the proximal portion 784 of guide member 780 extends out the elongated pusher 3710 (e.g., out through the lumen opening 3726' of handle 3722), as previously described. A clinician can pinch or hold the proximal portion 784 of guide member 780 extending through the handle 3722 against the handle outer surface 3725 and then advance the handle 3722 and guide member 780 into a micro catheter to advance the anchor 700 distally. The clinician can then retract elongated pusher 3710 proximally over the proximal portion 784 of guide member 780 (i.e., by releasing the proximal portion 784 of guide member 780 pinched or held against the handle outer surface 3725), and thereafter repeat the advancing and retracting acts until the anchor 700 reaches a desired location (e.g., distal end of micro catheter lumen). The use of the elongated pusher 3710 facilitates the anchor 700 delivery and navigation by leveraging the column strength of guide member 780, as an alternative to having an anchor pusher member that extends at least the length of the micro catheter.

The clinician then positions the distal portion of the micro catheter 3307 (i.e., with anchor 700 and guide member 780 packed inside) about the location for anchor deployment, and withdraws the micro catheter 3307 proximally while holding the anchor 700 in place using guide member 780 and/or advances anchor 700 via guide member 780 distally through the distal opening 3317 of the micro catheter 3307 while holding the micro catheter 3307 in place until the anchor 700 emerges from the catheter lumen and expands against the walls of the sinus lumen. As discussed above, the micro catheter 3307 can be formed to have improved tensile strength and force transmission due to the reinforcing members described herein. As such, the micro catheters described herein can make it easier and more precise for the clinician to move the guide member 780 and anchor 700 relative to the micro catheter 3307 without unintentionally disturbing (or limiting significant disturbance of) the position of the distal tip of the micro catheter 3307 because it is less likely to be stretched or be deflected under axial forces generated by moving the anchor 700 within the micro catheter.

At this point of the procedure, a distal portion of guide member 780 such as joint 744 coupling the guide member and anchor 700, can be disposed in the sinus lumen; the remainder of guide member 780 remains within the micro catheter lumen. If the clinician is satisfied with the anchor deployment location, he then withdraws the micro catheter from the patient, leaving behind the deployed anchor 700 with guide member 780 that extends proximally from the proximal portion of anchor 700 through the first curved portion 102A and junction 118 as shown in FIG. 55E, through the patient's venous vasculature and out of the patient via the femoral vein access point. Alternatively, he can recapture the deployed anchor 700 and guide member 780 into the micro catheter lumen and redeploy the anchor in the sinus lumen one or more times until he is satisfied with the anchor deployment location. Optionally, the clinician can use elongated pusher 3710 with micro catheter 3307 to facilitate anchor 700 recapture and redeployment in the sinus lumen.

To continue the procedure, the clinician introduces delivery catheter 3304 into the patient's vasculature via the femoral vein access point and navigates the catheter 3304 distally through the JV-IPS junction 118 (as shown in FIG. 55F) to the target penetration site 5000 along IPS wall 114 of the first curved portion 102A of the right IPS 102R. The clinician can feed the proximal end of guide member 780 through the first lumen 3315 of delivery catheter 3304, via distal opening 3315a and proximal opening 3315b of the first lumen. The clinician then advances delivery catheter 3304 over guide member 780, through the femoral vein access point and tracks the delivery catheter 3304 distally, over the guide member 780 and through the patient's venous vasculature, until the distal portion 3344 of the delivery catheter 3304 is positioned about the target penetration site 5000 along IPS wall 114 of the first curved portion 102A of the right IPS 102R as shown in FIG. 55G. While tracking the delivery catheter 3304 distally, the clinician can hold the guide member 780 stationary or pull proximally on the proximal portion 784 of the guide member 780 to facilitate advancement of the delivery catheter 3304 through the patient's venous anatomy. In addition, the clinician can rotate the delivery catheter 3304 while tracking distally over the guide member 780 to overcome any resistance, e.g., resistance encountered while tracking the catheter through JV-IPS junction 118 and/or into right IPS 102R.

The clinician can confirm the orientation of the delivery catheter 3304 and the trajectory of penetrating element 3350 through IPS wall 114 into CP angle cistern 138 relative to the target penetration site 5000 using one or more of the previously disclosed imaging techniques. The clinician may use the distal 3354*a* and proximal 3354*b* markers located on the distal portion 3344 of the delivery catheter 3304 in this confirmation step. The markers will be visible under various imaging modalities used during the procedure (e.g., bi- or single-plane fluoroscopy). To the extent the clinician has created a 3D reconstruction of the patient's anatomy about the target penetration site 5000 (e.g., using 3D-rotational angiography or venography), the clinician can confirm the orientation and/or trajectory of the penetrating element 3350 by combining the fluoroscopy and 3D reconstruction using a 3D road mapping technique. Optionally, the clinician can use the 3D reconstruction data to create a window representing the target penetration site 5000; the 3D window and live fluoroscopy can be overlaid with respect to each other to provide further guidance for the clinician to penetrate IPS wall 114 at target penetration site 5000.

Then, the clinician retracts the penetrating element guard or guard member 4000 to expose penetrating element 3350 in the IPS 102 at the target penetration site along IPS wall 114 of the first curved portion 102A of the right IPS 102R as shown in FIG. 55H. The clinician retracts the guard member 4000 by pulling proximally on pull wire 4010 while holding the remainder of delivery catheter 3304 in place. While retracting guard 4000 and using the previously disclosed imaging techniques, the clinician will observe marker 4015 in guard 4000 transition proximally towards and/or until it abuts or overlaps with distal marker 3354*a* located on the distal portion 3344 of delivery catheter 3304. Again, the clinician can confirm the trajectory of penetrating element 3350 through the IPS wall 114 into CP angle cistern 138 using one or more of the previously disclosed imaging techniques before penetrating IPS wall 114. If the clinician is unsatisfied with the trajectory of the penetrating element 3350 or perceived penetration site 5000 on IPS wall 114, the clinician can adjust the location of the distal portion 3344 of delivery catheter 3304 until the clinician is satisfied that penetrating element 3350 will penetrate the IPS wall 114 at the target location along the first curved portion 102A of the right IPS 102R. When adjusting the location of the distal portion 3344 of delivery catheter 3304 the clinician can re-sheath penetrating element 3350 by advancing the penetrating element guard 4000 distally via pull wire 4010 and then unsheath penetrating element by retracting guard 4000 proximally before penetrating IPS wall 114; this re-sheathing step can prevent inadvertent penetration or injury to the IPS walls that could occur if the penetrating element 3350 were uncovered or unprotected while the clinician repositioned delivery catheter 3304 in the IPS 102.

With the penetrating element 3350 oriented along a desired trajectory at the target penetration along IPS wall 114, the clinician advances delivery catheter 3304 distally so that penetrating element 3350 passes through the dura of IPS wall 114, arachnoid layer 115, and into the CSF-filled subarachnoid space of CP angle cistern 138 as shown in FIG. 55I. The clinician can pull proximally on the proximal portion of guide member 780 or hold the guide member 780 in place while advancing delivery catheter 3304 distally to cause the penetrating element 3350 to penetrate the IPS wall 114; these techniques allow the portion of delivery catheter 3304, distal of the lumen opening 3315*a* to track along the target trajectory and off-axis from the path of guide member 780 through the first curved portion 102A of the right IPS 102R. The clinician stops advancing delivery catheter 3304 distally when the clinician is satisfied that penetrating element 3350 and second lumen 3305 of delivery catheter 3304 have accessed CSF of the CP angle cistern 138; this can be confirmed via one or more of the previously disclosed imaging techniques, e.g., by 3D road mapping.

As an alternative method of confirming access to CP angle cistern 138, the clinician can aspirate CSF through the penetrating element 3350 and second lumen 3305 of delivery catheter 3304 to confirm that the penetrating element 3350 passed through IPS wall 114 and arachnoid layer 115 to access CSF within CP angle cistern 138 (e.g., aspirated CSF denoted by arrow-head lines in FIG. 55J). The clinician can use a syringe on the distal portion of handle (e.g., 10 cc syringe) to aspirate CSF proximally, through delivery catheter 3304. The presence of clear CSF in the syringe can confirm a successful penetration through the IPS into the CP angle cistern 138. If the clinician observes blood in the syringe, this can indicate that the penetrating element 3350 did not completely pass through IPS wall 114 or remained entirely within right IPS 102R. If the clinician did not penetrate IPS wall 114, the clinician can re-attempt to penetrate IPS wall 114 at the target site, attempt to penetrate IPS wall 114 at another target penetration site along the first curved portion 102A of right IPS 102R, attempt to penetrate IPS wall 114 along the second curved portion 102B of right IPS 102R as will be further described below, or abort the procedure.

After confirming that the penetrating element 3350 passed through IPS wall 114 and arachnoid layer 115 to access CSF within CP angle cistern 138, the clinician advances pusher member 3310 distally to advance shunt 200 distally from the lumen 3305 of delivery catheter 3304 until the distal anchoring mechanism 229 of the shunt deploys in CP angle cistern 138 in step 5050 of the procedure as shown in FIG. 55K. The clinician can confirm that the distal anchoring mechanism 229 of the shunt deployed in the cistern by observing a radiopaque marking(s) on a distal portion of the shunt as it emerges from the catheter into the subarachnoid space, using one the previously disclosed imaging techniques (e.g., by using live fluoroscopy to observe the RO makings in the distal portion of the shunt transition from a delivery configuration to a deployed configuration as described in connection with FIG. 55C). By pulling shunt pusher 3310 proximally (and, optionally, simultaneously pulling delivery catheter 3304 proximally), the clinician fully expands the distal anchoring mechanism 229 against arachnoid layer 115 in CP angle cistern 138.

The clinician continues deploying shunt 200 across the penetration tract in IPS wall 114 and in the right IPS 102R in step 5055 of the procedure as shown in FIG. 55L. By holding shunt pusher member 3310 in place while withdrawing delivery catheter 3304 proximally, shunt 200 emerges from the delivery catheter lumen 3305 and deploys in the lumen of IPS 102R. At this point in the procedure, the proximal portion of shunt 200 and, if included on the particular embodiment of shunt 200 being deployed, proximal anchoring mechanism 227 on the shunt remain inside lumen 3305 of delivery catheter 3304; the remainder of the shunt is deployed in the CP angle cistern and right IPS 102R.

The clinician finishes deploying shunt 200 in step 5060 of the procedure by deploying proximal anchoring mechanism 227 of shunt 200 about the JV-IPS junction 118 or in jugular vein 106 as shown in FIG. 55M. Again, by holding shunt pusher member 3310 in place while withdrawing delivery catheter 3304 proximally, shunt 200 emerges from delivery catheter lumen 3305. As the proximal anchoring mechanism 227 and interlocking elements 229 on the distal portion of the shunt pusher member 3310 emerge from within the delivery catheter lumen 3305, the shunt pusher member and shunt separate or disconnect, thereby releasing shunt 200 from pusher member 3310. The clinician, optionally, can pause the shunt deployment step before the shunt completely releases from the interlock (or the self-expanding distal end portion of the shunt delivery shuttle disclosed herein) of pusher member 3310 by holding delivery catheter 3304 in place (e.g., by not withdrawing delivery catheter 3304 proximally) to confirm that he is satisfied with the shunt deployment location in the patient before completely releasing shunt 200 from delivery catheter 3304. In embodiments of shunt 200 that do not include a proximal anchoring mechanism 227, step 5060 is completed in substantially the same manner, with shunt 200 releasing from the shunt delivery shuttle 4316 and proximal portion of shunt deployed in the JV.

In the next step 5065 of the procedure, the clinician removes delivery catheter 3304 from the patient by withdrawing it proximally through the venous vasculature and out of the patient at the femoral vein access point. Optionally, the clinician holds guide member 780 in place while withdrawing delivery catheter 3304 proximally to ensure that anchor 700 does not migrate proximally through IPS 102R and interfere with deployed shunt 200.

The clinician recaptures anchor 700 into the micro catheter (e.g., micro catheter 3307, which is omitted for clarity) and removes the anchor from the patient via the femoral vein access point in step 5070 of the procedure. By feeding the proximal portion of guide member 780 through the micro catheter lumen, the clinician can track the micro catheter distally over the guide member, around proximal anchoring mechanism 227 (if present) of the shunt deployed in the jugular vein 106 or JV-IPS junction 118, until the distal end of the micro catheter reaches the joint 744 between the guide member and anchor. He can then further advance the micro catheter distally and/or hold stationary or pull guide member 780 proximally to transition the anchor from its deployed or expanded configuration in the sinus lumen to its compressed configuration within the micro catheter lumen as shown in FIG. 55N. As discussed above, in some embodiments, the structural features detailed herein can improve structural characteristics of the reinforcing member of the micro catheter, for example, improved column strength and reduced likelihood of buckling. As a result, the micro catheter can, in some cases, more readily handle the user pulling the anchor 700 into the micro catheter without deforming or failing. With the anchor compressed in the micro catheter lumen, the clinician withdraws the micro catheter and anchor from the patient proximally, through the venous vasculature and out of the femoral vein access point. Thereafter, he withdraws the guide catheter from the patient.

The deployed shunt 200 (shown in FIG. 55O) and valve 2209 provide a one-way flow conduit to drain excess CSF from the patient's subarachnoid space into the jugular vein, thereby relieving the patient's elevated intracranial pressure. The arrows in FIG. 55O depict the direction of CSF flow from the CP angle cistern 138 into the shunt lumen 207, through valve 2209, and into jugular vein 106.

If in steps 5040 or 5045 of the procedure the clinician is unsuccessful at penetrating IPS wall 114 at the target penetration site along the first curved portion 102A, he can continue the procedure by attempting to penetrate IPS wall 114 along the second curved portion 102B of right IPS 102R (e.g., as shown in FIG. 2C). For example, in certain patient anatomies, an overhang of the petrous bone can prevent penetrating element 3350 from passing through IPS wall 114 into CP angle cistern 138. The presence of this bony overhang can be confirmed during the shunt implant procedure by using one or more of the previously disclosed imaging modalities. The clinician can then continue the procedure by re-sheathing penetrating element 3350 with penetrating element guard 4000, and advancing delivery catheter 3304 distally over guide member 780 until the distal portion of delivery catheter 3304 is positioned at a target penetration site along the second curved portion 102B of right IPS 102R. Optionally, the clinician can rotate delivery catheter 3304 from about 45 to 180 degrees while tracking distally from the first curved portion 102A toward the second curved portion 102B in IPS 102R; by rotating the delivery catheter, the clinician can orient penetrating element 3350 such that further distal advancement of delivery catheter 3304 will advance penetrating element 3350 through IPS wall 114 at a target penetration along the second curved portion 102B of right IPS 102R. The clinician can continue the procedure and deploy shunt 200 through IPS wall 114 along the second curved portion 102B of right IPS 102R as previously described in steps 5030-5070 of the procedure.

Embodiments of shunt 200 that have been deployed in IPS 102 can be retrieved using a minimally invasive retrieval procedure guided by one or more of the imaging methods previously disclosed. The clinician can advance a guide catheter through the patient's vasculature (e.g., from a femoral vein access point in the patient) to the JV-IPS junction 118. The guide catheter can be advanced until the proximal end of the catheter is proximate to the proximal end of shunt 200 deployed in the JV or further advanced until the proximal portion of the shunt 200 is contained within the distal portion of the guide catheter lumen. The clinician can then navigate a micro catheter (e.g., the micro catheter 3307) through the guide catheter until the distal opening 3317 of the micro catheter is proximate to the proximal end of the deployed shunt. An anchor 700 with elongate guide member 780 is then translated through the micro catheter, for example, using the elongated pusher 3710 and corresponding method of use as previously disclosed. The clinician can deploy anchor 700 from the distal opening 3317 of micro catheter 3307 and adjust the location of the expanded anchor 700 within the JV (and/or guide catheter lumen) until the proximal portion of the shunt is contained within the lumen of anchor 700 and/or the proximal portion of the shunt 200 has passed through one of the cells of anchor 700. The clinician then re-sheaths the anchor 700 into the micro catheter 3307, thereby compressing the proximal portion of shunt 200 within anchor 700 inside the micro catheter. Further to the discussion above, the improved maneuverability and strength (e.g., column strength) of the reinforcing members described herein can make it easier for the clinician to apply adequate axial force to the micro catheter to re-sheath the anchor 700 to collapse the anchor 700 and the proximal portion of the shunt 200 with few complications, such as collapsing or deforming the micro catheter. The clinician can then withdraw the micro catheter proximally until the distal anchoring mechanism 229 of the shunt in CP angle cistern 138 collapses and passes through IPS wall 114. The clinician can further withdraw the micro catheter into the guide catheter lumen and continue withdrawing the micro catheter from the patient to complete the shunt retrieval procedure. The retrieval procedure can also be completed using commercially available thrombectomy devices or embodiments of encapsulating shroud 7016 in addition to the anchor 700 as described above. After shunt retrieval, for example, to prevent bleeding into the CP angle cistern 138 through the penetration tract in IPS wall 114, the clinician can temporarily deploy a balloon in the IPS to stop bleeding, deploy a covered stent in the IPS at the penetration site, or embolize that portion of the IPS using commercially available embolization devices (e.g., coils, particles, foam, adhesives).

FIGS. 56A-E illustrate an alternate embodiment of shunt 2200. Shunt 2200 includes a distal anchoring mechanism 2229 (i.e., malelcot), as well as a retaining element 2230 comprising a radiopaque material, which element will be further described below. Distal anchoring mechanism 2229 includes arms or tines 2229*a* comprising a hinge, living joint, or the like 2229*b*, as previously described herein. The shunt 2200 further comprises a shunt body 2203, CSF lumen 2207, and a one-way valve 2209 located in the proximal portion 2204 of the shunt.

Figure 56A:
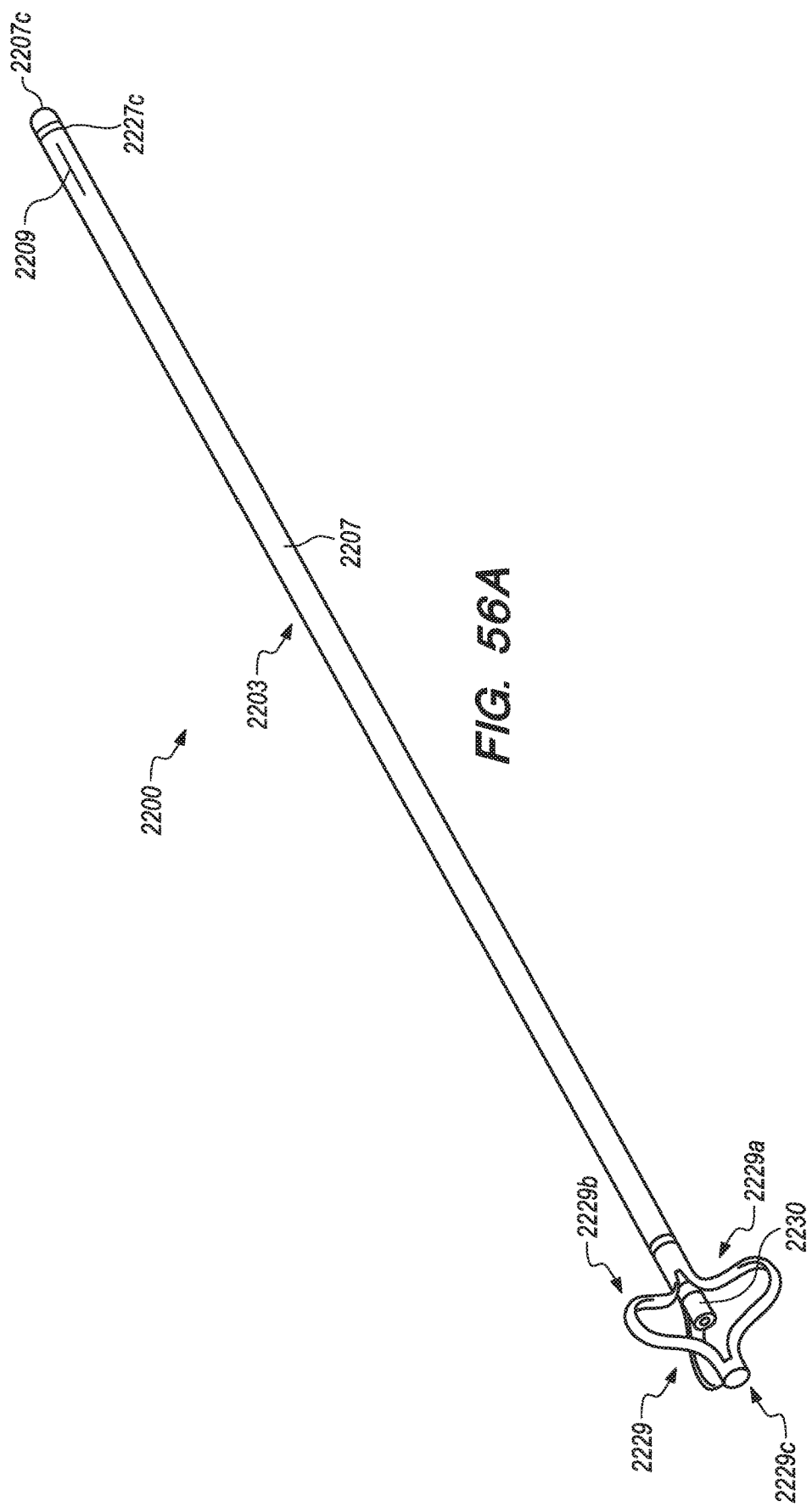
Figure 58A:
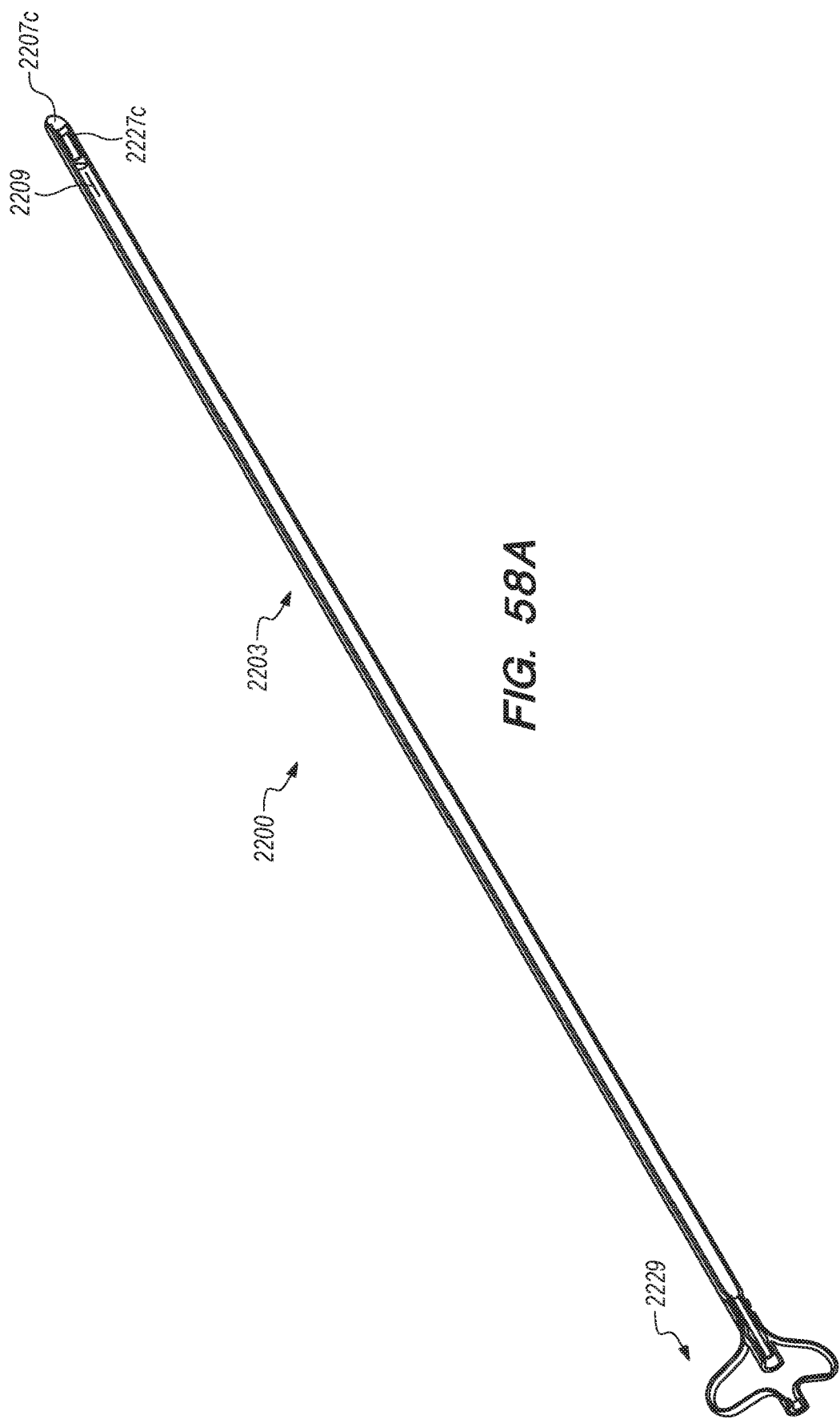

The shunt body 2203 can have an elongate cylindrical configuration as depicted in FIG. 56A and extend between the distal 2202 and proximal 2204 portions of the shunt. Shunt body comprises CSF lumen 2207, e.g., as illustrated in the cross-section views of FIGS. 56C-D. Shunt body 2203 can include an elastomeric polymer(s) suitable for implant applications including, but not limited to, silicone, polyurethane, polycarbonate urethane, thermoplastic polyurethane, aromatic or aliphatic polycarbonate thermoplastic polyurethane, silicone/polyurethane blends (e.g., thermoplastic silicone polycarbonate polyurethane comprising 20% silicone copolymer), or polyurethane silicone blends (e.g., polyurethane silicone copolymer). The durometer of the elastomer shunt body 2203 can range from about 15 A to about 80 A; for a silicone-based shunt body, the durometer can range from about 15 A to about 80 A, and for a urethane-based shunt body, the durometer can range from about 55 A to about 80 A. A shunt body 2203 comprised of an elastomeric polymer(s) advantageously resists thrombus formation on the portions of the implanted shunt in the blood flow of the IPS and jugular vein. Optionally, shunt 2200 can include an anti-thrombotic coating to prevent thrombus formation including, but not limited to, heparin-based or phosphorylcholine-based anti-thrombotic coatings. To further prevent thrombus formation, the length of shunt body 2203 can be configured such that the proximal portion 2204 and valve 2209 are located proximal to the IPS-JV junction 118 (e.g., by 0.25" or more) when implanted in the patient's vasculature; junction 118, a location where the IPS and JV blood flows intersect, can experience more turbulent blood flow and have a higher risk for thrombus formation on an implant and valve portion placed in the junction as compared to a location where the proximal portion of the shunt and valve are placed more proximally in the jugular vein, away from junction 118.

FIG. 56C illustrates a cross section of shunt 2200. The cross section of shunt body 2203 includes a shunt body wall thickness "W" in FIG. 56C. The wall thickness of an elastomer shunt body 2203 can range from about 0.001 inch to about 0.010 inch. The diameter of the CSF lumen 2207 of shunt 2200 can range from about 0.010 inch to about 0.020 inch. The outer diameter of shunt body 2203 can range from about 0.006 inch to about 0.040 inch. The length of shunt body 2203 can range from about 0.25" to 3.0" (6.35 mm 76.2 mm) to or more.

FIGS. 56B-D illustrate distal portion 2202 of shunt 2200. With reference to FIG. 56B, retaining element 2230 comprises a radiopaque material (e.g., gold or other radiopaque material disclosed herein) and the distal portion 2207*a* of CSF lumen 2207 (further described herein). Anchoring mechanism 2229 can include a radiopaque marker located in the distal collar 2229*c*. When shunt 2200 is deployed from a shunt delivery catheter, anchoring mechanism 2229 transitions (e.g., self-expands) from a compressed configuration within the delivery catheter (e.g., denoted by the dotted line portion "C" marked on FIG. 56B) to its open or deployed configuration shown in FIG. 56B; during deployment, the clinician can observe the marker of distal collar 2229*c* move toward the radiopaque retaining element 2230 to confirm that the distal anchoring mechanism 2229 has properly transitioned to its deployed state in CP angle cistern 138.

FIGS. 56C-D illustrate cross sections of the distal portion 2202 of shunt 2200 and the connection between distal anchoring mechanism 2229 and shunt body 2203 using one embodiment of a retaining element 2230. Retaining element 2230 includes a lumen that forms the distal or CSF inflow portion 2207*a* of CSF lumen 2207 of the shunt and embodiments can have the same range of internal diameters as described above for CSF lumen 2207 of shunt body 2203. Retaining element 2230 further includes a tapered portion 2233 to accommodate a curved portion of distal anchoring mechanism arms 2229*a* when the distal anchoring mechanism 2229 is in a compressed or delivery configuration; tapered portion 2233 also prevents retaining element 2230 from slipping proximally through the proximal portion 2229*e* of distal anchoring mechanism 2229 (e.g., during assembly).

The distal portion 2203*a* of shunt body 2203 is secured within the distal anchoring mechanism 2229. As shown in FIGS. 56C-D, distal portion 2203*a* of shunt body 2203 is compressed between the outer surface of retaining element 2203 and inner surface of the proximal portion 2229*e* of distal anchoring mechanism 2229. For example, distal portion 2229*e* of distal anchoring mechanism 2229 can be compressed (e.g., crimped, swaged) over the distal portion 2203*a* of the shunt body and retaining element 2230. Further, retaining element 2230 can include retaining features 2266 (e.g., circumferential threads as shown in FIGS. 60C-D, barbs, tines, hooks, or the like) to secure the distal portion 2203*a* of shunt body 2203 over retaining element 2230 and within the proximal portion 2229*e* of distal anchoring mechanism 2229.

FIG. 56E shows proximal portion 2204 of shunt 2200. Proximal portion 2204 includes a one-way valve 2209. Valve 2209 comprises a slit valve configuration with a single slit 2241 aligned with the longitudinal axis of shunt body 2203. This alignment can advantageously resist thrombus formation when implanted as it is also aligned generally with the direction of blood flow through the jugular vein and minimizes blood turbulence across the surface of proximal portion 2204 of the shunt. Proximal portion 2204 further includes a radiopaque marker 2227*c*, the marker may be disposed between a proximal plug 2207*c* and the valve 2209, or the plug 2207*c* may include radiopaque materials. The radiopaque marker 2227*c* is configured to assist shunt visualization in a patient during follow up clinical visits. The proximal plug 2207*c* is configured to close the proximal opening of the lumen 2207 of the shunt 2200.

Embodiments of valve 2209 can include one slit 2241 (e.g., as shown in FIGS. 29 and 56E) or multiple slits 2241 located around the circumference of shunt body 2203 to achieve a desired opening or cracking pressure for the valve and/or target CSF flow rate at a nominal differential between ICP and venous blood pressure (e.g., any of the opening or cracking pressures described herein, any of the CSF flow rates described herein). The slit 2241 can be orthogonal to the surface of shunt body 2203 (e.g., as shown in FIGS. 29 and 56E) or angled relative to such surface. Each slit 2241 can range from about 1 to 3 mm, or longer. Slit 2241 can be located in the proximal portion 2204 of shunt 2200 (e.g., as shown in FIG. 56E) or located more distally or proximally (e.g., extending to the proximal end of shunt 2200 and/or into plug 2207c described below). With a cylindrically configured shunt body 2203, the hoop strength of shunt body 2203 about slit 2241 prevents backflow of fluid (e.g., blood) through valve into CSF lumen 2207; for example, the valve remains closed and does not allow blood to leak into CSF lumen 2207 when venous blood pressures on the exterior of the shunt elevate above CSF pressure in the shunt lumen 2207 and intracranial compartment (e.g., CP angle cistern 138). Indeed, embodiments of valve 2209 have demonstrated backflow prevention with simulated venous blood pressures exceeding intracranial pressures by more than 175 mm Hg.

The proximal portion of CSF lumen 2007 can include a plug 2207c to close CSF lumen 2207 at its proximal end. Plug 2207c can comprise the same elastomeric material of shunt body 2203 or any of the other polymeric materials disclosed herein. Shunt 2200 can also include a radiopaque marker in the proximal portion of the shunt body 2203. Plug 2207c can be doped with a radiopaque material (e.g., barium sulfate, tantalum, or the like) or plug 2207c and/or proximal portion 2204 of the shunt can include a marker band comprising any of the radiopaque materials disclosed herein (e.g., a marker can be embedded in plug 2207c, shunt body 2203, or fixed thereto). The plug 2207c can have an atraumatic configuration (e.g., rounded end), as shown in FIG. 56E, or a more elongate tapering configuration, or be squared off with respect to the longitudinal axis of shunt body 2203.

FIGS. 57A-D illustrate the connection between distal anchoring mechanism 2229 and shunt body 2203 with an alternate embodiment of retaining element 2230. For ease in illustration and disclosure, the features, functions, and configurations of the shunt that are the same as in the shunt of the present disclosure (e.g., FIGS. 56A-E) are incorporated by reference herewith; the differences will be described in further detail below. Retaining element of FIG. 57A comprises a cylindrical element that forms the distal or CSF inflow portion 2207a of CSF lumen 2207 of shunt 2200, as illustrated in the cross-section views of FIGS. 57C-D. Retaining element 2230 can comprise titanium, stainless steel, Nitinol, or other super-elastic alloys. Retaining element 2230 can be connected to the proximal portion 2229e of distal anchoring mechanism 2229 (e.g., weld or adhesive placed through one or more openings 2229d in the distal anchoring mechanism 2229). A cylindrical marker band 2240 can be swaged over the distal portion 2203a of shunt body 2203 and retaining element 2230 to secure the connection between the shunt body and distal anchoring mechanism. The distal collar 2229c of anchoring mechanism 2229 can include a radiopaque marker (not shown in FIG. 57A-D). When shunt 2200 is deployed from a shunt delivery catheter, anchoring mechanism 2229 transitions (e.g., self-expands) from a compressed configuration within the delivery catheter (e.g., denoted by the dotted line portion "C" marked on FIG. 57C) to its open or deployed configuration shown in FIG. 57B; during deployment, the clinician can observe the marker of distal collar 2229c move toward the radiopaque marker band 2240 to confirm that the distal anchoring mechanism 2229 has properly transitioned to its deployed state.

Shunts comprising an elastomeric body 2203 (e.g., shunt 2200 of FIGS. 56A-58F) can advantageously compress and elongate to facilitate translation through a delivery catheter lumen in a deployment procedure. For example, shunt body 2203 can compress radially up to about 80% (e.g., such that compressed shunt diameter is about 20% of its resting diameter). Further, shunt body 2203 can extend, stretch, or elongate longitudinally up to about 400% of its resting length. The compression and elongation features of shunt body 2203 can be leveraged to maintain a relatively smaller profile (e.g., outer diameter) of a delivery catheter and facilitate delivery catheter access and navigation and shunt implantation through narrow and/or tortuous vasculature.

FIGS. 58A-F illustrate an embodiment of shunt 2200 that includes the connection between distal anchoring mechanism 2229 and shunt body 2203 with an retaining element 2230 illustrated in FIG. 57A-D. FIGS. 58A-F further include the valve 2209, marker 227c and proximal plug 2207c of FIG. 57A-D. As shown in FIGS. 58C-F, the distal collar 2229c of distal anchoring mechanism 2229 includes a radiopaque marker band 2240 to confirm that the distal anchoring mechanism 2229 has properly transitioned from a compressed configuration in the delivery catheter lumen to a deployed configuration in CP angle cistern 138.

FIGS. 59-63B illustrates an embodiment of a shunt delivery shuttle 7000 for translating and deploying a shunt 2200 (e.g., embodiments of shunt 2200 illustrated in FIGS. 56A-58F) through the second lumen 3305 of a delivery catheter 3304 (e.g., any of the delivery catheter embodiments disclosed herein including the delivery catheter illustrated in FIG. 64A-E). The shunt delivery shuttle 7000 includes a distal shuttle portion 7016 (e.g., mesh, braid, shroud, stent-like, funnel-like, tubular body, or other configurations), coupled to an elongate proximal pusher 7012 (e.g., wire or elongated pushing member) via a junction 7014. The distal shuttle portion 7016 of the shunt delivery shuttle 7000 comprises a proximal portion 7016a and a distal portion 7016b, having a lumen 7018 extending therebetween. The distal shuttle portion 7016 of the shunt delivery shuttle 7000 is configured to receive, retain, push and/or shuttle the shunt 2200. As illustrated in FIGS. 59A, 61A, 62A-C and 63C, the proximal portion 7016a of the distal shuttle portion 7016 tapers toward junction 7014.

The distal shuttle portion 7016 of the shunt delivery shuttle 7000 can comprise a self-expanding braid, and is shown in an expanded configuration in FIG. 59. The distal shuttle portion 7016 is configured to receive shunt 2200 (e.g., within the lumen 7018) and is configured to compress and elongate (e.g., FIG. 63A-B) suitable for translation within the second lumen 3305 of the delivery catheter for translating the shunt 2000 through the catheter, into the implantation site of a patient. With a lined lumen (e.g., PTFE-lined second lumen of delivery catheter 3304), the distal shuttle portion 7016 of the shunt delivery shuttle 7000 facilitates smooth transition of an elastomeric shunt 2200 through the delivery catheter. The expanded or resting diameter of distal shuttle portion 7016 of the shunt delivery shuttle 7000 can range from about 0.5 mm to about 6 mm. The compressed length of the shunt delivery shuttle 7000

(e.g., when compressed in a delivery catheter lumen) can range from about 0.25" to 3.0" (6.35 mm 76.2 mm) or more.

The distal shuttle portion 7016 of the shunt delivery shuttle 7000 includes multiple filaments 7020 that are weaved to form the braid structure, as illustrated by the inset of FIG. 59A. Filaments can comprise Nitinol (e.g., heat-set), stainless steel, or a polymer (e.g., PTFE, HDPE, PET, PEEK, Kevlar). Embodiments of the distal shuttle portion 7016 of the shunt delivery shuttle 7000 can include 8 to 144 filaments. Filaments 7020 of the distal shuttle portion 7016 can have round or non-round cross-sections; round cross-section filaments can have a diameter from about 0.0002 inch to about 0.005 inch. Filaments 7020 can be cut in the distal portion 7016b of the distal shuttle portion 7016 (e.g., as illustrated in FIG. 59), rounded, or braided back proximally toward the distal shuttle portion 7016 midsection to create a more atraumatic profile for the distal portion 7016b of the distal shuttle portion 7016.

The elongate proximal pusher 7012 can have a round or non-round cross-sectional profile. Embodiments of elongate proximal pusher 7012 with a round cross section can have a diameter of about 0.0006 to about 0.030 inch. The elongate proximal pusher 7012 can be solid or include a lumen to accommodate other delivery assembly components. Nitinol, stainless steel, or other like materials can be used for elongate proximal pusher 7012, provided the overall design provides sufficient column strength to deliver a shunt 2200 in the shunt delivery shuttle 7000 through a delivery catheter lumen and into a target implant site. The distal portion of the elongate proximal pusher 7012 can include a tapered grind or other features (e.g., cuts, slots, kerfs or the like) to increase the flexibility of such distal portion, which can facilitate shunt translation through the delivery catheter when the catheter is being used in tortuous anatomy. Junction 7014 can be formed by gathering the proximal ends of the filaments 4320 of the distal shuttle portion 7016 of the shunt delivery shuttle 7000 over the distal portion of the elongate proximal pusher 7012 and using a heat shrink material over the filaments and wire, by using a direct connection (e.g., by adhesive or welding, e.g., gathering the filaments over the wire and under a radiopaque marker band), or using any of the shunt-tether interlock configurations disclosed herein.

Alternate embodiments of shunt delivery shuttle 7000 can include any of the anchor 700 configurations disclosed herein as a substitute for the distal shuttle portion 7016 of the shunt delivery shuttle 7000 for translating shunt 2200 through delivery catheter 3304. For example, as shown in FIGS. 60A-63C, the shunt delivery shuttle 7000 can be formed from a hypo tube with a wall thickness from about 0.0005 inch to about 0.004 inch. The strut width of the shunt delivery shuttle 7000 can range from about 0.0002 inch to about 0.003 inch; the strut width can vary along the length of the shunt delivery shuttle 7000 (e.g., creating a stiffer proximal portion of the shunt delivery shuttle 7000 to facilitate translation of the shunt through the delivery catheter lumen and a more flexible distal portion of the shunt delivery shuttle 7000 radially capture shunt 2200). FIGS. 62A-62E illustrate alternative junction 7014 between the distal shuttle portion 7016 of the shunt delivery shuttle 7000 and the elongate proximal pusher 7012, the junction 7014 uses any suitable coupling mechanism or technique.

Figure 63A:
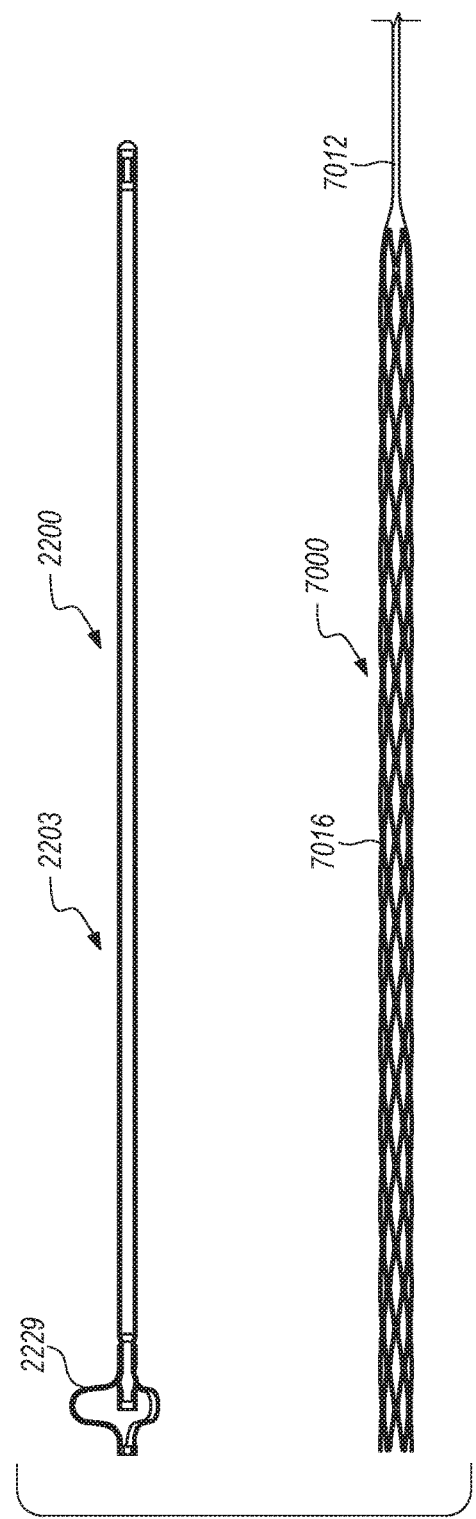
FIGS. 63A-C are perspective views of a shunt and a shunt delivery shuttle interface according to embodiments of the disclosed inventions.
Figure 63B:
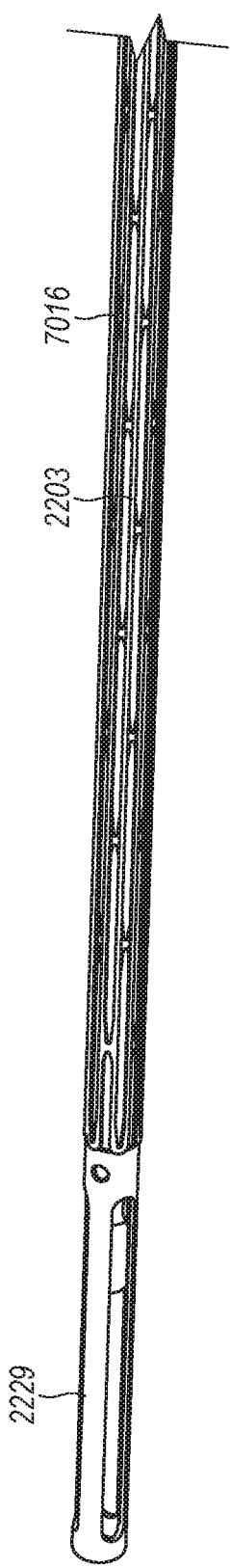
Figure 63C:
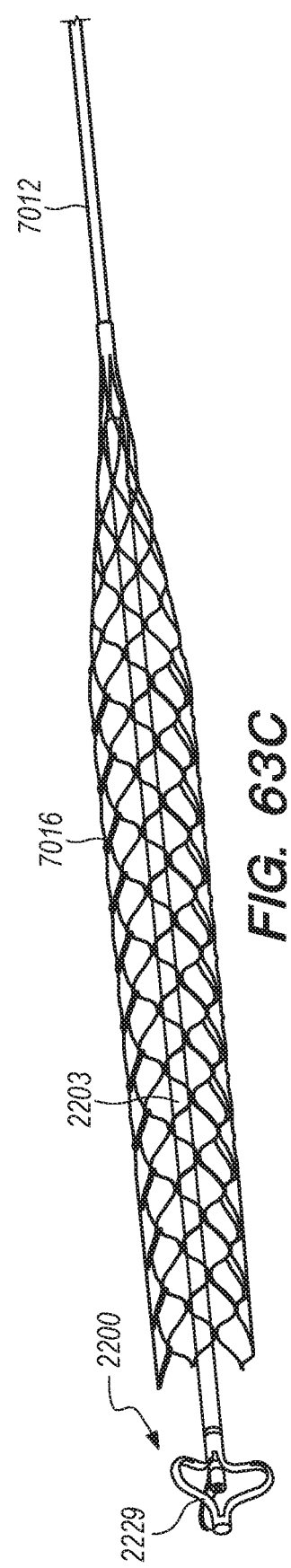

FIGS. 63A-C illustrate the shunt and the shunt delivery shuttle according to the embodiments of the invention. FIG. 63A shows the shunt 2200 and the shunt delivery shuttle 7000 separately, while FIGS. 63B and 63C show the interface between the shunt 2200 and the shunt delivery shuttle 7000. The shunt delivery shuttle 7000 is configured to be at least partially positioned within the lumen of, and movable relative to, the delivery catheter. The distal shuttle portion 7016 of the shunt delivery shuttle 7000 is configured to collapse around the elongate shunt body 2203 (FIG. 63B) to thereby transport the shunt body 2203 through the delivery catheter lumen, wherein the distal shuttle portion 7016 self-expands (FIG. 63C) to release the shunt body 2203 when the distal shuttle portion 7000 is advanced out of the delivery catheter lumen through the opening of the tissue penetrating element.

FIGS. 64A-E illustrate another embodiment of the delivery catheter 3304 embodiments described in connection with FIGS. 19A-I, 20, 21A-M, 30A-F. For ease in illustration and disclosure, the features, functions, and configurations of the delivery catheter that are the same as in the delivery catheter of the present disclosure (e.g., FIGS. 19A-I, 20, 21A-M, 30A-F) are incorporated by reference herewith; the differences will be described in further detail below. The delivery catheter illustrated in FIGS. 64A-E has received an elongate guide member 780 through first lumen 3315 of the penetrating element guard or guard member 4000 and delivery catheter 3304. Penetrating element guard 4000 is disposed over penetrating element 3350 to guard against inadvertent punctures in the vasculature while tracking the delivery catheter to the target penetration site in IPS wall 114. As described in connection with FIGS. 20, 21, and 31, the penetrating element guard 4000 can translate proximally over the distal portion of the delivery catheter to expose the penetrating element 3350 at the target penetration site in the IPS.

Figure 64A:
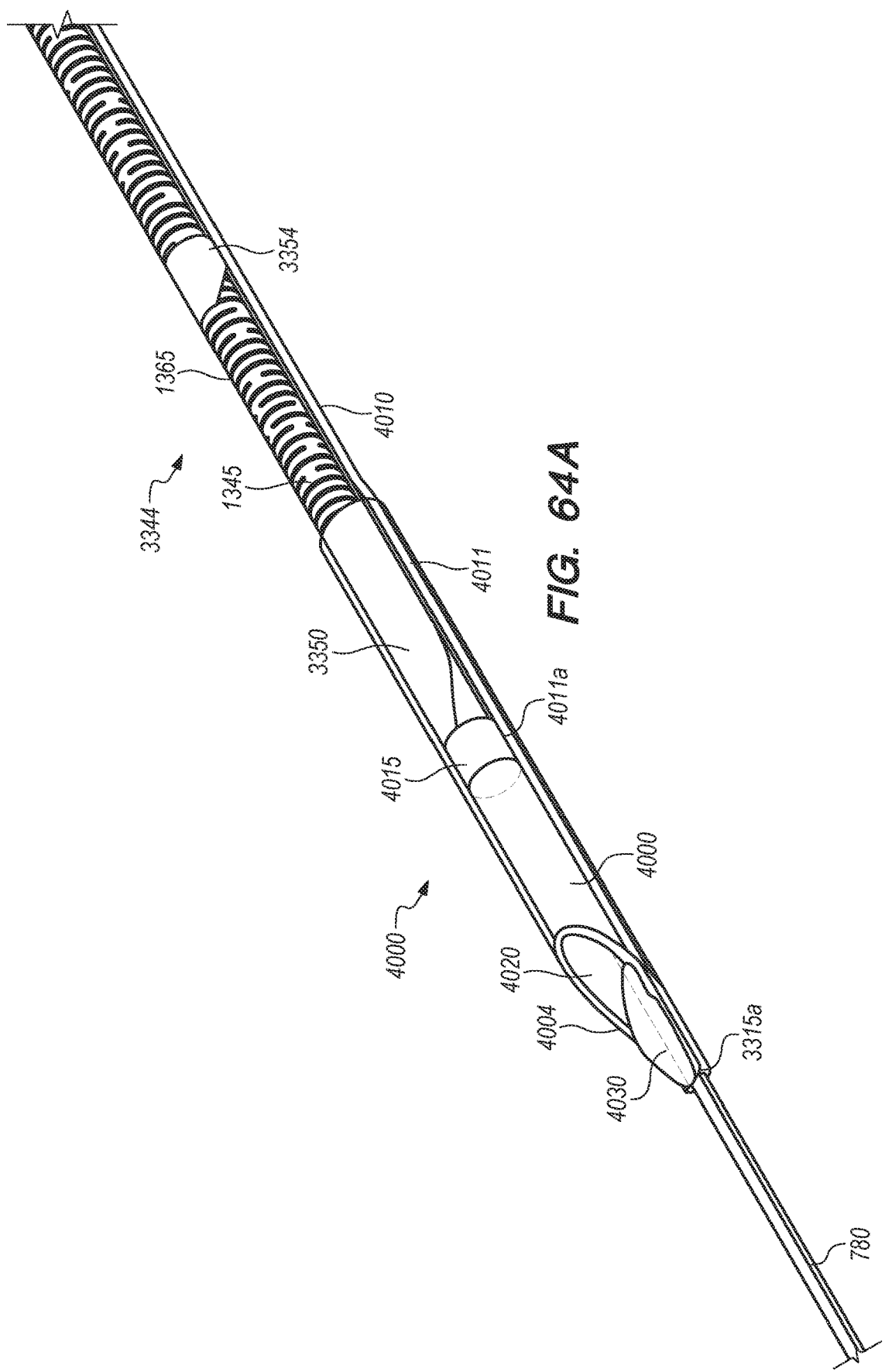
Figure 64B:
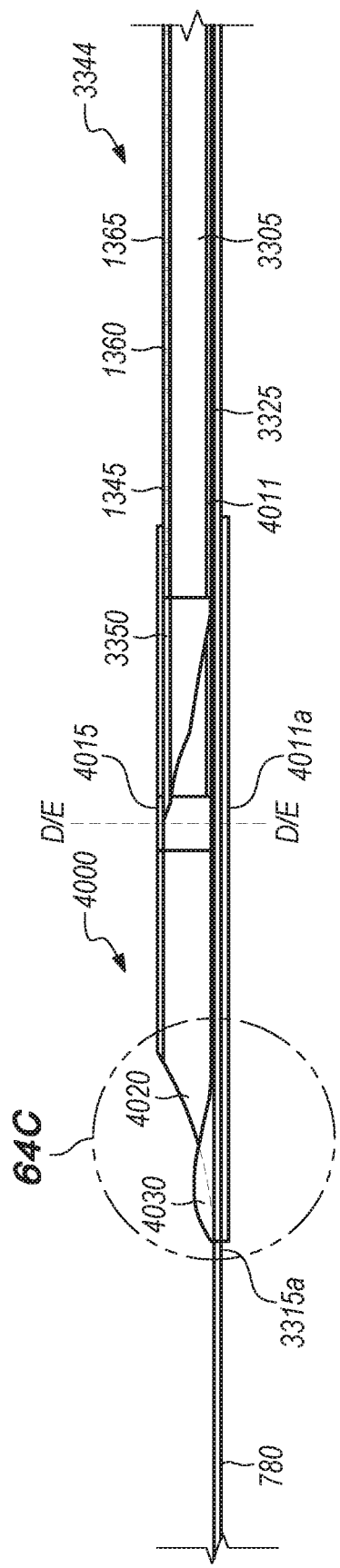
Figure 64C:
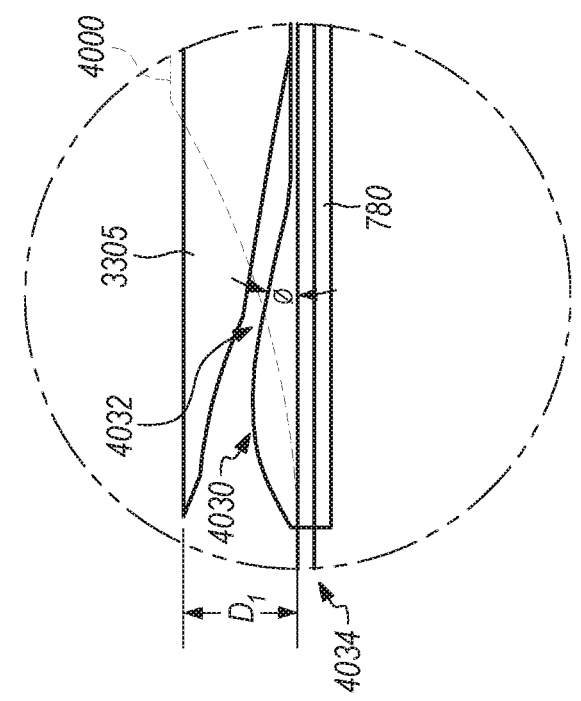

Penetrating element guard 4000 illustrated in FIGS. 64A-E includes a deflecting element 4030 to deflect penetrating element 3350 away from the elongate guide member 780 and towards a target penetration site in the patient's vasculature. FIG. 64B illustrates a cross-section of a distal portion of the delivery catheter including penetrating element guard 4000 and deflecting element 4030. FIG. 64C illustrates further details of the deflecting element 4030 illustrated in FIGS. 64A-B. Deflecting element 4030 includes proximal 4032 and distal 4034 portions. Distal portion 4034 can facilitate delivery catheter access into narrow or tortuous vasculature.

During a shunt deployment procedure, penetrating element guard 4000 is retracted proximally over the delivery catheter to expose penetrating element 3350 at the target penetration site; as the guard 4000 retracts proximally, the proximal portion 4032 of deflecting element 4032 contacts the bevel of penetrating element 3350. As the clinician further retracts penetrating element guard 4000 proximally, deflecting element 4030 (e.g., proximal portion 4032) deflects penetrating element away from elongate guide member 780. To achieve this deflection for penetrating element 3350, the angle of the proximal portion 4032 of deflecting element 4030 relative to the longitudinal axis of elongate guide member 780, as illustrated by angle "Φ" in FIG. 64C, can range from about five degrees to about 30 degrees, or more. Deflecting element 4030, by increasing the angle of the penetrating element relative to the plane of the elongate guide member 780, increases the distance or separation between the penetrating element tip and guide member 780 (e.g., illustrated as D1 in FIG. 64C). Deflecting element 4030 facilitates tissue puncture in challenging patient anatomies, e.g., in a portion of the IPS 102 or CS 104 that runs relatively parallel to CP angle cistern 138. For example, if the patient has a significant petrous bone overhang that prevents penetration through IPS wall 114 at the first turn 102A of IPS 102 (see FIGS. 2A-B), the clinician can use a delivery catheter and shuttle embodiment as illustrated in FIGS. 64A-E to penetrate IPS wall 114 beyond the petrous bone overhang, for example, between the first 102A and second 102B turns of IPS 102.

Deflecting element 4030 can be added to penetrating element guard 4000 using an ultraviolet light-cured adhesive or epoxy material. Alternatively, penetrating element guard 4000 and deflecting element 4030 can be molded as a single part. Materials for molded embodiments of the penetrating element guard and deflecting element can include Nylon, Pebax, polyurethane, or any other polymeric material disclosed herein for use with guard 4000 or delivery catheter 3304.

FIGS. 64D-E illustrate cross-section views of the delivery catheter 3304 shown in FIGS. 64A-C at reference line "D/E" of FIG. 64B (e.g., through marker band 4015 embedded in guard 4000). As shown in FIGS. 64D-E, delivery catheter 3304 includes a second shuttle pull wire 4012. Pull wire 4012 includes a distal portion 4013 and connection point 4013a, which are illustrated in FIGS. 64D-E. Delivery catheter 3304 includes a fourth lumen 3335 (not shown) configured to receive the second pull wire 4012. A dual pull wire configuration of delivery catheter 3304 can provide smoother penetrating element guard 4000 retraction proximally over penetrating element and provide smoother distal retraction of guard 4000 to re-cover penetrating element 3350 compared to single pull wire embodiments.

Figure 65A:
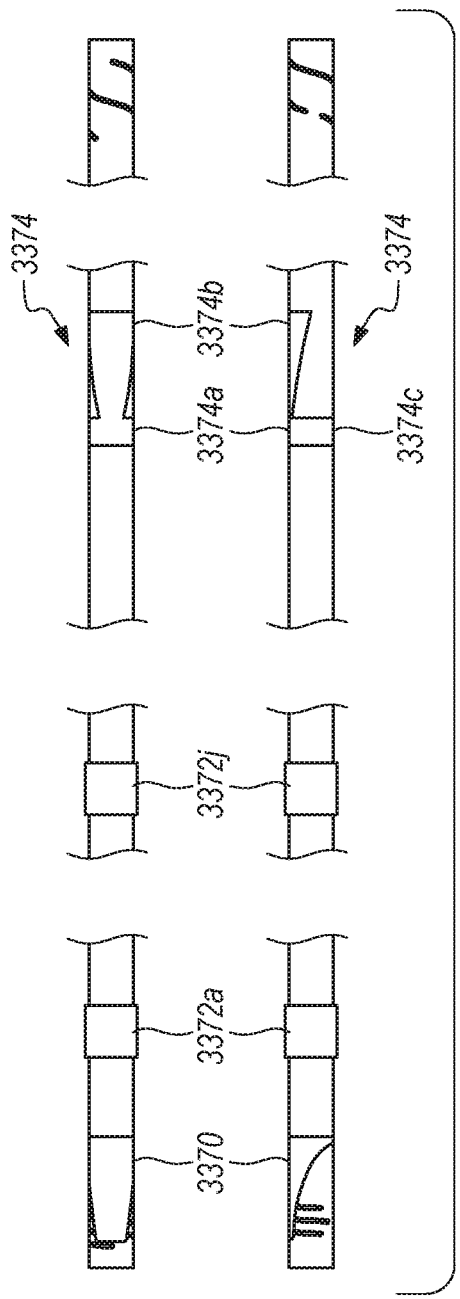
FIGS. 65A-C are side and perspective views of radiopaque markers constructed according to embodiments of the disclosed inventions.
Figure 65B:
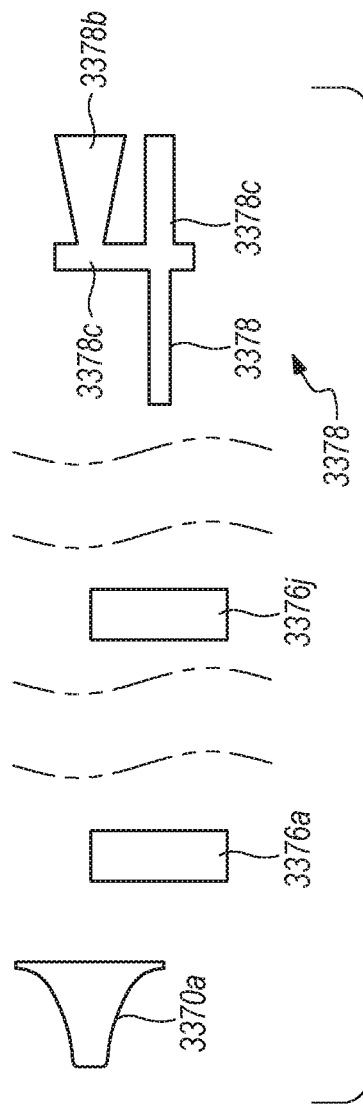
Figure 65C:
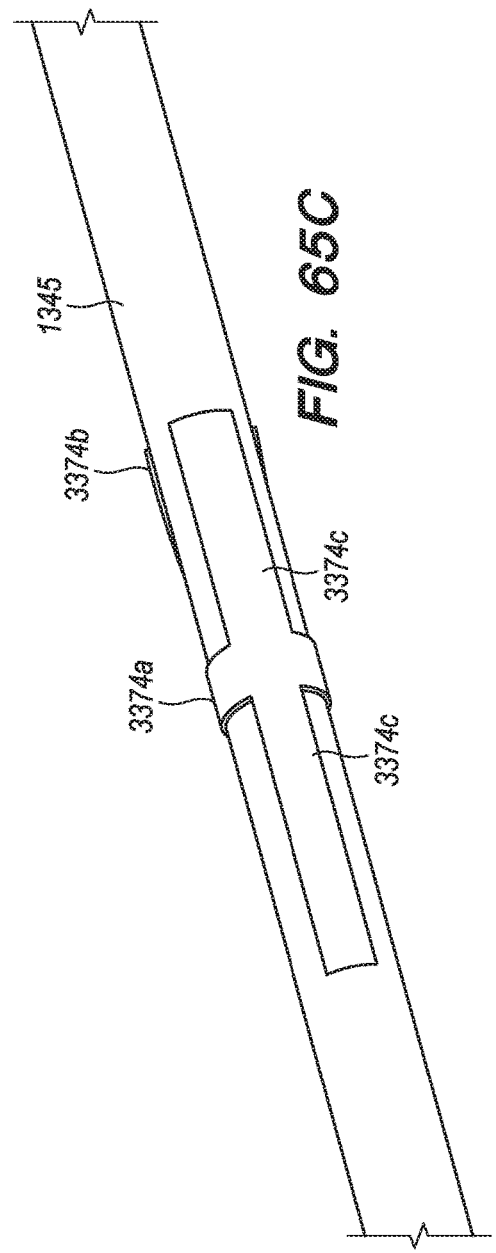

FIGS. 65A-C illustrate embodiments of radiopaque markers that enable an clinician to discern delivery catheter 3304 and penetrating element 3350 orientation in the patient's vasculature under flouroscopy. FIG. 65A illustrates marker bands 3370, 3372, and 3374 applied to reinforcing member 1345 of a delivery catheter 3304. FIG. 65B illustrates the patterns used to apply the marker bands shown in FIG. 65A; pattern 3370a of FIG. 65B corresponds to marker 3370 of FIG. 65A, patterns 3376a through 3376j of FIG. 65B corresponds to markers 3372a through 3372j of FIG. 65A, and pattern 3378 of FIG. 65B corresponds to marker 3374 of FIG. 65A. FIG. 65A illustrates catheter assembly alignment features 3374a-c of marker band 3374.

The markers illustrated in FIG. 65A can comprise gold plating (or other radiopaque materials) applied in the patterns reflected in FIG. 65B to reinforcing member 1345. The plating can range in thickness from about 0.0002 inch to about 0.002 inch. Distal marker band 3370 includes orienting features illustrated in FIGS. 65A-B and can be aligned axially with the bevel of penetrating element 3350 to help the clinician discern penetrating element orientation in vivo (e.g., under flouroscopy when deliver catheter 3304 has advanced into IPS 102). Additional dimensions of marker band 3370 and pattern 3370a used to form marker band 3370 are included in FIGS. 65A-B. Markers 3372a through 3372j comprise a series of marker bands placed with equal spacing between each band (e.g., 1 cm spacing between marker bands as illustrated in FIG. 65A) to provide the clinician with a reference point and measurement tool when delivery catheter has navigated to IPS 102. Each marker band 3372a through 3372j is approximately 1 mm wide, although other widths are possible. While FIG. 65A illustrates ten marker bands at equal 1 cm spacing between each band as the bands extend proximally from marker band 3372a, other configurations and spacing are possible. Orienting feature 3374b of marker band 3374 can also be aligned axially with the bevel of penetrating element 3350 to help the clinician discern penetrating element orientation in vivo. Orienting feature 3374c provides a reference point during manufacturing to ensure proper assembly and function of delivery catheter 3304. For example, elongate guide member 780 and first lumen 3315 of the delivery catheter can be axially aligned to orienting feature 3374c. In addition, one or more shuttle pull wires (e.g., pull wire 4010, pull wire 4012) and the corresponding pull wire lumens (e.g., third lumen 3325, fourth lumen 3335) can be axially aligned to orienting feature 3374c. Additional dimensions and features of marker 3374 are included in FIGS. 65A-B.

Figure 66:
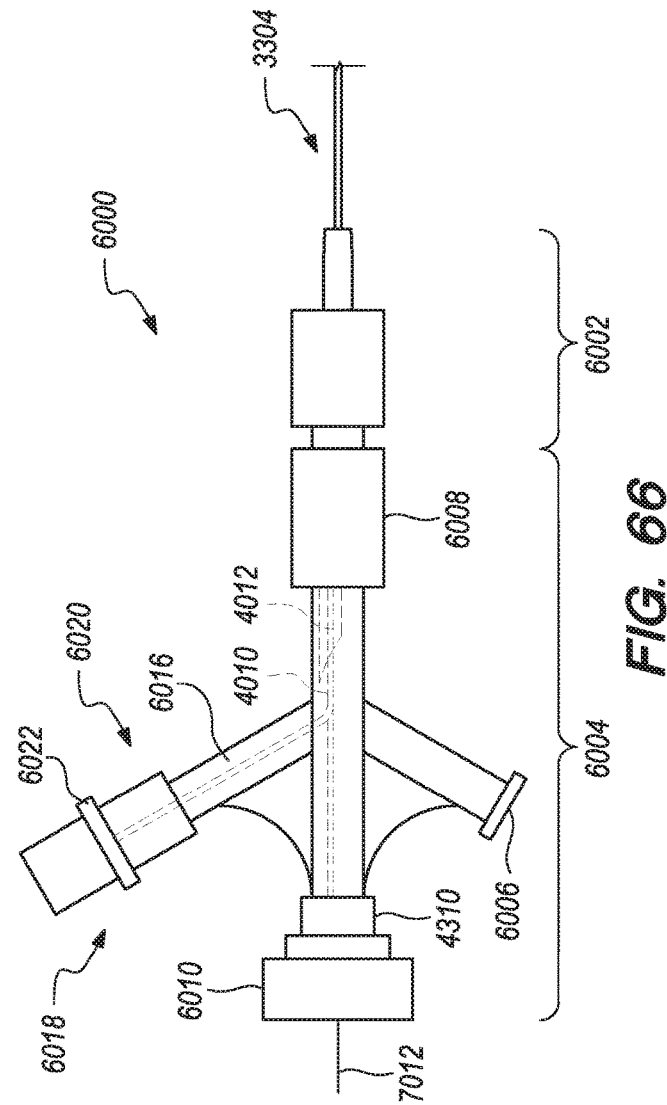
FIG. 66 is perspective view of a handle assembly constructed according to embodiments of the disclosed inventions.

FIG. 66 illustrates an embodiment of a handle assembly 6000 for use with a delivery catheter 3304. Handle assembly 6000 includes three main components: a needle hub 6002, a double hemostasis valve "Y" connector 6004, and a vented male Luer cap 6018; vendor and part number details are provided for these components on FIG. 66. The proximal end of delivery catheter 3304 extends through needle hub 6002 into the distal hub of Y connector 6004 as illustrated in FIG. 66. The elongate proximal pusher 7012 of shunt delivery shuttle 7000 extends proximally from the delivery catheter 3304 through a first hemostasis valve 6010 in Y connector 6004 as illustrated in FIG. 66. Shuttle pull wires 4010 and 4012 extend proximally from their respective lumens in delivery catheter 3304 through a second hemostasis valve 6020 in Y connector 6004. The proximal ends of shuttle pull wires 4010, 4012 extend through a female Luer lock and are fixed (e.g., welded, bonded with adhesive) to the underside of male Luer cap 6018. Hypotubes are used to provide additional support to shuttle pull wires 4010, 4012 in the second hemostasis valve portion 6020 of Y connector 6004: a smaller hypotube 6012, 6014 is placed over each of shuttle pull wires 4010 and 4012. The pull wire and smaller hypotubes are passed through a larger hypotube 6016 shown in FIG. 66. Hypotubes can have any suitable dimensions compatible with handle 6000 (e.g., standard hypotube gauging, dimensions, and materials can be ascertained from https://www.vitaneedle.com/hypodermic-tube-gauge-chart/). Dimensions and other details of hypotubes 6012, 6014, and 6014 are as follows: larger hypotube 6016 is 15 regular wall×1.89"; smaller hypotubes 6012, 6014 are 26 thin wall×2.05 inches. The hypotubes 6012, 6014, and 6014 subassembly in the second hemostasis valve 4020 portion of Y connector 6004 provides additional support and column strength for shuttle pull wires 4010, 4012 to enable smooth and consistent proximal and distal actuation of penetrating element guard 4000 via cap 6018.

When handle assembly 6000 is in use with a delivery catheter 3304, unscrewing cap 6018 from Luer lock 6022 initiates proximal retraction of penetrating element guard 4000; after unscrewing cap 6018 from Luer lock 6022, the clinician can pull proximally on cap 6018 to further retract guard 4000 over penetrating element 3350. The clinician can then use delivery catheter 3304 to penetrate IPS wall. Handle assembly 6000 includes an aspiration/flush port 6006 that includes a lumen fluidically contiguous with second lumen 3305 of delivery catheter 3304; by attaching a syringe (e.g., 1 ml syringe) to the proximal end of port 6006, the operator can aspirate CSF from CP angle cistern 138, through penetrating element lumen 3355, delivery catheter lumen 3305, and port 6006 to observe CSF collecting in the syringe and confirm penetration through IPS wall into the subarachnoid space; alternative embodiments of handle assembly 6000 do not include aspiration/flush port 6006. The shunt delivery shuttle 7000 can be used to advance shunt 2200 from delivery catheter lumen 3305 and penetrating element lumen 3355 until distal anchoring mechanism 2229 deploys in CP angle cistern 138. Port 6006 can also be used to flush saline or contrast through lumen 3305 and out of penetrating element lumen 3355 into the patient's vasculature at different points during the shunt implant procedure. By reversing the foregoing sequence described for cap 6018 (e.g., pushing distally on cap 6018 and screwing cap 6018 onto Luer lock 6022, the operator can advance guard 4000 distally clinician and re-cover penetrating element 3350 (e.g., after shunt implantation and while withdrawing delivery catheter from the patient).

It should be appreciated that if the clinician inadvertently causes a tear in IPS wall 114, the clinician may elect to abort the procedure. If using an embodiment of anchor 700 that includes an outer polymeric layer that covers the cells of the anchor and a guide member 780 that can detach from anchor 700, he can, redeploy anchor 700 in the sinus lumen across the tear and leave the anchor 700 in the IPS 102 by detaching guide member 780; in this scenario, the anchor can prevent venous blood from leaving into the subarachnoid space and/or uncontrolled CSF leaking from the subarachnoid space into the venous system.

FIGS. 67-A-H illustrates alternative delivery catheter, pusher member 3310 and shunt 2200 interfaces, and respective interlocking members 3336, constructed according to embodiments of the disclosed inventions. As shown in FIG. 67A, the interlocking member 3336 of the pusher 3310 engages the outer surface of the shunt 2200, which radially compresses without longitudinally stretching the shunt 2200 and thereby reduces friction of the shunt 2200 with the delivery catheter inner wall.

Figure 67A:
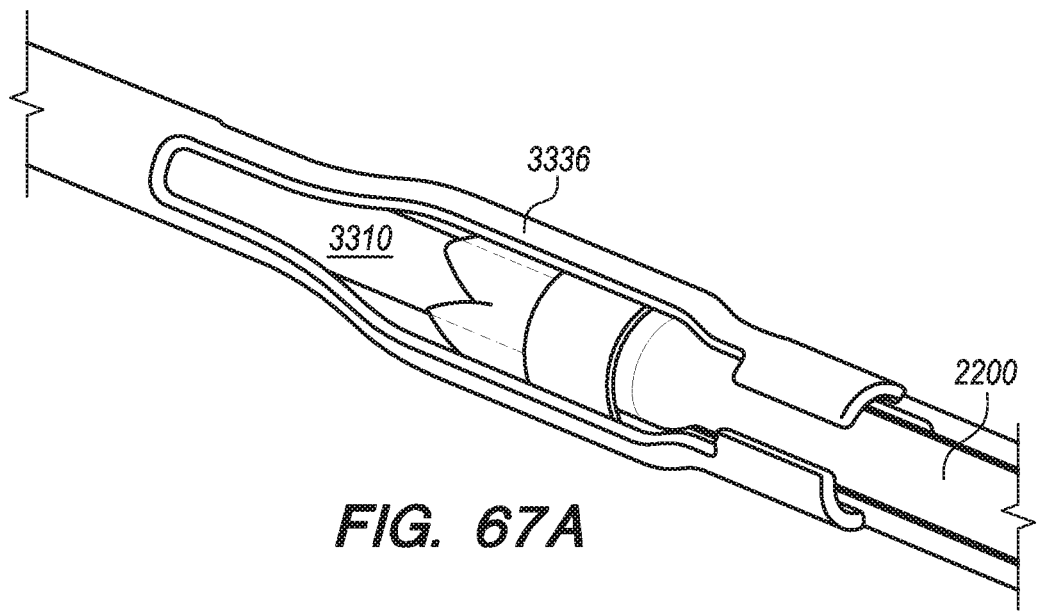
FIGS. 67A-I are side views of a shunt pusher constructed according to embodiments of the disclosed inventions.
Figure 67B:
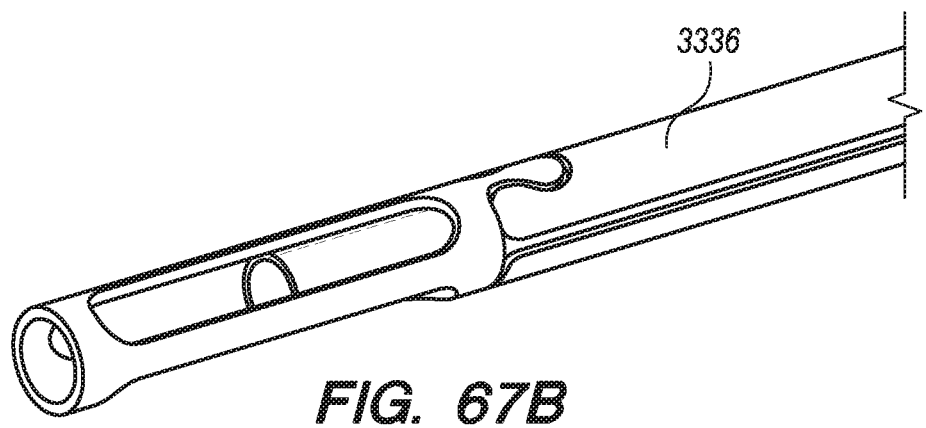
Figure 67C:
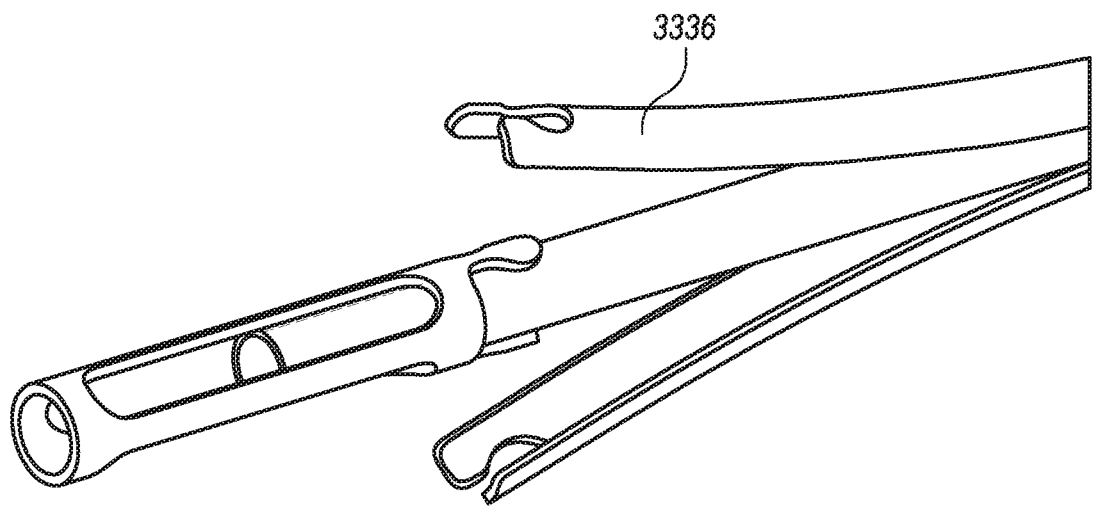

In FIGS. 67B-C, the interlocking member of the pusher 3310 engages the outer surface of the delivery catheter. In these embodiments, friction of the shunt 2200 with the delivery catheter may be reduced and the valve (not shown) of the shunt would be not engaged with the pusher member 3310, since the interlock member is mounted on the outer surface of the catheter. In alternative embodiments, the interlocking member 3336 of the pusher depicted in FIGS. 67B-C can be constrained within the lumen of a delivery catheter, as previously described in connection with other pusher embodiments disclosed herein.

Figure 67D:
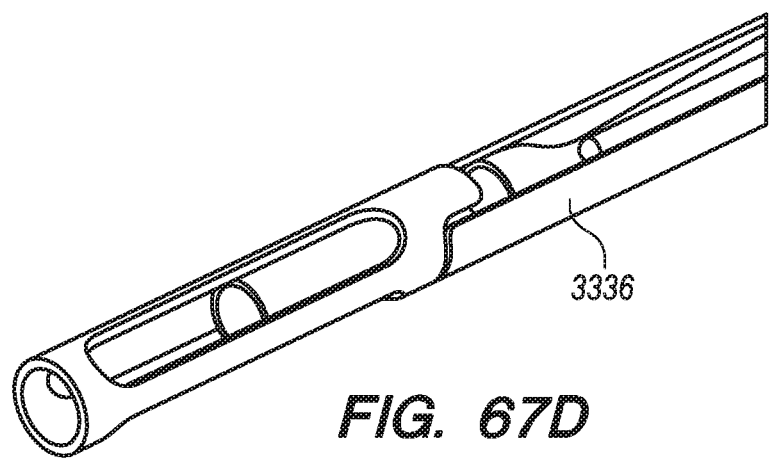
Figure 67E:
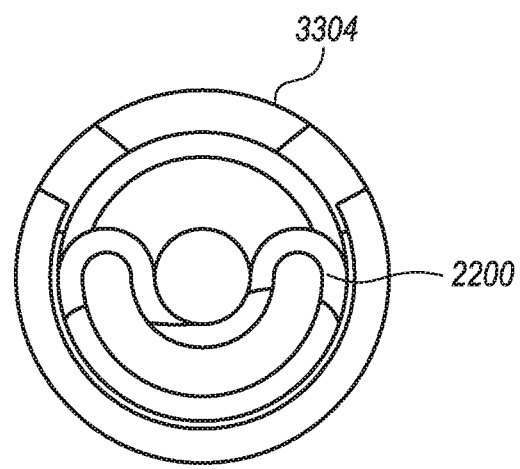

As shown in FIG. 67D-E, the shunt 2200 may be further compressed (e.g., folded, bent, or the like) within the lumen of the delivery catheter 3304 for more efficient packing during delivery of the shunt at the target site.

Figure 67F:
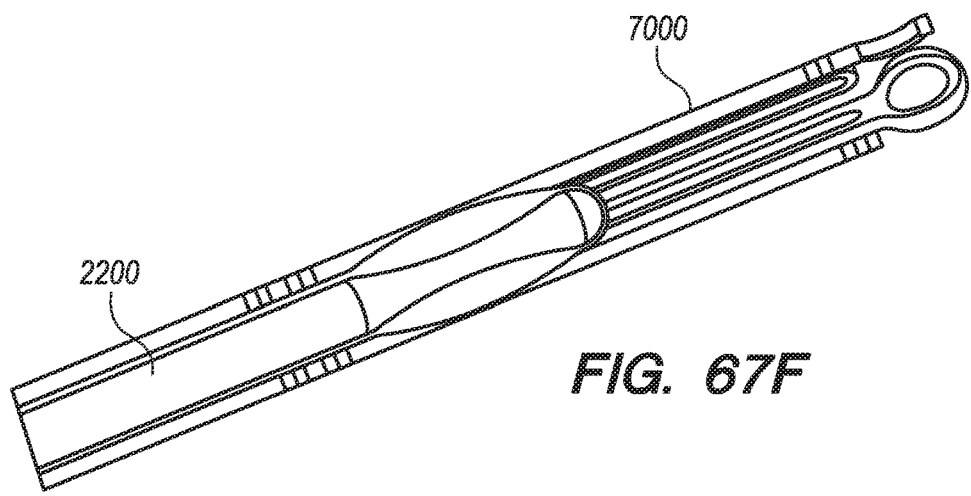
Figure 67G:
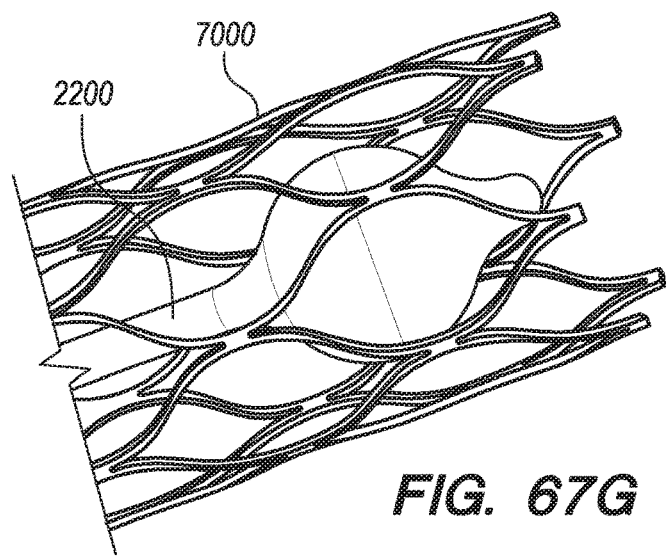

Alternatively or additionally, the shunt 2200 may be compressed during delivery by the shunt delivery shuttle 7000 having a stent-like structure, as shown in FIGS. 67F-G. In these embodiments, the shunt comprises a polymeric body and anchoring mechanism (e.g., silicon) as it will be described in further detail below.

Figure 67H:
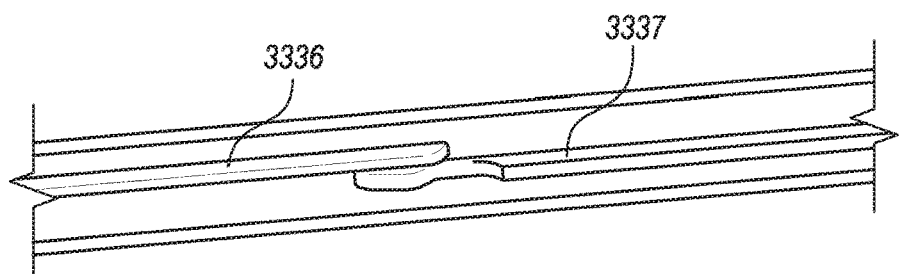
Figure 67I:
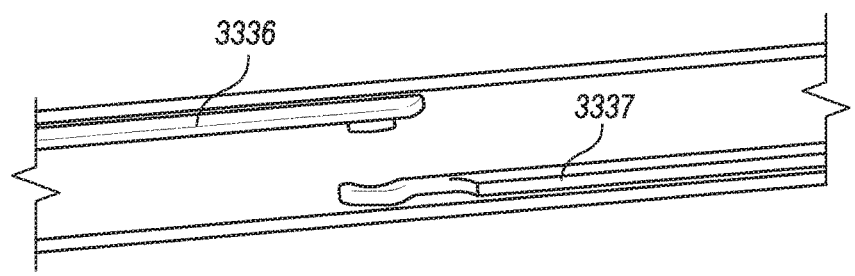

In yet another alternative embodiment, the interlocking members 3336 of the pusher and the interlocking members 3337 of the shunt include mating elements, such as a protrusion and a slot, as shown in FIGS. 67H-I. The engagement of the interlocking members may be further assisted by a reduced inner diameter of the delivery catheter (not shown), magnetic elements, or the like.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

The invention claimed is:

1. A catheter device comprising:
 a reinforcing member having a proximal end and a distal end and defining a central opening therebetween, the reinforcing member comprising:
  a plurality of discrete longitudinally arranged structural regions disposed between the proximal end and the distal end and comprising:
   a first structural region, disposed at or near the proximal end and defining a first series of wall perforations setting a first stiffness of the first structural region, the first series of wall perforations having a pitch of about 0.014 inches to about 0.018 inches and a cut frequency of about 2 to about 3 cuts per rotation;
   a second structural region, disposed distally relative to the first structural region and defining a second series of wall perforations setting a second stiffness of the second structural region, the second series of wall perforations having a pitch starting at about 0.014 inches to about 0.018 inches and decreasing to about 0.003 inches to about 0.007 inches and a cut frequency of about 2 to about 3 cuts per rotation;
   a third structural region, disposed distally relative to the second structural region and defining a third series of wall perforations setting a third stiffness of the third structural region, the third series of wall perforations having a pitch starting at about 0.008 inches to about 0.012 inches and decreasing to about 0.002 inches to about 0.006 inches and a cut frequency of about 1 to about 2 cuts per rotation;
   a fourth structural region, disposed distally relative to the third structural region and defining a fourth series of wall perforations setting a fourth stiffness of the fourth structural region, the fourth series of wall perforations having a pitch of about 0.002 inches to about 0.006 inches and a cut frequency of about 1 to about 2 cuts per rotation; and
   a distal structural region substantially free of perforations and disposed distally relative to the fourth structural region.

2. The catheter device of claim 1 wherein a width of any one or more of the first, second, third, or fourth series of wall perforations is about 0.0005 inches to about 0.0015 inches.

3. The catheter device of claim 1 wherein:
 the first series of wall perforations has a cut balance of about 106 degrees to about 110 degrees on and about 34 degrees to about 38 degrees off;
 the second series of wall perforations has a cut balance of about 106 degrees to about 110 degrees on and about 34 degrees to about 38 degrees off;
 the third series of wall perforations has a cut balance of about 208 degrees to about 212 degrees on and about 28 degrees to about 32 degrees off; and
 the fourth series of wall perforations has a cut balance of about 208 degrees to about 212 degrees on and about 28 degrees to about 32 degrees off.

4. The catheter device of claim 3 wherein:
 the first series of wall perforations has a cut balance of about 108 degrees on and about 36 degrees off;
 the second series of wall perforations has a cut balance of about 108 degrees on and about 36 degrees off;

the third series of wall perforations has a cut balance of about 210 degrees on and about 30 degrees off; and the fourth series of wall perforations has a cut balance of about 210 degrees on and about 30 degrees off.

5. The catheter device of claim 3 wherein:

the first series of wall perforations is formed along a substantially left-helical path; and the fourth series of wall perforations is formed along a substantially left-helical path.

6. The catheter device of claim 5 wherein:

the second series of wall perforations is formed along a substantially left-helical path; and the third series of wall perforations is formed along a substantially left-helical path.

7. The catheter device of claim 1 further comprising a liner material along an inner surface of the central opening and an outer jacket material disposed along an outer surface of the reinforcing member.

8. The catheter device of claim 1 wherein the distal structural region has a length that is less than about 0.020 inches; the fourth structural region has a length that is about 6 inches to about 8 inches; the third structural region has a length that is about 4 to about 8 inches; and the second structural region has a length that is about 6 to about 9 inches.

9. The catheter device of claim 8 wherein the distal structural region has a length that is about 0.012 inches; the fourth structural region has a length that is about 7.862 inches; the third structural region has a length that is about 5.906 inches; and the second structural region has a length that is about 7.874 inches.

10. A method for deploying an elongate guide member into a body lumen of a patient using a pusher tool, the method comprising:

(a) navigating a catheter device of claim 1 to a target location in the body lumen of the patient, wherein the catheter device of claim 1 is configured to deploy the guide member;

(b) inserting the guide member through respective handle and tubular body portion lumens of the pusher tool;

(c) grasping the pusher tool;

(d) pinching to thereby secure a portion of the guide member in pinched engagement against a proximal facing surface of the handle;

(e) advancing the pusher tool while maintaining the pinched engagement of the guide member against the proximal facing surface of the handle so as to advance the guide member distally into, or further into, a first end opening of the catheter device of claim 1;

(f) releasing the pinched engagement of the guide member from the proximal facing surface of the handle; and (g) withdrawing the pusher tool proximally relative to the guide member.

11. The method of claim 10, further comprising repeatedly performing steps (d) through (g) until a distal end portion of the guide member is deployed from a second end opening of the catheter device of claim 1 and positioned at the target location in the patient's body.

12. The method of claim 11, wherein the advancing of the pusher tool while maintaining the pinched engagement of the guide member against the proximal facing surface of the handle so as to advance the guide member distally into, or further into, the first end opening of the catheter device of claim 1 comprises:

providing an axial force to the first structural region of the catheter device of claim 1.

13. The method of claim 10, wherein a single hand is used for grasping the pusher tool.

14. The method of claim 13, wherein a finger or thumb of the single hand is used for pinching to thereby secure the portion of the guide member against the proximal facing surface of the handle.

15. The method of claim 10, wherein the body lumen comprises a blood vessel, and wherein the catheter device of claim 1 is advanced into the blood vessel through an introducer sheath having a proximal opening outside of the patient and a distal opening within the blood vessel.

16. The method of claim 10, wherein the first end opening of the catheter device of claim 1 is accessed via an introducer hub, the method further comprising grasping to thereby stabilize the introducer hub while advancing a distal portion of the tubular body through the introducer hub.

17. The method of claim 10, wherein the proximal facing surface of the handle is configured to mate with a human thumb or finger.

18. The method of claim 10, wherein the targeted location in the patient's body comprises inferior petrosal sinus (IPS) or cavernous sinus (CS) of the patient at a location distal to a curved wall portion of the IPS that separates the IPS from a cerebellopontine (CP) angle cistern of the patient.

* * * * *